(12) United States Patent
Maxwell et al.

(10) Patent No.: US 12,005,127 B2
(45) Date of Patent: Jun. 11, 2024

(54) DNA-PK INHIBITORS

(71) Applicant: VERTEX PHARMACEUTICALS INCORPORATED, Boston, MA (US)

(72) Inventors: John Patrick Maxwell, Hingham, MA (US); Katrina Lee Jackson, Weston, MA (US); Qing Tang, Boxborough, MA (US); Mark A. Morris, Somerville, MA (US); Steven M. Ronkin, Watertown, MA (US); Jinwang Xu, Framingham, MA (US); Kevin M. Cottrell, Cambridge, MA (US); Paul S. Charifson, Framingham, MA (US)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 899 days.

(21) Appl. No.: 16/962,442

(22) PCT Filed: Jan. 16, 2019

(86) PCT No.: PCT/US2019/013788
§ 371 (c)(1),
(2) Date: Jul. 15, 2020

(87) PCT Pub. No.: WO2019/143678
PCT Pub. Date: Jul. 25, 2019

(65) Prior Publication Data
US 2020/0353101 A1  Nov. 12, 2020

Related U.S. Application Data

(60) Provisional application No. 62/618,339, filed on Jan. 17, 2018.

(51) Int. Cl.
| | | |
|---|---|---|
| *C07D 239/74* | (2006.01) |
| *A61K 48/00* | (2006.01) |
| *C07D 239/88* | (2006.01) |
| *C07D 239/94* | (2006.01) |
| *C07D 401/12* | (2006.01) |
| *C07D 403/12* | (2006.01) |
| *C07D 417/12* | (2006.01) |
| *C07D 491/048* | (2006.01) |

(52) U.S. Cl.
CPC ...... *A61K 48/0066* (2013.01); *A61K 48/0075* (2013.01); *C07D 239/74* (2013.01); *C07D 239/88* (2013.01); *C07D 239/94* (2013.01); *C07D 401/12* (2013.01); *C07D 403/12* (2013.01); *C07D 417/12* (2013.01); *C07D 491/048* (2013.01)

(58) Field of Classification Search
CPC ............ A61K 48/0066; A61K 48/0075; C07D 239/74; C07D 239/99; C07D 239/94; C07D 401/12; C07D 403/12; C07D 417/12; C07D 491/048
See application file for complete search history.

(56) References Cited

U.S. PATENT DOCUMENTS

| | | |
|---|---|---|
| 3,773,919 A | 11/1973 | Boswell et al. |
| 4,186,183 A | 1/1980 | Steck et al. |
| 4,217,344 A | 8/1980 | Vanlerberghe et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,774,085 A | 9/1988 | Fidler |
| 4,797,368 A | 1/1989 | Carter et al. |
| 4,837,028 A | 6/1989 | Allen |
| 4,897,355 A | 1/1990 | Eppstein et al. |
| 4,946,787 A | 8/1990 | Eppstein et al. |
| 5,049,386 A | 9/1991 | Eppstein et al. |
| 5,173,414 A | 12/1992 | Lebkowski et al. |
| 5,356,802 A | 10/1994 | Chandrasegaran |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,008,336 A | 12/1999 | Hanson et al. |
| 6,013,453 A | 1/2000 | Choo et al. |
| 6,140,081 A | 10/2000 | Barbas |
| 6,140,466 A | 10/2000 | Barbas, III et al. |
| 6,200,759 B1 | 3/2001 | Dove et al. |

(Continued)

FOREIGN PATENT DOCUMENTS

| | | |
|---|---|---|
| AU | 2019209293 | 1/2019 |
| CN | 105246883 A | 1/2016 |

(Continued)

OTHER PUBLICATIONS

Brinkman, E.K. et al., "Easy Quantitative Assessment of Genome Editing by Sequence Trace Decomposition," Nucleic Acids Research, 8 pages, Dec. 16, 2014, vol. 42, No. 22, p. e168, Oxford University Press, Oxford, UK.

(Continued)

*Primary Examiner* — D Margaret M Seaman
(74) *Attorney, Agent, or Firm* — Barnes & Thornburg LLP

(57) ABSTRACT

The present invention relates to compounds useful as inhibitors of DNA-PK. The invention also provides pharmaceutically acceptable compositions comprising said compounds and methods of using the compositions in the treatment of various diseases, conditions, or disorders.

48 Claims, 3 Drawing Sheets
Specification includes a Sequence Listing.

(56) References Cited

U.S. PATENT DOCUMENTS

| | | |
|---|---|---|
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,689,558 B2 | 2/2004 | Case |
| 6,794,136 B1 | 9/2004 | Eisenberg et al. |
| 6,903,185 B2 | 6/2005 | Kim et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,074,596 B2 | 7/2006 | Darzynkiewicz et al. |
| 7,153,949 B2 | 12/2006 | Kim et al. |
| 7,253,273 B2 | 8/2007 | Collingwood |
| 7,262,054 B2 | 8/2007 | Jamieson et al. |
| 7,361,635 B2 | 4/2008 | Miller et al. |
| 8,153,773 B2 | 4/2012 | Jemielity et al. |
| 8,404,681 B2 | 3/2013 | Halbrook et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Le Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,145,565 B2 | 9/2015 | Carroll et al. |
| 9,181,535 B2 | 11/2015 | Liu et al. |
| 9,365,964 B2 | 6/2016 | Kim |
| 9,771,333 B2 * | 9/2017 | Zhang ................. A61P 35/04 |
| 2005/0064474 A1 | 3/2005 | Urnov et al. |
| 2005/0267061 A1 | 12/2005 | Martin |
| 2006/0188987 A1 | 8/2006 | Guschin et al. |
| 2007/0218528 A1 | 9/2007 | Miller |
| 2008/0131962 A1 | 6/2008 | Miller |
| 2011/0201055 A1 | 8/2011 | Doyon et al. |
| 2013/0281431 A1 | 10/2013 | Charifson et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0275059 A1 | 9/2014 | Maxwell et al. |
| 2014/0287938 A1 | 9/2014 | Zhang et al. |
| 2014/0310830 A1 | 10/2014 | Zhang et al. |
| 2020/0353101 A1 | 11/2020 | Maxwell et al. |

FOREIGN PATENT DOCUMENTS

| | | |
|---|---|---|
| EP | 1381857 | 1/2004 |
| EP | 1417038 | 5/2004 |
| EP | 2771468 | 9/2014 |
| EP | 2 784 162 A1 | 10/2014 |
| EP | 2 771 468 B1 | 2/2015 |
| EP | 2784162 B1 | 4/2015 |
| EP | 2 764 103 B1 | 8/2015 |
| EP | 3740480 A1 | 11/2020 |
| GB | 2338237 | 2/2001 |
| JP | 2006-523681 | 10/2006 |
| JP | 2016-509063 A | 3/2016 |
| JP | 2016-516706 | 6/2016 |
| JP | 2016-522190 | 7/2016 |
| JP | 2017-535271 A | 11/2017 |
| JP | 2021-511038 | 5/2021 |
| JP | 2021-511312 | 5/2021 |
| JP | 2021-511314 A | 5/2021 |
| WO | WO 1991/016024 | 10/1991 |
| WO | WO 1991/017424 | 11/1991 |
| WO | WO 1993/024641 | 12/1993 |
| WO | WO 1995/019431 | 7/1995 |
| WO | WO 1996/006166 | 2/1996 |
| WO | WO 1998/037186 | 8/1998 |
| WO | WO 1998/053057 | 11/1998 |
| WO | WO 1998/053058 | 11/1998 |
| WO | WO 1998/053059 | 11/1998 |
| WO | WO 1998/053060 | 11/1998 |
| WO | WO 1998/054311 | 12/1998 |
| WO | WO 2000/027878 | 5/2000 |
| WO | WO 2001/060970 | 8/2001 |
| WO | WO 2001/088197 | 11/2001 |
| WO | WO 2002/016536 | 2/2002 |
| WO | WO 2002/077227 | 10/2002 |
| WO | WO 2002/099084 | 12/2002 |
| WO | WO 2003/016496 | 2/2003 |
| WO | WO 2007/014275 | 2/2007 |
| WO | WO 2010/017562 | 2/2010 |
| WO | 2013072015 A1 | 5/2013 |
| WO | WO 2013/130824 | 9/2013 |
| WO | WO 2014/018423 | 1/2014 |
| WO | WO 2014/093595 | 6/2014 |
| WO | WO 2014/093622 | 6/2014 |
| WO | WO 2014/093635 | 6/2014 |
| WO | WO 2014/093655 | 6/2014 |
| WO | WO 2014/093661 | 6/2014 |
| WO | WO 2014/093694 | 6/2014 |
| WO | WO 2014/093701 | 6/2014 |
| WO | WO 2014/093709 | 6/2014 |
| WO | WO 2014/093712 | 6/2014 |
| WO | WO 2014/093718 | 6/2014 |
| WO | WO 2014/130955 | 8/2014 |
| WO | 2014/159690 | * 10/2014 |
| WO | 2014/183850 | * 10/2014 |
| WO | 2014159690 A1 | 10/2014 |
| WO | WO 2014/172458 | 10/2014 |
| WO | 2014183850 A1 | 11/2014 |
| WO | WO 2014/204723 | 12/2014 |
| WO | WO 2014/204724 | 12/2014 |
| WO | WO 2014/204725 | 12/2014 |
| WO | WO 2014/204726 | 12/2014 |
| WO | WO 2014/204727 | 12/2014 |
| WO | WO 2014/204728 | 12/2014 |
| WO | WO 2014/204729 | 12/2014 |
| WO | WO 2015/048557 | 4/2015 |
| WO | WO 2015/048577 | 4/2015 |
| WO | WO 2015/058067 | 4/2015 |
| WO | WO 2015/077375 A1 | 5/2015 |
| WO | WO 2015/168079 | 11/2015 |
| WO | WO 2016/028682 | 2/2016 |
| WO | WO 2016/081923 | 5/2016 |
| WO | WO 2017/165655 | 9/2017 |
| WO | WO 2018/013840 | 1/2018 |
| WO | WO 2019/143675 | 7/2019 |
| WO | WO 2019/143677 | 7/2019 |
| WO | WO 2019/143678 | 7/2019 |

OTHER PUBLICATIONS

International Search Report dated Mar. 19, 2019, prepared in International Application No. PCT/US2019/013783.

International Search Report dated Mar. 21, 2019, prepared in International Application No. PCT/US2019/013785.

Ahmad, I., and Allen, T.M., "Antibody-Mediated Specific Binding and Cytotoxicity of Liposome-Entrapped Doxorubicin to Lung Cancer Cells in Vitro," Cancer Research, pp. 4817-4820, Sep. 1,

(56) References Cited

OTHER PUBLICATIONS 1992, vol. 52, No. 17, American Society for Cancer Research, Philadelphia, PA, US.
Bae, S., et al., "Cas-OFFinder: A Fast and Versatile Algorithm That Searches for Potential Off-Target Sites of Cas9 RNA-Guided Endonucleases," *Bioinformatics*, pp. 1473-1475, Jan. 24, 2014, vol. 30, No. 10, Oxford University Press, Oxford, UK.
Beerli, R.R., and Barbas, C.F. III., "Engineering Polydactyl Zinc-Finger Transcription Factors," Nature Biotechnology, Feb. 2002, pp. 135-141, vol. 20, Nature Portfolio, London, UK.
Behr, J.-P., "Gene Transfer with Synthetic Cationic Amphiphiles: Prospects for Gene Therapy," Bioconjugate Chemistry, Sep. 1, 1994, pp. 382-389, vol. 5, No. 5, American Chemical Society, Washington, DC.
Bell, C.C., et al., "A High-Throughput Screening Strategy for Detecting CRISPR-Cas9 Induced Mutations Using Next-Generation Sequencing," BMC Genomics, 7 pages, Nov. 20, 2014, 15, No. 1, Article No. 1002, Springer Nature, London, UK.
Bennardo, N., et al., "Alternative-NHEJ is a Mechanistically Distinct Pathway of Mammalian Chromosome Break Repair," PLoS Genetics, 10 pages, Jun. 27, 2008, vol. 4, Issue 6, e1000110, Public Library of Science, San Francisco, CA, US.
Berge, S.M., et al., "Pharmaceutical Salts", Journal of Pharmaceutical Sciences, Jan. 1977, pp. 1-19, vol. 66, No. 1, vol. 66, Elsevier, Amsterdam, NL.
Bitinaite, J., et al., "FokI Dimerization is Required for DNA Cleavage," Proceedings of the National Academy of Sciences of the United States of America, pp. 10570-10575, Sep. 1998, vol. 95, United States National Academy of Sciences, Washington, DC, US.
Blaese, M., et al., "Vectors in Cancer Therapy: How Will They Deliver?" Cancer Gene Therapy, pp. 291-297, 1995, vol. 2, No. 4, Nature Portfolio, London, UK.
Certo, M.T. et al., "Tracking Genome Engineering Outcome at Individual DNA Breakpoints", *Nature Methods*, Aug. 2011, pp. 671-676, vol. 8, No. 8, Nature Portfolio, London, UK.
Choo, Y., and Isalan, M., "Advances in Zinc Finger Engineering," Current Opinion in Structural Biology, pp. 411-416, Aug. 1, 2000, vol. 10, Issue 4, Elsevier, Amsterdam, NL.
Crystal, R.G., "Transfer of Genes to Humans: Early Lessons and Obstacles to Success," Science, Oct. 20, 1995, pp. 404-410, vol. 270, American Association for the Advancement of Science, Washington, DC, US.
Dexheimer, T.S., "DNA Repair Pathways and Mechanisms," DNA Repair of Cancer Stem Cells, Dordrecht: Springer; 2013. pp. 19-32.
Fonfara, Ines et al., "The CRISPR-associated DNA-cleaving enzyme Cpf1 also processes precursor CRISPR RNA", Nature, vol. 532, pp. 517-521.
Fu, Y. et al., "Improving CRISPR-Cas Nuclease Specificity Using Truncated Guide RNAs," *Nature Biotechnology*, pp. 279-284, Mar. 2014, vol. 32, No. 3, Nature Portfolio, London, UK.
Gao, F., et al., "DNA-guided Genome Editing Using the *Natronobacterium gregoryi* Argonaute," *Nature Biotechnology*, pp. 768-773, May 2016, vol. 34, No. 7, Nature Portfolio, London, UK, with Aug. 1, 2017 Retraction.
Gao, X., and Huang, L., "Cationic Liposome-Mediated Gene Transfer," Gene Therapy, 1995, pp. 710-722, vol. 2, Nature Portfolio, London, UK.
Heigwer, F., et al., "E-CRISP: Fast CRISPR Target Site Identification," Nature Methods, Feb. 2014, pp. 122-123, vol. 11, No. 2, Nature Portfolio, London, UK.
Heppell, Jacob T., and Jasim Al-Rawi, "Synthesis, structures elucidation, DNA-PK, P13K and antiplatelet activity of a series of novel 7- or 8-(N-substituted)-2-morpholino-quinazolines." Medicinal Chemistry Research, 2016, 25(8): pp. 1695-1704.
Hermonat, P.L., and Muzyczka, N., "Use of Adeno-Associated Virus as a Mammalian DNA Cloning Vector: Transduction of Neomycin Resistance into Mammalian Tissue Culture Cells," Proceedings of the National Academy of Sciences of the United States of America, pp. 6466-6470, Oct. 1984, vol. 81, United States National Academy of Sciences, Washington, DC, US.

Heyer, W.-D., et al., "Regulation of Homologous Recombination in Eukaryotes," Annual Review of Genetics, 2010, pp. 113-139, vol. 44, Annual Reviews, San Mateo, CA.
Hsu, P.D., et al., "DNA Targeting Specificity of RNA-Guided Cas9 Nucleases," *Nature Biotechnology*, pp. 827-832, Sep. 2013, vol. 31, No. 9, Nature Portfolio, London, UK.
Isalan, M., et al., "A Rapid, Generally Applicable Method to Engineer Zinc Fingers Illustrated by Targeting the HIV-1 Promoter," Nature Biotechnology, pp. 656-660, Jul. 2001, vol. 19, Nature Portfolio, London, UK.
Kim, Y.-G., et al., "Chimeric Restriction Endonuclease," Proceedings of the National Academy of Sciences of the United States of America, pp. 883-887, Feb. 1994, vol. 91, United States National Academy of Sciences, Washington, DC, US.
Kim, Y.-G., et al., "Insertion and Deletion Mutants of FokI Restriction Endonuclease," The Journal of Biological Chemistry, pp. 31978-31982, Dec. 16, 1994, vol. 269, No. 50, The American Society for Biochemistry and Molecular Biology, Rockville, MD, US.
Kotin, R.M., "Prospects for the Use of Adeno-Associated Virus as a Vector for Human Gene Therapy," Human Gene Therapy, pp. 793-801, 1994, vol. 5, Mary Ann Liebert, Inc., Larchmont, NY, US.
Li, L., and Chandrasegaran, S., "Alteration of the Cleavage Distance of FokI Restriction Endonuclease by Insertion Mutagenesis," Proceedings of the National Academy of Sciences of the United States of America, pp. 2764-2768, Apr. 1993, vol. 90, United States National Academy of Sciences, Washington, DC, US.
Li, L., et al., "Functional Domains in FokI Restriction Endonuclease," Proceedings of the National Academy of Sciences of the United States of America, pp. 4275-4279, May 1992, vol. 89, United States National Academy of Sciences, Washington, DC, US.
Lin, S., et al., "Enhanced Homology-Directed Human Genome Engineering by Controlled Timing of CRISPR/Cas9 Delivery," eLife, 13 pages, Dec. 15, 2014, e04766, eLife Sciences Publications Ltd., Cambridge, UK.
MacDiarmid, J.A., et al., "Sequential Treatment of Drug-Resistant Tumors with Targeted Minicells Containing siRNA or a Cytotoxic Drug," Nature Biotechnology, pp. 643-651, Jul. 2009, vol. 27, No. 7, Nature Portfolio, London, UK.
Mali, P., et al., "RNA-Guided Human Genome Engineering via Cas9," Science, pp. 823-826, Feb. 15, 2013, vol. 339, American Association for the Advancement of Science, Washington, DC, US.
Miyaoka, Y., et al., "Systematic Quantification of HDR and NHEJ Reveals Effects of Locus, Nuclease, and Cell Type on Genome-Editing," *Scientific Reports*, 12 pages, Mar. 31, 2016, 6, Article No. 23549, Scientific Reports, London, UK.
Muzyczka, N., "Adeno-Associated Virus (AAV) Vectors: Will They Work?" Journal of Clinical Investigation, p. 1351, Oct. 1994, vol. 94, The American Society for Clinical Investigation, Inc., Ann Arbor, MI, US.
Pabo, C.O, et al., "Design and Selection of Novel Cys2His2 Zinc Finger Proteins," Annual Review of Biochemistry, pp. 313-340, 2001, vol. 70, Annual Reviews, San Mateo, CA, US.
Remy, J.-S., et al., "Gene Transfer with a Series of Lipophilic DNA-Binding Molecules," Bioconjugate Chemistry, pp. 647-654, Nov. 1, 1994, vol. 5, Issue 6, American Chemical Society, Washington, DC, US.
Robert, Francis, et al., "Pharmacological inhibition of DNA-PK stimulates Cas9-mediated genome editing." Genome medicine, 2015, 7(1); pp. 1-11.
Roberts, R.J., et al., "REBASE: Restriction Enzymes and Methyltransferases," Nucleic Acids Research, Jan. 1, 2003, pp. 418-420, vol. 31, No. 1, Oxford University Press, Oxford, UK.
Samulski, R.J., et al., "Helper-Free Stocks of Recombinant Adeno-Associated Viruses: Normal Integration Does Not Require Viral Gene Expression," Journal of Virology, pp. 3822-3828, Sep. 1989, vol. 63, No. 9, American Society for Microbiology, Washington, DC, US.
Segal, D.J., and Barbas, C.F. III, "Custom DNA-Binding Proteins Come of Age: Polydactyl Zinc-Finger Proteins," Current Opinion in Biotechnology, pp. 632-637, 2001, vol. 12, Elsevier, Amsterdam, NL.

(56) References Cited

OTHER PUBLICATIONS

Swiech, L. et al., "In vivo Interrogation of Gene Function in the Mammalian Brain Using CRISPR-Cas9", Nature Biotechnology, pp. 102-106, (2015), vol. 33, No. 1, Nature Portfolio, London, UK.

Tratschin, J. D., et al., "A Human Parvovirus, Adeno-Associated Virus, as a Eucaryotic Vector: Transient Expression and Encapsidation of the Procaryotic Gene for Chloramphenicol Acetyltransferase," Molecular and Cellular Biology, pp. 2072-2081, Oct. 1984, vol. 4, No. 10, American Society for Microbiology, Washington, DC, US.

Tratschin, J. D., et al., "Adeno-Associated Virus Vector for High-Frequency Integration, Expression, and Rescue of Genes in Mammalian Cells," Molecular and Cellular Biology, pp. 3251-3260, Nov. 1985, vol. 5, No. 11, American Society for Microbiology, Washington, DC, US.

West, M.H.P., et al., "Gene Expression in Adeno-Associated Virus Vectors: The Effects of Chimeric mRNA Structure, Helper Virus, and Adenovirus VAI RNA," Virology, pp. 38-47, 1987, vol. 160, Elsevier, Amsterdam, NL.

Wiedenheft, B., et al., "RNA-guided genetic silencing systems in bacteria and archaea," Nature, Feb. 15, 2012, 482 (7385, pp. 331-338.

Xiao, A., et al., "CasOT: A Genome-Wide Cas9/gRNA Off-Target Searching Tool," *Bioinformatics*, pp. 1180-1182, (2014), vol. 30, No. 8, Oxford University Press, Oxford, UK.

Zetsche, B., et al., "Cpf1 is a Single RNA-Guided Endonuclease of a Class 2 CRISPR-Cas System," Cell, pp. 759-771, Oct. 22, 2015, vol. 163, No. 3, Elsevier, Amsterdam, NL.

Zhu, F. et al, "Nickel-Catalyzed Cross-Coupling of Aryl Fluorides and Organozinc Reagents," Journal of Organic Chemistry, 2014, 79, pp. 4285-4292.

International Search Report dated Mar. 19, 2019, prepared in International Application No. PCT/US2019/013788.

Peng, R., et al, "Potential Pitfalls of CRISPR/Cas9-Mediated Genome Editing", The FEBS Journal, Nov. 4, 2015, pp. 1218-1231, vol. 283, No. 7, John Wiley and Sons, Hoboken, NJ, U.S.

Robert, F., et al. "Pharmacological inhibition of DNA-PK stimulates Cas9-mediated genome editing", Genome Medicine, Aug. 27, 2015, pp. 1-11, vol. 7, No. 1.

\* cited by examiner

DNA-PK INHIBITORS

CROSS-REFERENCE TO RELATED APPLICATIONS

This application is a National Stage application of International Application No. PCT/US2019/013788, filed Jan. 16, 2019, which claims the benefit of U.S. Provisional Application No. U.S. 62/618,339, filed Jan. 17, 2018, the entire contents of which are hereby incorporated herein by reference.

SEQUENCE LISTING

The instant application contains a Sequence Listing which has been submitted electronically in ASCII format and is hereby incorporated by reference in its entirety. The ASCII copy, created on Jan. 16, 2019, is named 67573-322059 Sequence listing_ST25.txt and is 4.1 KB in size.

TECHNICAL FIELD OF THE INVENTION

The present invention relates to compounds useful as inhibitors of DNA-dependent protein kinase (DNA-PK). The invention also provides pharmaceutically acceptable compositions comprising the compounds of the invention and methods of using the compositions in the treatment of cancer, and for increasing genome editing efficiency by administering a DNA-PK inhibitor and a genome editing system to a cell(s).

BACKGROUND OF THE INVENTION

Ionizing radiation (IR) induces a variety of DNA damage of which double strand breaks (DSBs) are the most cytotoxic. These DSBs can lead to cell death via apoptosis and/or mitotic catastrophe if not rapidly and completely repaired. In addition to IR, certain chemotherapeutic agents including topoisomerase II inhibitors, bleomycin, and doxorubicin also cause DSBs. These DNA lesions trigger a complex set of signals through the DNA damage response network that function to repair the damaged DNA and maintain cell viability and genomic stability. In mammalian cells, the predominant repair pathway for DSBs is the Non-Homologous End Joining Pathway (NHEJ). This pathway functions regardless of the phase of the cell cycle and does not require a template to re-ligate the broken DNA ends. NHEJ requires coordination of many proteins and signaling pathways. The core NHEJ machinery consists of the Ku70/80 heterodimer and the catalytic subunit of DNA-dependent protein kinase (DNA-PKcs or DNA-PK), which together comprise the active DNA-PK enzyme complex. DNA-PKcs is a member of the phosphatidylinositol 3-kinase-related kinase (PIKK) family of serine/threonine protein kinases that also includes ataxia telangiectasia mutated (ATM), ataxia telangiectasia and Rad3-related (ATR), mTOR, and four PI3K isoforms. However, while DNA-PKcs is in the same protein kinase family as ATM and ATR, these latter kinases function to repair DNA damage through the Homologous Recombination (HR) pathway and are restricted to the S and $G_2$ phases of the cell cycle. While ATM is also recruited to sites of DSBs, ATR is recruited to sites of single stranded DNA breaks.

NHEJ is thought to proceed through three key steps: recognition of the DSBs, DNA processing to remove non-ligatable ends or other forms of damage at the termini, and finally ligation of the DNA ends. Recognition of the DSB is carried out by binding of the Ku heterodimer to the ragged DNA ends followed by recruitment of two molecules of DNA-PKcs to adjacent sides of the DSB; this serves to protect the broken termini until additional processing enzymes are recruited. Recent data supports the hypothesis that DNA-PKcs phosphorylates the processing enzyme, Artemis, as well as itself to prepare the DNA ends for additional processing. In some cases DNA polymerase may be required to synthesize new ends prior to the ligation step. The auto-phosphorylation of DNA-PKcs is believed to induce a conformational change that opens the central DNA binding cavity, releases DNA-PKcs from DNA, and facilitates the ultimate religation of the DNA ends.

It has been known for some time that DNA-PK$^{-/-}$ mice are hypersensitive to the effects of IR and that some non-selective small molecule inhibitors of DNA-PKcs can radiosensitize a variety of tumor cell types across a broad set of genetic backgrounds. While it is expected that inhibition of DNA-PK will radiosensitize normal cells to some extent, this has been observed to a lesser degree than with tumor cells likely due to the fact that tumor cells possess higher basal levels of endogenous replication stress and DNA damage (oncogene-induced replication stress) and DNA repair mechanisms are less efficient in tumor cells. Most importantly, an improved therapeutic window with greater sparing of normal tissue will be imparted from the combination of a DNA-PK inhibitor with recent advances in precision delivery of focused IR, including image-guide RT (IGRT) and intensity-modulated RT (IMRT).

Inhibition of DNA-PK activity induces effects in both cycling and non-cycling cells. This is highly significant since the majority of cells in a solid tumor are not actively replicating at any given moment, which limits the efficacy of many agents targeting the cell cycle. Equally intriguing are recent reports that suggest a strong connection between inhibition of the NHEJ pathway and the ability to kill traditionally radioresistant cancer stem cells (CSCs). It has been shown in some tumor cells that DSBs in dormant CSCs predominantly activate DNA repair through the NHEJ pathway; it is believed that CSCs are usually in the quiescent phase of the cell cycle. This may explain why half of cancer patients may experience local or distant tumor relapse despite treatment as current strategies are not able to effectively target CSCs. A DNA-PK inhibitor may have the ability to sensitize these potential metastatic progenitor cells to the effects of IR and select DSB-inducing chemotherapeutic agents.

Given the involvement of DNA-PK in DNA repair processes, an application of specific DNA-PK inhibitory drugs would be to act as agents that will enhance the efficacy of both cancer chemotherapy and radiotherapy. Accordingly, it would be desirable to develop compounds useful as inhibitors of DNA-PK.

In addition, precise genome targeting technologies are needed to enable systematic engineering of genetic variations. The use of genome editing systems, specifically Clustered Regularly Interspaced Short Palindromic Repeats (CRISPR)-endonuclease based genome editing technology has grown exponentially in the past few years. The type II CRISPR-Cas9 bacterial innate immune system has emerged as an effective genome editing tool for targeted modification of the human genome (Wiedenheft, B. 2012; Hsu, P. D. eta. 2014). Recently, CRISPR-Cpf genome editing systems have been described. CRISPR-endonuclease based genome editing is dependent, in part, upon non-homologous end joining (NHEJ) and homology directed repair (HDR) pathways to repair DNA double strand breaks. Cellular repair mechanism favors NHEJ over HDR.

While the achievement of insertion or deletions (indels) from NHEJ is up to 70% effective in some reports, the efficiency of HDR remains challenging, with rates at less than 1%.

Accordingly, a need exists for increasing genome editing efficiency, in particular, HDR efficiency. Another application of specific DNA-PK inhibitory drugs would be to act as agents that will enhance the efficacy of genome editing systems.

SUMMARY OF THE INVENTION

It has been found that compounds of this invention, and pharmaceutically acceptable compositions thereof, are effective as inhibitors of DNA-PK. Accordingly, in one aspect, the invention features compounds represented by Formula (I):

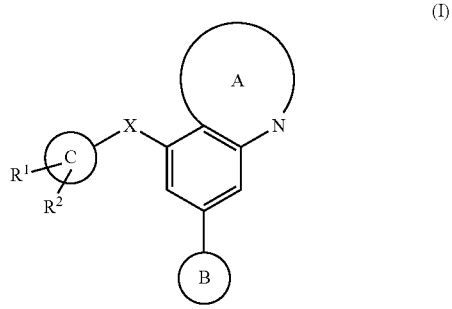

or pharmaceutically acceptable salts thereof, where each of $R^1$, $R^2$, X, Ring A, Ring B and Ring C independently is as defined elsewhere herein.

In one embodiment, the compounds of the invention are represented by Formula (I) or pharmaceutically acceptable salts thereof, wherein:

Ring A is an aromatic ring system selected from

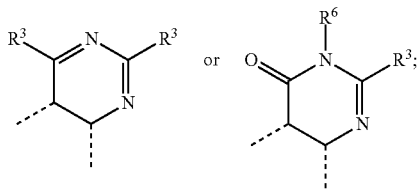

Ring B is a ring system selected from

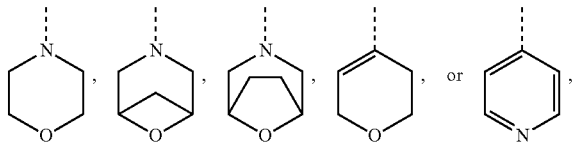

wherein Ring B is optionally substituted with one or more substituents selected from the group consisting of —F, —OH, and $C_{1-4}$alkyl optionally substituted with one or more substituents selected from the group consisting of —F, —Cl, —OH, and —OC$_{1-2}$alkyl;

Ring C is a $C_{4-6}$ cycloalkyl, 5-6-membered heteroaryl, or phenyl group, wherein Ring C is optionally further substituted with one or more substituents selected from the group consisting of halogen, $C_{1-2}$ alkyl, —OH, and —OC$_{1-2}$alkyl;

X is —NH—, —O—, —OC$_{1-4}$ alkyl-, —S—, or —CH$_2$—;

each of $R^1$ and $R^2$ is, independently, hydrogen, —C(O)NHR$^4$, —C(O)OR$^4$, —NHC(O)R$^4$, —NHC(O)OR$^4$, —NHC(O)NHR$^4$, —NHS(O)$_2$R$^4$, —NHR$^4$, —C$_{1-4}$ alkyl-NHR$^4$, —OR$^4$, or R$^7$ wherein $R^1$ and $R^2$ cannot simultaneously be hydrogen;

each $R^3$ independently is hydrogen, —C$_{1-4}$alkyl, halogen, —OC$_{1-2}$alkyl, —C(O)OH, —C(O)OC$_{1-2}$alkyl, —CN, —C(O)NHC$_{1-2}$alkyl, —C(O)NH$_2$, C$_{3-4}$ cycloalkyl, or —NRR', wherein each of said $R^3$ alkyl and cycloalkyl independently is optionally substituted with one or more substituents selected from the group consisting of —F, —Cl, —OH and —OC$_{1-2}$alkyl;

each $R^4$ independently is hydrogen, C$_{1-4}$alkyl, C$_{2-4}$alkenyl, C$_{2-4}$alkynyl, C$_{3-10}$ cycloalkyl, 6-10 membered aryl, 5-10-membered heteroaryl, or 4-10-membered heterocyclyl, wherein each of said $R^4$ groups is optionally substituted with one or more substituents selected from the group consisting of —Br, —Cl, —F, C$_{1-4}$alkyl, CN, NO$_2$, C$_{2-4}$alkenyl, C$_{2-4}$alkynyl, C$_{3-6}$cycloalkyl, C$_{0-4}$ alkyl-C$_{3-5}$ cycloalkyl, C$_{0-4}$ alkyl-O—C$_{1-4}$ alkyl, C$_{0-4}$ alkyl-O—C$_{0-4}$ alkyl-C$_{3-5}$ cycloalkyl, C(O)OC$_{1-4}$ alkyl, C(O)OC$_{0-4}$ alkyl-C$_{3-5}$ cycloalkyl, C$_{0-4}$ alkyl-C(O)NH$_2$, C(O)NHC$_{1-4}$ alkyl, C(O)N(C$_{1-4}$ alkyl)$_2$, C(O)NH(C$_{0-4}$ alkyl-C$_{3-5}$ cycloalkyl), CH$_2$OR$^5$, C$_{0-4}$ alkyl-C(O)R$^5$, C$_{0-4}$ alkyl-C(O)N(R$^5$)$_2$, C$_{0-4}$ alkyl-C(O)OR$^5$, C$_{0-4}$ alkyl-NHC(O)R$^5$, C$_{0-4}$ alkyl-N(R$^5$)$_2$, 5-6 membered heterocyclyl, —O(C$_{1-4}$ alkyl)OR$^5$, —OR$^5$, and oxo, and wherein each of said optional $R^4$ substituents is optionally and independently substituted with one or more substituents selected from the group consisting of —F, —Cl, C$_{1-4}$alkyl, —OH, —OC$_{1-4}$alkyl, —SC$_{1-4}$alkyl, —C(O)C$_{1-4}$ alkyl, —C(O)OC$_{1-4}$ alkyl, and —C(O)OC$_{0-4}$ alkyl-C$_{3-5}$ cycloalkyl; and each $R^5$ independently is hydrogen, C$_{1-4}$alkyl, phenyl, 5-6-membered heteroaryl, or 4-7-membered heterocyclyl, wherein each $R^5$ independently is optionally substituted with one or more substituents selected from the group consisting of —F, —Cl, C$_{1-2}$alkyl, —CH$_2$OH, —CN, —OH, —OC$_{1-2}$alkyl, 5-6-membered heteroaryl, and 4-7 membered heterocyclyl, or two $R^5$ groups together with the intervening nitrogen atom optionally form a morpholine ring, azetidine ring, pyrrolidine ring, piperidine ring, or piperazine ring; and $R^6$ is hydrogen or C$_{1-4}$alkyl optionally substituted with one or more substituents selected from the group consisting of —F, —Cl, —CH$_2$OH, —CN, —OH, and —OC$_{1-2}$alkyl;

$R^7$ is 6-10-membered aryl, 5-10-membered heteroaryl, or 4-7-membered heterocyclyl, each of which is optionally substituted with one or more substituents selected from the group consisting of —F, —Cl, C$_{1-2}$alkyl, —CH$_2$OH, —CN, and —OR; and each of R and R' independently is hydrogen or C$_{1-4}$alkyl, or R and R' together with the nitrogen atom to which they are attached optionally form a morpholine ring, azetidine ring, pyrrolidine ring, piperidine ring, or piperazine ring.

or a pharmaceutically acceptable salt thereof, where each of $R^1$, $R^2$, X, Ring A, Ring B and Ring C is as defined elsewhere herein.

The invention also provides pharmaceutical compositions that include a compound of Formula (I) and a pharmaceutically acceptable carrier, adjuvant, or vehicle. These compounds and pharmaceutical compositions are useful for treating or lessening the severity of cancer.

The compounds and compositions provided by this invention are also useful for the study of DNA-PK in biological and pathological phenomena; the study of intracellular signal transduction pathways mediated by such kinases; and the comparative evaluation of new kinase inhibitors.

The present invention can also improve HDR efficiency by suppressing NHEJ enzymes such as DNA-PK using DNA-PK inhibitors.

In some embodiments, the disclosure provides a method of editing one or more target genomic regions, the method includes administering to one or more cells that have one or more target genomic regions, a genome editing system and a compound represented by Formula (I):

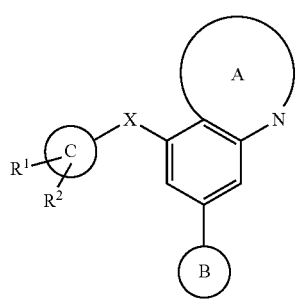

(I)

or pharmaceutically acceptable salts thereof, where each of $R^1$, $R^2$, X, Ring A, Ring B and Ring C independently is as defined elsewhere herein.

Ring A is an aromatic ring system selected from

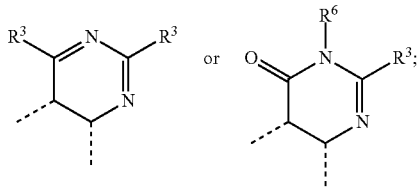

Ring B is a ring system selected from

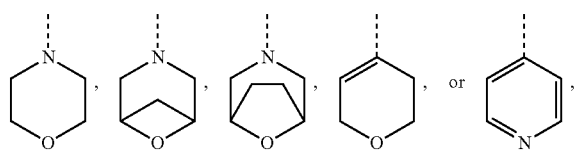

wherein Ring B is optionally substituted with one or more substituents selected from the group consisting of —F, —OH, and $C_{1-4}$alkyl optionally substituted with one or more substituents selected from the group consisting of —F, —Cl, —OH, and —$OC_{1-2}$alkyl;

Ring C is a $C_{4-6}$ cycloalkyl, 5-6-membered heteroaryl, or phenyl group, wherein Ring C is optionally further substituted with one or more substituents selected from the group consisting of halogen, $C_{1-2}$ alkyl, —OH, and —$OC_{1-2}$alkyl;

X is —NH—, —O—, —$OC_{1-4}$ alkyl-, —S—, or —$CH_2$—;

each of $R^1$ and $R^2$ is, independently, hydrogen, —C(O)NHR$^4$, —C(O)OR$^4$, —NHC(O)R$^4$, —NHC(O)OR$^4$, —NHC(O)NHR$^4$, —NHS(O)$_2$R$^4$, —NHR$^4$, —$C_{1-4}$alkyl-NHR$^4$, —OR$^4$, or R$^7$ wherein $R^1$ and $R^2$ cannot simultaneously be hydrogen;

each $R^3$ independently is hydrogen, —$C_{1-4}$alkyl, halogen, —$OC_{1-2}$alkyl, —C(O)OH, —C(O)$OC_{1-2}$alkyl, —CN, —C(O)NH$C_{1-2}$alkyl, —C(O)NH$_2$, $C_{3-4}$ cycloalkyl, or —NRR', wherein each of said $R^3$ alkyl and cycloalkyl independently is optionally substituted with one or more substituents selected from the group consisting of —F, —Cl, —OH and —$OC_{1-2}$alkyl;

each $R^4$ independently is hydrogen, $C_{1-4}$alkyl, $C_{2-4}$alkenyl, $C_{2-4}$alkynyl, $C_{3-10}$ cycloalkyl, 6-10 membered aryl, 5-10-membered heteroaryl, or 4-10-membered heterocyclyl, wherein each of said $R^4$ groups is optionally substituted with one or more substituents selected from the group consisting of —Br, —Cl, —F, $C_{1-4}$alkyl, CN, NO$_2$, $C_{2-4}$alkenyl, $C_{2-4}$alkynyl, $C_{3-6}$cycloalkyl, $C_{0-4}$ alkyl-$C_{3-5}$ cycloalkyl, $C_{0-4}$ alkyl-O—$C_{1-4}$ alkyl, $C_{0-4}$ alkyl-O—$C_{0-4}$ alkyl-$C_{3-5}$ cycloalkyl, C(O)$OC_{1-4}$ alkyl, C(O)$OC_{0-4}$ alkyl-$C_{3-5}$ cycloalkyl, $C_{0-4}$ alkyl-C(O)NH$_2$, C(O)NH$C_{1-4}$ alkyl, C(O)N($C_{1-4}$ alkyl)$_2$, C(O)NH($C_{0-4}$ alkyl-$C_{3-5}$ cycloalkyl), $CH_2OR^5$, $C_{0-4}$ alkyl-C(O)R$^5$, $C_{0-4}$ alkyl-C(O)N(R$^5$)$_2$, $C_{0-4}$ alkyl-C(O)OR$^5$, $C_{0-4}$ alkyl-NHC(O)R$^5$, $C_{0-4}$ alkyl-N(R$^5$)$_2$, 5-6 membered heterocyclyl, —O($C_{1-4}$ alkyl)OR$^5$, —OR', and oxo, and wherein each of said optional $R^4$ substituents is optionally and independently substituted with one or more substituents selected from the group consisting of —F, —Cl, $C_{1-4}$alkyl, —OH, —$OC_{1-4}$alkyl, —$SC_{1-4}$alkyl, —C(O)$C_{1-4}$ alkyl, —C(O)$OC_{1-4}$ alkyl, and —C(O)$OC_{0-4}$ alkyl-$C_{3-5}$ cycloalkyl; and each $R^5$ independently is hydrogen, $C_{1-4}$alkyl, phenyl, 5-6-membered heteroaryl, or 4-7-membered heterocyclyl, wherein each $R^5$ independently is optionally substituted with one or more substituents selected from the group consisting of —F, —Cl, $C_{1-2}$alkyl, —CH$_2$OH, —CN, —OH, —$OC_{1-2}$alkyl, 5-6-membered heteroaryl, and 4-7 membered heterocyclyl, or two $R^5$ groups together with the intervening nitrogen atom optionally form a morpholine ring, azetidine ring, pyrrolidine ring, piperidine ring, or piperazine ring; and $R^6$ is hydrogen or $C_{1-4}$alkyl optionally substituted with one or more substituents selected from the group consisting of —F, —Cl, —CH$_2$OH, —CN, —OH, and —$OC_{1-2}$alkyl;

$R^7$ is 6-10-membered aryl, 5-10-membered heteroaryl, or 4-7-membered heterocyclyl, each of which is optionally substituted with one or more substituents selected from the group consisting of —F, —Cl, $C_{1-2}$alkyl, —CH$_2$OH, —CN, and —OR; and each of R and R' independently is hydrogen or $C_{1-4}$alkyl, or R and R' together with the nitrogen atom to which they are attached optionally form a morpholine ring, azetidine ring, pyrrolidine ring, piperidine ring, or piperazine ring.

In some embodiments, the disclosure also provides a method of repairing a DNA break in one or more target genomic regions via a homology directed repair (HDR) pathway, the method includes administering to one or more cells that have one or more target genomic regions, a genome editing system and a compound represented by Formula (I) or pharmaceutically acceptable salts thereof.

The genome editing system interacts with a nucleic acid(s) of the target genomic regions, resulting in a DNA break, and wherein the DNA break is repaired at least in part via a HDR pathway.

In some embodiments, the disclosure also provides a method of inhibiting or suppressing repair of a DNA break in one or more target genomic regions via a NHEJ pathway, the method includes administering to one or more cells that have one or more target genomic regions, a genome editing system and a compound represented by Formula (I) or pharmaceutically acceptable salts thereof.

The genome editing system interacts with a nucleic acid(s) of the one or more target genomic regions, resulting in a DNA break, and wherein repair of the DNA break via a NHEJ pathway is inhibited or suppressed.

In some embodiments, the disclosure also provides a method of modifying expression of one or more genes or proteins, the method includes administering to one or more cells that comprise one or more target genomic regions, a genome editing system and a compound represented by Formula (I) or pharmaceutically acceptable salts thereof.

The genome editing system interacts with a nucleic acid(s) of the one or more target genomic regions of a target gene(s), resulting in editing the one or more target genomic regions and wherein the edit modifies expression of a downstream gene(s) and/or protein(s) associated with the target gene(s).

In some embodiments, a kit or composition is provided for editing one or more target genomic regions. In some embodiments, the kit or composition includes a genome editing system; and a compound represented by Formula (I) or pharmaceutically acceptable salts thereof.

Other features, objects, and advantages of the invention are apparent in the detailed description that follows. It should be understood, however, that the detailed description, while indicating embodiments and aspects of the invention, is given by way of illustration only, not limitation. Various changes and modification within the scope of the invention will become apparent to those skilled in the art from the detailed description.

BRIEF DESCRIPTION OF THE DRAWINGS

FIG. 1A depicts the design of a bicistronic construct targeting the human AAVS1 locus (SBI).

FIG. 1B depicts the cell line, and the targeted polynucleotide region, used in the traffic light reporter assay for monitoring HDR efficiency.

FIG. 1C is a schematic of the experimental workflow used in the traffic light reporter assay for monitoring HDR efficiency.

DETAILED DESCRIPTION OF THE INVENTION

Figure 1A:
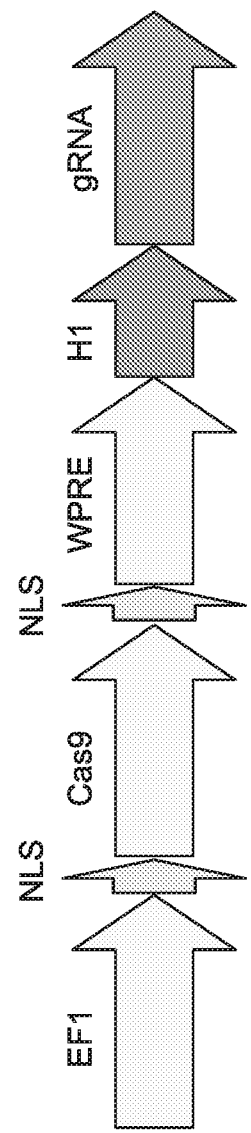
FIGS. 1A-1C are a series of schematics and sequences relating to the use of a traffic light reporter assay used for monitoring HDR efficiency.

Unless otherwise defined, scientific and technical terms used in connection with this disclosure shall have the meanings that are commonly understood by those of ordinary skill in the art. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout this disclosure. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients. Generally, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference. As utilized in accordance with this disclosure, the terms defined in this disclosure, unless otherwise indicated, shall be understood to have the meanings as defined herein.

Compounds of the Invention

In one embodiment, the compounds of the invention are represented by Formula (I):

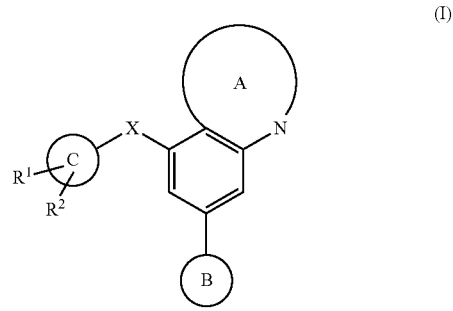

(I)

or pharmaceutically acceptable salts thereof, wherein the variables of Formula (I) are each independently as described below. The first set of the variables of Formula (I) is as follows:

Ring A is an aromatic ring system selected from

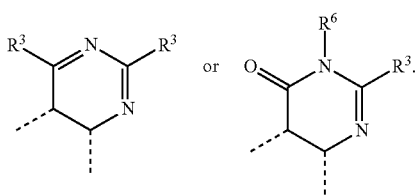

Ring B is a ring system optionally substituted and selected from

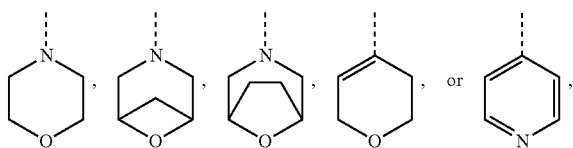

wherein Ring B is optionally substituted with one or more substituents selected from the group consisting of —F, —OH, and $C_{1-4}$alkyl optionally substituted with one or more substituents selected from the group consisting of —F, —Cl, —OH, and —$OC_{1-2}$alkyl. In one specific embodiment, Ring B is optionally substituted and selected from

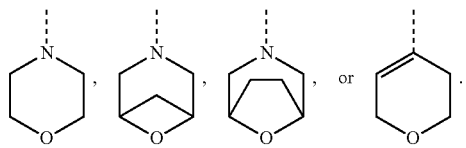

In another specific embodiment, Ring B is optionally substituted

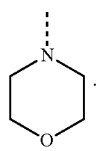

Ring C is a $C_{4-6}$ cycloalkyl, 5-6-membered heteroaryl, or phenyl, wherein Ring C is optionally further substituted with one or more substituents selected from the group consisting of halogen, $C_{1-2}$ alkyl, —OH, and —$OC_{1-2}$alkyl. In a specific embodiment, Ring C is optionally substituted $C_{4-6}$ cycloalkyl or optionally substituted 5-6 membered heteroaryl. In a specific embodiment, Ring C is optionally substituted $C_{4-6}$ cycloalkyl. In a specific embodiment, Ring C is optionally substituted 5-6 membered heteroaryl or optionally substituted phenyl.

X is —NH—, —O—, —$OC_{1-4}$ alkyl-, —S—, or —$CH_2$—. In a specific embodiment, X is —NH—, —O—, or —$CH_2$—. In another specific embodiment, X is —NH— or —O—. In another specific embodiment, X is —O—. In another specific embodiment, X is —NH—. In another specific embodiment, X is —$OC_{1-4}$ alkyl-. In another specific embodiment, X is —$CH_2$—.

Each of $R^1$ and $R^2$ is independently hydrogen, —C(O)NHR$^4$, —C(O)OR$^4$, —NHC(O)R$^4$, —NHC(O)OR$^4$, —NHC(O)NHR$^4$, —NHS(O)$_2$R$^4$, —NHR$^4$, —$C_{1-4}$ alkyl-NHR$^4$, —OR$^4$, or R$^7$ wherein $R^1$ and $R^2$ cannot simultaneously be hydrogen. In a specific embodiment, at least one of $R^1$ and $R^2$ is —NHR$^4$ or —OR$^4$. In another specific embodiment, each of $R^1$ and $R^2$ independently is hydrogen, —C(O)NHR$^4$, —C(O)OR$^4$, —NHC(O)R$^4$, —NHC(O)OR$^4$, —$C_{1-4}$ alkyl-NHR$^4$, —NHR$^4$, —OR$^4$, or R$^7$. In another specific embodiment, $R^2$ is hydrogen and $R^1$ is —C(O)NHR$^4$, —C(O)OR$^4$, —NHC(O)R$^4$, —NHC(O)OR$^4$, —NHC(O)NHR$^4$, —NHS(O)$_2$R$^4$, —NHR$^4$, —$C_{1-4}$ alkyl-NHR$^4$, —OR$^4$, or R$^7$; and R. In another specific embodiment, $R^2$ is hydrogen and $R^1$ is —C(O)NHR$^4$, —C(O)OR$^4$, —NHC(O)R$^4$, —NHC(O)OR$^4$, —$C_{1-4}$ alkyl-NHR$^4$, —NHR$^4$, —OR$^4$, or R$^7$. In another specific embodiment, $R^2$ is hydrogen and $R^1$ is —NHR$^4$, —OR$^4$, or R$^7$. In another specific embodiment, $R^2$ is hydrogen and $R^1$ is —NHR$^4$ or —OR$^4$.

Each $R^3$ independently is hydrogen, —$C_{1-4}$alkyl, halogen, —$OC_{1-2}$alkyl, —C(O)OH, —C(O)$OC_{1-2}$alkyl, —CN, —C(O)NH$C_{1-2}$alkyl, —C(O)NH$_2$, $C_{3-4}$ cycloalkyl, or —NRR', wherein each of said $R^3$ alkyl and cycloalkyl independently is optionally substituted with one or more substituents selected from the group consisting of —F, —Cl, —OH and —$OC_{1-2}$alkyl. In a specific embodiment, each $R^3$ independently is hydrogen, —$C_{1-4}$alkyl, halogen, —$OC_{1-2}$alkyl, —CN, —$C_{3-4}$ cycloalkyl, or —NRR', wherein each of said $R^3$ alkyl and cycloalkyl independently is optionally substituted. In another specific embodiment, each $R^3$ independently is hydrogen, methyl, —Cl, —OCH$_3$, —CN, cyclopropyl, —NHCH$_3$, or —N(CH$_3$)$_2$.

Each $R^4$ independently is hydrogen, $C_{1-4}$alkyl, $C_{2-4}$alkenyl, $C_{2-4}$alkynyl, $C_{3-10}$ cycloalkyl, 6-10 membered aryl, 5-10-membered heteroaryl, or 4-10-membered heterocyclyl. Each of the $R^4$ groups is optionally and independently substituted with one or more substituents selected from the group consisting of —Br, —Cl, —F, $C_{1-4}$alkyl, CN, NO$_2$, $C_{2-4}$alkenyl, $C_{2-4}$alkynyl, $C_{3-6}$cycloalkyl, $C_{0-4}$ alkyl-$C_{3-5}$ cycloalkyl, $C_{0-4}$ alkyl-O—$C_{1-4}$ alkyl, $C_{0-4}$ alkyl-O—$C_{0-4}$ alkyl-$C_{3-5}$ cycloalkyl, C(O)$OC_{1-4}$ alkyl, C(O)$OC_{0-4}$ alkyl-$C_{3-5}$ cycloalkyl, $C_{0-4}$ alkyl-C(O)NH$_2$, C(O)NH$C_{1-4}$ alkyl, C(O)N($C_{1-4}$ alkyl)$_2$, C(O)NH($C_{0-4}$ alkyl-$C_{3-5}$ cycloalkyl), CH$_2$OR$^5$, $C_{0-4}$ alkyl-C(O)R$^5$, $C_{0-4}$ alkyl-C(O)N(R$^5$)$_2$, $C_{0-4}$ alkyl-C(O)OR$^5$, $C_{0-4}$ alkyl-NHC(O)R$^5$, $C_{0-4}$ alkyl-N(R$^5$)$_2$, 5-6 membered heterocyclyl, —O($C_{1-4}$ alkyl)OR$^5$, —OR$^5$, and oxo. Each of the optional $R^4$ substituents is optionally and independently substituted with one or more substituents selected from the group consisting of —F, —Cl, $C_{1-4}$alkyl, —OH, —$OC_{1-4}$alkyl, —$SC_{1-4}$alkyl, —C(O)$C_{1-4}$ alkyl, —C(O)$OC_{1-4}$ alkyl, and —C(O)$OC_{0-4}$ alkyl-$C_{3-5}$ cycloalkyl. Specific examples of the heteroaryl group for $R^4$ include a pyrrole, imidazole, pyrazole, triazole, thiazole, isothiazole, oxazole, pyridine, furopyridine

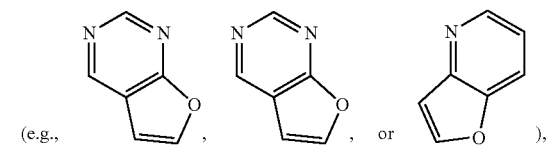

pyrimidine, pyrimidinone, pyrazine, pyridazine, quinolone, furopyrimidine

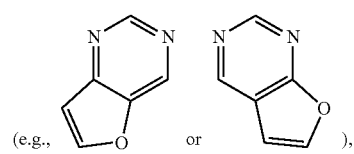

pyrrolopyrimidine, benzimidazole, benzothiazole, and benzoxazole. In a specific embodiment, each of the $C_{1-4}$ alkyl, $C_{1-4}$alkyl, $C_{2-4}$alkenyl, and $C_{2-4}$alkynyl for $R^4$ is optionally and independently substituted with one or more substituents selected from the group consisting of —F and —O(C$_{1-4}$ alkyl), and each of the C$_{3-10}$ cycloalkyl, 6-10 membered aryl, 5-10-membered heteroaryl, and 4-10-membered heterocyclyl group for R$^4$ is optionally and independently substituted with one or more C$_{1-4}$alkyl, —O(C$_{1-4}$ alkyl), C$_{0-4}$ alkyl-O—C$_{1-4}$ alkyl, C(O)NHC$_{1-4}$ alkyl, C(O)N(C$_{1-4}$ alkyl)$_2$, or piperazine, wherein each of the optional R$^4$ substituents is optionally substituted with one or more C$_{1-4}$alkyl.

Specific examples of the heterocyclyl group for R$^4$ include a tetrahydrofuran, oxetane, tetrahydropyran, dihydroisoxazole, pyrimidine-2,4(1H,3H)-dione, dihydrofuropyrimidine

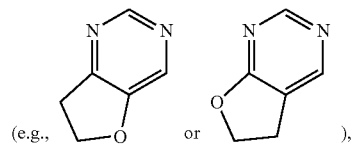

(e.g., or ), dihydropyranopyrimidine

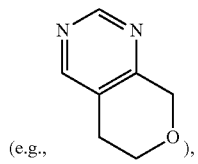

(e.g., ), dihydropyrrolopyrimidine, tetrahydropyridopyrimidine, dihydropyridopyrimidine

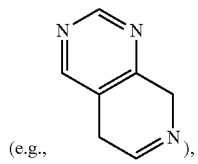

(e.g., ), dihydrofuropyridine

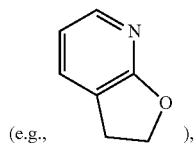

(e.g., ), dihydropyridopyridine, tetrahydropteridine, and isoindoline-1,3-dione. Specific examples of the heterocyclic group for the R$^4$ substituents include an oxetane, azetidine, tetrahydrofuran, dihydropyran, tetrahydropyran, morpholine, piperidine, pyrrolidine, piperazine, furan, oxazole, oxadiazole, pyrrole, pyrazole, triazole, oxadiazole and tetrazole.

In a specific embodiment, each R$^4$ independently is hydrogen or an optionally substituted group selected from C$_{1-4}$alkyl, C$_{2-4}$alkenyl, C$_{2-4}$alkynyl, C$_{3-5}$cycloalkyl, or a phenyl. In another specific embodiment, each R$^4$ independently is an optionally substituted group selected from a pyrrole, imidazole, pyrazole, triazole, thiazole, isothiazole, oxazole, pyridine, furopyridine, pyrimidine, pyrimidinone, pyrazine, pyridazine, quinolone, furopyrimidine, pyrrolopyrimidine, benzimidazole, benzothiazole, benzoxazole, tetrahydrofuran, oxetane, tetrahydropyran, dihydroisoxazole, pyrimidine-2,4(1H,3H)-dione, dihydrofuropyrimidine, dihydropyranopyrimidine, dihydropyrrolopyrimidine, tetrahydropyridopyrimidine, dihydropyridopyrimidine, dihydrofuropyridine, dihydropyridopyridine, tetrahydropteridine, or isoindoline-1,3-dione. In another specific embodiment, each R$^4$ independently is an optionally substituted group selected from imidazole, pyrazole, pyrimidine, furopyrimidine, oxetane or dihydrofuropyrimidine.

In another specific embodiment, each R$^4$ independently is hydrogen or an optionally substituted group selected from C$_{1-4}$ alkyl,

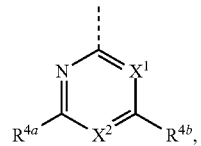

or a ring group selected from a C$_{3-5}$ cycloalkyl group, pyrrole, imidazole, pyrazole, triazole, thiazole, isothiazole, oxazole, tetrahydrofuran, oxetane, tetrahydropyran, dihydroisoxazole, or phenyl, wherein X$^1$ is N or CR$^{4d}$; X$^2$ is N or CR$^{4c}$, wherein X$^1$ and X$^2$ cannot simultaneously be N; each of R$^{4a}$, R$^{4b}$, and R$^{4c}$ independently is hydrogen, F, Cl, Br, CN, NO$_2$, C$_{1-4}$ alkyl, C$_{0-4}$ alkyl-C$_{3-5}$ cycloalkyl, C$_{0-4}$ alkyl-O—C$_{1-4}$ alkyl, C$_{0-4}$ alkyl-O—C$_{0-4}$ alkyl-C$_{3-5}$ cycloalkyl, C$_{2-4}$ alkenyl, C$_{2-4}$ alkynyl, C(O)OC$_{1-4}$ alkyl, C(O)OC$_{0-4}$ alkyl-C$_{3-5}$ cycloalkyl, C(O)NH$_2$, C(O)NHC$_{1-4}$ alkyl, C(O)N(C$_{1-4}$ alkyl)$_2$, C(O)NH(C$_{0-4}$ alkyl-C$_{3-5}$ cycloalkyl), a heterocyclic group selected from an oxetane, azetidine, tetrahydrofuran, dihydropyran, tetrahydropyran, morpholine, piperidine, or piperazine, or a heteroaryl group selected from a furan, oxazole, oxadiazole, pyrrole, pyrazole, triazole, or tetrazole; or R$^{4c}$ and R$^{4a}$, or R$^{4c}$ and R$^{4b}$, together with the intervening atoms, optionally form a dihydrofuran, dihydropyran, or tetrahydropiperidine heterocyclic group; and R$^{4d}$ independently is hydrogen, F, Cl, Br, CN, NO$_2$, C$_{1-4}$ alkyl, C$_{0-4}$ alkyl-O—C$_{1-4}$ alkyl, C$_{2-4}$ alkenyl, C$_{2-4}$ alkynyl, C(O)OC$_{1-4}$ alkyl, C(O)NH$_2$, C(O)NHC$_{1-4}$ alkyl, or C(O)N(C$_{1-4}$ alkyl)$_2$. Each of said heterocyclic and heteroaryl groups for R$^{4a}$, R$^{4b}$ and R$^{4c}$, and for the substituents of R$^4$ is optionally and independently substituted with one or more substituents selected from the group consisting of —F, C$_{1-4}$ alkyl, —OH, —C(O)C$_{1-4}$ alkyl, —C(O)OC$_{1-4}$ alkyl, or —C(O)OC$_{0-4}$ alkyl-C$_{3-5}$ cycloalkyl; and each of the alkyl and cycloalkyl groups for R$^{4a}$, R$^{4b}$ and R$^{4c}$, and for the substituents of R$^4$ is optionally and independently substituted with one or more substituents selected from the group consisting of —F and —OH. In a specific embodiment, R$^{4d}$ is hydrogen, CF, CCl, or CC-2 alkyl optionally substituted with one or more —F.

In another specific embodiment, each R$^4$ independently is C$_{1-4}$ alkyl or a ring group selected from C$_{3-5}$ cycloalkyl, pyrazole, imidazole, oxetane,

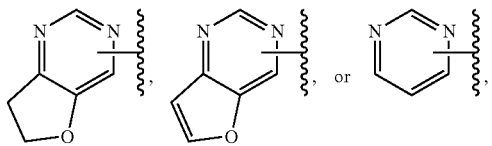

, , or , wherein the $R^4$ $C_{1-4}$ alkyl is optionally substituted with one or more substituents selected from the group consisting of —Br, —Cl, —F, and —O($C_{1-4}$ alkyl), and wherein each of the $R^4$ ring groups is optionally and independently substituted with one or more substituents selected from the group consisting of —Br, —Cl, —F, $C_{1-4}$alkyl, —CN, —O($C_{1-4}$ alkyl), $C_{3-6}$cycloalkyl, $C_{0-4}$ alkyl-O—$C_{1-4}$ alkyl, C(O)NH$C_{1-4}$ alkyl, C(O)N($C_{1-4}$ alkyl)$_2$, and a piperazine, wherein each of the optional $R^4$ substituents is optionally substituted with one or more substitutents selected from the group consisting of —F, $C_{1-4}$alkyl, —OH, and —O$C_{1-4}$alkyl. In a specific embodiment, the $R^4$ $C_{1-4}$ alkyl is optionally substituted with one or more substituents selected from the group consisting of —F and —O($C_{1-4}$ alkyl), and each of the $R^4$ ring groups is optionally and independently substituted with one or more substituents selected from the group consisting of $C_{1-4}$alkyl, —O($C_{1-4}$ alkyl), $C_{0-4}$ alkyl-O—$C_{1-4}$ alkyl, C(O)NH$C_{1-4}$ alkyl, C(O)N($C_{1-4}$ alkyl)$_2$, and a piperazine, wherein each of the optional $R^4$ substituents is optionally substituted with one or more $C_{1-4}$alkyl.

Each $R^5$ independently is hydrogen, $C_{1-4}$alkyl, phenyl, 5-6-membered heteroaryl, or 4-7-membered heterocyclyl, wherein each $R^5$ independently is optionally substituted with one or more substituents selected from the group consisting of —F, —Cl, $C_{1-2}$alkyl, —CH$_2$OH, —CN, —OH, —O$C_{1-2}$alkyl, 5-6-membered heteroaryl, and 4-7 membered heterocyclyl, or two $R^5$ groups together with the intervening nitrogen atom optionally form a morpholine, azetidine, pyrrolidine, piperidine, or piperazine. Specific examples of the optionally substituted heteroaryl group for $R^5$ include an imidazole, triazole, thiazole, pyridine, and pyrimidine. Specific examples of the optionally substituted heterocyclyl group for $R^5$ include an oxetane, tetrahydrofuran, and tetrahydropyran.

$R^6$ is hydrogen or $C_{1-4}$alkyl optionally substituted with one or more substituents selected from the group consisting of —F, —Cl, —CH$_2$OH, —CN, —OH, and —O$C_{1-2}$alkyl. In a specific embodiment, $R^6$ is hydrogen or methyl.

$R^7$ is 6-10-membered aryl, 5-10-membered heteroaryl, or 4-7-membered heterocyclyl, each of which is optionally substituted with one or more substituents selected from the group consisting of —F, —Cl, $C_{1-2}$alkyl, —CH$_2$OH, —CN, and —OR. Specific examples of $R^7$ include a pyrrole, imidazole, pyrazole, triazole, thiazole, isothiazole, oxazole, pyridine, furopyridine, pyrimidine, pyrimidinone, pyrazine, pyridazine, quinolone, furopyrimidine, pyrrolopyrimidine, benzimidazole, benzothiazole, benzoxazole, tetrahydrofuran, oxetane, tetrahydropyran, dihydroisoxazole, pyrimidine-2,4(1H,3H)-dione, dihydrofuropyrimidine, dihydropyranopyrimidine, dihydropyrrolopyrimidine, tetrahydropyridopyrimidine, dihydropyridopyrimidine, dihydrofuropyridine, dihydropyridopyridine, tetrahydropteridine, and isoindoline-1,3-dione. In a specific embodiment, $R^7$ is optionally substituted and selected from a pyrimidine, imidazole, pyrazole, thiazole, furopyrimidine, pyrrolopyrimidine, benzimidazole, benzothiazole, benzoxazole, oxetane, dihydrofuropyrimidine, or isoindoline-1,3-dione. In another specific embodiment, $R^7$ is optionally substituted and selected from a pyrimidine, imidazole, pyrazole, thiazole, furopyrimidine, oxetane, dihydrofuropyrimidine, or isoindoline-1,3-dione. In yet another specific embodiment, $R^7$ is optionally substituted and selected from a pyrimidine, pyrazole, furopyrimidine, thiazole, or isoindoline-1,3-dione.

Each of R and R' independently is hydrogen or $C_{1-4}$alkyl, or R and R' together with the nitrogen atom to which they are attached optionally form a morpholine ring, azetidine ring, pyrrolidine ring, piperidine ring, or piperazine ring. In a specific embodiment, each of R and R' independently is hydrogen or $C_{1-4}$alkyl. In another specific embodiment, each of R and R' independently is hydrogen or $C_{1-2}$alkyl.

In the second set of variables of Formula (I), each $R^4$ independently is hydrogen, $C_{1-4}$alkyl, $C_{2-4}$alkenyl, $C_{2-4}$alkynyl, $C_{3-10}$ cycloalkyl, a phenyl, a naphthalene, a 5-10-membered heteroaryl group selected from the group consisting of a pyrrole, imidazole, pyrazole, triazole, thiazole, isothiazole, oxazole, pyridine, furopyridine, pyrimidine, pyrimidinone, pyrazine, pyridazine, quinolone, furopyrimidine, pyrrolopyrimidine, benzimidazole, benzothiazole, and benzoxazole, or a 4-10-membered heterocyclyl group selected from the group consisting of a tetrahydrofuran, oxetane, tetrahydropyran, dihydroisoxazole, pyrimidine-2,4 (1H,3H)-dione, dihydrofuropyrimidine, dihydropyranopyrimidine, dihydropyrrolopyrimidine, tetrahydropyridopyrimidine, dihydropyridopyrimidine, dihydrofuropyridine, dihydropyridopyridine, tetrahydropteridine, and isoindoline-1,3-dione. Each of $R^4$ is optionally and independently substituted. In a specific embodiment, the heterocyclic group for the $R^4$ substituents is optionally substituted and selected from an oxetane, azetidine, tetrahydrofuran, dihydropyran, tetrahydropyran, morpholine, piperidine, pyrrolidine, piperazine, furan, oxazole, oxadiazole, pyrrole, pyrazole, triazole, oxadiazole or tetrazole. The remaining variables of Formula (I) are each and independently as described in the first set of variables of Formula (I).

In the third set of variables of Formula (I), each $R^5$ independently is hydrogen or an optionally substituted group selected from $C_{1-4}$alkyl, phenyl, a 5-6-membered heteroaryl group selected from an imidazole, triazole, thiazole, pyridine, or pyrimidine, or a 4-6-membered heterocyclyl group selected from an oxetane, tetrahydrofuran, or tetrahydropyran. Each $R^4$ independently is as described in the second set of variables of Formula (I). The remaining variables of Formula (I) are each and independently as described in the first or second set of variables of Formula (I).

In the fourth set of variables of Formula (I), Ring C is optionally substituted $C_{4-6}$ cycloalkyl or optionally substituted 5-6 membered heteroaryl; each of $R^4$ and $R^5$ independently are as described in the third set of variables of Formula (I); and the remaining variables of Formula (I) are each and independently as described in any of the first through third sets of variables of Formula (I).

In the fifth set of variables of Formula (I), X is —O— or —NH—; Ring C Ring C is optionally substituted $C_{4-6}$ cycloalkyl or optionally substituted 5-6 membered heteroaryl; and the remaining variables of Formula (I) are each and independently as described in any of the first through fourth sets of variables of Formula (I).

In the sixth set of variables of Formula (I), X is —O— or —NH—; Ring C Ring C is optionally substituted $C_{4-6}$ cycloalkyl or optionally substituted 5-6 membered heteroaryl; each of $R^4$ and $R^5$ independently are as described in the third set of variables of Formula (I); and the remaining variables of Formula (I) are each and independently as described in any of the first through fifth sets of variables of Formula (I).

In the seventh set of variables of Formula (I), Ring B

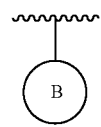

is optionally substituted and selected from

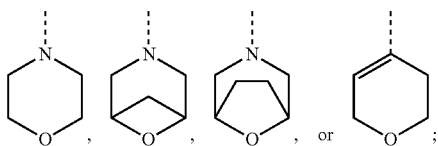

X is —O— or —NH—; and the remaining variables of Formula (I) are each and independently as described in any one of the first through sixth sets of variables of Formula (I).

In the eighth set of variables of Formula (I), Ring B

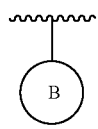

is optionally substituted and selected from

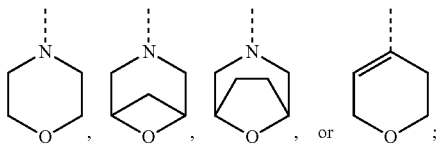

X is —O— or —NH—; Ring C Ring C is optionally substituted $C_{4-6}$ cycloalkyl or optionally substituted 5-6 membered heteroaryl; each of $R^4$ and $R^5$ independently are as described in the third set of variables of Formula (I); and the remaining variables of Formula (I) are each and independently as described in any of the first through seventh sets of variables of Formula (I).

In the ninth set of variables of Formula (I), each $R^3$ independently is hydrogen, —$C_{1-4}$alkyl, halogen, —$OC_{1-2}$alkyl, —CN, —$C_{3-4}$ cycloalkyl, or —NRR', wherein each of said $R^3$ alkyl and cycloalkyl independently is optionally substituted; and the remaining variables of Formula (I) are each and independently as described in any of the first through eighth sets of variables of Formula (I).

In the tenth set of variables of Formula (I), each $R^4$ independently is hydrogen or an optionally substituted group selected from $C_{1-4}$alkyl, $C_{2-4}$alkenyl, $C_{2-4}$alkynyl, $C_{3-5}$cycloalkyl, or phenyl; and the remaining variables of Formula (I) are each and independently as described in any of the first through ninth sets of variables of Formula (I).

In the eleventh set of variables of Formula (I), each $R^4$ independently is an optionally substituted group selected from a pyrrole, imidazole, pyrazole, triazole, thiazole, isothiazole, oxazole, pyridine, furopyridine, pyrimidine, pyrimidinone, pyrazine, pyridazine, quinolone, furopyrimidine, pyrrolopyrimidine, benzimidazole, benzothiazole, benzoxazole, tetrahydrofuran, oxetane, tetrahydropyran, dihydroisoxazole, pyrimidine-2,4(1H,3H)-dione, dihydrofuropyrimidine, dihydropyranopyrimidine, dihydropyrrolopyrimidine, tetrahydropyridopyrimidine, dihydropyridopyrimidine, dihydrofuropyridine, dihydropyridopyridine, tetrahydropteridine, or isoindoline-1,3-dione; and the remaining variables of Formula (I) are each and independently as described in any of the first through tenth sets of variables of Formula (I).

In the twelfth set of variables of Formula (I), each $R^4$ independently is an optionally substituted group selected from imidazole, pyrazole, pyrimidine, furopyrimidine, oxetane or dihydrofuropyrimidine; and the remaining variables of Formula (I) are each and independently as described in any of the first through eleventh sets of variables of Formula (I).

In the thirteenth set of variables of Formula (I), each $R^4$ independently is hydrogen or an optionally substituted group selected from $C_{1-4}$ alkyl,

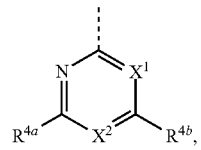

or a ring group selected from $C_{3-5}$ cycloalkyl, pyrrole, imidazole, pyrazole, triazole, thiazole, isothiazole, oxazole, tetrahydrofuran, oxetane, tetrahydropyran, dihydroisoxazole, or phenyl, wherein $X^1$ is N or $CR^{4d}$; $X^2$ is N or $CR^{4c}$, wherein $X^1$ and $X^2$ cannot simultaneously be N; each of $R^{4a}$, $R^{4b}$, and $R^{4c}$ independently is hydrogen, F, Cl, Br, CN, $NO_2$, $C_{1-4}$ alkyl, $C_{0-4}$ alkyl-$C_{3-5}$ cycloalkyl, $C_{0-4}$ alkyl-O—$C_{1-4}$ alkyl, $C_{0-4}$ alkyl-O—$C_{0-4}$ alkyl-$C_{3-5}$ cycloalkyl, $C_{2-4}$ alkenyl, $C_{2-4}$ alkynyl, C(O)O$C_{1-4}$ alkyl, C(O)O$C_{0-4}$ alkyl-$C_{3-5}$ cycloalkyl, C(O)$NH_2$, C(O)NH$C_{1-4}$ alkyl, C(O)N($C_{1-4}$ alkyl)$_2$, C(O)NH($C_{0-4}$ alkyl-$C_{3-5}$ cycloalkyl), a heterocyclic group selected from oxetane, azetidine, tetrahydrofuran, dihydropyran, tetrahydropyran, morpholine, piperidine, or piperazine, or a heteroaryl group selected from furan, oxazole, oxadiazole, pyrrole, pyrazole, triazole, or tetrazole; or $R^{4c}$ and $R^{4a}$, or $R^{4c}$ and $R^{4b}$, together with the intervening atoms, optionally form a dihydrofuran, dihydropyran, or tetrahydropiperidine heterocyclic ring group; $R^{4d}$ independently is hydrogen, F, Cl, Br, CN, $NO_2$, $C_{1-4}$ alkyl, $C_{0-4}$ alkyl-O—$C_{1-4}$ alkyl, $C_{2-4}$ alkenyl, $C_{2-4}$ alkynyl, C(O)O$C_{1-4}$ alkyl, C(O)$NH_2$, C(O)NH$C_{1-4}$ alkyl, or C(O)N($C_{1-4}$ alkyl)$_2$; each of the $R^4$ ring groups is optionally and independently substituted with one or more substituents selected from the group consisting of F, Cl, Br, CN, $NO_2$, $C_{1-4}$ alkyl, $C_{0-4}$ alkyl-$C_{3-5}$ cycloalkyl, $C_{0-4}$ alkyl-O—$C_{1-4}$ alkyl, $C_{0-4}$ alkyl-O—$C_{0-4}$ alkyl-$C_{3-5}$ cycloalkyl, $C_{2-4}$ alkenyl, $C_{2-4}$ alkynyl, C(O)O$C_{1-4}$ alkyl, C(O)O$C_{0-4}$ alkyl-$C_{3-5}$ cycloalkyl, C(O)$NH_2$, C(O)NH$C_{1-4}$ alkyl, C(O)N($C_{1-4}$ alkyl)$_2$, C(O)NH($C_{0-4}$ alkyl-$C_{3-5}$ cycloalkyl), a heterocyclic group selected from oxetane, azetidine, tetrahydrofuran, dihydropyran, tetrahydropyran, morpholine, piperidine, or piperazine, and a heteroaryl group selected from furan, oxazole, oxadiazole, pyrrole, pyrazole, triazole, or tetrazole; each of said heterocyclic and heteroaryl groups for $R^{4a}$, $R^{4b}$ and $R^{4c}$, and for the substituents of $R^4$ is optionally and independently substituted with one or more substituents selected from the group consisting of —F, $C_{1-4}$ alkyl, —OH, —C(O)$C_{1-4}$ alkyl, —C(O)O$C_{1-4}$ alkyl, or —C(O)O$C_{0-4}$ alkyl-$C_{3-5}$ cycloalkyl; and each of said alkyl and cycloalkyl groups for $R^{4a}$, $R^{4b}$ and $R^{4c}$, and for the substituents of $R^4$ is optionally and independently substituted with one or more substituents selected from the group consisting of —F and —OH. The remaining variables of Formula (I) are each and independently as described in any of the first through thirteenth sets of variables of Formula (I).

In the fourteenth set of variables of Formula (I), each $R^4$ independently is $C_{1-4}$ alkyl or a ring group selected from $C_{3-5}$ cycloalkyl, pyrazole, imidazole, oxetane,

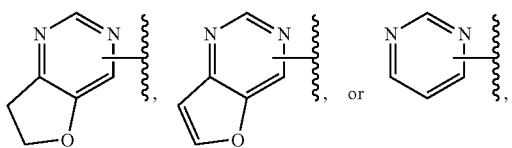

wherein said R⁴ $C_{1-4}$ alkyl is optionally substituted with one or more substituents selected from the group consisting of —Br, —Cl, —F, and —O($C_{1-4}$ alkyl), and wherein each of said R⁴ ring groups is optionally and independently substituted with one or more substituents selected from the group consisting of —Br, —Cl, —F, $C_{1-4}$alkyl, —CN, —O($C_{1-4}$ alkyl), $C_{3-6}$cycloalkyl, $C_{0-4}$ alkyl-O—$C_{1-4}$ alkyl, C(O)NH$C_{1-4}$ alkyl, C(O)N($C_{1-4}$ alkyl)₂, and a piperazine, wherein each of said optional R⁴ substituents is optionally and independently substituted with one or more substitutents selected from the group consisting of —F, $C_{1-4}$alkyl, —OH, and —O$C_{1-4}$alkyl. The remaining variables of Formula (I) are each and independently as described in any of the first through thirteenth sets of variables of Formula (I).

In the fifteenth set of variables of Formula (I), each R⁴ independently is as described in the fourteenth set of variables of Formula (I), wherein the R⁴ $C_{1-4}$ alkyl is optionally substituted with one or more substituents selected from the group consisting of —F and —O($C_{1-4}$ alkyl), and each of the R⁴ ring groups is optionally and independently substituted with one or more substituents selected from the group consisting of $C_{1-4}$alkyl, —O($C_{1-4}$ alkyl), $C_{1-4}$ alkyl-O—$C_{1-4}$ alkyl, C(O)NH$C_{1-4}$ alkyl, C(O)N($C_{1-4}$ alkyl)₂, and a piperazine, and wherein each of the optional R⁴ substituents is optionally substituted with one or more $C_{1-4}$alkyl. The remaining variables of Formula (I) are each and independently as described in any of the first through fourteenth sets of variables of Formula (I).

In the sixteenth set of variables of Formula (I), each of R¹ and R² independently is hydrogen, —C(O)NHR⁴, —C(O)OR⁴, —NHC(O)R⁴, —NHC(O)OR⁴, —$C_{0-4}$ alkyl-NHR⁴, —OR⁴, or R⁷. The remaining variables of Formula (I) are each and independently as described in any of the first through fifteenth sets of variables of Formula (I).

In the seventeenth set of variables of Formula (I), R⁷ is optionally substituted and selected from a pyrrole, imidazole, pyrazole, triazole, thiazole, isothiazole, oxazole, pyridine, furopyridine, pyrimidine, pyrimidinone, pyrazine, pyridazine, quinolone, furopyrimidine, pyrrolopyrimidine, benzimidazole, benzothiazole, benzoxazole, tetrahydrofuran, oxetane, tetrahydropyran, dihydroisoxazole, pyrimidine-2,4(1H,3H)-dione, dihydrofuropyrimidine, dihydropyranopyrimidine, dihydropyrrolopyrimidine, tetrahydropyridopyrimidine, dihydropyridopyrimidine, dihydrofuropyridine, dihydropyridopyridine, tetrahydropteridine, or isoindoline-1,3-dione. The remaining variables of Formula (I) are each and independently as described in any of the first through sixteenth sets of variables of Formula (I).

In the eighteenth set of variables of Formula (I), R⁷ is optionally substituted and selected from a pyrimidine, imidazole, pyrazole, thiazole, furopyrimidine, pyrrolopyrimidine, benzimidazole, benzothiazole, benzoxazole, oxetane, dihydrofuropyrimidine, or isoindoline-1,3-dione. The remaining variables of Formula (I) are each and independently as described in any of the first through seventeenth sets of variables of Formula (I).

In the nineteenth set of variables of Formula (I), R⁷ is optionally substituted and selected from a pyrimidine, pyrazole, furopyrimidine, thiazole, or isoindoline-1,3-dione; and the remaining variables of Formula (I) are each and independently as described in any of the first through eighteenth sets of variables of Formula (I).

In the twentieth set of variables of Formula (I), X is —O—; and the remaining variables of Formula (I) are each and independently as described in any of the first through eighteenth sets of variables of Formula (I).

In the twenty first set of variables of Formula (I), X is —NH—; and the remaining variables of Formula (I) are each and independently as described in any of the first through eighteenth sets of variables of Formula (I).

In the twenty second set of variables of Formula (I), X is —CH₂—; and the remaining variables of Formula (I) are each and independently as described in any of the first through eighteenth sets of variables of Formula (I).

In the twenty third set of variables of Formula (I), X is —O$C_{1-4}$alkyl-; and the remaining variables of Formula (I) are each and independently as described in any of the first through eighteenth sets of variables of Formula (I).

In the twenty fourth set of variables of Formula (I), Ring C is optionally substituted $C_{4-6}$ cycloalkyl; and the remaining variables of Formula (I) are each and independently as described in any of the first through twenty third sets of variables of Formula (I).

In the twenty fifth set of variables of Formula (I), Ring C is optionally substituted cyclohexane; and the remaining variables of Formula (I) are each and independently as described in any of the first through twenty fourth sets of variables of Formula (I).

In the twenty sixth set of variables of Formula (I), R¹ is —C(O)NHR⁴, —C(O)OR⁴, —NHC(O)R⁴, —NHC(O)OR⁴, —NHC(O)NHR⁴, —NHS(O)₂R⁴, —$C_{0-4}$ alkyl-NHR⁴, —OR⁴, or R⁷; R² is hydrogen; and the remaining variables of Formula (I) are each and independently as described in any of the first through twenty fifth sets of variables of Formula (I).

In the twenty seventh set of variables of Formula (I), each R³ independently is hydrogen, methyl, —Cl, —OCH₃, —CN, cyclopropyl, —NHCH₃, or —N(CH₃)₂; R⁶ is hydrogen or methyl; and the remaining variables of Formula (I) are each and independently as described in any of the first through twenty sixth sets of variables of Formula (I).

In the twenty eighth set of variables of Formula (I), Ring C is optionally substituted 5-6 membered heteroaryl; and the remaining variables of Formula (I) are each and independently as described in any of the first through twenty seventh sets of variables of Formula (I).

In the twenty ninth set of variables of Formula (I), Ring C is optionally substituted phenyl; and the remaining variables of Formula (I) are each and independently as described in any of the first through twenty seventh sets of variables of Formula (I).

In the thirtieth set of variables of Formula (I), Ring C is optionally substituted phenyl; X is —O$C_{1-4}$ alkyl-; and the remaining variables of Formula (I) are each and independently as described in any of the first through twenty seventh sets of variables of Formula (I).

In another embodiment, the compounds of the invention are represented by Formula (II) or pharmaceutically acceptable salts thereof:

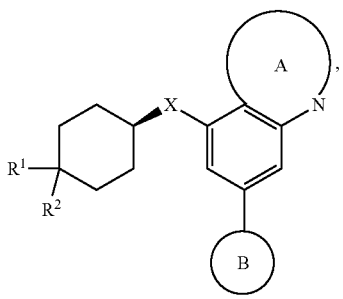

(II)

wherein the variables of Formula (II) are each independent as described below.

In the first set of variables of Formula (II), each of the variables of Formula (II) is independently as described above in any of the first through twenty seventh sets of variables of Formula (I).

In the second set of variables of Formula (II), $R^1$ is —C(O)NHR$^4$, —C(O)OR$^4$, —NHC(O)R$^4$, —NHC(O)OR$^4$, —NHC(O)NHR$^4$, —NHS(O)$_2$R$^4$, —C$_{0-4}$ alkyl-NHR$^4$, —OR$^4$, or R$^7$; and $R^2$ is hydrogen. The remaining variables of Formula (I) are each and independently as described in any of the first through twenty seventh sets of variables of Formula (I).

In another embodiment, the compounds of the invention are represented by Formula (III-A-1), (III-A-2), (III-B-1), or (III-B-2), or pharmaceutically acceptable salts thereof:

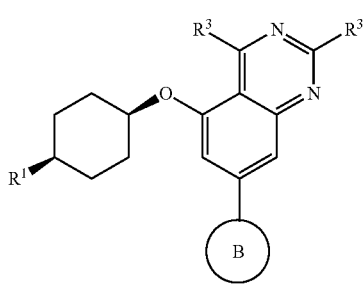

(III-A-1)

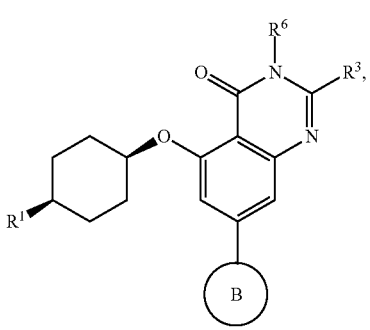

(III-B-1)

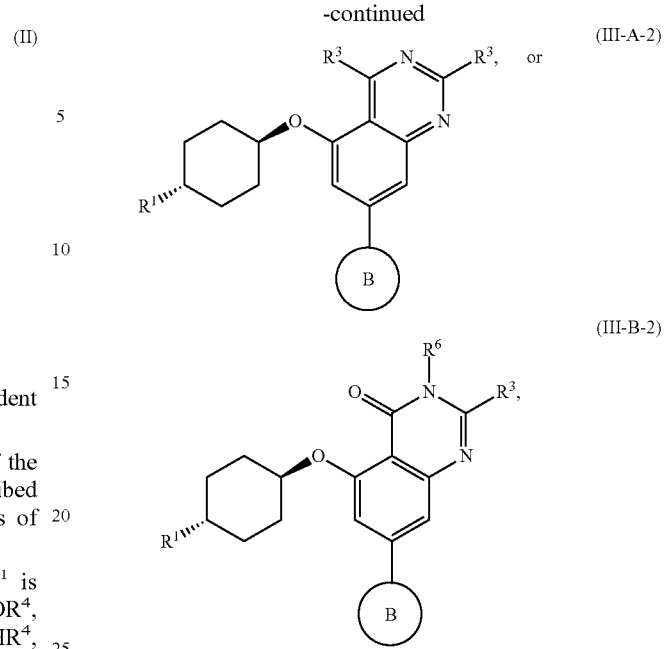

wherein the variables of Formula (II) are each independently as described below.

In the first set of variables of Formula (III-A-1), (III-A-2), (III-B-1), or (III-B-2), each of the variables of (III-A-1), (III-A-2), (III-B-1), or (III-B-2) is independently as described above in any of the first through twenty seventh sets of variables of Formula (I).

In the second set of variables of Formula (III-A-1), (III-A-2), (III-B-1), or (III-B-2), $R^1$ is —C(O)NHR$^4$, —C(O)OR$^4$, —NHC(O)R$^4$, —NHC(O)OR$^4$, —NHC(O)NHR$^4$, —NHS(O)$_2$R$^4$, —C$_{0-4}$ alkyl-NHR$^4$, —OR$^4$, or R$^7$; and the remaining variables of Formula (I) are each and independently as described in any of the first through twenty seventh sets of variables of Formula (I).

In the third set of variables of Formula (III-A-1), (III-A-2), (III-B-1), or (III-B-2), $R^1$ is —C$_{1-4}$ alkyl-NHR$^4$, —NHR$^4$, or —OR$^4$; and the remaining variables of Formula (I) are each and independently as described in any of the first or second set of variables of (III-A-1), (III-A-2), (III-B-1), or (III-B-2).

In the fourth set of variables of Formula (III-A-1), (III-A-2), (III-B-1), or (III-B-2), $R^1$ is —NHR$^4$; and the remaining variables of Formula (I) are each and independently as described in any of the first through third sets of variables of Formula (III-A-1), (III-A-2), (III-B-1), or (III-B-2).

In the fifth set of variables of Formula (III-A-1), (III-A-2), (III-B-1), or (III-B-2), $R^1$ is —OR$^4$; and the remaining variables of Formula (I) are each and independently as described in any of the first through fourth sets of variables of Formula (III-A-1), (III-A-2), (III-B-1), or (III-B-2).

In the sixth set of variables of Formula (III-A-1), (III-A-2), (III-B-1), or (III-B-2), $R^3$ independently is hydrogen, methyl, —Cl, —OCH$_3$, —CN, cyclopropyl, —NHCH$_3$, or —N(CH$_3$)$_2$; $R^6$ is hydrogen or methyl; and the remaining variables of Formula (I) are each and independently as described in any of the first through fifth sets of variables of Formula (III-A-1), (III-A-2), (III-B-1), or (III-B-2).

In yet another embodiment, the compounds of the invention are represented by Formula (IV) or pharmaceutically acceptable salts thereof:

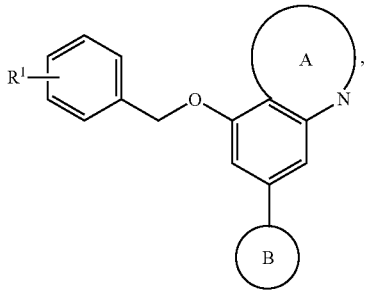

(IV)

wherein the variables of Formula (IV) are each and independently as described below.

In the first set of variables of Formula (IV), each of the variables independently is as described in any one of the first through thirtieth sets of variables of Formula (I).

In the second set of variables of Formula (IV), R¹ is hydrogen, —C(O)NHR⁴, —C(O)OR⁴, —NHC(O)R⁴, —NHC(O)OR⁴, —NHC(O)NHR⁴, —NHS(O)₂R⁴, —C₀₋₄ alkyl-NHR⁴, —OR⁴, or R⁷; and the remaining variables of Formula (IV) are each and independently as described in any of the first through thirtieth sets of variables of Formula (I).

In the third set of variables of Formula (IV), Ring B is optionally substituted

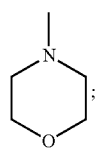

and the remaining variables of Formula (IV) are each and independently as described in the first or second set of variables of Formula (IV).

In yet another embodiment, the compounds of the invention are represented by Formula (V-A) or (V-B), or pharmaceutically acceptable salts thereof:

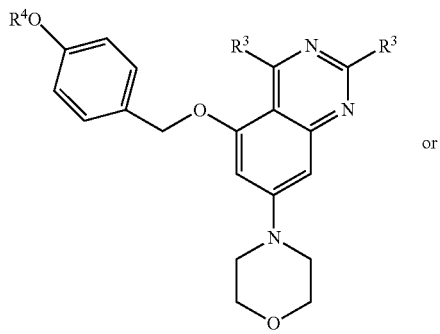

(V-A)

or

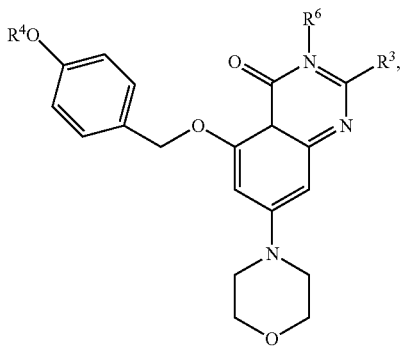

(V-B)

wherein each of the variables of Formula (V-A) or (V-B) is independently as described below.

In the first set of variables of Formula (V-A) or (V-B), each of the variables independently is as described in any one of the first through thirtieth sets of variables of Formula (I).

In the second set of variables of Formula (V-A) or (V-B), R³ is hydrogen, methyl, cyclopropyl, —F, —Cl, —OC₁₋₂alkyl, —NRR', or —CN, wherein each of said R³ alkyl is optionally substituted with one or more substituents selected from the group consisting of —F, —OH, and —O(C₁₋₂ alkyl); each R⁴ independently is optionally substituted C₁₋₄ alkyl optionally substituted with one or more substituents selected from the group consisting of —F, —OH, and —O(C₁₋₂ alkyl); and R and R' are each and independently hydrogen or C₁₋₂ alkyl. The remaining variables of Formula (V-A) or (V-B) are each and independently as described in any one of the first through thirtieth sets of variables of Formula (I).

In the third set of variables of Formula (V-A) or (V-B), each R³ independently is hydrogen, methyl, —Cl, —OCH₃, —CN, cyclopropyl, —NHCH₃, or —N(CH₃)₂; and R⁶ is hydrogen or methyl. The remaining variables of Formula (V-A) or (V-B) are each and independently as described in the first or second set of variables of Formula (V-A) or (V-B).

In yet another embodiment, the compounds of the invention are represented by any one of Formulae (I), (II), (III-A-1), (III-A-2), (III-B-1), (III-B-2), (IV), (V-A) and (V-B), or pharmaceutically acceptable salts thereof, wherein each of the variables of these Formulae independently as depicted in the structural formulae of Tables 1 and 2.

In yet another embodiment, the compounds of the invention are as depicted in Tables 1 and 2, or pharmaceutically acceptable salts thereof. In one specific embodiment, the invention features a compound selected from the group of compounds listed in Table 1, or a pharmaceutically acceptable salt thereof. In another specific embodiment, the invention features a compound selected from the group of compounds listed in Table 2, or a pharmaceutically acceptable salt thereof.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted," whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. For example, if X is halogen; optionally substituted $C_{1-3}$ alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$ alkyl, or phenyl, wherein X is optionally substituted by $J^X$, then both $C_{1-3}$ alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups. As is also apparent to a skilled person, a heteroaryl or heterocyclic ring containing an NH group can be optionally substituted by replacing the hydrogen atom with the substituent. If a substituent radical or structure is not identified or defined as "optionally substituted," the substituent radical or structure is unsubstituted.

Combinations of substituents envisioned by this invention are preferably those that result in the formation of stable or chemically feasible compounds. The term "stable," as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "alkyl" or "alkyl group," as used herein, means a straight-chain (i.e., unbranched) or branched, substituted or unsubstituted hydrocarbon chain that is completely saturated. Unless otherwise specified, alkyl groups contain 1-8 carbon atoms. In some embodiments, alkyl groups contain 1-6 carbon atoms, and in yet other embodiments, alkyl groups contain 1-4 carbon atoms (represented as "$C_{1-4}$ alkyl"). In other embodiments, alkyl groups are characterized as "$C_{0-4}$ alkyl" representing either a covalent bond or a $C_{1-4}$ alkyl chain. Examples of alkyl groups include methyl, ethyl, propyl, butyl, isopropyl, isobutyl, sec-butyl, and tert-butyl. The term "alkylene," as used herein, represents a saturated divalent straight or branched chain hydrocarbon group and is exemplified by methylene, ethylene, isopropylene and the like. The term "alkylidene," as used herein, represents a divalent straight chain alkyl linking group. The term "alkenyl," as used herein, represents monovalent straight or branched chain hydrocarbon group containing one or more carbon-carbon double bonds. The term "alkynyl," as used herein, represents a monovalent straight or branched chain hydrocarbon group containing one or more carbon-carbon triple bonds.

The term "cycloalkyl" (or "carbocycle") refers to a monocyclic $C_3$-$C_8$ hydrocarbon or bicyclic $C_8$-$C_{12}$ hydrocarbon that is completely saturated and has a single point of attachment to the rest of the molecule, and wherein any individual ring in said bicyclic ring system has 3-7 members. Suitable cycloalkyl groups include, but are not limited to, cyclopropyl, cyclobutyl, cyclopentyl, cyclohexyl, and cycloheptyl.

The term "heterocycle," "heterocyclyl," "heterocycloalkyl," or "heterocyclic" as used herein refers to a monocyclic, bicyclic, or tricyclic ring system in which at least one ring in the system contains one or more heteroatoms, which is the same or different, and that is completely saturated or that contains one or more units of unsaturation, but which is not aromatic, and that has a single point of attachment to the rest of the molecule. In some embodiments, the "heterocycle," "heterocyclyl," "heterocycloalkyl," or "heterocyclic" group has three to fourteen ring members in which one or more ring members is a heteroatom independently selected from oxygen, sulfur, nitrogen, or phosphorus, and each ring in the system contains 3 to 8 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydro-imidazol-2-one.

The term "heteroatom" means one or more of oxygen, sulfur, nitrogen, or phosphorus, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated," as used herein, means that a moiety has one or more units of unsaturation.

The term "alkoxy," or "thioalkyl," as used herein, refers to an alkyl group, as previously defined, attached to the principal carbon chain through an oxygen ("alkoxy") or sulfur ("thioalkyl") atom.

The terms "haloalkyl," "haloalkenyl," and "haloalkoxy" mean alkyl, alkenyl, or alkoxy, as the case may be, substituted with one or more halogen atoms. The term "halogen" means F, Cl, Br, or I.

The term "aryl" used alone or as part of a larger moiety as in "aralkyl," "aralkoxy," or "aryloxyalkyl," refers to a monocyclic, bicyclic, or tricyclic carbocyclic ring system having a total of six to fourteen ring members, wherein said ring system has a single point of attachment to the rest of the molecule, at least one ring in the system is aromatic and wherein each ring in the system contains 4 to 7 ring members. The term "aryl" may be used interchangeably with the term "aryl ring." Examples of aryl rings include phenyl, naphthyl, and anthracene.

The term "heteroaryl," used alone or as part of a larger moiety as in "heteroaralkyl," or "heteroarylalkoxy," refers to a monocyclic, bicyclic, and tricyclic ring system having a total of five to fourteen ring members, wherein said ring system has a single point of attachment to the rest of the molecule, at least one ring in the system is aromatic, at least one ring in the system contains one or more heteroatoms independently selected from nitrogen, oxygen, sulfur or phosphorus, and wherein each ring in the system contains 4 to 7 ring members. The term "heteroaryl" may be used interchangeably with the term "heteroaryl ring" or the term "heteroaromatic."

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As described herein, a bond drawn from a substituent to the center of one ring within a multiple-ring system (as shown below) represents substitution of the substituent at any substitutable position in any of the rings within the multiple ring system. For example, Structure a represents possible substitution in any of the positions shown in Structure b.

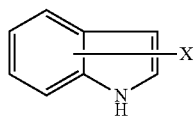

Structure a

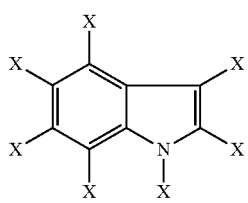

Structure b

This also applies to multiple ring systems fused to optional ring systems (which would be represented by dotted lines). For example, in Structure c, X is an optional substituent both for ring A and ring B.

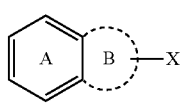

Structure c

If, however, two rings in a multiple ring system each have different substituents drawn from the center of each ring, then, unless otherwise specified, each substituent only represents substitution on the ring to which it is attached. For example, in Structure d, Y is an optionally substituent for ring A only, and X is an optional substituent for ring B only.

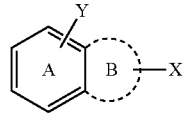

Structure d

The term "protecting group," as used herein, represent those groups intended to protect a functional group, such as, for example, an alcohol, amine, carboxyl, carbonyl, etc., against undesirable reactions during synthetic procedures. Commonly used protecting groups are disclosed in Greene and Wuts, *Protective Groups In Organic Synthesis*, $3^{rd}$ Edition (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz). Examples of hydroxyl protecting groups include ethers, such as tetrahydropyranyl, tert butyl, benzyl, allyl, and the like; silyl ethers such as trimethyl silyl, triethyl silyl, triisopropylsilyl, tert-butyl diphenyl silyl, and the like; esters such as acetyl, trifluoroacetyl, and the like; and carbonates. Hydroxyl protecting groups also include those appropriate for the protection of phenols.

Unless otherwise depicted or stated, structures recited herein are meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Compounds that have been drawn with stereochemical centers defined, usually through the use of a hatched ( ⋯⋯ⵊⵊⵊⵊⵊ ) or bolded ( ◂━━▬ ) bond, are stereochemically pure, but with the absolute ⋯⋯ⵊⵊⵊⵊⵊ stereochemistry still undefined. Such compounds can have either the R or S configuration. In those cases where the absolute configuration has been determined, the chiral center(s) are labeled (R) or (S) in the drawing.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools, probes in biological assays, or as DNA-PK inhibitors with an improved therapeutic profile.

Compositions, Formulations, and Administration of Compounds of the Invention

In another embodiment, the invention provides a pharmaceutical composition comprising a compound of any of the formulae described herein and a pharmaceutically acceptable excipient. In a further embodiment, the invention provides a pharmaceutical composition comprising a compound of Table 1. In a further embodiment, the invention provides a pharmaceutical composition comprising a compound of Table 2. In a further embodiment, the compositions additionally comprise an additional therapeutic agent.

According to another embodiment, the invention provides a composition comprising a compound of this invention or a pharmaceutically acceptable derivative thereof and a pharmaceutically acceptable carrier, adjuvant, or vehicle. In one embodiment, the amount of compound in a composition of this invention is such that is effective to measurably inhibit a DNA-PK in a biological sample or in a patient. In another embodiment, the amount of compound in the compositions of this invention is such that is effective to measurably inhibit DNA-PK. In one embodiment, the composition of this invention is formulated for administration to a patient in need of such composition. In a further embodiment, the composition of this invention is formulated for oral administration to a patient.

The term "patient," as used herein, means an animal, preferably a mammal, and most preferably a human.

The term "agent" is used herein to denote a chemical compound, a small molecule, a mixture of chemical compounds, a biological macromolecule, or an extract made from biological materials.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. These terms also mean the treatment of a disease in a mammal, e.g., in a human, including (a) inhibiting the disease, i.e., arresting or preventing its development; (b) relieving the disease, i.e., causing regression of the disease state; or (c) curing the disease.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

As used herein, "administer" refers to contacting, injecting, dispensing, delivering, or applying a DNA-PK inhibitor to a subject, a genomic editing system and/or a DNA-PK inhibitor to a cell or a subject. In some embodiments, the administration is contacting a genomic editing system and/or a DNA-PK inhibitor with a cell(s). In some embodiments, the administration is delivering a genomic editing system and/or a DNA-PK inhibitor to a cell(s). In some embodiments, the administration is applying a genomic editing system and/or a DNA-PK inhibitor to a cell(s). In some embodiments, the administration is injecting a genomic editing system and/or a DNA-PK inhibitor to a cell(s). Administering can occur in vivo, ex vivo, or in vitro. Administering a genomic editing system and a DNA-PK inhibitor to a cell(s) can be done simultaneously or sequentially.

The term "acquired" in reference to a condition or disease as used herein means a disorder or medical condition which develops post-fetally; in contrast with a congenital disorder, which is present at birth. A congenital disorder may be antecedent to an acquired disorder.

The terms "congenital" or "inherited" condition or disease is a genetic disorder found in the genome of a subject that is present in a subject at birth. The "genome" as used herein includes all of the genetic material in the nucleus and the cytoplasm, and further includes the mitochondrial genome and ribosomal genome. The congenital or inherited may be expressed at any time during the subject's life, for example at birth or at adulthood.

The term "genetic disorder" or "genetic disease" includes inherited or acquired mutations in the genome of a subject that causes or may cause disease.

The terms "polymorphisms" or "genetic variations" means different forms of a gene at a genetic locus.

It will also be appreciated that certain of the compounds of the present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof. As used herein, the term "inhibitory active metabolite or residue thereof" means that a metabolite or residue thereof is also an inhibitor of DNA-PK.

As used herein, the term "pharmaceutically acceptable salt" refers to those salts which are, within the scope of sound medical judgment, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in *J. Pharmaceutical Sciences*, 66:1-19, 1977, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional, epidural, intraspinal, and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Depending upon the particular proliferative condition or cancer to be treated, additional therapeutic agents, which are normally administered to treat or prevent that condition, may also be present in the compositions of this invention. As used herein, additional therapeutic agents which are normally administered to treat or prevent a particular proliferative condition or cancer are known as "appropriate for the disease, or condition, being treated." Examples of additional therapeutic agents are provided infra.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions of the Invention

In one embodiment, the invention provides a method of sensitizing a cell to a therapeutic agent or a disease state that induces a DNA lesion comprising the step of contacting the cell with one or more DNA-PK inhibitors of Formulae (I), (II), (III-A-1), (III-A-2), (III-B-1), (III-B-2), (IV), (V-A) and (V-B), or a pharmaceutically acceptable salt thereof. In one specific embodiment, the methods of the invention employ one or more DNA-PK inhibitors of Formulae (I), (II), (III-A-1), (III-A-2), (III-B-1), and (III-B-2), or pharmaceutically acceptable salts thereof.

The invention further provides methods of potentiating a therapeutic regimen for treatment of cancer comprising the step of administering to an individual in need thereof an effective amount of a DNA-PK inhibitor of (I), (II), (III-A-1), (III-A-2), (III-B-1), (III-B-2), (IV), (V-A) and (V-B), or a pharmaceutically acceptable salt thereof. In one specific embodiment, the methods of the invention employ one or more DNA-PK inhibitors of Formulae (I), (II), (III-A-1), (III-A-2), (III-B-1), and (III-B-2), or pharmaceutically acceptable salts thereof. In one aspect, the therapeutic regimen for treatment of cancer includes radiation therapy.

Compounds of the invention are useful in instances where radiation therapy is indicated to enhance the therapeutic benefit of such treatment. In addition, radiation therapy frequently is indicated as an adjuvant to surgery in the treatment of cancer. The goal of radiation therapy in the adjuvant setting is to reduce the risk of recurrence and enhance disease-free survival when the primary tumor has been controlled. Adjuvant radiation therapy is indicated in several diseases including colon, rectal, lung, gastroesophageal, and breast cancers as described below.

The invention also can be practiced by including another anti-cancer chemotherapeutic agent with a compound of the invention in a therapeutic regimen for the treatment of cancer, with or without radiation therapy. The combination of a DNA-PK inhibitor compound of the invention with such other agents can potentiate the chemotherapeutic protocol. For example, the inhibitor compound of the invention can be administered with etoposide or bleomycin, agents known to cause DNA strand breakage.

The invention further relates to radiosensitizing tumor cells utilizing the compounds of the invention, such as DNA-PK inhibitors of Formulae (I), (II), (III-A-1), (III-A-2), (III-B-1), and (III-B-2), or pharmaceutically acceptable salts thereof. The preferred compounds are those as described for the pharmaceutical compositions of the invention. A compound that can "radiosensitize" a cell, as used herein, is defined as a molecule, preferably a low molecular weight molecule, administered to animals in therapeutically effective amount to increase the sensitivity of cells to electromagnetic radiation and/or to promote the treatment of diseases that are treatable with electromagnetic radiation (e.g., X-rays). Diseases that are treatable with electromagnetic radiation include neoplastic diseases, benign and malignant tumors, and cancerous cells.

The present invention also provides methods of treating cancer in an animal that includes administering to the animal an effective amount of a DNA-PK inhibitor such as, for example, a compound of the invention. The invention further is directed to methods of inhibiting cancer cell growth, including processes of cellular proliferation, invasiveness, and metastasis in biological systems. Methods include use of a compound of the invention as an inhibitor of cancer cell growth. Preferably, the methods are employed to inhibit or reduce cancer cell growth, invasiveness, metastasis, or tumor incidence in living animals, such as mammals. The compounds of the invention can be used, either alone or in combination with the use of IR or one or more chemotherapeutic agents, in treating cancer or inhibiting cancer cell growth. Methods of the invention also are readily adaptable for use in assay systems, e.g., assaying cancer cell growth and properties thereof, as well as identifying compounds that affect cancer cell growth.

Tumors or neoplasms include growths of tissue cells in which the multiplication of the cells is uncontrolled and progressive. Some such growths are benign, but others are termed "malignant" and can lead to death of the organism. Malignant neoplasms or "cancers" are distinguished from benign growths in that, in addition to exhibiting aggressive cellular proliferation, they can invade surrounding tissues and metastasize. Moreover, malignant neoplasms are characterized in that they show a greater loss of differentiation (greater "dedifferentiation") and their organization relative to one another and their surrounding tissues. This property is also called "anaplasia."

Neoplasms treatable by the present invention also include solid tumors, i.e., carcinomas and sarcomas. Carcinomas include those malignant neoplasms derived from epithelial cells which infiltrate (invade) the surrounding tissues and give rise to metastases. Adenocarcinomas are carcinomas derived from glandular tissue, or from tissues which form recognizable glandular structures. Another broad category of cancers includes sarcomas, which are tumors whose cells are embedded in a fibrillar or homogeneous substance like embryonic connective tissue. The invention also enables treatment of cancers of the myeloid or lymphoid systems, including leukemias, lymphomas, and other cancers that typically do not present as a tumor mass, but are distributed in the vascular or lymphoreticular systems.

DNA-PK activity can be associated with various forms of cancer in, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer, including small cell lung carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas and osteosarcomas, skin cancers, including malignant melanoma, tumor progression of human skin keratinocytes, squamous cell cancer, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma. Methods to potentiate treatment of these and other forms of cancer are embraced by the invention.

The invention provides a method of inhibiting DNA-PK activity in a biological sample that includes contacting the biological sample with a compound or composition of the invention. The term "biological sample," as used herein, means a sample outside a living organism and includes, without limitation, cell cultures or extracts thereof, biopsied material obtained from a mammal or extracts thereof, and blood, saliva, urine, feces, semen, tears, or other body fluids or extracts thereof. Inhibition of kinase activity, particularly DNA-PK activity, in a biological sample is useful for a variety of purposes known to one of skill in the art. Examples of such purposes include, but are not limited to, biological specimen storage and biological assays. In one embodiment, the method of inhibiting DNA-PK activity in a biological sample is limited to non-therapeutic methods.

In some embodiments, this disclosure provides methods, compositions and kits for editing a target genome, e.g., by correcting a mutation. Such methods, compositions and kits can increase genome editing efficiency by the use of a DNA-PK inhibitor.

A genomic editing system can stimulate or induce a DNA break(s), such as DSB(s) at the desired locus in the genome (or target genomic region). The creation of DNA cleavage prompts cellular enzymes to repair the site of break through either the error prone NHEJ pathway or through the error-free HDR pathway. In NHEJ, the DNA lesion is repaired by fusing the two ends of the DNA break in a series of enzymatic processes involving Ku70/80 heterodimer and DNA dependent protein kinase (DNA-PK) enzymes. The repair mechanism involves tethering and alignment of two DNA ends, resection, elongation and ligation (Rouet et al.; Dexheimer T. DNA repair pathways and mechanisms. In: Mathews L, Cabarcas S, Hurt E, editors. DNA repair of cancer stem cells. Dordrecht: Springer; 2013. p. 19-32.) resulting in the formation of small insertion or deletion mutations (indels) at the break site. Indels introduced into the coding sequence of a gene can cause either premature stop codon or frame-shift mutations that lead to the production of nonfunctional, truncated proteins. The mechanism of HDR pathway is less understood and involves a different set of repair proteins such as Rad51 that stimulate strand invasion by a donor repair template for base insertion or gene replacement. Hence, HDR allows introduction of exogenous DNA template to obtain a desired outcome of DNA editing within a genome and can be a powerful strategy for translational disease modeling and therapeutic genome editing to restore gene function.

Of the two DNA repair pathways, NHEJ occurs at a much higher frequency and reports of more than 70% efficiency can be achieved even in neurons (Swiech et al., "In vivo interrogation of gene function in the mammalian brain using CRISPR-Cas9," *Nat Biotechnol.* 2015 January; 33(1):102-62014). The HDR gene correction however, occurs at very low frequency and during S and G2 phase when DNA replication is completed and sister chromatids are available to serve as repair templates (Heyer et al., Regulation of homologous recombination in eukaryotes. Annual Review of Genetics 44:113-139, 2010). Since NHEJ occurs throughout the cell cycle, in competition and is favored over HDR during the S and G2 phase, targeted insertion through the HDR pathway remains a challenge and a focus of continued studies.

DNA protein-kinase (DNA-PK) plays a role in various DNA repair processes. DNA-PK participates in DNA double-stranded break repair through activation of the non-homologous end-joining (NHEJ) pathway. NHEJ is thought to proceed through three steps: recognition of the DSBs, DNA processing to remove non-ligatable ends or other forms of damage at the termini, and finally ligation of the DNA ends. Recognition of the DSB is carried out by binding of the Ku heterodimer to the ragged DNA ends followed by recruitment of two molecules of DNA-dependent protein kinase catalytic subunit (DNA-PKcs) to adjacent sides of the DSB; this serves to protect the broken termini until additional processing enzymes are recruited. Recent data supports the hypothesis that DNA-PKcs phosphorylates the processing enzyme, Artemis, as well as itself to prepare the DNA ends for additional processing. In some cases DNA polymerase may be required to synthesize new ends prior to the ligation step. The auto-phosphorylation of DNA-PKcs is believed to induce a conformational change that opens the central DNA binding cavity, releases DNA-PKcs from DNA, and facilitates the ultimate re-ligation of the DNA ends.

In some embodiments, this disclosure provides methods, compositions, and kits to enhance gene editing, in particular increasing the efficiency of repair of DNA break(s) via a HDR pathway, or the efficiency of inhibiting or suppressing repair of DNA break(s) via a NHEJ pathway, in genome editing systems, including CRISPR-based HDR repair in cells. While not being bound by a particular theory, it is believed that a genome editing system administered to a cell(s) interacts with a nucleic acid(s) of the target gene, resulting in or causing a DNA break; such DNA break is repaired by several repair pathways, e.g., HDR, and a DNA-PK inhibitor administered to a cell(s) inhibits, blocks, or suppresses a NHEJ repair pathway, and the frequency or efficiency of HDR DNA repair pathway can be increased or promoted.

The interaction between a genome editing system with a nucleic acid(s) of the target gene can be hybridization of at least part of the genome editing system with the nucleic acid(s) of the target gene, or any other recognition of the nucleic acid(s) of the target gene by the genome editing system. In some embodiments, such interaction is a protein-DNA interactions or hybridization between base pairs.

In some embodiments, this disclosure provides methods of editing one or more target genomic regions in a cell(s) by administering to the cell(s) a genome editing system and a DNA-PK inhibitor. The editing can occur simultaneously or sequentially. Editing of the one or more target genomic regions includes any kind of genetic manipulations or engineering of a cell's genome. In some embodiments, the editing of the one or more target genomic regions can include insertions, deletions, or replacements of genomic regions in a cell(s). Genomic regions comprise the genetic material in a cell(s), such as DNA, RNA, polynucleotides, and oligonucleotides. Genomic regions in a cell(s) also comprise the genomes of the mitochondria or chloroplasts contained in a cell(s).

In some embodiments, the insertions, deletions or replacements can be either in a coding or a non-coding genomic region, in intronic or exonic regions, or any combinations thereof including overlapping or non-overlapping segments thereof. As used herein, a "non-coding region" refers to genomic regions that do not encode an amino acid sequence. For example, non-coding regions include introns. Coding regions refer to genomic regions that code for an amino acid sequence. For example, coding regions include exons.

In some embodiments, the editing of one or more target genomic regions can occur in any one or more target regions in a genome of a cell(s). In some embodiments, the editing of one or more target genomic regions can occur, for example, in an exon, an intron, a transcription start site, in a promoter region, an enhancer region, a silencer region, an insulator region, an antirepressor, a post translational regulatory element, a polyadenylation signal (e.g. minimal poly A), a conserved region, a transcription factor binding site, or any combinations thereof.

In some embodiments, administration to a cell(s) with a DNA-PK inhibitor and a genomic editing system results in increased targeted genome editing efficiency as compared to conditions in which a DNA-PK inhibitor and a genomic editing system is not administered to a cell(s). In some embodiments, the increased editing efficiency is about 1-fold, 2-fold, 3-fold, 4-fold, 5-fold, 10-fold, 15-fold, 20-fold, 25-fold, 30-fold, 40-fold, 50-fold, or 100-fold, in comparison to a condition in which a DNA-PK inhibitor and a genome editing system is not administered to a cell(s), or compared to a condition in which only a genome editing system and not a DNA-PK inhibitor is administered to a cell(s). The efficiency of genomic editing can be measured by any method known in the art, for example, by any method that ascertains the frequency of targeted polynucleotide integration or by measuring the frequency of targeted mutagenesis. Targeted polynucleotide integrations can also result in alteration or replacement of a sequence in a genome, chromosome or a region of interest in cellular chromatin. Targeted polynucleotide integrations can result in targeted mutations including, but not limited to, point mutations (i.e., conversion of a single base pair to a different base pair), substitutions (i.e., conversion of a plurality of base pairs to a different sequence of identical length), insertions or one or more base pairs, deletions of one or more base pairs and any combination of the aforementioned sequence alterations.

In some embodiments, the methods of editing one or more target genomic regions in a cell(s) involve administering to the cell(s) a genome editing system and a DNA-PK inhibitor. In some embodiments, the cell(s) is synchronized at the S or the G2 cell cycle phase. Synchronization of the cell(s) at the S or G2 cell cycle phase can be achieved by any method known in the art. As a non-limiting example, agents that can be used to synchronize a cell(s) at the S or G2 cell cycle phase include aphidicolin, dyroxyurea, lovastatin, mimosine, nocodazole, thymidine, or any combinations thereof (See, Lin et al. "Enhanced homology-directed human genome engineering by controlled timing of CRISPR/Cas9 delivery," *Elife*. 2014 Dec. 15; 3). In some embodiments, the agents for cell synchronization can be administered at any time during the gene-editing process. In some embodiments, a cell(s) can be synchronized at the S or the G2 phase of the cell cycle before, during, or after administering to a cell(s) a genome editing system and/or a DNA-PK inhibitor.

In some embodiments, the methods of editing one or more target genomic regions in a cell(s) by administering to the cell(s) a genome editing system and a DNA-PK inhibitor results in increased cell survival in comparison to conditions in which a genome editing system and a DNA-PK inhibitor were not administered to a cell(s), or in comparison to conditions in which only a gene editing system is contacted or administered into a cell(s) and not a DNA-PK inhibitor.

In some embodiments, provided herein are methods of repairing a DNA break in one or more target genomic regions via an HDR pathway. The administering to a cell(s) a genome editing system and a DNA-PK inhibitor results in a DNA break of a targeted region of the genome, and the DNA break is subsequently repaired, at least in part, by a HDR pathway. These methods result in increased amounts of HDR-mediated repair (e.g. HDR pathway) in the one or more target genomic regions resulting in greater efficiency of HDR-mediated repair as compared to conditions in which a DNA-PK inhibitor and a genomic editing system is not administered to a cell(s). In some embodiments, the efficiency of HDR pathway mediated repair of the DNA break is about 1-fold, 2-fold, 3-fold, 4-fold, 5-fold, 10-fold, 15-fold, 20-fold, 25-fold, 30-fold, 40-fold, 50-fold, or 100-fold, in comparison to a condition in which a DNA-PK inhibitor and a genome editing system is not administered to a cell(s), or compared to a condition in which only a genome editing system and not a DNA-PK inhibitor is administered to a cell(s). The efficiency of HDR pathway mediated repair can be measured by any method known in the art, for example, by ascertaining the frequency of targeted polynucleotide integration or by measuring the frequency of targeted mutagenesis.

In some embodiments, the methods herein provide for repairing the DNA break by increasing the efficiency of the HDR pathway.

The HDR pathway can be "canonical" or "alternative." "HDR" (homology directed repair) refers to a specialized form of DNA repair that takes place, for example, during repair of double-strand breaks or a DNA nick in a cell(s). HDR of double stranded breaks is generally based on nucleotide sequence homology, uses a "donor" molecule to template repair of a "target" molecule (e.g., the one that experienced the double-strand break), and can lead to the transfer of genetic information from the donor to the target. Canonical HDR of double stranded breaks is generally based on BRCA2 and RAD51 and typically employs a dsDNA donor molecule. Non-canonical, or "alternative," HDR is an HDR mechanism that is suppressed by BRCA2, RAD51, and/or functionally-related genes. Alternative HDR may use a ssDNA or nicked dsDNA donor molecule. See, for example, WO 2014172458.

In some embodiments, the methods of repairing a DNA break in one or more target genomic regions via an HDR pathway by administering to the cell(s) a genome editing system and a DNA-PK inhibitor result in increased cell survival in comparison to conditions in which a genome editing system and a DNA-PK inhibitor are not administered to a cell(s), or in comparison to conditions in which only a gene editing system is administered to a cell(s) and not a DNA-PK inhibitor.

In some embodiments, provided herein are methods of inhibiting or suppressing NHEJ-mediated repair of a DNA break in one or more target genomic regions in a cell(s). In some embodiments, the inhibiting or suppressing of NHEJ-mediated repair of a DNA break is performed by inhibiting or suppressing the NHEJ pathway. The NHEJ pathway can be either classical ("canonical") or an alternative NHEJ pathway (alt-NHEJ, or microhomology-mediated end joining (MMEJ)). The NHEJ pathway or alt-NHEJ pathway is suppressed in a cell(s) by administering to a cell(s) a genome editing system and a DNA-PK inhibitor.

The classical NHEJ repair pathway is a DNA double stranded break repair pathway in which the ends of the double stranded break are ligated without extensive homology. Classical NHEJ repair uses several factors, including KU70/80 heterodimer (KU), XRCC4, Ligase IV, and DNA protein kinases catalytic subunit (DNA-PKcs). Alt-NHEJ is another pathway for repairing double strand breaks. Alt-NHEJ uses a 5-25 base pair microhomologous sequence during alignment of broken ends before joining the broken ends. Alt-NHEJ is largely independent of KU70/80 heterodimer (KU), XRCC4, Ligase IV, DNA protein kinases catalytic subunit (DNA-PKcs), RAD52, and ERCC1. See, Bennardo et al., "Alternative-NHEJ is a Mechanistically Distinct Pathway of Mammalian Chromosome Break Repair," *PLOS Genetics*, Jun. 27, 2008.

In some embodiments, the methods of inhibiting or suppressing NHEJ-mediated repair of a DNA break via the NHEJ pathway in one or more target genomic regions in a cell(s) by inhibiting or suppressing the NHEJ pathway though the administering to a cell(s) a genomic editing system and a DNA-PK inhibitor result in increased efficiency of inhibiting or suppressing the NHEJ-mediated repair of the DNA break in comparison to a cell(s) that have not received a genomic editing system and a DNA-PK inhibitor, or in comparison to a condition in which a cell(s) receives a genomic editing system and not a DNA-PK inhibitor. In some embodiments, the increased efficiency of inhibiting or suppressing repair of a DNA break via the NHEJ pathway by contacting a cell(s) with a DNA-PK inhibitor and a genome editing system is about 1-fold, 2-fold, 3-fold, 4-fold, 5-fold, 10-fold, 15-fold, 20-fold, 25-fold, 30-fold, 40-fold, 50-fold, or 100-fold, in comparison to a condition in which a DNA-PK inhibitor and a genome editing system is not administered to a cell(s), or compared to a condition in which only a genome editing system and not a DNA-PK inhibitor is administered to a cell(s). The efficiency inhibiting or suppressing repair of a DNA break via the NHEJ pathway can be measured by any method known in the art, for example, by ascertaining the frequency of targeted polynucleotide integration or by measuring the frequency of targeted mutagenesis.

In some embodiments, the methods of inhibiting or suppressing NHEJ-mediated repair of a DNA break in one or more target genomic regions in a cell(s) by inhibiting or suppressing the NHEJ pathway though the administering to a cell(s) a genomic editing system and a DNA-PK inhibitor result in increased cell survival in comparison to conditions in which a genome editing system and a DNA-PK inhibitor were not contacted or administered to a cell(s), or in comparison to conditions in which only a gene editing system is contacted or administered into a cell(s) and not a DNA-PK inhibitor.

The DNA break can be a double stranded break (DSB) or two single stranded breaks (e.g. two DNA nicks). The DSB can be blunt ended or have either a 5' or 3' overhang, if the strands are each cleaved too far apart, the overhangs will continue to anneal to each other and exist as two nicks, not one DSB.

In some embodiments, provided herein are methods of modifying expression of one or more genes (a target gene(s)), and/or corresponding or downstream proteins, by administering to a cell(s) a genome editing system and a DNA-PK inhibitor. In some embodiments, the genome editing system can create, for example, insertions, deletions, replacements, modification or disruption in a target genomic region(s) of a target gene(s) of the cell(s), resulting in modified expression of the target gene(s). In some embodiments, the insertion, deletions, replacement, modification or disruption can result in targeted expression of a specific protein, or group of proteins, or of downstream proteins. In some embodiments, the genome editing system can create insertions, deletions or replacements in non-coding regions or coding regions. In some embodiments, the genome editing system can create insertions, deletions, replacements, modification or disruption in a promoter region, enhancer region, and/or any other gene regulatory element, including an exon, an intron, a transcription start site, a silencer region, an insulator region, an antirepressor, a post translational regulatory element, a polyadenylation signal (e.g. minimal poly A), a conserved region, a transcription factor binding site, or any combinations thereof. In some embodiments, the genome editing system can create the insertions, deletions, replacements, modification or disruption in more than one target region, simultaneously or sequentially. In some embodiments, administering to a cell(s) with a genome editing system and a DNA-PK inhibitor can allow for targeted modified gene expression in the cell(s). Such targeted modified gene expression can lead to expression of specific proteins and downstream proteins thereof.

In some embodiments, the expression of a downstream gene and/or protein is increased by at least 10%, 20%, 30%, 40%, 50%, 60%, 70%, 80%, 90%, 1, 1.5-fold, 2-fold, 2.5-fold, 3-fold, 3.5-fold, 4-fold, 4.5-fold, 5-fold, or 10-fold in comparison to a condition in which a DNA-PK inhibitor and a genome editing system is not administered to a cell(s), or compared to a condition in which only a genome editing system and not a DNA-PK inhibitor is administered to a cell(s).

In some embodiments, the gene expression of a downstream gene and/or protein is decreased by at least 10%, 20%, 30%, 40%, 50%, 60%, 70%, 80%, 90%, 95%, 96%, 97%, 98%, or 99% in comparison to a condition in which a DNA-PK inhibitor and a genome editing system is not administered to a cell(s), or compared to a condition in which only a genome editing system and not a DNA-PK inhibitor is administered to a cell(s).

The cell of the methods herein can be any cell. In some embodiments, the cell is a vertebrate cell. In some embodiments, the vertebrate cell is a mammalian cell. In some embodiment, the vertebrate cell is a human cell.

The cell can be any kind of cell at any developmental stage. In some embodiments, the cell can be a differentiated cell, a totipotent stem cell, a pluripotent stem cell, an embryonic stem cell, an embryonic germ cell, an adult stem cell, a precursor cell, an induced pluripotent stem cell, or any combinations thereof. A differentiated cell is a specialized cell that performs a specific function in a tissue. A totipotent stem cell is an undifferentiated cell from an embryo, fetus or adult that can divide for extended periods and has the capability of differentiating into any cell type of any of the three germ layers of an organism. A pluripotent stem cell is an undifferentiated cell from an embryo, fetus or adult that can divide for extended periods and has the capability of differentiating into any cell type of an organism except extra-embryonic tissue or the placenta. An embryonic stem cell is an undifferentiated stem cell that is found in the inner cell mass of an embryo and has the capability to differentiate into any type of cell of any of the three germ layers. An embryonic germ cell is an embryonic cell that can give rise to reproductive cells, such as sperm cells or egg cells. An adult stem cell is an undifferentiated cell that is found in differentiated tissue, is capable of self-renewal and can differentiate into any of the cells of the tissue in which it resides. A precursor or progenitor cell is a partially differentiated cell which typically can only differentiate into one kind of cell (e.g. a unipotent cell). An induced pluripotent stem cell is a kind of pluripotent stem cell that is generated from an adult differentiated or partially differentiated cell. See, for example, WO/2010/017562.

As used herein, the singular form "a", "an" and "the" include plural references unless the context clearly dictates otherwise. For example, the term "a cell" includes a plurality of cells, including mixtures thereof. For example "one or more cells" and "a cell(s)" are interchangeably used herein. Similarly, "one or more target genomic regions" and "a target genomic region(s)" are interchangeably used herein.

The terms, "approximately" and "about" are used interchangeably herein. The term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The terms "polynucleotide", "nucleotide", "nucleotide sequence", "nucleic acid" and "oligonucleotide" are used interchangeably. They refer to a polymeric form of nucleotides of any length, either deoxyribonucleotides (DNA) or ribonucleotides (RNA), or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term "ssDNA" means a single stranded DNA molecule. The term "ssODN" means single stranded oligodeoxynucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselerloate, phosphorodiselenoate, phosphoroanilothioate, phoshoraniladate, phosphoronmidate, and the like. An oligonucleotide can include a label for detection, if desired.

The term "synthetic RNA" refers to RNA that is engineered or non-naturally occurring.

As used herein the term "wild type" is a term of the art understood by skilled persons and means the typical form of an organism, strain, gene or characteristic as it occurs in nature as distinguished from mutant or variant forms.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%. 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "expression" refers to the process by which a polynucleotide is transcribed from a DNA template (such as into mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

A "viral vector" is defined as a recombinantly produced virus or viral particle that comprises a polynucleotide to be delivered into a host cell, either in vivo, ex vivo or in vitro. Examples of viral vectors include retroviral vectors, adenoviral vectors, adeno-associated virus vectors, adenoviral vectors, lentiviral vectors, herpes simplex viral vectors, and chimeric viral vectors and the like. In some embodiments s where gene transfer is mediated by a retroviral vector, a vector construct refers to the polynucleotide comprising the retroviral genome or part thereof.

Some embodiments of the disclosure relate to vector systems comprising one or more vectors, or vectors as such. Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells.

The cells can be primary cells, induced pluripotent stem cells (iPSCs), embryonic stem cells (hESCs), adult stem cells, progenitor cells or cell lines. "Primary cells" are cells taken directly from living tissue and placed in vitro for growth. Primary cells have few population doublings, and have a finite lifespan for population doublings in vitro. "Stem cells," "embryonic stem cells," and "induced pluripotent stem cells," are unspecialized and undifferentiated cells capable of self-renewal and having the potential to differentiate into cells of different types with specialized function. "Cell lines" include cell cultures that are derived from one cell type or a set of cells of the same type which can proliferate indefinitely. Non-limiting examples of mammalian cell lines can include CD34 cells, 293 cells, HEK cells, CHO cells, BHK cells, CV-1 cells, Jurkat cells, HeLa cells, or any variants thereof.

In some embodiments, a vector is capable of driving expression of one or more sequences in mammalian cells using a mammalian expression vector. Examples of mammalian expression vectors include pCDM8 and pMT2PC. When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. Other promoters can include, for example, EF1 promoter, or EF1 alpha promoter. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

As used herein, "substantially pure" means an object species is the predominant species present (i.e., on a molar basis it is more abundant than any other individual species in the composition). In some embodiments, a substantially purified fraction is a composition wherein the object species comprises at least about 50 percent (on a molar basis) of all macromolecular species present.

Generally, a substantially pure composition will comprise more than about 80 percent of all macromolecular species present in the composition. In some embodiments, a substantially pure composition will comprise more than about 85%, 90%, 95%, and 99% of all macromolecular species present in the composition. In some embodiments, the object species is purified to essential homogeneity (contaminant species are not detected in the composition by conventional detection methods) wherein the composition consists essentially of a single macromolecular species.

Genome Editing System

Various types of genome engineering systems can be used. The terms "genome editing system," "gene editing system," and the like, are used interchangeably herein, and refer to a system or technology which edits a target gene or the function or expression thereof. A genome editing system comprises: at least one endonuclease component enabling cleavage of a target genomic region(s) (or target sequence(s)); and at least one genome-targeting element which brings or targets the endonuclease component to a target genomic region(s). Examples of genome-targeting element include a DNA-binding domain (e.g., zinc finger DNA-binding protein or a TALE DNA-binding domain), guide RNA elements (e.g., CRISPR guide RNA), and guide DNA elements (e.g., NgAgo guide DNA). Programmable genome-targeting and endonuclease elements enable precise genome editing by introducing DNA breaks, such as double strand breaks (DSBs) at specific genomic loci. DSBs subsequently recruit endogenous repair machinery for either non-homologous end-joining (NHEJ) or homology directed repair (HDR) to the DSB site to mediate genome editing. The "endonuclease component" comprises an endonuclease or a nucleic acid comprising a nucleotide sequence(s) encoding such endonuclease.

The term "endonuclease" refers to any wild-type, mutant, variant, or engineered enzyme capable of catalyzing the hydrolysis (cleavage) of a bond between nucleic acids within a DNA or RNA molecule. Endonucleases can recognize and cleave a DNA or RNA molecule at its target genomic regions. Examples of endonucleases include a homing endonuclease; restriction enzyme such as FokI; a chimeric Zinc-Finger nuclease (ZFN) resulting from the fusion of engineered zinc-finger domains with the catalytic domain of a restriction enzyme such as FokI; Cas enzymes, and Cpf enzymes. Chemical endonucleases in which a chemical or peptidic cleaver is conjugated either to a polymer of nucleic acids or to another DNA recognizing a specific target sequence, thereby targeting the cleavage activity to a specific sequence, are comprised in the term "endonuclease". Examples of chemical enonucleases include synthetic nucleases like conjugates of orthophenanthroline, a DNA cleaving molecule, and triplex-forming oligonucleotides (TFOs).

By "variant" it is intended a recombinant protein obtained by replacement of at least one residue in the amino acid sequence of the parent protein with a different amino acid.

In some embodiments, endonucleases such as ZFNs, TALENs and/or meganucleases comprise a cleavage domain and/or cleavage half-domain. The cleavage domain may be homologous or heterologous to the DNA-binding domain. For example, a zinc finger DNA-binding domain and a cleavage domain from a nuclease or a meganuclease DNA-binding domain and cleavage domain from a different nuclease can be used. Heterologous cleavage domains can be obtained from any endonuclease or exonuclease. Exemplary endonucleases from which a cleavage domain can be derived include, but are not limited to, restriction endonucleases and homing endonucleases. See, for example, WO2013/130824. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

A cleavage half-domain can be derived from any nuclease or portion thereof, as set forth above, that requires dimerization for cleavage activity. In some embodiments, two fusion proteins are required for cleavage if the fusion proteins comprise cleavage half-domains. In some embodiments, a single protein comprising two cleavage half-domains can be used. In some embodiments, the two cleavage half-domains can be derived from the same endonuclease (or functional fragments thereof). In some embodiments, each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-50 nucleotides, 5-8 nucleotides or by 15-18 nucleotides. It is noted that any integral number of nucleotides or nucleotide pairs can intervene between two target sites (e.g., from 2 to 50 nucleotide pairs or more). In some embodiments, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31, 978-31, 982.

In some embodiments, the endonuclease component comprises a fusion protein(s) that include a cleavage domain (or cleavage half-domain) from at least one Type IIS restriction enzyme and one or more zinc finger binding domains, which may or may not be engineered. An exemplary Type IIS restriction enzyme, whose cleavage domain is separable from the binding domain, is Fok I. This particular enzyme is active as a dimer. Bitinaite et al. (1998) Proc. Natl. Acad. Sci. USA 95: 10,570-10,575. The portion of the Fok I enzyme used in such fusion proteins is considered a cleavage half-domain. Thus, for targeted double-stranded cleavage and/or targeted replacement of cellular sequences using zinc finger- or TALE-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used.

Exemplary Type IIS restriction enzymes are described in International Publication WO 07/014275, incorporated herein in its entirety. Additional restriction enzymes also contain separable binding and cleavage domains, and these are contemplated by the disclosure. See, for example, Roberts et al. (2003) Nucleic Acids Res. 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474 and 20060188987 and WO 2013/130824. Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499. See, e.g., U.S. Patent Publication No. 2008/0131962 and 2011/0201055. Engineered cleavage half-domains described herein can be prepared using any suitable method, for example, by site-directed mutagenesis of wild-type cleavage half-domains (Fok I) as described in U.S. Patent Publication Nos. 20050064474 and 20080131962.

The term "edit", "edits," "editing," and the like refer to any kind of engineering, altering, modifying or modulating (in each case which includes, but not limited to, by means of gene knockout, gene tagging, gene disruption, gene mutation, gene insertion, gene deletion, gene activation, gene silencing or gene knock-in).

As used herein, "genetic modification," "genome editing," "genome modification," "gene modification," and "gene editing," refer to any gene addition, deletion, knock-out, knock-in, tagging, mutation, activation, silencing, modification, and/or disruption to a cell's nucleotides. The cell in this context can be in vitro, in vivo, or ex vivo.

By "target genomic region," "target gene," "DNA target", "DNA target sequence", "target sequence", "target nucleotide sequence", "target-site", "target", "site of interest", "recognition site", "polynucleotide recognition site", "recognition sequence", "cleavage site" is intended a polynucleotide sequence that is recognized and cleaved by a genome editing system. These terms refer to a distinct DNA location, preferably a genomic location, at which a DNA break (cleavage) is to be induced by the genome editing system.

The aforesaid editing, including engineering, altering, modifying and modulating, can occur simultaneously or sequentially. Any genome editing system known in the art can be used. In some embodiments, the genome editing system is a meganuclease based system, a zinc finger nuclease (ZFN) based system, a Transcription Activator-Like Effector-based Nuclease (TALEN) based system, a CRISPR-based system, or NgAgo-based system.

Meganuclease-based, ZFN-based and TALEN-based each comprise at least one DNA-binding domain or a nucleic acid comprising a nucleic acid sequence(s) encoding the DNA-binding domain, and achieve specific targeting or recognition of a target genomic region(s) via protein-DNA interactions. A CRISPR-based system comprises at least one guide RNA element or a nucleic acid comprising a nucleic acid sequence(s) encoding the guide RNA element, and achieves specific targeting or recognition of a target genomic region(s) via base-pairs directly with the DNA of the target genomic region(s). A NgAgo-based system comprises at least one guide DNA element or a nucleic acid comprising a nucleic acid sequence(s) encoding the guide DNA element, and achieves specific targeting or recognition of a target genomic region(s) via base-pairs directly with the DNA of the target genomic region(s).

In some embodiments, the genome editing system is a meganuclease-based system. A meganuclease-based system employs meganucleases which are endonucleases with large (>14 bp) recognition sites, and its DNA binding domains are also responsible for cleavage of target sequences. The DNA-binding domain of meganucleases may have a double-stranded DNA target sequence of 12 to 45 bp. In some embodiments, the meganuclease is either a dimeric enzyme, wherein each meganuclease domain is on a monomer, or a monomeric enzyme comprising the two domains on a single polypeptide. Not only wild-type meganucleases but also various meganuclease variants have been generated by protein engineering to cover a myriad of unique sequence combinations. In some embodiments, chimeric meganucleases with a recognition site composed of a half-site of meganuclease A and a half-site of protein B can also be used. Specific examples of such chimeric meganucleases comprising the protein domains of I-DmoI and I-CreI. Examples of meganucleases include homing endonucleases from the LAGLIDADG family.

The LAGLIDADG meganuclease can be I-SceI, I-ChuI, I-CreI, I-CsmI, PI-SceI, PI-TliI, PI-MtuI, I-CeuI, I-SceII, I-SceIII, HO, PI-CivI, PI-CtrI, PI-AaeI, PI-BsuI, PI-DhaI, PI-DraI, PI-MavI, PI-MchI, PI-MfuI, PI-MflI, PI-MgaI, PI-MgoI, PI-MinI, PI-MkaI, PI-MleI, PI-MmaI, PI-MshI, PI-MsmI, PI-MthI, PI-MtuI, PI-MxeI, PI-NpuI, PI-PfuI, PI-RmaI, PI-SpbI, PI-SspI, PI-FacI, PI-MjaI, PI-PhoI, PI-TagI, PI-ThyI, PI-TkoI, PI-TspI, or I-MsoI; or can be a functional mutant or variant thereof, whether homodimeric, heterodimeric or monomeric. In some embodiments, the LAGLIDADG meganuclease is a I-CreI derivative. In some embodiments, the LAGLIDADG meganuclease shares at least 80% similarity with the natural I-CreI LAGLIDADG meganuclease. In some embodiments, the LAGLIDADG meganuclease shares at least 80% similarity with residues 1-152 of the natural I-CreI LAGLIDADG meganuclease. In some embodiments, the LAGLIDADG meganuclease may consists of two monomers sharing at least 80% similarity with residues 1-152 of the natural I-CreI LAGLIDADG meganuclease linked together, with or without a linker peptide.

The "LAGLIDADG meganuclease" refers to a homing endonuclease from the LAGLIDADG family, as defined in Stoddard et al (Stoddard, 2005), or an engineered variant comprising a polypeptide sharing at least 80%, 85%, 90%, 95%, 97.5%, 99% or more identity or similarity with said natural homing endonuclease. Such engineered LAGLIDADG meganucleases can be derived from monomeric or dimeric meganucleases. When derived from dimeric meganucleases, such engineered LAGLIDADG meganucleases can be single-chain or dimeric endonucleases.

By "I-CreI" is intended the natural wild-type I-CreI meganuclease having the sequence of pdb accession code 1g9y.

The DNA recognition and cleavage functions of meganucleases are generally intertwined in a single domain. Unlike meganucleases, the DNA binding domains of ZFN-based and TALEN-based systems are distinct from the endonuclease for cleavage function. The ZFN-based system comprises: at least one zinc finger protein or a variant thereof, or a nucleic acid comprising a nucleotide sequence(s) encoding the zinc finer protein or variant thereof as its DNA-binding domain; and an endonuclease element, such as zinc finger nuclease (ZFN) or Fok1 cleavage domain. The zinc finder protein (ZFP) is non-naturally occurring in that it is engineered to bind to a target site of choice. See, for example, Beerli et al. (2002) Nature Biotechnol. 20: 135-141; Pabo et al. (2001) Ann. Rev. Biochem. 70:313-340; Isalan ei al. (2001) Nature Biotechnol. 19:656-660; Segal et al. (2001) Curr. Opin. Biotechnol. 12:632-637; Choo et al. (2000) Curr. Opin. Struct Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Various kinds of selection methods can be used with the methods herein. Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in WO 02/077227. In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. Selection of target sites; ZFPs and methods for design and construction of fusion proteins (and polynucleotides encoding same) are known to those of skill in the art and described in detail in U.S. Pat. Nos. 6,140,815; 789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

A Transcription Activator-Like Effector-based Nuclease (TALEN) system refers to a genome editing system that employs one or more Transcription Activator-Like Effector (TALE)-DNA binding domain and an endonuclease element, such as Fok1 cleavage domain. The TALE-DNA binding domain comprises one or more TALE repeat units, each having 30-38 (such as, 31, 32, 33, 34, 35, or 36) amino acids in length. The TALE-DNA binding domain may employ a full length TALE protein or fragment thereof, or a variant thereof. The TALE-DNA binding domain can be fused or linked to the endonuclease domain by a linker.

The terms "CRISPR-based system," "CRISPR-based gene editing system," "CRISPR-genome editing," "CRISPR-gene editing," "CRISPR-endonuclease based genome editing," and the like are used interchangeably herein, and collectively refer to a genome editing system that comprises one or more guide RNA elements; and one or more RNA-guided endonuclease elements. The guide RNA element comprises a targeter RNA comprising a nucleotide sequence substantially complementary to a nucleotide sequence at the one or more target genomic regions or a nucleic acid comprising a nucleotide sequence(s) encoding the targeter RNA. The RNA-guided endonuclease element comprises an endonuclease that is guided or brought to a target genomic region(s) by a guide RNA element; or a nucleic acid comprising a nucleotide sequence(s) encoding such endonuclease. Examples of such CRISPR-based gene editing system includes CRISPR-based system is a CRISPR-Cas system or a CRISPR-Cpf system.

As used herein, the terms "guide RNA element," "guide RNA", "gRNA," "gRNA molecule," and "synthetic guide RNA" are used interchangeably and refer to the polynucleotide sequence comprising a targeter RNA that hybridizes with a target nucleic sequence or a nucleic acid comprising a nucleotide sequence(s) encoding the targeter RNA. A targeter RNA of gRNA comprises a targeting domain that includes a nucleotide sequence substantially complementary to the nucleotide sequence at a target genomic region. The phrase "substantially complementary" means a degree of complementarity that is at least 60%, 65%, 70%, 75%, 80%, 85%, 90%. 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

A guide RNA element can further comprise an activator RNA that is capable of hybridizing with the targeter RNA, or a nucleic acid comprising a nucleotide sequence(s) encoding the activator RNA. The activator RNA and targeter RNA can be separate or fused as a single nucleic acid via a linker loop sequence to form a single gRNA molecule. A gRNA molecule may comprise a number of domains. For example, such gRNA comprises, for example from 5' to 3': a targeting domain (which is complementary to a target nucleic acid); a first complementarity domain; a linking domain; a second complementarity domain (which is complementary to the first complementarity domain); a proximal domain; and a optionally, a tail domain. See WO2015048557.

A "first complementarity domain" has substantial complementarity with the second complementarity domain, and may form a duplexed region under at least some physiological conditions.

A "linking domain" serves to link the first complementarity domain with the second complementarity domain of a unimolecular gRNA. The linking domain can link the first and the second complementarity domains covalently or non-covalently.

A "proximal domain" can be 3-25 nucleotides in length, or 5-20 nucleotides in length. The proximal domain can share homology with or be derived from a naturally occurring proximal domain.

A "tail domain" can be absent, or be 1, 2, 3, 4, 5, 6, 7, 8, 9, or 10 nucleotides in length. The tail domain may include sequences that are complementary to each other and which, under at least some physiological conditions, form a duplexed region.

The guide RNA element may form a complex with an endonuclease of the RNA-guided endonuclease element, such as Cas endonuclease ("gRNA/nuclease complex"). An example of gRNA/nuclease complex is a CRISPR complex as described below with respect to a CRISR-based system. In some embodiments, the CRISPR complex comprises an endonuclease of RNA-guided endonuclease system that is complexed with the targeter RNA. In some embodiments, the CRISPR complex comprises an endonuclease of RNA-guided endonuclease system that is complexed with the targeter RNA and the activator RNA.

The targeting domain of targeter RNA promotes specific targeting or homing of a gRNA/nuclease complex to a target nucleotide sequence. In some embodiments, the targeting domain can be 10-30 bp, such as 15-25 bp, 18-22 bp, or 20 bp.

Methods for designing gRNAs are known in the art, including methods for selecting, designing, and validating target domain. See, for example, WO2015048577, Mali et al., 2013 SCIENCE 339(6121): 823-826; Hsu et al., 2013 NATBIOTECHNOL, 31(9): 827-32; Fu et al., 2014 NATBTOTECHNOL, doi: 10.1038/nbt.2808. PubMed PMID: 24463574; Heigwer et al., 2014 NAT METHODS 11 (2): 122-3. doi: 10.1038/nmeth.2812. PubMed PMID: 24481216; Bae et al., 2014 BIOINFORMATICS PubMed PMID: 24463181; Xiao A et al., 2014 BIOINFORMATICS Pub Med PMID: 24389662.

In some embodiments, RNA-guided endonucleases, such as a Cas enzyme or protein (e.g., Type-II Cas9 protein) or Cpf enzyme or protein (e.g., Cpf1 protein) can be used. In some embodiments, a modified version of such Cas or Cpf enzyme or protein can also be used.

In some embodiments, the CRISPR-based system is a CRISPR-Cas system. The CRISPR-Cas system comprises: (a) at least one guide RNA element or a nucleic acid comprising a nucleotide sequence(s) encoding the guide RNA element, the guide RNA element comprising a targeter RNA that includes a nucleotide sequence substantially complementary to a nucleotide sequence at the one or more target genomic regions, and an activator RNA that includes a nucleotide sequence that is capable of hybridizing with the targeter RNA; and (b) a Cas protein element comprising a Cas protein or a nucleic acid comprising a nucleotide sequence encoding the Cas protein. The targeter RNA and activator RNAs can be separate or fused together into a single RNA.

In some embodiments, the CRISPR-based system includes Class 1 CRISPR and/or Class 2 CRISPR systems. Class 1 systems employ several Cas proteins together with a CRISPR RNAs (crRNA) as the targeter RNA to build a functional endonuclease. Class 2 CRISPR systems employ a single Cas protein and a crRNA as the targeter RNA. Class 2 CRISPR systems, including the type II Cas9-based system, comprise a single Cas protein to mediate cleavage rather than the multi-subunit complex employed by Class 1 systems. The CRISPR-based system also includes Class II, Type V CRISPR system employing a Cpf1 protein and a crRNA as the targeter RNA.

The Cas protein is a CRISPR-associated (Cas) double stranded nuclease. In some embodiments, CRISPR-Cas system comprises a Cas9 protein. In some embodiments, the Cas9 protein is SaCas9, SpCas9, SpCas9n, Cas9-HF, Cas9-H840A, FokI-dCas9, or D10A nickase. The term "Cas protein," such as Cas9 protein, include wild-type Cas protein or functional derivatives thereof (such as truncated versions or variants of the wild-type Cas protein with a nuclease activity).

In some embodiments, Cas9 proteins from species other than *S. pyogenes* and *S. thermophiles* can be used. Additional Cas9 protein species may be obtained and used herein include: *Acidovorax avenae, Actinobacillus pleuropneumoniae, Actinobacillus succinogenes, Actinobacillus suis, Actinomyces* sp., *Cycliphilus denitrificans, Aminomonas paucivorans, Bacillus cereus; Bacillus smithii, Bacillus thuringiensis, Bacteroides* sp., *Blastopirellula marina, Bradyrhizobium* sp., *Brevibacillus laterosporus, Campylobacter coli, Campylobacter jejuni, Campylobacter lari, Candidatus Puniceispirillum, Clostridium cellulolyticum, Clostridium perfingens, Corynebacterium accolens, Corynebacterium dolichum, Corynebacterium matruchotii, Dinoroseobacter shibae, Eubacterium dolichum, gamma proteobacterium, Gluconacetobacter diazotrophicus, Haemoplzilus parainfluenzae, Haemophilus sputorum, Helicobacter canadensis, Helicohacter cinaedi, Helicobacter mustelae, Llyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria* sp., *Neisseria wadsworthii, Nitrosomonas* sp., *Parvibaculum lavamentivorans, Pasteurella multocida, Phascolarctobacterium succinatutells, Ralstonia syzygii, Rhodopseudomonas palustris, Rhodovulum* sp., *Simonsiella muelleri, Sphingomonas* sp., *Sporolactobacillus vineae, Staphylococcus lugdunensis, Streptococcus* sp., *Subdoligranulum* sp., *Tistrella mobilis, Treponema* sp., or *Verminephrobacter eiseniae*.

In some embodiments, one or more elements of a CRISPR-based system is derived from a type I, type II, or type III CRISPR system In some embodiments, one or more elements of a CRISPR-based system is derived from a particular organism comprising an endogenous CRISPR system, such as *Streptococcus pyogenes, Staphylococcus aureus, Francisella tularensis, Prevotella* sp., *Acidaminococcus* sp., and *Lachnospiraceae* sp. In general, a CRISPR-based system is characterized by elements that promote the formation of a CRISPR complex at the target genomic regions or the site of a target sequence (also referred to as a protospacer in the context of an endogenous CRISPR system). In the context of formation of a CRISPR complex, "target sequence" refers to a sequence to which a guide sequence is designed to have substantial complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, a target sequence is located in the nucleus or cytoplasm of a cell(s). In some embodiments, the target sequence may be within an organelle of a eukaryotic cell(s), for example, mitochondrion or chloroplast.

A sequence or template that may be used for recombination into the targeted locus comprising the target sequences is referred to as an "editing template" or "editing polynucleotide" or "editing sequence". An exogenous template polynucleotide may be referred to as an editing template or donor template. In some embodiments, single stranded DNA and double stranded DNA from either synthetic or biologic origin may be used. By way of non-limiting example, suitable editing templates include ssODN, dsODN, PCR products, plasmids, and viruses including AAV, Adenovirus, Retrovirus, lentivirus, etc. Additional editing templates are also possible. In some embodiments, the recombination is homologous recombination.

In some embodiments, the CRISPR-based system is a CRISPR-Cas9 system. The targeter RNA of the CRISPR-Cas9 system comprises a CRISPR targeting RNA (crRNA) and the activator RNA of the CRISPR-Cas 9 system comprises a trans-activating CRISPR RNA (tracRNA). The Cas protein element of the CRISPR-Cas9 system employs a Cas9 protein. The crRNA and the tracrRNA can be separate or combined into a single RNA construct via a linker loop sequence. This combined RNA construct is called a single-guide RNA (sgRNA; or guide RNA).

With respect to general information on CRISPR-Cas systems, components thereof, and delivery of such components, including methods, materials, delivery vehicles, vectors, particles, AAV, and making and using thereof, including as to amounts and formulations can be found in: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830, US 2014-0287938 A1, US 2014-0273234 A1, US2014-0273232 A1, US 2014-0273231, US 2014-0256046 A1, US 2014-0248702 A1, US 2014-0242700 A1, US 2014-0242699 A1, US 2014-0242664 A1, US 2014-0234972 A1, US 2014-0227787 A1, US 2014-0189896 A1, US 2014-0186958, US 2014-0186919 A1, US 2014-0186843 A1, US 2014-0179770 A1 and US 2014-0179006 A1, US 2014-0170753; European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661, WO 2014/093694, WO 2014/093595, WO 2014/093718, WO 2014/093709, WO 2014/093622, WO 2014/093635, WO 2014/093655, WO 2014/093712, WO2014/093701, WO2014/018423, WO 2014/204723, WO 2014/204724, WO 2014/204725, WO 2014/204726, WO 2014/204727, WO 2014/204728, WO 2014/204729, and WO2016/028682.

In some embodiments, the CRISPR-based system is a CRISPR-Cpf system. The "CRISPR-Cpf system" comprises: (a) at least one guide RNA element or a nucleic acid comprising a nucleotide sequence(s) encoding the guide RNA element, the guide RNA comprising a targeter RNA having a nucleotide sequence complementary to a nucleotide sequence at a locus of the target nucleic acid; and (b) a Cpf protein element or a nucleic acid comprising a nucleotide sequence encoding the Cpf protein element.

An example of a Cpf protein element includes a Cpf1 nucleases, such as *Francisella* Cpf1 (FnCpf1) and any variants thereof. See, for example, Zetsche et al., "Cpf1 is a single RNA-guided endonuclease of a class 2 CRISPR-Cas system," *Cell,* 163(3): pages 759-71; and Fonfara et al., "The CRISPR-associated DNA-cleaving enzyme Cpf1 also processes precursor CRISPR RNA," *Nature* 532 (7600): pages, 517-21. Cpf1's preferred PAM is 5'-TTN, differing from that of Cas9 (3'-NGG) in both genomic location and GC-content. The CRISPR-Cpf system may not employ an activator RNA (tracrRNA). Both Cpf1 and its guide RNAs are in general smaller than their SpCas9 counterparts. The Cpf1 locus contains a mixed alpha/beta domain, a RuvC-I followed by a helical region, a RuvC-II and a zinc finger-like domain. The Cpf1 protein has a RuvC-like endonuclease domain that is similar to the RuvC domain of Cas9. Furthermore, Cpf1 does not have a HNH endonuclease domain, and the N-terminal of Cpf1 does not have the alfa-helical recognition lobe of Cas9. The Cpf1 loci encode Cas1, Cas2 and Cas4 proteins more similar to types I and III than from type II systems. Cpf1-family proteins can be found in many bacterial species.

Without being bound to a particular theory, the CRISPR-Cpf system employs a Cpf1-crRNA complex which cleaves target DNA or RNA by identification of a protospacer adjacent motif 5'-YEN-3=(where "Y" is a pyrimidine and "N" is any nucleobase) or 5'-TTN-3 in contrast to the G-rich PAM targeted by Cas9. After identification of PAM, Cpf1 introduces a sticky-end-like DNA double-stranded break of 4 or 5 nucleotides overhang.

In some embodiments, the genome editing system is a NgAgo-based system. The NgAgo-based system comprises at least one guide DNA element or a nucleic acid comprising a nucleic acid sequence(s) encoding the guide DNA element; and a DNA-guided endonuclease. The NgAgo-based system employs DNA as a guide element. Its working principle is similar to that of CRISPR-Cas9 technology, but its guide element is a segment of guide DNA(dDNA) rather than gRNA in CRISPR-Cas9 technology. An example of DNA-guided endonuclease is an Argonaute endonuclease (NgAgo) from *Natronobacterium gregoryi*. See, for example, Feng Gao et al. "DNA-guided genome editing using the *Natronobacterium gregoryi* Argonaute," *Nature Biotechnology*, (2016): doi:10.1038/nbt.3547.

By "linker," "peptide linker", "peptidic linker" or "peptide spacer" it is intended to mean a peptide sequence that allows the connection of different monomers in a fusion protein and the adoption of the correct conformation for said fusion protein activity and which does not alter the activity of either of the monomers. Peptide linkers can be of various sizes from 1, 2, 3, 4, 5, 10, 15, 20, 30, 40 to 50 amino acids as a non limiting indicative range or any intermediate value within this range.

DNA-PK Inhibitors for Increasing Genomic Editing Efficiency

Targeted genome editing efficiency can be increased by administering to a cell(s) with one or more compounds (e.g., DNA-PK inhibitors) described herein and a genome editing system. Genome editing systems suitable for use include, for example, a meganuclease based system, a zinc finger nuclease (ZFN) based system, a Transcription Activator-Like Effector-based Nuclease (TALEN) system, a CRISPR-based system or NgAgo-based system. The methods, compositions, and kits of the disclosure provide DNA-PK inhibitors and/or a genome editing system for increasing genome editing efficiency. In some embodiments, HDR genome editing efficiency is increased following administering to a cell(s) with a DNA-PK inhibitor.

In some embodiments, the genome editing system is a CRISPR-based genome editing system. The CRISPR-based genome editing system can be a CRISPR-Cas system or variants thereof. The CRISPR-Cas system can use any Cas endonucleases, such as Cas 9 endonucleases and variants thereof. Examples of Cas 9 endonucleases includes Cas9 endonucleases or variants thereof, such as SaCas9, SpCas9, SpCas9n, Cas9-HF, Cas9-H840A, FokI-dCas9, or CasD10A nickase. The Cas endonuclease can be wild type, engineered, or a nickase mutant, or any variations thereof.

In some embodiments, the CRISPR-based genome editing system includes a CRISPR sequence, a trans-activating cr (tracr) sequence, a guide sequence and a Cas endonuclease or any combinations thereof.

In some embodiments, the CRISPR-based genome editing system includes a RNA comprising a CRISPR sequence (crRNA), a RNA comprising a trans-activating cr (tracr) sequence (tracrRNA) and a Cas endonuclease or any combinations thereof.

In some embodiments, the CRISPR-based genome editing system includes a CRISPR sequence sequence, a guide sequence, and a Cas endonuclease or a Cpf endonuclease, or any combinations thereof.

In some embodiments, the CRISPR-based genome editing system is a CRISPR-Cpf system. The Cpf nuclease is a Class 2 CRISPR-Cas system endonuclease. Cpf is a single RNA-guided endonuclease. The Cpf nuclease can be wild type, engineered or a nickase mutant, or any variations thereof. See, for example, Zetsche et al., "CPF1 is a single RNA-guided endonuclease of a Class 2 CRISPR-Cas System," Cell, 163(3):759-71. In some embodiments, the Cpf nuclease is a Cpf 1 endonuclease.

In some embodiments, the genome editing system is a meganuclease based system. Meganuclease-based genome editing uses sequence-specific endonucleases that recognize large DNA target sites (e.g. typically about >12 bp). See, for example, U.S. Pat. No. 9,365,964. Meganucleases can cleave unique chromosomal sequences without affecting overall genome integrity. In some embodiments, the meganuclease can be a homing endonuclease. In some embodiments, the meganuclease can be an intron endonuclease or an intein endonuclease. The homing endonucleases can belong to the LAGLIDADG family. The meganucleases can be wild type, engineered or a nickase mutant.

In some embodiments, the gene-editing system is a zinc finger nuclease (ZFN) based system. The ZFN is an artificial restriction enzyme engineered based on the fusion between a zing finger DNA-binding domain and a DNA-cleavage domain. See, for example, U.S. Pat. No. 9,145,565.

In some embodiments, the gene-editing system is a Transcription Activator-Like Effector-based Nuclease (TALEN). TALENs are engineered restriction enzymes that are made by the fusion of a TAL effector DNA-binding domain to a DNA cleavage domain. See, for example, U.S. Pat. No. 9,181,535.

In some embodiments, the gene editing system is an Argonaute based system. Argonaute based gene editing systems include an Argonaute derived endonuclease and a 5' phosphorylated ssDNA. In some embodiments, the phosphorylated ssDNA can be 10-40 nucleotides, 15-30 nucleotide or 18-30 nucleotides (e.g. about 24 nucleotides) in length. In some embodiments, the Argonaute endonuclease can be any endonuclease. In some embodiments, the Argonaute endonuclease is derived from *Thermus thermophiles* (TtAgo), *Pyrococcus furiosus* (PfAgo), or *Natronobacterium gregoryi* (NgAgo). In some embodiments, the *Natronobacterium gregoryi* (NgAgo) is strain 2 (i.e. *N. gregoryi* SP2). In some embodiments, the Argonaute endonuclease is NgAgo. See, for example, Gao et al., "DNA-guided genome editing using the *Natronobacterium gregoryi* Argonaute," Nature Biotechnology, May 2016.

The DNA-PK inhibitors can be any DNA-PK inhibitor. The DNA-PK inhibitor can be any compound or substance that causes inhibition of a DNA-PK. The DNA-PK inhibitor can be a compound, small molecule, antibody, or nucleotide sequence. In some embodiments, the DNA-PK inhibitors are compounds represented by Formula (I), (II), (III-A-1), (III-A-2), (III-B-1), (III-B-2), (IV), (V-A) and (V-B).

In some embodiments, the disclosure provides a method of editing one or more target genomic regions, the method includes administering to one or more cells that have one or more target genomic regions, a genome editing system and a compound represented by Formula (I):

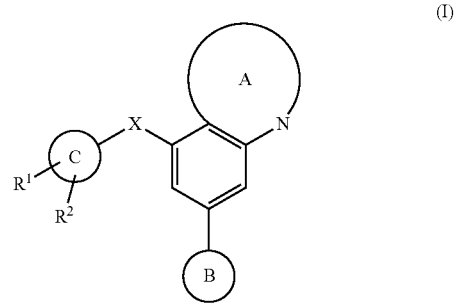

(I)

or pharmaceutically acceptable salts thereof, where each of $R^1$, $R^2$, X, Ring A, Ring B and Ring C independently is as defined elsewhere herein.

Ring A is an aromatic ring system selected from

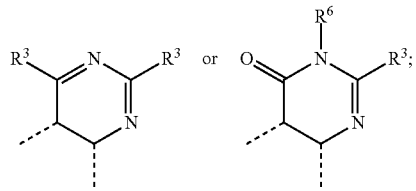

Ring B is a ring system selected from

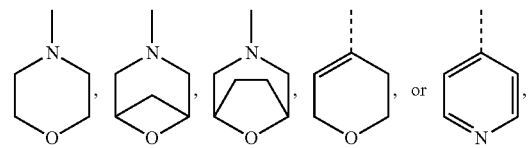

wherein Ring B is optionally substituted with one or more substituents selected from the group consisting of —F, —OH, and $C_{1-4}$alkyl optionally substituted with one or more substituents selected from the group consisting of —F, —Cl, —OH, and —$OC_{1-2}$alkyl;

Ring C is a C$_{4-6}$ cycloalkyl, 5-6-membered heteroaryl, or phenyl group, wherein Ring C is optionally further substituted with one or more substituents selected from the group consisting of halogen, C$_{1-2}$ alkyl, —OH, and —OC$_{1-2}$alkyl;

X is —NH—, —O—, —OC$_{1-4}$ alkyl-, —S—, or —CH$_2$—;

each of R$^1$ and R$^2$ is, independently, hydrogen, —C(O)NHR$^4$, —C(O)OR$^4$, —NHC(O)R$^4$, —NHC(O)OR$^4$, —NHC(O)NHR$^4$, —NHS(O)$_2$R$^4$, —NHR$^4$, —C$_{1-4}$ alkyl-NHR$^4$, —OR$^4$, or R$^7$ wherein R$^1$ and R$^2$ cannot simultaneously be hydrogen;

each R$^3$ independently is hydrogen, —C$_{1-4}$alkyl, halogen, —OC$_{1-2}$alkyl, —C(O)OH, —C(O)OC$_{1-2}$alkyl, —CN, —C(O)NHC$_{1-2}$alkyl, —C(O)NH$_2$, C$_{3-4}$ cycloalkyl, or —NRR', wherein each of said R$^3$ alkyl and cycloalkyl independently is optionally substituted with one or more substituents selected from the group consisting of —F, —Cl, —OH and —OC$_{1-2}$alkyl;

each R$^4$ independently is hydrogen, C$_{1-4}$alkyl, C$_{2-4}$alkenyl, C$_{2-4}$alkynyl, C$_{3-10}$ cycloalkyl, 6-10 membered aryl, 5-10-membered heteroaryl, or 4-10-membered heterocyclyl, wherein each of said R$^4$ groups is optionally substituted with one or more substituents selected from the group consisting of —Br, —Cl, —F, C$_{1-4}$alkyl, CN, NO$_2$, C$_{2-4}$alkenyl, C$_{2-4}$alkynyl, C$_{3-6}$cycloalkyl, C$_{0-4}$ alkyl-C$_{3-5}$ cycloalkyl, C$_{0-4}$ alkyl-O—C$_{1-4}$ alkyl, C$_{0-4}$ alkyl-O—C$_{0-4}$ alkyl-C$_{3-5}$ cycloalkyl, C(O)OC$_{1-4}$ alkyl, C(O)OC$_{0-4}$ alkyl-C$_{3-5}$ cycloalkyl, C$_{0-4}$ alkyl-C(O)NH$_2$, C(O)NHC$_{1-4}$ alkyl, C(O)N(C$_{1-4}$ alkyl)$_2$, C(O)NH(C$_{0-4}$ alkyl-C$_{3-5}$ cycloalkyl), CH$_2$OR$^5$, C$_{0-4}$ alkyl-C(O)R$^5$, C$_{0-4}$ alkyl-C(O)N(R$^5$)$_2$, C$_{0-4}$ alkyl-C(O)OR$^5$, C$_{0-4}$ alkyl-NHC(O)R$^5$, C$_{0-4}$ alkyl-N(R$^5$)$_2$, 5-6 membered heterocyclyl, —O(C$_{1-4}$ alkyl)OR$^5$, —OR$^5$, and oxo, and wherein each of said optional R$^4$ substituents is optionally and independently substituted with one or more substituents selected from the group consisting of —F, —Cl, C$_{1-4}$alkyl, —OH, —OC$_{1-4}$alkyl, —SC$_{1-4}$alkyl, —C(O)C$_{1-4}$ alkyl, —C(O)OC$_{1-4}$ alkyl, and —C(O)OC$_{0-4}$ alkyl-C$_{3-5}$ cycloalkyl; and each R$^5$ independently is hydrogen, C$_{1-4}$alkyl, phenyl, 5-6-membered heteroaryl, or 4-7-membered heterocyclyl, wherein each R$^5$ independently is optionally substituted with one or more substituents selected from the group consisting of —F, —Cl, C$_{1-2}$alkyl, —CH$_2$OH, —CN, —OH, —OC$_{1-2}$alkyl, 5-6-membered heteroaryl, and 4-7 membered heterocyclyl, or two R$^5$ groups together with the intervening nitrogen atom optionally form a morpholine ring, azetidine ring, pyrrolidine ring, piperidine ring, or piperazine ring; and R$^6$ is hydrogen or C$_{1-4}$alkyl optionally substituted with one or more substituents selected from the group consisting of —F, —Cl, —CH$_2$OH, —CN, —OH, and —OC$_{1-2}$alkyl;

R$^7$ is 6-10-membered aryl, 5-10-membered heteroaryl, or 4-7-membered heterocyclyl, each of which is optionally substituted with one or more substituents selected from the group consisting of —F, —Cl, C$_{1-2}$alkyl, —CH$_2$OH, —CN, and —OR; and each of R and R' independently is hydrogen or C$_{1-4}$alkyl, or R and R' together with the nitrogen atom to which they are attached optionally form a morpholine ring, azetidine ring, pyrrolidine ring, piperidine ring, or piperazine ring.

In some embodiments, the disclosure provides a method of editing one or more target genomic regions, the method includes administering to one or more cells that have one or more target genomic regions, a genome editing system and a compound represented by Formula (II) or pharmaceutically acceptable salts thereof:

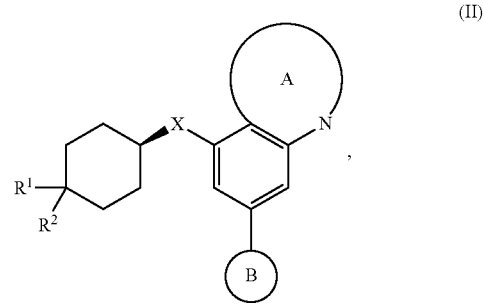

(II)

wherein the variables of Formula (II) are each independently as described below.

In the first set of variables of Formula (II), each of the variables of Formula (II) is independently as described above in any of the first through twenty seventh sets of variables of Formula (I).

In the second set of variables of Formula (II), R$^1$ is —C(O)NHR$^4$, —C(O)OR$^4$, —NHC(O)R$^4$, —NHC(O)OR$^4$, —NHC(O)NHR$^4$, —NHS(O)$_2$R$^4$, —C$_{0-4}$ alkyl-NHR$^4$, —OR$^4$, or R$^7$; and R$^2$ is hydrogen. The remaining variables of Formula (I) are each and independently as described in any of the first through twenty seventh sets of variables of Formula (I).

In some embodiments, the disclosure provides a method of editing one or more target genomic regions, the method includes administering to one or more cells that have one or more target genomic regions, a genome editing system and a compound represented by Formula (III-A-1), (III-A-2), (III-B-1), or (III-B-2), or pharmaceutically acceptable salts thereof:

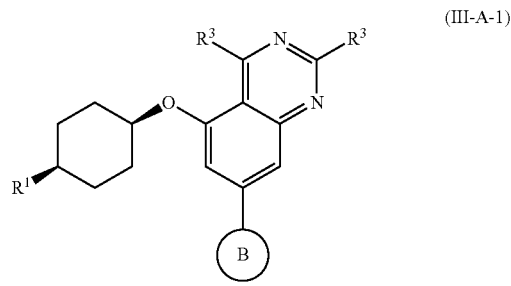

(III-A-1)

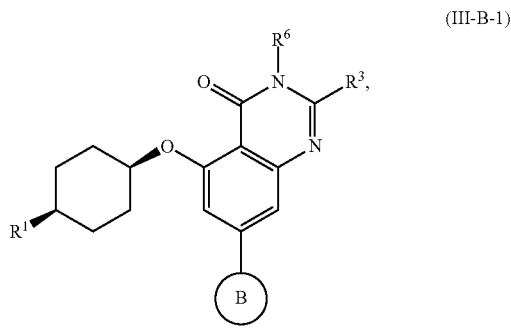

(III-B-1)

-continued (III-A-2)

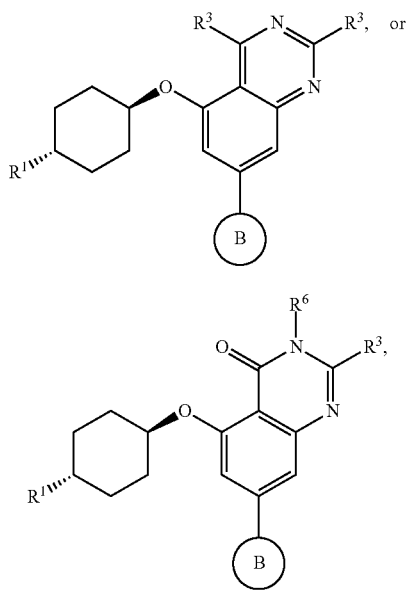

(III-B-2)

wherein the variables of Formula (II) are each independently as described below.

In the first set of variables of Formula (III-A-1), (III-A-2), (III-B-1), or (III-B-2), each of the variables of (III-A-1), (III-A-2), (III-B-1), or (III-B-2) is independently as described above in any of the first through twenty seventh sets of variables of Formula (I).

In the second set of variables of Formula (III-A-1), (III-A-2), (III-B-1), or (III-B-2), $R^1$ is —C(O)NHR$^4$, —C(O)OR$^4$, —NHC(O)R$^4$, —NHC(O)OR$^4$, —NHC(O)NHR$^4$, —NHS(O)$_2$R$^4$, —C$_{0-4}$ alkyl-NHR$^4$, —OR$^4$, or R$^7$; and the remaining variables of Formula (I) are each and independently as described in any of the first through twenty seventh sets of variables of Formula (I).

In the third set of variables of Formula (III-A-1), (III-A-2), (III-B-1), or (III-B-2), $R^1$ is —C$_{1-4}$ alkyl-NHR$^4$, —NHR$^4$, or —OR$^4$; and the remaining variables of Formula (I) are each and independently as described in any of the first or second set of variables of (III-A-1), (III-A-2), (III-B-1), or (III-B-2).

In the fourth set of variables of Formula (III-A-1), (III-A-2), (III-B-1), or (III-B-2), $R^1$ is —NHR$^4$; and the remaining variables of Formula (I) are each and independently as described in any of the first through third sets of variables of Formula (III-A-1), (III-A-2), (III-B-1), or (III-B-2).

In the fifth set of variables of Formula (III-A-1), (III-A-2), (III-B-1), or (III-B-2), $R^1$ is —OR$^4$; and the remaining variables of Formula (I) are each and independently as described in any of the first through fourth sets of variables of Formula (III-A-1), (III-A-2), (III-B-1), or (III-B-2).

In the sixth set of variables of Formula (III-A-1), (III-A-2), (III-B-1), or (III-B-2), $R^3$ independently is hydrogen, methyl, —Cl, —OCH$_3$, —CN, cyclopropyl, —NHCH$_3$, or —N(CH$_3$)$_2$; $R^6$ is hydrogen or methyl; and the remaining variables of Formula (I) are each and independently as described in any of the first through fifth sets of variables of Formula (III-A-1), (III-A-2), (III-B-1), or (III-B-2).

In yet another embodiment, the compounds of the invention are represented by Formula (IV) or pharmaceutically acceptable salts thereof:

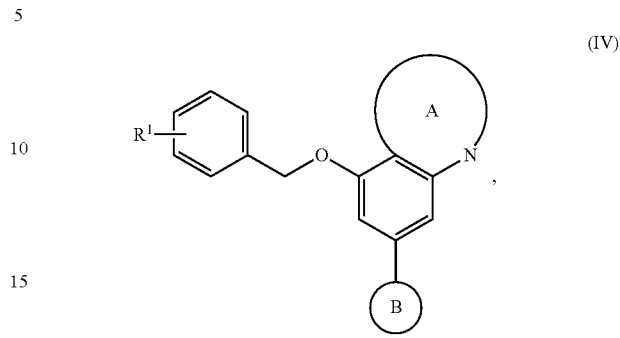

(IV)

wherein the variables of Formula (IV) are each and independently as described below.

In the first set of variables of Formula (IV), each of the variables independently is as described in any one of the first through thirtieth sets of variables of Formula (I).

In the second set of variables of Formula (IV), $R^1$ is hydrogen, —C(O)NHR$^4$, —C(O)OR$^4$, —NHC(O)R$^4$, —NHC(O)OR$^4$, —NHC(O)NHR$^4$, —NHS(O)$_2$R$^4$, —C$_{0-4}$ alkyl-NHR$^4$, —OR$^4$, or R$^7$; and the remaining variables of Formula (IV) are each and independently as described in any of the first through thirtieth sets of variables of Formula (I).

In the third set of variables of Formula (IV), Ring B is optionally substituted

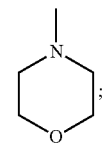

and the remaining variables of Formula (IV) are each and independently as described in the first or second set of variables of Formula (IV).

In some embodiments, the disclosure provides a method of editing one or more target genomic regions, the method includes administering to one or more cells that have one or more target genomic regions, a genome editing system and a compound represented by Formula (V-A) or (V-B), or pharmaceutically acceptable salts thereof:

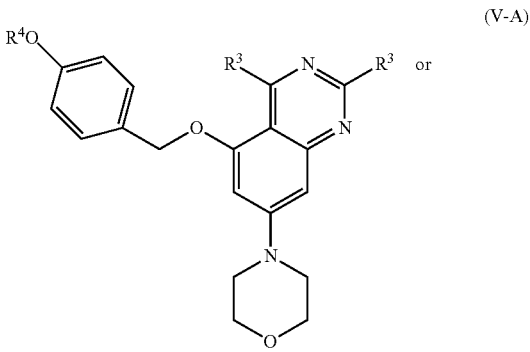

(V-A)

-continued

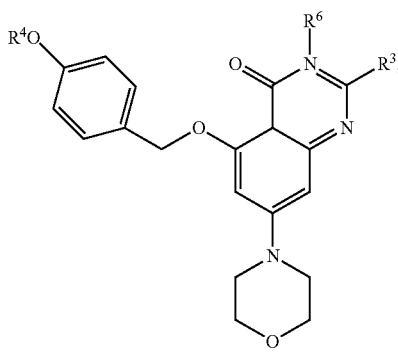

(V-B)

wherein each of the variables of Formula (V-A) or (V-B) is independently as described below.

In the first set of variables of Formula (V-A) or (V-B), each of the variables independently is as described in any one of the first through thirtieth sets of variables of Formula (I).

In the second set of variables of Formula (V-A) or (V-B), $R^3$ is hydrogen, methyl, cyclopropyl, —F, —Cl, —OC$_{1-2}$alkyl, —NRR', or —CN, wherein each of said $R^3$ alkyl is optionally substituted with one or more substituents selected from the group consisting of —F, —OH, and —O(C$_{1-2}$ alkyl); each $R^4$ independently is optionally substituted C$_{1-4}$ alkyl optionally substituted with one or more substituents selected from the group consisting of —F, —OH, and —O(C$_{1-2}$ alkyl); and R and R' are each and independently hydrogen or C$_{1-2}$ alkyl. The remaining variables of Formula (V-A) or (V-B) are each and independently as described in any one of the first through thirtieth sets of variables of Formula (I).

In the third set of variables of Formula (V-A) or (V-B), each $R^3$ independently is hydrogen, methyl, —Cl, —OCH$_3$, —CN, cyclopropyl, —NHCH$_3$, or —N(CH$_3$)$_2$; and $R^6$ is hydrogen or methyl. The remaining variables of Formula (V-A) or (V-B) are each and independently as described in the first or second set of variables of Formula (V-A) or (V-B).

In yet another embodiment, the compounds of the invention are represented by any one of Formulae (I), (II), (III-A-1), (III-A-2), (III-B-1), (III-B-2), (IV), (V-A) and (V-B), or pharmaceutically acceptable salts thereof, wherein each of the variables of these Formulae independently as depicted in the structural formulae of Tables 1 and 2.

In some embodiments, the disclosure also provides a method of repairing a DNA break in one or more target genomic regions via a homology directed repair (HDR) pathway, the method includes administering to one or more cells that have one or more target genomic regions, a genome editing system and a compound represented by Formula (I), (II), (III-A-1), (III-A-2), (III-B-1), (III-B-2), (IV), (V-A) and (V-B) or pharmaceutically acceptable salts thereof.

The genome editing system interacts with a nucleic acid(s) of the target genomic regions, resulting in a DNA break, and wherein the DNA break is repaired at least in part via a HDR pathway.

In some embodiments, the disclosure also provides a method of inhibiting or suppressing repair of a DNA break in one or more target genomic regions via a NHEJ pathway, the method includes administering to one or more cells that have one or more target genomic regions, a genome editing system and a compound represented by Formula (I), (II), (III-A-1), (III-A-2), (III-B-1), (III-B-2), (IV), (V-A) and (V-B) or pharmaceutically acceptable salts thereof.

The genome editing system interacts with a nucleic acid(s) of the one or more target genomic regions, resulting in a DNA break, and wherein repair of the DNA break via a NHEJ pathway is inhibited or suppressed.

In some embodiments, the disclosure also provides a method of modifying expression of one or more genes or proteins, the method includes administering to one or more cells that comprise one or more target genomic regions, a genome editing system and a compound represented by Formula (I), (II), (III-A-1), (III-A-2), (III-B-1), (III-B-2), (IV), (V-A) and (V-B) or pharmaceutically acceptable salts thereof.

The genome editing system interacts with a nucleic acid(s) of the one or more target genomic regions of a target gene(s), resulting in editing the one or more target genomic regions and wherein the edit modifies expression of a downstream gene (s) and/or protein(s) associated with the target gene(s).

In some embodiments, the DNA break includes a DNA double strand break (DSB).

In some embodiments, the compound is a co-crystal that includes a compound having a structure of Formula (I) and a co-crystal former selected from adipic acid, citric acid, fumaric acid, maleic acid, succinic acid, or benzoic acid.

In some embodiments, the efficiency of editing the target genomic regions in the one or more cells is increased as compared to that in otherwise identical cell or cells but without the compound.

In some embodiments, the efficiency of the repair of the DNA break at the target genomic regions in the one or more cells via a HDR pathway is increased as compared to that in otherwise identical cell or cells but without the compound.

In some embodiments, the efficiency of inhibiting or suppressing the repair of the DNA break at the target genomic regions in the one or more cells via a NHEJ pathway is increased as compared to that in otherwise identical cell or cells but without the compound.

In some embodiments, the efficiency is increased by at least 2-fold, 3-fold, 4-fold, 5-fold, 10-fold, 15-fold, 20-fold, 25-fold, 30-fold, 40-fold, 50-fold, or 100-fold as compared to that in otherwise identical cell or cells but without compound.

In some embodiments, the efficiency is measured by frequency of targeted polynucleotide integration. In some embodiments, the efficiency is measured by frequency of targeted mutagenesis. In some embodiments, the targeted mutagenesis comprises point mutations, deletions, and/or insertions.

In some embodiments, the expression of a downstream gene (s) and/or protein(s) associated with the target gene(s) is increased as compared to the baseline expression level in the one or more cells prior to the administration. For example, said expression is increased by at least 10%, 20%, 30%, 40%, 50%, 60%, 70%, 80%, 90%, 1-fold, 1.5-fold, 2-fold, 2.5-fold, 3-fold, 3.5-fold, 4-fold, 4.5-fold, 5-fold, or 10-fold as compared to the baseline expression level in the one or more cells prior to the administration.

In some embodiments, the expression of a downstream gene (s) and/or protein(s) associated with the target gene(s) is decreased as compared to the baseline expression level in the one or more cells prior to the administration. For example, the gene expression is decreased by at least 10%, 20%, 30%, 40%, 50%, 60%, 70%, 80%, 90%, 95%, 96%, 97%, 98%, or 99% as compared to the baseline expression level in the one or more cells prior to the administration.

In some embodiments, the expression of a downstream gene (s) and/or protein(s) associated with the target gene(s) is substantially eliminated in the one or more cells.

In some embodiments, the cell is synchronized at the S or the G2 cell cycle phase.

In some embodiments, the one or more cells that are administered or contacted with said compound have increased survival in comparison to one or more cells that have not been administered or contacted with said compound.

In some embodiments, the genome editing system and the compound are administered into the one or more cells simultaneously. In some embodiments, the genome editing system and the compound are administered into the one or more cells sequentially. In some embodiments, the genome editing system is administered into the one or more cells prior to the compound. In some embodiments, the compound is administered into the one or more cells prior to the genome editing system.

In some embodiments, the one or more cells are cultured cells. In some embodiments, the one or more cells are in vivo cells within an organism. In some embodiments, the one or more cells are ex vivo cells from an organism.

In some embodiments, the organism is a mammal. In some embodiments, the organism is a human.

In some embodiments, the genome editing system and the compound are administered via a same route. In some embodiments, the genome editing system and the compound are administered via a different route. In some embodiments, the genome editing system is administered intravenously and the compound is administered orally.

In some embodiments, the genome editing system is selected from a meganuclease based system, a zinc finger nuclease (ZFN) based system, a Transcription Activator-Like Effector-based Nuclease (TALEN) system, a CRISPR-based system, or a NgAgo-based system.

In some embodiments, the genome editing system is a CRISPR-based system. In some embodiments, the CRISPR-based system is a CRISPR-Cas system or a CRISPR-Cpf system.

In some embodiments, the CRISPR-based system is a CRISPR-Cas system and wherein the CRISPR-Cas system includes: (a) at least one guide RNA element that includes: (i) a targeter RNA that includes a nucleotide sequence substantially complementary to a nucleotide sequence at the one or more target genomic regions or a nucleic acid that includes a nucleotide sequence(s) encoding the targeter RNA; (ii) and an activator RNA that includes a nucleotide sequence that is capable of hybridizing with the targeter RNA or a nucleic acid that includes a nucleotide sequence(s) encoding the activator RNA; and (b) a Cas protein element that includes a Cas protein or a nucleic acid that includes a nucleotide sequence(s) encoding the Cas protein.

In some embodiments, the targeter RNA and activator RNA are fused as a single molecule.

In some embodiments, the Cas protein is a Type-II Cas9 protein. In some embodiments, the Cas9 protein is a SaCas9, SpCas9, SpCas9n, Cas9-HF, Cas9-H840A, FokI-dCas9, or D10A nickase, or any combinations thereof.

In some embodiments, the CRISPR-based system is a CRISPR-Cpf system and the CRISPR-Cpf system includes: (a) at least one guide RNA element or a nucleic acid that includes a nucleotide sequence(s) encoding the guide RNA element, the guide RNA that includes a targeter RNA that that includes a nucleotide sequence substantially complementary to a nucleotide sequence at the one or more target genomic regions; and (b) a Cpf protein element that includes a Cpf protein or a nucleic acid comprising a nucleotide sequence encoding the Cpf protein.

In some embodiments, the genome editing system is delivered by one or more vectors.

In some embodiments, the one or more vectors are selected from viral vectors, plasmids, or ssDNAs.

In some embodiments, the viral vectors are selected from retroviral, lentiviral, adenoviral, adeno-associated and herpes simplex viral vectors.

In some embodiments, the genome editing system is delivered by synthetic RNA.

In some embodiments, the genome editing system is delivered by a nanoformulation.

In some embodiments, a kit or composition is provided for editing one or more target genomic regions. In some embodiments, the kit or composition includes a genome editing system; and a compound represented by Formula (I), (II), (III-A-1), (III-A-2), (III-B-1), (III-B-2), (IV), (V-A) and (V-B) or pharmaceutically acceptable salts thereof.

In some embodiments, the genome editing system of the kit or composition is a meganuclease based system, a zinc finger nuclease (ZFN) based system, a Transcription Activator-Like Effector-based Nuclease (TALEN) system, a CRISPR-based system, or NgAgo-based system. In some embodiments, the genome editing system of the kit or composition is a CRISPR-based system. In some embodiments, the CRISPR-based system of the kit or composition is a CRISPR-Cas system or a CRISPR-Cpf system.

In some embodiments, the CRISPR-based system of the kit or composition is a CRISPR-Cas system and wherein the CRISPR-Cas system includes: (a) at least one guide RNA element that includes: (i) a targeter RNA that includes a nucleotide sequence substantially complementary to a nucleotide sequence at the one or more target genomic regions or a nucleic acid that includes a nucleotide sequence(s) encoding the targeter RNA; (ii) and an activator RNA that includes a nucleotide sequence that is capable of hybridizing with the targeter RNA, or a nucleic acid that includes a nucleotide sequence(s) encoding the activator RNA; and (b) a Cas protein element that includes a Cas protein or a nucleic acid that includes a nucleotide sequence(s) encoding the Cas protein.

In some embodiments, the Cas protein of the kit or composition is a Type-II Cas9 protein. In some embodiments, the Cas9 protein of the kit or composition is a SaCas9, SpCas9, SpCas9n, Cas9-HF, Cas9-H840A, FokI-dCas9, or D10A nickase, or any combination thereof.

In some embodiments, the CRISPR-based system of the kit or composition is a CRISPR-Cpf system, and wherein the CRISPR-Cpf system includes: (a) a targeter RNA that includes a nucleotide sequence substantially complementary to a nucleotide sequence at the one or more target genomic regions, or a nucleic acid that includes a nucleotide sequence(s) encoding the targeter RNA; and (b) a Cpf protein element that includes a Cpf protein or a nucleic acid that includes a nucleotide sequence(s) encoding the Cpf protein.

In some embodiments, the genome editing system of the kit or composition is included or packaged in one or more vectors. In some embodiments, the one or more vectors are selected from viral vectors, plasmids, or ssDNAs. In some embodiments, the viral vectors are selected from the group consisting of retroviral, lentiviral, adenoviral, adeno-associated and herpes simplex viral vectors.

In some embodiments, the increased genome editing efficiency is about 1-fold, 2-fold, 3-fold, 4-fold, 5-fold, 10-fold, 15-fold, 20-fold, 25-fold, 30-fold, 40-fold, 50-fold, or 100-fold, in comparison to a condition in which a DNA-PK inhibitor and a genome editing system is not administered to a cell(s), or compared to a condition in which only a genome editing system and not a DNA-PK inhibitor is administered to a cell(s).

Use of DNA-PK Inhibitors and Genome Editing System, Kits, and Compositions Thereof Genome editing, in which particular genomic regions are precisely altered, holds great therapeutic potential.

In some embodiments, provided herein are methods for editing one or more target genomic regions, for repairing a DNA break in one or more target genomic regions via a HDR pathway, for inhibiting or suppressing NHEJ-mediated repair of a DNA break in one or more target genomic, and for modifying the expression of one or more genes or proteins via administering to a cell(s) a genome editing system and a DNA-PK inhibitor.

In some embodiments, provided herein are methods of modifying expression of one or more genes or proteins comprising administering to one or more cells that comprise one or more target genomic regions, a genome editing system and a DNA-PK inhibitor described herein, wherein the genome editing system interacts with a nucleic acid(s) of the one or more target genomic regions of a target gene(s), resulting in editing the one or more target genomic regions and wherein the edit modifies expression of a downstream gene (s) and/or protein(s) associated with the target gene(s).

The genome editing system can be any genome editing system that can edit a target genomic region in a cell(s). Exemplary genome editing systems are described in detail above and can include, for example, a meganuclease based system, a zinc finger nuclease (ZFN) based system, a Transcription Activator-Like Effector-based Nuclease (TALEN) system, a CRISPR-based system, or NgAgo-based system Editing of the one or more target genomic regions includes any kind of genetic manipulations or engineering of a cell's genome. The editing of the one or more target genomic regions can include insertions, deletions, or replacements of genomic regions in a cell(s) performed by one or more endonucleases. Genomic regions comprise the genetic material in a cell(s), such as DNA, RNA, polynucleotides, and oligonucleotides. Genomic regions in a cell(s) also comprise the genomes of the mitochondria or chloroplasts contained in a cell(s).

In some embodiments, provided herein are methods of treating a subject having a disease or condition in need of editing one or more target genomic regions in a cell(s) of the subject, comprising administering to one or more cells a genome editing system and a DNA-PK inhibitor.

In some embodiments, the methods provided herein are used to modify expression of a gene, an RNA molecule, a protein, a group of proteins, or downstream proteins in a pathway. Such modification can be used to treat a disease, a dysfunction, abnormal organismal homeostasis, either acquired or inherited or those due to the aging process. As used herein, the term "modify" or "modifying" includes modulating, enhancing, decreasing, increasing, inserting, deleting, knocking-out, knocking-in, and the like.

One of skill in the art understands that diseases, either acquired or inherited, or otherwise obtained, involve a dysregulation of homeostatic mechanisms including involvement of gene or protein function. To this end, a skilled artisan can use the methods provided herein to modulate, modify, enhance, decrease, or provide an otherwise gene function in a subject.

Modifying expression of gene and consequent protein expression in a cell(s) can be achieved by the methods provided herein, for example, by specific editing (e.g. replacing, inserting or deleting, any combinations thereof) a nucleic acid sequence in any of an exon, an intron, a transcription start site, a promoter region, an enhancer region, a silencer region, an insulator region, an antirepressor, a post translational regulatory element, a polyadenylation signal (e.g. minimal poly A), a conserved region, a transcription factor binding site, or any combinations thereof.

In some embodiments, the methods, kits and compositions provided herein are used to treat a subject that has cancer. The method of treating a subject having a cancer or cancer related condition comprises administering to a cell(s) of the subject a DNA-PK inhibitor and a genome editing system. The administration of the DNA-PK inhibitor and the genome editing system can be in vivo or ex vivo.

The cancer can be of any kind of cancer. Cancer includes solid tumors such as breast, ovarian, prostate, lung, kidney, gastric, colon, testicular, head and neck, pancreas, brain, melanoma, and other tumors of tissue organs and cancers of the blood cells, such as lymphomas and leukemias, including acute myelogenous leukemia, chronic lymphocytic leukemia, T cell lymphocytic leukemia, and B cell lymphomas. The cancers can include melanoma, leukemia, astocytoma, glioblastoma, lymphoma, glioma, Hodgkins lymphoma, chronic lymphocyte leukemia and cancer of the pancreas, breast, thyroid, ovary, uterus, testis, pituitary, kidney, stomach, esophagus and rectum.

In some embodiments, the methods, kits and compositions provided herein are used to treat a subject having any one or more of the following cancers: Acute lymphoblastic leukemia (ALL), Acute myeloid leukemia, Adrenocortical carcinoma, AIDS-related cancers, AIDS-related lymphoma, Anal cancer, Appendix cancer, Astrocytoma, childhood cerebellar or cerebral, Basal-cell carcinoma, Bile duct cancer, extrahepatic (see cholangiocarcinoma), Bladder cancer, Bone tumor, osteosarcoma/malignant fibrous histiocytoma, Brainstem glioma, Brain cancer, Brain tumor, cerebellar astrocytoma, Brain tumor, cerebral astrocytoma/malignant glioma, Brain tumor, ependymoma, Brain tumor, medulloblastoma, Brain tumor, supratentorial primitive neuroectodermal tumors, Brain tumor, visual pathway and hypothalamic glioma, Breast cancer, Bronchial adenomas/carcinoids, Burkitt's lymphoma, Carcinoid tumor, childhood, Carcinoid tumor, gastrointestinal, Carcinoma of unknown primary, Central nervous system lymphoma, primary, Cerebellar astrocytoma, childhood, Cerebral astrocytoma/malignant glioma, childhood, Cervical cancer, Childhood cancers, Chondrosarcoma, Chronic lymphocytic leukemia, Chronic myelogenous leukemia, Chronic myeloproliferative disorders, Colon cancer, Cutaneous T-cell lymphoma, Desmoplastic small round cell tumor, Endometrial cancer, Ependymoma, Epitheliod Hemangioendothelioma (EHE), Esophageal cancer, Ewing's sarcoma in the Ewing family of tumors, Extracranial germ cell tumor, Extragonadal germ cell tumor, Extrahepatic bile duct cancer, Eye cancer, intraocular melanoma, Eye cancer, retinoblastoma, Gallbladder cancer, Gastric (stomach) cancer, Gastrointestinal carcinoid tumor, Gastrointestinal stromal tumor (GIST), Germ cell tumor: extracranial, extragonadal, or ovarian, Gestational trophoblastic tumor, Glioma of the brain stem, Glioma, childhood cerebral astrocytoma, Glioma, childhood visual pathway and hypothalamic, Gastric carcinoid, Hairy cell leukemia, Head and neck cancer, Heart cancer, Hepatocellular (liver) cancer, Hodgkin lymphoma, Hypopharyngeal cancer, Hypothalamic and visual pathway glioma, childhood, Intraocular melanoma, Islet cell carcinoma (endocrine pancreas), Kaposi sarcoma, Kidney cancer (renal cell cancer), Laryngeal cancer, Leukaemias, Leukaemia, acute lymphoblastic (also called acute lymphocytic leukaemia), Leukaemia, acute myeloid (also called acute myelogenous leukemia), Leukaemia, chronic lymphocytic (also called chronic lymphocytic leukemia), Leukemia, chronic myelogenous (also called chronic myeloid leukemia), Leukemia, hairy cell, Lip and oral cavity cancer, Liposarcoma, Liver cancer (primary), Lung cancer, non-small cell, Lung cancer, small cell, Lymphomas, AIDS-related Lymphoma, Burkitt Lymphoma, cutaneous T-Cell Lymphoma, Hodgkin Lymphomas, Non-Hodgkin (an old classification of all lymphomas except Hodgkin's) Lymphoma, primary central nervous system Macroglobulinemia, Waldenström, Male breast cancer, Malignant fibrous histiocytoma of bone/osteosarcoma, Medulloblastoma, childhood Melanoma, Melanoma, intraocular (eye), Merkel cell cancer, Mesothelioma, adult malignant Mesothelioma, childhood Metastatic squamous neck cancer with occult primary, Mouth cancer, Multiple endocrine neoplasia syndrome Multiple myeloma/plasma cell neoplasm, Mycosis fungoides, Myelodysplastic syndromes, Myelodysplastic/myeloproliferative diseases, Myelogenous leukemia, chronic Myeloid leukemia, adult acute Myeloid leukemia, childhood acute Myeloma, multiple (cancer of the bone-marrow), Myeloproliferative disorders, chronic Myxoma, Nasal cavity and paranasal sinus cancer, Nasopharyngeal carcinoma, Neuroblastoma, Non-Hodgkin lymphoma, Non-small cell lung cancer, Oligodendroglioma, Oral cancer, Oropharyngeal cancer, Osteosarcoma/malignant fibrous histiocytoma of bone, Ovarian cancer, Ovarian epithelial cancer (surface epithelial-stromal tumor), Ovarian germ cell tumor, Ovarian low malignant potential tumor, Pancreatic cancer, islet cell Pancreatic cancer, Paranasal sinus and nasal cavity cancer, Parathyroid cancer, Penile cancer, Pharyngeal cancer, Pheochromocytoma, Pineal astrocytoma, Pineal germinoma, Pineoblastoma and supratentorial primitive neuroectodermal tumors, Pituitary adenoma, Plasma cell neoplasia/Multiple myeloma, Pleuropulmonary blastoma, Primary central nervous system lymphoma, Prostate cancer, Rectal cancer, Renal cell carcinoma (kidney cancer), Renal pelvis and ureter cancer, transitional cell cancer, Retinoblastoma, Rhabdomyosarcoma, Salivary gland cancer, Sarcoma, Ewing family of tumors, Kaposi Sarcoma, soft tissue Sarcoma, uterine sarcoma, Sezary syndrome, Skin cancer (non-melanoma), Skin cancer (melanoma), Skin carcinoma, Merkel cell, Small cell lung cancer, Small intestine cancer, Soft tissue sarcoma, Squamous cell carcinoma—see skin cancer (non-melanoma), Squamous neck cancer with occult primary, metastatic, Stomach cancer, Supratentorial primitive neuroectodermal tumor, T-Cell lymphoma, cutaneous (Mycosis Fungoides and Sezary syndrome), Testicular cancer, Throat cancer, Thymoma, Thymoma and thymic carcinoma, Thyroid cancer, Thyroid cancer, Transitional cell cancer of the renal pelvis and ureter, Gestational Trophoblastic tumor, Unknown primary site carcinoma of adult, Unknown primary site cancer of, childhood, Ureter and renal pelvis, transitional cell cancer, Urethral cancer, Uterine cancer, endometrial cancer, Uterine sarcoma, Vaginal cancer, Visual pathway and hypothalamic glioma, Vulvar cancer, Waldenström macroglobulinemia, or Wilms tumor (kidney cancer).

In some embodiments, exemplary target genes associated with cancer include ABL1, ABL2, ACSL3, AF15Q14, AF1Q, AF3p21, AF5q31, AKAP9, A T1, AKT2, ALDH2, AL, AL017, APC, ARHGEF12, ARHH, ARID1A, ARID2, ARNT, ASPSCR1, ASXL1, ATF1, ATIC, ATM, ATRX, AXIN1, BAP1, BCL10, BCL11A, BCL11B, BCL2, BCL3, BCL5, BCL6, BCL7A, BCL9, BCOR, BCR, BHD, BIRC3, BLM, BMPRIA, BRAF, BRCA1, BRCA2, BRD3, BRD4, BRIPI, BTG1, BUB1B, C12orf9, C15orf21, C15orf55, C16orf75, C2orf44, CAMTA1, CANT1, CARD11, CARS, CBFA2T1, CBFA2T3, C.BFB, CBL, CBLB, CBLC, CCDC6, CCNB1IP1, CCND1, CCND2, CCND3, CCNE1, CD273, CD274, CD74, CD79A, CD79B, CDH1, CDH11, CDK12, CDK4, CDK6, CD N2A, CD N2a(pl4), CD N2C, CDX2, CEBPA, CEPl, CHCHD7, CHEK2, CHIC2, CHN1, CIC, CinA, CLTC, CLTCL1, CMKOR1, CNOT3, COL1Al, COPEB, COX6C, CREB1, CREB3L1, CREB3L2, CREBBP, CRLF2, CRTC3, CTNNB1, CYLD, D10S170, DAXX, DDB2, DDIT3, DDX10, DDX5, DDX6, DEK, D1CER1, DNM2, DNMT3A, DUX4, EBFI, ECT2L, EGFR, E1F4A2, ELF4, ELK4, ELKS, ELL, ELN, EML4, EP300, EPS 15, ERBB2, ERCC2, ERCC3, ERCC4, ERCC5, ERG, ETV1, ETV4, ETV5, ETV6, EVI1, EWSR1, EXT1, EXT2, EZH2, EZR, FACL6, FAM22A, FAM22B, FAM46C, 1ANCA, EANCC, FANCD2, FANCE, FANCF, FANCG, FBXO1 1, FBXW7, FCGR2B, FEV, FGFR1, FGFRIOP, FGFR2, FGFR3, FTI, FIIT, FIP1L1, FLU, FLJ27352, FLT3, FNBP1, FOXL2, FOXOIA, FOX03A, FOXP1, FSTL3, FUBP1, FUS, FVT1, GAS7, GATA1, GATA2, GATA3, GMPS, GNA11, GNAQ, GNAS, GOLGA5, GOPC, GPC3, GPHN, GRAF, H3F3A, IICMOGT-1, IIEAB, HERPUD1, IIEY1, IIIPl, HISTIIT3B, IIISTIII4I, IILF, HLXB9, HMGA1, HMGA2, HNRNPA2BI, HOOK3, HOXA11, HOXA13, HOXA9, HOXC11, HOXC13, HOXD11, HOXD13, HRAS, IIRPT2, HSPCA, HSPCB, IDH1, IDH2, IGH, IGK, IGL, IKZF1, IL2, TL21R, IL6ST, IL7R, IRF4, IRTA1, ITK, JAK1, JAK2, JAK3, JAZF1, JUN, KCNJ5, KDM5A, KDM5C, KDM6A, KDR, KIAA1549, KIF5B, KIT, KLF4, KLK2, KRAS, KTN1, LAF4, LASPl, LCK, LCP1, LCX, LHFP, LIFR, LMO1, LM02, LPP, LRIG3, LYL1, MADH4, MAF, MAFB, MALT1, MAML2, MAP2KL MAP2K2, MλP2K4, MAX, MDM2, MDM4, MDS1, MDS2, MECT1, MED12, MEN1, MET, MITF, MKL1, MLF1, MLIII, MLL, MLL2, MLL3, MLLT1, MLLT10, MLLT2, MLLT3, MLLT4, MLLT6, MLLT7, MN1, MPL, MSF, MSH2, MSH6, MSI2, MSN, MTCP1, MUC1, MUTYH, MYB, MYC, MYCL1, MYCN, MYD88, MYH11, MYH9, MYST4, NACA, NBS1, NCOA1, NCOA2, NCOA4, NDRG1, NF1, NF2, NFE2L2, NFIB, NFKB2, NIN, NKX2-1, NONO, NOTCH I, NOTCH2, NPMl, NR4A3, NRAS, NSDl, NT5C2, NTRKl, NTRK3, NUMAl, NUP214, NUP98, OLIG2, OMD, P2RY8, PAFAH1B2, PALB 2, PAX3, PAX5, PAX7, PAX8, PBRM1, PBX1, PCM1, PCSK7, PDE4DIP, PDGFB, PDGFRA, PDGFRB, PERI, PIIF6, PHOX2B, PICALM, PIK3CA, PIK3R1, PIM1, PLAG 1, PML, PMS1, PMS2, PMX1, PNUTL1, POT1, POU2AF1, POU5F1, PPARG, PPP2R1A, PRCC, PRDM1, PRDM16, PRF1, PRKAR1 A, PRO1073, PSIP2, PTCH, PTEN, PTPN11, RABSEP, RACl, RAD51L1, RAFl, RALGDS, RANBP17, RAPIGDSI, RARA, RBI, RBM15, RECQL4, REL, RET, RNF43, ROS1, RPL10, RPL22, RPL5, RPN1, RUNDC2A, RUNX1, RUNXBP2, SBDS, SDC4, SDH5, SDHB, SDHC, SDHD, SEPT6, SET, SETBP1, SETD2, SF3B1, SFPQ, SFRS3, SH2B3, SH3GL1, SIL, SLC34A2, SLC45A3, SMARCA4, SMARCB1, SMARCE1, SMO, SOCS1, SOX2, SRGAP3, SRSF2, SSI8, SS18L1, SSH3BP1, SSX1, SSX2, SSX4, STAT3, STK11, STL, SUFU, SIJZ12, SYK, TAF15, TALI, TAL2, TCEA1, TCF1, TCF12, TCF3, TCF7L2, TCL1A, TCL6, TERT, TET2, TFE3, TFEB, TFG, TFPT, TFRC, THRAP3, TIF1, TLX1, TLX 3, TMPRSS2, TNFAIP3, TNFRSF14, TNFRSF17, TNFRSF6, TOPI, TP53, TPM3, TPM4, TPR, TRA, TRAF7, TRB, TRD, TRIM27, TRIM33, TRIP11, TSC1, TSC2, TSHR, TTL, U2AF1, USP6, VHL, VTUA, WAS, WHSC1, WHSC1L1, WIF1, WRN, WT1, WTX, WWTR1, XPA, XPC, XPOl, YWHAE, ZNF145, ZNF198, ZNF278, ZNF331, ZNF384, ZNF521, ZNF9, ZRSR2 or any combinations thereof.

In some embodiments, the methods provided herein are used to treat a subject that has an inherited disorder. The method of treating a subject having a genetic disease or condition or inherited disorder, comprises administering to a cell(s) of the subject a DNA-PK inhibitor and a genome editing system. The administration of or the DNA-PK inhibitor and the genome editing system can be in vivo or ex vivo.

The inherited disorder can result from mutations or duplications in chromosomal regions (e.g. from point mutations, deletions, insertions, frameshift, chromosomal duplications or deletions). The inherited disorder can be any inherited disorder.

In some embodiments, the inherited disorder is 2211.2 deletion syndrome, Angelman syndrome, Canavan disease, Charcot-Marie-Tooth disease, Color blindness, Cri du chat, Down syndrome, Duchenne muscular dystrophy, Haemochromatosis, Haemophilia, Klinefelter syndrome, Neurofibromatosis, Phenylketonuria, Polycystic kidney disease, Prader-Willi syndrome, Sickle-cell disease, Spinal muscular atrophy, Spinal muscular atrophy, Tay-Sachs disease, Turner syndrome, a hemoglobinopathy, or any combinations thereof.

In some embodiments, the inherited disorder is 1p36 deletion syndrome, 18p deletion syndrome, 21-hydroxylase deficiency, 47 XXX (triple X syndrome), 47 XXY (Klinefelter syndrome), 5-ALA dehydratase-deficient porphyria, ALA dehydratase deficiency, 5-aminolaevulinic dehydratase deficiency porphyria, 5p deletion syndrome, Cri du chat (AKA 5p-syndrome), ataxia telangiectasia (AKA A-T), alpha 1-antitrypsin deficiency (AAT), aceruloplasminemia, achondrogenesis type II (ACG2), achondroplasia (ACH), Acid beta-glucosidase deficiency, Gaucher disease (any type, e.g. type 1, type 2, type 3), Acrocephalosyndactyly (Apert), Apert syndrome, acrocephalosyndactyly (any type, e.g., type 1, type 2, type 3, type 5), Pfeiffer syndrome, Acrocephaly, Acute cerebral Gaucher's disease, acute intermittent porphyria, (AIP) ACY2 deficiency, Alzheimer's disease (AD), Adelaide-type craniosynostosis, Muenke syndrome, Adenomatous Polyposis Coli, familial adenomatous polyposis, Adenomatous Polyposis of the Colon, familial adenomatous polyposis (ADP), adenylosuccinate lyase deficiency, Adrenal gland disorders, Adrenogenital syndrome, Adrenoleukodystrophy, androgen insensitivity syndrome (AIS), alkaptonuria (AKU), ALA dehydratase porphyria, ALA-D porphyria, ALA dehydratase deficiency, Alagille syndrome, Albinism, Alcaptonuria, alkaptonuria, Alexander disease, alkaptonuria, Alkaptonuric ochronosis, alkaptonuria, alpha-1 proteinase inhibitor disease, alpha-1 related emphysema, Alpha-galactosidase A deficiency, Fabry disease, Alstrom syndrome, Alexander disease (ALX), Amelogenesis imperfecta, Amino levulinic acid dehydratase deficiency, Aminoacylase 2 deficiency, Canavan disease, Anderson-Fabry disease, androgen insensitivity syndrome, Anemia, hereditary sideroblastic, X-linked sideroblastic anemiasplenic and/or familial anemia, Angiokeratoma Corporis Diffusum, Angiokeratoma diffuse, Angiomatosis retinae, von Hippel-Lindau disease, APC resistance, Leiden type, factor V Leiden thrombophilia, Apert syndrome, AR deficiency, androgen insensitivity syndrome, Charcot-Marie-Tooth disease (any type, e.g., CMT1, CMTX, CMT2, CMT4, severe early onset CMT), Arachnodactyly, Marfan syndrome, ARNSHL, Nonsyndromic deafness (autosomal recessive, autosomal dominant, x-linked, or mitochondria), Arthro-ophthalmopathy, hereditary progressive, Stickler syndrome (e.g. COL2A1, COL11A1, COL11A2, COL9A1), Arthrochalasis multiplex congenita, Ehlers-Danlos syndrome (e.g. hypermobility type, arthrochalasia type, classical type, vascular type, kyphoscoliosis type, dermatosparaxis type) Asp deficiency, Aspa deficiency, Aspartoacylase deficiency, ataxia telangiectasia, Autism-Dementia-Ataxia-Loss of Purposeful Hand Use syndrome, Rett syndrome, autosomal dominant juvenile ALS, Autosomal dominant opitz G/BBB syndrome, autosomal recessive form of juvenile ALS type 3, Amyotrophic lateral sclerosis (any type; e.g. ALS1, ALS2, ALS3, ALS4, ALS5, ALS5, ALS6, ALS7, ALS8, ALS9, ALS10, ALS11, ALS12, ALS13, ALS14, ALS15, ALS16, ALS17, ALS18, ALS19, ALS20, ALS21, ALS22, FTDALS1, FTDALS2, FTDALS3, FTDALS4, FTDALS4, IBMPFD2), Autosomal recessive nonsyndromic hearing loss, Autosomal Recessive Sensorineural Hearing Impairment and Goiter, Pendred syndrome, Alexander disease (AxD), Ayerza syndrome, familial pulmonary arterial hypertension, B variant of the Hexosaminidase GM2 gangliosidosis, Sandhoff disease, BANF-related disorder, neurofibromatosis (any type, e.g., NF1, NF2, schwannomatosis), Beare-Stevenson cutis gyrata syndrome, Benign paroxysmal peritonitis, Benjamin syndrome, beta-thalassemia, BH4 Deficiency, tetrahydrobiopterin deficiency, Bilateral Acoustic Neurofibromatosis, biotinidase deficiency, bladder cancer, Bleeding disorders, factor V Leiden thrombophilia, Bloch-Sulzberger syndrome, incontinentia pigmenti, Bloom syndrome, Bone diseases, Bourneville disease, tuberous sclerosis, Brain diseases, prion disease, breast cancer, Birt-Hogg-Dubé syndrome, Brittle bone disease, osteogenesis imperfecta, Broad Thumb-Hallux syndrome, Rubinstein-Taybi syndrome, Bronze Diabetes, hemochromatosis, Bronzed cirrhosis, Bulbospinal muscular atrophy, X-linked Spinal and bulbar muscular atrophy, Burger-Grutz syndrome, lipoprotein lipase deficiency, familial CADASIL syndrome, CGD Chronic granulomatous disorder, Campomelic dysplasia, Cancer Family syndrome, hereditary nonpolyposis colorectal cancer, breast cancer, bladder cancer, Carboxylase Deficiency, Multiple Late-Onset biotinidase deficiency, Cat cry syndrome, Caylor cardiofacial syndrome, Ceramide trihexosidase deficiency, Cerebelloretinal Angiomatosis, familial von Hippel-Lindau disease, Cerebral arteriopathy, CADASIL syndrome, Cerebral autosomal dominant ateriopathy, CADASIL syndrome, Cerebroatrophic Hyperammonemia, Rett syndrome, Cerebroside Lipidosis syndrome, Charcot disease, CHARGE syndrome, Chondrodystrophia, Chondrodystrophy syndrome, Chondrodystrophy with sensorineural deafness, otospondylomegaepiphyseal dysplasia, Chondrogenesis imperfecta, Choreoathetosis self-mutilation hyperuricemia syndrome, Lesch-Nyhan syndrome, Classic Galactosemia, galactosemia, Cleft lip and palate, Stickler syndrome, Cloverleaf skull with thanatophoric dwarfism, Thanatophoric dysplasia (e.g. type 1 or type 2), Coffin-Lowry syndrome (CLS), Cockayne syndrome, Coffin-Lowry syndrome, collagenopathy types II and XI, familial Nonpolyposis, hereditary nonpolyposis colorectal cancer, familial Colon cancer, familial adenomatous polyposis, Colorectal cancer, Complete HPRT deficiency, Lesch-Nyhan syndrome, Complete hypoxanthine-guanine phosphoribosyltransferase deficiency, Compression neuropathy, hereditary neuropathy with liability to pressure palsies, Connective tissue disease, Conotruncal anomaly face syndrome, Cooley's Anemia, beta-thalassemia, Copper storage disease, Wilson's disease, Copper transport disease, Menkes disease, Coproporphyria, hereditary coproporphyria, Coproporphyrinogen oxidase deficiency, Cowden syndrome, CPX deficiency, Craniofacial dysarthrosis, Crouzon syndrome, Craniofacial Dysostosis, Crouzon syndrome, Crohn's disease, fibrostenosing, Crouzon syndrome, Crouzon syndrome with acanthosis nigricans, Crouzonodermoskeletal syndrome, Crouzonodermoskeletal syndrome, Cockayne syndrome (CS), Cowden syndrome, Curschmann-Batten-Steinert syndrome, cutis gyrata syndrome of Beare-Stevenson, Beare-Stevenson cutis gyrata syndrome, D-glycerate dehydrogenase deficiency, hyperoxaluria, primary, Dappled metaphysis syndrome, spondyloepimetaphyseal dysplasia, Strudwick type, Dementia Alzheimer's type (DAT), Genetic hypercalciuria, Dent's disease, muscular dystrophy (e.g. Duchenne and Becker types), Deafness with goiter, Pendred syndrome, Deafness-retinitis pigmentosa syndrome, Usher syndrome, Deficiency disease, Phenylalanine Hydroxylase, Degenerative nerve diseases, de Grouchy syndrome 1, De Grouchy syndrome, Dejerine-Sottas syndrome, Delta-aminolevulinate dehydratase deficiency porphyria, Dementia, CADASIL syndrome, demyelinogenic leukodystrophy, Alexander disease, Dermatosparactic type of Ehlers-Danlos syndrome, Dermatosparaxis, inherited developmental disabilities, distal hereditary motor neuropathy (dHMN), distal hereditary motor neuropathy (e.g. DHMN-V), DHTR deficiency, androgen insensitivity syndrome, Diffuse Globoid Body Sclerosis, Krabbe disease, Di George's syndrome, Dihydrotestosterone receptor deficiency, androgen insensitivity syndrome, distal hereditary motor neuropathy, Myotonic dystrophy (type 1 or type 2), distal spinal muscular atrophy (any type, including e.g. type 1, type 2, type 3, type 4, type 5, type 6), Duchenne/Becker muscular dystrophy, Dwarfism (any kind, e.g. achondroplastic, achondroplasia, thanatophoric dysplasia), Dwarfism-retinal atrophy-deafness syndrome, Cockayne syndrome, dysmyelinogenic leukodystrophy, Alexander disease, Dystrophia myotonica, dystrophia retinae pigmentosa-dysostosis syndrome, Usher syndrome, Early-Onset familial alzheimer disease (EO-FAD), Alzheimer disease (including e.g. type 1, type 2, type 3, or type 4) Ekman-Lobstein disease, osteogenesis imperfecta, Entrapment neuropathy, hereditary neuropathy with liability to pressure palsies, erythropoietic protoporphyria (EPP), Erythroblastic anemia, beta-thalassemia, Erythrohepatic protoporphyria, Erythroid 5-aminolevulinate synthetase deficiency, X-linked sideroblastic anemia, Eye cancer, retinoblastoma FA—Friedreich ataxia, Friedreich's ataxia, FA, fanconi anemia, Facial injuries and disorders, factor V Leiden thrombophilia, FALS, amyotrophic lateral sclerosis, familial acoustic neuroma, familial adenomatous polyposis, familial Alzheimer disease (FAD), familial amyotrophic lateral sclerosis, amyotrophic lateral sclerosis, familial dysautonomia, familial fat-induced hypertriglyceridemia, lipoprotein lipase deficiency, familial, familial hemochromatosis, hemochromatosis, familial LPL deficiency, lipoprotein lipase deficiency, familial, familial nonpolyposis colon cancer, hereditary nonpolyposis colorectal cancer, familial paroxysmal polyserositis, familial PCT, porphyria cutanea tarda, familial pressure-sensitive neuropathy, hereditary neuropathy with liability to pressure palsies, familial primary pulmonary hypertension (FPPH), familial vascular leukoencephalopathy, CADASIL syndrome, FAP, familial adenomatous polyposis, FD, familial dysautonomia, Ferrochelatase deficiency, ferroportin disease, Haemochromatosis (any type, e.g., type 1, type 2A, type 2B, type 3, type 4, neonatal haemochromatosis, acaeruloplasminaemia, congenital atransferrinaemia, gracile syndrome) Periodic fever syndrome, Familial Mediterranean fever (FMF), FG syndrome, FGFR3-associated coronal synostosis, Fibrinoid degeneration of astrocytes, Alexander disease, Fibrocystic disease of the pancreas, Folling disease, fra(X) syndrome, fragile X syndrome, Fragilitas ossium, osteogenesis imperfecta, FRAXA syndrome, Friedreich's ataxia (FRDA), G6PD deficiency, Galactokinase deficiency disease, galactosemia, Galactose-1-phosphate uridyl-transferase deficiency disease, galactosemia, Galactosylceramidase deficiency disease, Krabbe disease, Galactosylceramide lipidosis, Krabbe disease, galactosylcerebrosidase deficiency, galactosylsphingosine lipidosis, GALC deficiency, GALT deficiency, galactosemia, Gaucher-like disease, pseudo-Gaucher disease, GBA deficiency, Genetic brain disorders, genetic emphysema, genetic hemochromatosis, hemochromatosis, Giant cell hepatitis, neonatal, Neonatal hemochromatosis, GLA deficiency, Glioblastoma, retinal, retinoblastoma, Glioma, retinal, retinoblastoma, globoid cell leukodystrophy (GCL, GLD), Krabbe disease, globoid cell leukoencephalopathy, Glucocerebrosidase deficiency, Glucocerebrosidosis, Glucosyl cerebroside lipidosis, Glucosylceramidase deficiency, Glucosylceramide beta-glucosidase deficiency, Glucosylceramide lipidosis, Glyceric aciduria, hyperoxaluria, primary, Glycine encephalopathy, Nonketotic hyperglycinemia, Glycolic aciduria, hyperoxaluria, primary, GM2 gangliosidosis, Tay-Sachs disease, Goiter-deafness syndrome, Pendred syndrome, Graefe-Usher syndrome, Usher syndrome, Gronblad-Strandberg syndrome, pseudoxanthoma elasticum, Haemochromatosis, hemochromatosis, Hallgren syndrome, Usher syndrome, Harlequin type ichthyosis, Hb S disease, hypochondroplasia (HCH), hereditary coproporphyria (HCP), Head and brain malformations, Hearing disorders and deafness, Hearing problems in children, HEF2A, HEF2B, Hematoporphyria, porphyria, Heme synthetase deficiency, Hemochromatoses, hemoglobin M disease, methemoglobinemia beta-globin type, Hemoglobin S disease, hemophilia, hepatoerythropoietic porphyria (HEP), hepatic AGT deficiency, hyperoxaluria, primary, Hepatolenticular degeneration syndrome, Wilson disease, Hereditary arthro-ophthalmopathy, Stickler syndrome, Hereditary dystopic lipidosis, Hereditary hemochromatosis (HHC), hemochromatosis, Hereditary hemorrhagic telangiectasia (HHT), Hereditary Inclusion Body Myopathy, skeletal muscle regeneration, Hereditary iron-loading anemia, X-linked sideroblastic anemia, Hereditary motor and sensory neuropathy, Hereditary motor neuronopathy, type V, distal hereditary motor neuropathy, Hereditary multiple exostoses, Hereditary nonpolyposis colorectal cancer, Hereditary periodic fever syndrome, Hereditary Polyposis Coli, familial adenomatous polyposis, Hereditary pulmonary emphysema, Hereditary resistance to activated protein C, factor V Leiden thrombophilia, Hereditary sensory and autonomic neuropathy type III, familial dysautonomia, Hereditary spastic paraplegia, infantile-onset ascending hereditary spastic paralysis, Hereditary spinal ataxia, Friedreich's ataxia, Hereditary spinal sclerosis, Friedreich's ataxia, Herrick's anemia, Heterozygous OSMED, Weissenbacher-Zweymuller syndrome, Heterozygous otospondylomegaepiphyseal dysplasia, Weissenbacher-Zweymuller syndrome, HexA deficiency, Tay-Sachs disease, Hexosaminidase A deficiency, Tay-Sachs disease, Hexosaminidase alpha-subunit deficiency (any variant, e.g. variant A, variant B), Tay-Sachs disease, HFE-associated hemochromatosis, hemochromatosis, HGPS, Progeria, Hippel-Lindau disease, von Hippel-Lindau disease, hemochromatosis (HLAH), distal hereditary motor neuropathy (HMN V), hereditary nonpolyposis colorectal cancer (HNPCC), hereditary neuropathy with liability to pressure palsies (HNPP), homocystinuria, Homogentisic acid oxidase deficiency, alkaptonuria, Homogentisic acidura, alkaptonuria, Homozygous porphyria cutanea tarda, hepatoerythropoietic porphyria, hyperoxaluria, primary (HP1), hyperoxaluria (HP2), hyperphenylalaninemia (HPA), HPRT—Hypoxanthine-guanine phosphoribosyltransferase deficiency, Lesch-Nyhan syndrome, HSAN type III, familial dysautonomia, familial dysautonomia (HSAN3), Hereditary Sensory Neuropathy (any type, e.g. HSN-1, HSN-II, HSN-III), familial dysautonomia, Human dermatosparaxis, Huntington's disease, Hutchinson-Gilford progeria syndrome, progeria, Hyperandrogenism, nonclassic type due to 21-hydroxylase deficiency, Hyperchylomicronemia, familial lipoprotein lipase deficiency, familial, Hyperglycinemia with ketoacidosis and leukopenia, propionic acidemia, Hyperlipoproteinemia type I, lipoprotein lipase deficiency, familial hyperoxaluria, primary hyperphenylalaninaemia, hyperphenylalaninemia, hyperphenylalaninemia, Hypochondrodysplasia, hypochondroplasia, Hypochondrogenesis, Hypochondroplasia, Hypochromic anemia, X-linked sideroblastic anemia, Hypoxanthine phosphoribosyltransferse (HPRT) deficiency, Lesch-Nyhan syndrome, infantile-onset ascending hereditary spastic paralysis (IAHSP), ICF syndrome, Immunodeficiency, centromere instability and facial anomalies syndrome, Idiopathic hemochromatosis, hemochromatosis, type 3, Idiopathic neonatal hemochromatosis, hemochromatosis, neonatal, Idiopathic pulmonary hypertension, Immune system disorders, X-linked severe combined immunodeficiency, Incontinentia pigmenti, Infantile cerebral Gaucher's disease, Infantile Gaucher disease, infantile-onset ascending hereditary spastic paralysis, Infertility, inherited emphysema, inherited tendency to pressure palsies, hereditary neuropathy with liability to pressure palsies, Insley-Astley syndrome, otospondylomegaepiphyseal dysplasia, Intermittent acute porphyria syndrome, acute intermittent porphyria, Intestinal polyposis-cutaneous pigmentation syndrome, Peutz-Jeghers syndrome, incontinentia pigmenti (IP), Iron storage disorder, hemochromatosis, Isodicentric 15, isodicentric 15, Isolated deafness, nonsyndromic deafness, Jackson-Weiss syndrome, Joubert syndrome, Juvenile Primary Lateral Sclerosis (JPLS), juvenile amyotrophic lateral sclerosis, Juvenile gout, choreoathetosis, mental retardation syndrome, Lesch-Nyhan syndrome, juvenile hyperuricemia syndrome, Lesch-Nyhan syndrome, Jackson-Weiss syndrome (JWS), spinal and bulbar muscular atrophy, Kennedy disease, spinal and bulbar muscular atrophy, Kennedy spinal and bulbar muscular atrophy, spinal and bulbar muscular atrophy, Kerasin histiocytosis, Kerasin lipoidosis, Kerasin thesaurismosis, ketotic glycinemia, propionic acidemia, ketotic hyperglycinemia, propionic acidemia, Kidney diseases, hyperoxaluria, primary, Kniest dysplasia, Krabbe disease, Kugelberg-Welander disease, spinal muscular atrophy, Lacunar dementia, CADASIL syndrome, Langer-Saldino achondrogenesis, Langer-Saldino dysplasia, Late-onset Alzheimer disease, late-onset Krabbe disease (LOKD), Krabbe disease, Learning Disorders, Learning disability, Lentiginosis, perioral, Peutz-Jeghers syndrome, Lesch-Nyhan syndrome, Leukodystrophies, leukodystrophy with Rosenthal fibers, Alexander disease, Leukodystrophy, spongiform, Li-Fraumeni syndrome (LFS), Li-Fraumeni syndrome, Lipase D deficiency, lipoprotein lipase deficiency, familial LIPD deficiency, lipoprotein lipase deficiency, familial Lipidosis, cerebroside, Lipidosis, ganglioside, infantile, Tay-Sachs disease, Lipoid histiocytosis (kerasin type), lipoprotein lipase deficiency, familial Liver diseases, galactosemia, Lou Gehrig disease, Louis-Bar syndrome, ataxia telangiectasia, Lynch syndrome, hereditary nonpolyposis colorectal cancer, Lysyl-hydroxylase deficiency, Machado-Joseph disease, Spinocerebellar ataxia (any type, e.g. SCA1, SCA2, SCA3, SCA 18, SCA20, SCA21, SCA23, SCA26, SCA28, SCA29), Male breast cancer, breast cancer, Male genital disorders, Malignant neoplasm of breast, breast cancer, malignant tumor of breast, breast cancer, Malignant tumor of urinary bladder, bladder cancer, Mammary cancer, breast cancer, Marfan syndrome, Marker X syndrome, fragile X syndrome, Martin-Bell syndrome, fragile X syndrome, McCune-Albright syndrome, McLeod syndrome, MEDNIK syndrome, Mediterranean Anemia, beta-thalassemia, Mega-epiphyseal dwarfism, otospondylomegaepiphyseal dysplasia, Menkea syndrome, Menkes disease, Menkes disease, Mental retardation with osteocartilaginous abnormalities, Coffin-Lowry syndrome, Metabolic disorders, Metatropic dwarfism, type II, Kniest dysplasia, Metatropic dysplasia type II, Kniest dysplasia, Methemoglobinemia (any type, e.g. congenital, beta-globin type, congenital methemoglobinemia type II), methylmalonic acidemia, Marfan syndrome (MFS), MHAM, Cowden syndrome, Micro syndrome, Microcephaly, MMA, methylmalonic acidemia, Menkes disease (AKA MK or MNK), Monosomy 1p36 syndrome, Motor neuron disease, amyotrophic lateral sclerosis, amyotrophic lateral sclerosis, Movement disorders, Mowat-Wilson syndrome, Mucopolysaccharidosis (MPS I), Mucoviscidosis, Multi-Infarct dementia, CADASIL syndrome, Multiple carboxylase deficiency, late-onset, biotinidase deficiency, Multiple hamartoma syndrome, Cowden syndrome, Multiple neurofibromatosis, Muscular dystrophy (any type, including, e.g., Duchenne and Becker type), Myotonia atrophica, myotonic dystrophy, Myotonia dystrophica, Nance-Insley syndrome, otospondylomegaepiphyseal dysplasia, Nance-Sweeney chondrodysplasia, otospondylomegaepiphyseal dysplasia, NBIA1, pantothenate kinase-associated neurodegeneration, Neill-Dingwall syndrome, Cockayne syndrome, Neuroblastoma, retinal, retinoblastoma, Neurodegeneration with brain iron accumulation type 1, pantothenate kinase-associated neurodegeneration, Neurologic diseases, Neuromuscular disorders, distal hereditary motor neuronopathy, Niemann-Pick, Niemann-Pick disease, Noack syndrome, Nonketotic hyperglycinemia, Glycine encephalopathy, Non-neuronopathic Gaucher disease, Non-phenylketonuric hyperphenylalaninemia, tetrahydrobiopterin deficiency, nonsyndromic deafness, Noonan syndrome, Norrbottnian Gaucher disease, Ochronosis, alkaptonuria, Ochronotic arthritis, alkaptonuria, Ogden syndrome, osteogenesis imperfecta (OI), Osler-Weber-Rendu disease, Hereditary hemorrhagic telangiectasia, OSMED, otospondylomegaepiphyseal dysplasia, osteogenesis imperfecta, Osteopsathyrosis, osteogenesis imperfecta, Osteosclerosis congenita, Oto-spondylo-megaepiphyseal dysplasia, otospondylomegaepiphyseal dysplasia, otospondylomegaepiphyseal dysplasia, Oxalosis, hyperoxaluria, primary, Oxaluria, primary, hyperoxaluria, primary, pantothenate kinase-associated neurodegeneration, Patau Syndrome (Trisomy 13), PBGD deficiency, acute intermittent porphyria, PCC deficiency, propionic acidemia, porphyria cutanea tarda (PCT), PDM disease, Pendred syndrome, Periodic disease, Mediterranean fever, Familial Periodic peritonitis, Periorificial lentiginosis syndrome, Peutz-Jeghers syndrome, Peripheral nerve disorders, familial dysautonomia, Peripheral neurofibromatosis, Peroneal muscular atrophy, peroxisomal alanine:glyoxylate aminotransferase deficiency, hyperoxaluria, primary Peutz-Jeghers syndrome, Phenylalanine hydroxylase deficiency disease, Pheochromocytoma, von Hippel-Lindau disease, Pierre Robin syndrome with fetal chondrodysplasia, Weissenbacher-Zweymuller syndrome, Pigmentary cirrhosis, hemochromatosis, Peutz-Jeghers syndrome (PJS), pantothenate kinase-associated neurodegeneration (PKAN), PKU, phenylketonuria, Plumboporphyria, ALA deficiency porphyria, PMA, Polycystic kidney disease, polyostotic fibrous dysplasia, McCune-Albright syndrome, familial adenomatous polyposis, hamartomatous intestinal polyposis, polyps-and-spots syndrome, Peutz-Jeghers syndrome, Porphobilinogen synthase deficiency, ALA deficiency porphyria, porphyrin disorder, PPOX deficiency, variegate porphyria, Prader-Labhart-Willi syndrome, Prader-Willi syndrome, presenile and senile dementia, Primary ciliary dyskinesia (PCD), primary hemochromatosis, hemochromatosis, primary hyperuricemia syndrome, Lesch-Nyhan syndrome, primary senile degenerative dementia, procollagen type EDS VII, mutant, progeria, Hutchinson Gilford Progeria Syndrome, Progeria-like syndrome, Cockayne syndrome, progeroid nanism, Cockayne syndrome, progressive chorea, chronic hereditary (Huntington), Huntington's disease, progressively deforming osteogenesis imperfecta with normal sclerae, Osteogenesis imperfecta (any type, e.g. Type I, Type II, Type III, Type IV, Type V, Type VI, Type VII, Type VIII), proximal myotonic dystrophy (PROMM), propionic acidemia, propionyl-CoA carboxylase deficiency, protein C deficiency, protein S deficiency, protoporphyria, protoporphyrinogen oxidase deficiency, variegate porphyria, proximal myotonic dystrophy, Myotonic dystrophytype 2, proximal myotonic myopathy, pseudo-Gaucher disease, pseudoxanthoma elasticum, psychosine lipidosis, Krabbe disease, pulmonary arterial hypertension, pulmonary hypertension, pseudoxanthoma elasticum (PXE), pseudoxanthoma elasticum, retinoblastoma (Rb), Recklinghausen disease, Recurrent polyserositis, Retinal disorders, Retinitis pigmentosa-deafness syndrome, Usher syndrome, Retinoblastoma, Rett syndrome, RFALS type 3, Ricker syndrome, Riley-Day syndrome, familial dysautonomia, Roussy-Levy syndrome, Rubinstein-Taybi syndrome (RSTS), Rett syndrome (RTS), Rubinstein-Taybi syndrome, Rubinstein-Taybi syndrome, Sack-Barabas syndrome, SADDAN disease, sarcoma family syndrome of Li and Fraumeni, Li-Fraumeni syndrome, SBLA syndrome (sarcoma, breast, leukemia, and adrenal gland syndrome), Li-Fraumeni syndrome, Spinal and bulbar muscular atrophy (SBMA), Schwannoma, acoustic, bilateral, neurofibromatosis type II, Schwartz-Jampel syndrome, X-linked severe combined immunodeficiency (SCIDX1), SED congenita, spondyloepiphyseal dysplasia congenita, SED Strudwick, spondyloepimetaphyseal dysplasia, Strudwick type, spondyloepiphyseal dysplasia congenita (SEDc), Spondyloepimetaphyseal dysplasia (SEMD), Strudwick type SEMD, senile dementia, severe achondroplasia with developmental delay and acanthosis nigricans, SADDAN disease, Shprintzen syndrome, Siderius X-linked mental retardation syndrome caused by mutations in the PHF8 gene, skeleton-skin-brain syndrome, Skin pigmentation disorders, spinal muscular atrophy (SMA), Spondylo-meta-epiphyseal dysplasia (SMED) (any type, e.g. Studwick type, type 1), Smith-Lemli-Opitz syndrome, Smith Magenis Syndrome, South-African genetic porphyria, infantile onset ascending spastic paralysis, infantile-onset ascending hereditary spastic paralysis, Speech and communication disorders, sphingolipidosis, Tay-Sachs, Tay-Sachs disease, spinal and bulbar muscular atrophy, spinal muscular atrophy, spinal muscular atrophy, distal type V, distal hereditary motor neuropathy, spinal muscular atrophy distal with upper limb predominance, distal hereditary motor neuropathy, spinocerebellar ataxia, spondyloepiphyseal dysplasia congenita, spondyloepiphyseal dysplasia, collagenopathy (any type, e.g. types II and XI), spondyloepimetaphyseal dysplasia, spondylometaphyseal dysplasia (SMD), spondyloepimetaphyseal dysplasia, spongy degeneration of central nervous system, spongy degeneration of the brain, spongy degeneration of white matter in infancy, sporadic primary pulmonary hypertension, SSB syndrome, steely hair syndrome, Menkes disease, Steinert disease, myotonic dystrophy, Steinert myotonic dystrophy syndrome, myotonic dystrophy, Stickler syndrome, stroke, CADASIL syndrome, Strudwick syndrome, subacute neuronopathic Gaucher disease, Swedish genetic porphyria, acute intermittent porphyria, acute intermittent porphyria, Swiss cheese cartilage dysplasia, Kniest dysplasia, Tay-Sachs disease, TD—thanatophoric dwarfism, thanatophoric dysplasia, TD with straight femurs and cloverleaf skull, thanatophoric dysplasia Type 2, Telangiectasia, cerebello-oculocutaneous, ataxia telangiectasia, Testicular feminization syndrome, androgen insensitivity syndrome, tetrahydrobiopterin deficiency, testicular feminization syndrome (TFM), androgen insensitivity syndrome, thalassemia intermedia, beta-thalassemia, Thalassemia Major, beta-thalassemia, thanatophoric dysplasia, Thrombophilia due to deficiency of cofactor for activated protein C, Leiden type, factor V Leiden thrombophilia, Thyroid disease, Tomaculous neuropathy, hereditary neuropathy with liability to pressure palsies, Total HPRT deficiency, Lesch-Nyhan syndrome, Total hypoxanthine-guanine phosphoribosyl transferase deficiency, Lesch-Nyhan syndrome, Treacher Collins syndrome, Trias fragilitis ossium, triple X syndrome, Triplo X syndrome, Trisomy 21Trisomy X, Troisier-Hanot-Chauffard syndrome, hemochromatosis, Tay-Sachs disease (TSD), Tuberous Sclerosis Complex (TSC), Tuberous sclerosis, Turner-like syndrome, Noonan syndrome, UDP-galactose-4-epimerase deficiency disease, galactosemia, UDP glucose 4-epimerase deficiency disease, galactosemia, UDP glucose hexose-1-phosphate uridylyltransferase deficiency, galactosemia, Undifferentiated deafness, nonsyndromic deafness, UPS deficiency, acute intermittent porphyria, Urinary bladder cancer, bladder cancer, UROD deficiency, Uroporphyrinogen decarboxylase deficiency, Uroporphyrinogen synthase deficiency, acute intermittent porphyria, Usher syndrome, UTP hexose-1-phosphate uridylyltransferase deficiency, galactosemia, Van Bogaert-Bertrand syndrome, Van der Hoeve syndrome, Velocardiofacial syndrome, VHL syndrome, von Hippel-Lindau disease, Vision impairment and blindness, Alstrom syndrome, Von Bogaert-Bertrand disease, von Hippel-Lindau disease, Von Recklenhausen-Applebaum disease, hemochromatosis, von Recklinghausen disease, neurofibromatosis type I, Vrolik disease, osteogenesis imperfecta, Waardenburg syndrome, Warburg Sjo Fledelius Syndrome, Micro syndrome, Wilson disease (WD), Weissenbacher-ZweymWller syndrome, Werdnig-Hoffmann disease, spinal muscular atrophy, Williams Syndrome, Wilson disease, Wilson's disease, Wilson disease, Wolf-Hirschhom syndrome, Wolff Periodic disease, Weissenbacher-Zweymwller syndrome (WZS), Xeroderma pigmentosum, X-linked mental retardation and macroorchidism, fragile X syndrome, X-linked primary hyperuricemia, Lesch-Nyhan syndrome, X-linked severe combined immunodeficiency, X-linked sideroblastic anemia, X-linked spinal-bulbar muscle atrophy, spinal and bulbar muscular atrophy, X-linked uric aciduria enzyme defect, Lesch-Nyhan syndrome, X-SCID, X-linked severe combined immunodeficiency, X-linked sideroblastic anemia (XLSA), X-SCID, X-linked severe combined immunodeficiency, X-linked sideroblastic anemia (XLSA), XSCID, X-linked severe combined immunodeficiency, XXX syndrome, triple X syndrome, XXXX syndrome, XXXXX syndrome, XXXXX, XXY syndrome, XXY trisomy, Klinefelter syndrome, XYY syndrome, triplet repeat disorders, or any combinations thereof.

In embodiments, a specific post-transcriptional control modulator is targeted for modulation, modification, enhancement or decrease in activity by administering a DNA-PK inhibitor and a genomic editing system. For example, post-transcriptional control modulators can include PARN, PAN, CPSF, CstF, PAP, PABP, PAB2, CFI, CFII, RNA triphosphatase, RNA gluanyltransferase, RNA methyltransferase, SAM synthase, ubiquitin-conjugating enzyme E2R, SR proteins SFRS1 through SFR11, hnRNP proteins (e.g. HNRNPA0, HNRNPA1, HNRNPA1L1, HNRNPA1L2, HNRNPA2, HNRNPA2B1, HNRNPAB, HNRNPB1, HNRNPC, HNRNPCL1, HNRNPD, HNRNPDL, HNRNPF, HNRNHP1, HNRNPH2, HNRNPH3, HNRNPK, HNRNPL, HNRNPLL, HNRNPM, HNRNPR, HNRNPU, HNRNPUL1, HNRNPUL2, HNRNPUL3, ADAR, Mex 67, Mtr2, Nab2, Dead-box helicase, eIF4A, eIF4B, eIF4E, eIF4G, GEF, GCN2, PKR, HRI, PERK, eEF1, eEF2, GCN, eRF3, ARE-specific binding proteins, EXRN1, DCP1, DCP2, RCK/p54, CPEB, eIF4E, microRNAS and siRNAs, DICER, Ago proteins, Nonsence-mediated mRNA decay proteins, UPF3A, UPF3BeIF4A3, MLN51, Y14/MAGOH, MG-1, SMG-5, SMG-6, SMG-7, or any combinations thereof.

In some embodiments, genetic pathways associated with the cell cycle are modulated, enhanced or decreased in activity by administering a DNA-PK inhibitor and a genomic editing system. Exemplary pathways and genes associated with the cell cycle include ATM, PMS2, FAS-L, MRE11, MLH1, FasR, NBS1, MSH6, Trail-L, RAD50, MSH2, Trail-R, 53BP1, RFC, TNF-Ct, P53, PCNA, TNF-R1, CHKE, MSH3, FADD, E2F1, MutS, homolog, TRADD, PML, MutL, homolog, R1P1, FANCD2, Exonuclease, MyD88, SMC1, DNA, Polymerase, delta, IRAK, BLM1, (POLD1, POLD2, POLD3, NIL, BRCA1, and, POLD4, -genes, IKK, H2AX, encoding, subunits), NFKβ, ATR, Topoisomerase, 1, IκBα, RPA, Topoisomerase, 2, IAP, ATRIP, RNAseH1, Caspase, 3, RAD9, Ligase, 1, Caspase, 6, RAD1, DNA, polymerase, 1, Caspase, 7, HUS, DNA, polymerase, 3, Caspase, 8, RAD17, Primase, Caspase, 10, RFC, Helicase, HDAC1, CHK1, Single strand, binding, HDAC2, TLK1, proteins, Cytochrome, C, CDCl25, Bxl-xL, STAT3, STAT5, DFF45, Vcl-2, ENDO-G, PI3K, Akt, Calpain, Bad, Bax, Ubiqiiitin-mediated proteolysis, Hypoxia, Cell Proliferation, HIF-loc, MAPK, El, HERC1, TRAF6, HIF-Iβ, MAPKK, E2, UBE2Q, MEKKl1, Refl, MAPKKK, E3, UBE2R, COP!, HSP90, c-Met, UBLE1A, UBE2S, PIFH2, VEGF, HGF, UBLE1B, UBE2U, cIAP, PAS, ER, S1/2, UBLEIC, UBE2W, PIAS, ARNT, ATK, UBE2A, UBE2Z, SYVN, VHL, PKCs, UBE2B, AFC, LLC, N, NHLRC1, HLF, Paxilin, UBE2C, UBE1, AIRE, EPF, FAK, UBE2A, E6AP, MGRN1, VDU2, Adducin, UBE2E, UBE3B, BRCA1, SUMORESUME, PYK1, UBE2F, Smurf, FANCL, SENP1, RB, UBE2G1, Itch, MIDI, Calcineurin, A, RBI, UBE2G2, HERC2, Cdc20, RACK1, Raf-1, UBE2I, HERC3, Cdhl, PTB, A-Raf, UBE2J1, HERC4, Apcl, Hur, B-raf, UBE2J2, UBE4A, Apc2, PHD2, MEK1/2, UBE2L3, UBE4B, Apc3, SSAT2, ERK1/2, UBE2L6, CHIP, Apc4, SSAT1, Ets, UBE2M, CYC4, Apc5, GSK3, Elkl, UBE2N, PPR19, Apc6, CBP, SAP1, UBE20, UIP5, Apc7, FOX04, cPLA2, WWPI, Mdm2, Apc8, FlH-1, WWP2, Parkin, Apc9, TRIP, 12, Trim32, Ape, 10, NEED4, Trim37, Ape, 11, ARF-BP1, SIAH-1, Ape, 12, EDD1, PML, Cell, survival, Cell, cycle, arrest, SMADI, P21, SMAD5, BAX, SAMD8, MDR, LEF1, DRAIL, IGFBP3, TCF3, GADD45, TCF4, P300, HAT1, PI3, Akt, GF1, or any combinations thereof.

In some embodiments, genes associated with angiogenesis are modulated, enhanced or decreased in activity by administering a DNA-PK inhibitor and a genomic editing system to a cell(s). Exemplary genes and genetic pathways associated with angiogenesis, and angiogenesis-related conditions include VEGF, VEGFR2, SHC, E2F7, VEGFB, VEGFR3, PI3, VEGFC, Nrp 1, PIP3, EGFDIP3, DAG, GRB2, SOS, Akt, PB, PKC, Ras, RAF1, DAG, eNOS, NO, ERK1, ER2, cPLA2, ME1, MEK2, or any combinations thereof.

In some embodiments, genetic pathways and/or genes associated with mitochondrial function are modulated, enhanced or decreased in activity by administering a DNA-PK inhibitor and a genomic editing system to a cell(s). Exemplary genes and genetic pathways associated with mitochondrial function include Malate dehydrogenase Aminotransferase, Hydratase, Deacylase, Dehydrogenase, Carboxylase, Mutase, Fatty acid oxidation Leucine Oxidation Isoleucine disorders (enzyme Pathway oxidation pathway deficiencies) Aminotransferase Aminotransferase, OCTN2 Branched chain Branched chain, FATP1-6 aminotransferase 2, aminotransferase 2, CPT-1 mitochondrial mitochondrial, CACT Isobutytyl-CoA 2-methylbutytyl-CoA, CPT-II dehydrogenase Dehydrogenase, SCAD (Branched Chain (Branched Chain, MCAD Keto Acid Keto Acid, VLCAD Dehydrogase Dehydrogenase, ETF-DH Complex) Complex), Alpha-ETF Hydratase Hydratase, Beta-ETF HMG-CoA lyase 2-methyl-3-OH-SCHAD butyryl-CoA, LCHAD dehydrogenase, MTP 3-Oxothiolase, LKAT, DECR 1, HMGCS2, HMGCL, or any combinations thereof.

In some embodiments, genetic pathways and/or genes associated with DNA damage or genomic instability are modulated, enhanced or decreased in activity. Exemplary genes and genetic pathways associated with pathways and/or genes relating to DNA Damage and genomic instability include 53BP1, BLM, MBD2, DNA, ligase, 4, MDC1, H2AX, XLF, SMC1, 53BP1, Rad50, P53, P53, Artemis, Rad27, TdT, APE1, PMS2, APE2, UvrA, RecA, MLH1, NEIL1, UvrB, SSB, MSH6, NEIL2, UvrC, Mrell, MSH2, NEIL3, XPC, Rad50, RFC, XRCC1, Rad23B, Nbsl, PCNA, PNKP, CEN2, CtIP, MSH3, Tdpl, DDB, RPA, MutS, APTX, XPE, Rad51, MutL, DNA, polymerase β CSA, Rad52, DNA polymerase δ, CSB, Rad54, Topoisomerase, 1, DNA, TFT1H, BRCA1, Topoisomerase, 2, PCNA, XPB, BRCA2, RNAseHl, FEN1, XPD, Exol, Ligase 1, RFC, XPA, BLM, DNA, polymerase, 1, PAR, 1, RPA, ToplIla, DNA, Ligl, XPG, GEN1, Primase, Lig3, ERCC Yenl Helicase, UNG, XPF, Slxl, SSBs, MUTY DNA polymerase δ, Slx4, SMUG DNA polymerase ε, Mus8, MBD4, Emel, Dssl, ASH1L, SETD4, DQT1L, SETD5, EHMT1, SETD6, EHMT2, SETD7, EZH1, SETD8, EZH2, SETD9, MLL, SETDB1, MLL2, SETDB2, MLL3, SETMAR, MLL4, SMYD, 1, MLL5, SMYD2, NSD, 1, SMYD3, PRDM2, SMYD4, SET, SMYD5, SETBP1, SUV39H1, SETD 1A, SUV39H2, SETD 1B, SUV420H1, SETD2, SUV420 H2, SETD3, or any combinations thereof.

In some embodiments, genes encoding for mammalian transcription factors are modulated, enhanced, decreased or provided to a cell. Exemplary human transcription factors include AFF4, AFF3, AFF2, AFF1, AR, TFAP2B, TFAP2D, TFAP2C, TFAP2E, TFAP2A, JARID2, KDM5D, ARID4A, ARID4B, KDM5A, ARID3A, KDM5B, KDM5C, ARID5B, ARID3B, ARID2, ARID5A, ARID3C, ARID1A, ARID1B, HIF1A, NPAS1, NPAS3, NPAS4, MLXIPL, ARNTL2, MXD1, AHRR, TFE3, HES2, MNT, TCF3, SREBF1, TFAP4, TCFL5, LYL1, USF2, TFEC, AHR, MLX, MYF6, MYF5, SIM1, TFEB, HAND1, HES1, ID2, MYCL1, ID3, TCF21, MXI1, SOHLH2, MYOG, TWIST1, NEUROG3, BHLHE41, NEUROD4, MXD4, BHLHE23, TCF15, MAX, ID1, MYOD1, ARNTL, BHLHE40, MYCN, CLOCK, HEY2, MYC, ASCL1, TCF12, ARNT, HES6, FERD3L, MSGN1, USF1, TAL1, NEUROD1, TCF23, HEYL, HAND2, NEUROD6, HEY1, SOHLH1, MESP1, PTF1A, ATOH8, NPAS2, NEUROD2, NHLH1, ID4, ATOH1, ARNT2, HES3, MLXIP, ASCL3, KIAA2018, OLIG3, NHLH2, NEUROG2, MSC, HES7, ATOH7, BHLHA15, BHLHE22, NEUROG1, FIGLA, ASCL2, OLIG1, TAL2, MITF, SCXB, HELT, ASCL4, MESP2, HES4, SCXA, TCF4, HES5, SREBF2, BHLHA9, OLIG2, MXD3, TWIST2, LOC388553, C13orf38-SOHLH2, CEBPE, XBP1, BATF3, CREB5, CEBPG, ATF3, ATF7, CEBPB, CEBPD, CEBPA, CEBPA, CBFB, CAMTA2, CAMTA, EBF4, EBF3, EBF1, EBF2, NR2F6, NR2F1, NR2F2, GRHL2, TFCP2L1, GRHL1, TFCP2, UBP1, GRHL3, YBX2, CSDET, CSDA, YBX1, LIN28A, CARHSP1, CSDC2, LIN28B, NFIX, NFIC, NFIB, NFIA, CUX2, ONECUT2, CUX1, ONECUT1, SATB1, ONECUT3, SATB2, DMRT3, DMRT1, DMRTC2, DMRTA2, DMRTB1, DMRT2, DMRTA1, E2F2, E2F1, E2F3, TFDP2, E2F8, E2F5, E2F7, E2F6, TFDP3, TFDP1, E2F4, NR1H3, NR1H2, ETV1, ETV7, SPIT, ELF4, ETV2, ERF, ELF2, ELK3, ETV3, ELF1, SPDEF, ELK1, ETS1, EHF, ELF5, ETV6, SPIB, FLI1, GABPA, ERG, ETS2, ELK4, ELF3, FEV, SPIC, ETV4, ETV5, FOXN3, FOXC1, FOXJ2, FOXF1, FOXN1, FOXM1, FOXP1, FOXO3, FOXA2, FOXP2, FOXJ1, FOXP4, FOXF2, FOXN4, FOXK2, FOXO1, FOXH1, FOXQ1, FOXK1, FOXI1, FOXD4, FOXA3, FOXN2, FOXB1, FOXG1, FOXR1, FOXL1, FOXC2, FOXE1, FOXS1, FOXL2, FOXO4, FOXD4L1, FOXD4L4, FOXD2, FOXI2, FOXE3, FOXD3, FOXD4L3, FOXR2, FOXJ3, FOXO6, FOXB2, FOXD4L5, FOXD4L6, FOXD4L2, KIAA0415, FOXA1, FOXP3, GCM2, GCM1, NR3C1, GTF2IRD1, GTF2I, GTF2IRD2B, GTF2IRD2, SOX8, SOX30, PMS1, CIC, TCF7, TOX4, SOX10, HMGXB4, HBP1, TFAM, UBTF, WHSC1, SOX6, HMGXB3, BBX, TOX2, SOX4, SOX21, SOX9, SOX15, SOX5, SOX3, LEF1, HMG20A, SOX13, TCF7L2, SSRP1, TCF7L1, SOX17, SOX14, PINX1, SOX7, SOX11, SOX12, SOX2, SOX1, SRY, SOX18, UBTFL1, UBTFL2, TOX, HMGB1, HMGB2, PBRM1, TOX3, SMARCE1, HMG20B, HMGB3, HMGA2, HMGA1, ARX, HOXA11, MEOX1, DLX6, ISL1, HOXC8, BARX2, ALX4, GSC2, DLX3, PITX1, HOXA9, HOXA10, LHX5, LASS4, ZFHX4, SIX4, VSX1, ADNP, RHOXF1, MEIS3, PBX4, DLX5, HOXA1, HOXA2, HOXA3, HOXA5, HOXA6, HOXA13, EVX1, NOBOX, MEOX2, LHX2, LHX6, LHX3, TLX1, PITX3, HOXB6, HNF1B, DLX4, SEBOX, VTN, PHOX2B, NKX3-2, DBX1, NANOG, IRX4, CDX1, TLX2, DLX2, VAX2, PRRX1, TGIF2, VSX2, NKX2-3, HOXB8, HOXB5, HOXB7, HOXB3, HOXB1, MSX2, LHX4, HOXA7, HOXC13, HOXC11, HOXC12, ESX1, BARHL1, NKX2-4, NKX2-2, SIX1, HOXD1, HOXD3, HOXD9, HOXD10, HOXD11, HOXD13, MNX1, CDX4, BARX1, RHOXF2, LHX1, GSC, MEIS2, RAX, EMX1, NKX2-8, NKX2-1, HLX, LMX1B, SIX3, LBX1, PDX1, LASS5, ZFHX3, BARHL2, LHX9, LASS2, MEIS1, DLX1, HMBOX1, ZEB1, VAX1, NKX6-2, VENTX, HHEX, TGIF2LX, LASS3, ALX3, HOXB13, IRX6, ISL2, PKNOX1, LHX8, LMX1A, EN1, MSX1, NKX6-1, HESX1, PITX2, TLX3, EN2, UNCX, GBX1, NKX6-3, ZHX1, HDX, PHOX2A, PKNOX2, CDX2, DRGX, NKX3-1, PBX3, PRRX2, GBX2, SHOX2, GSX1, HOXD4, HOXD12, EMX2, IRX1, IRX2, SIX2, HOXB9, HOPX, OTP, LASS6, HOXC5, HOXB2, RAX2, EVX2, ZHX3, PROP1, ISX, HOXD8, TGIF2LY, IRX5, SIX5, TGIF1, IRX3, ZHX2, LBX2, NKX2-6, ALX1, GSX2, HOXC9, HOXC10, HOXB4, NKX2-5, SIX6, MIXL1, DBX2, PBX1, SHOX, ARGFX, HMX3, HMX2, BSX, HOXA4, DMBX1, HOXC6, HOXC4, RHOXF2B, PBX2, DUXA, DPRX, LEUTX, NOTO, HOMEZ, HMX1, DUX4L5, DUX4L2, DUX4L3, DUX4L6, NKX1-1, HNF1A, HSF4, HSFY2, HSFX1, HSFX2, HSFY1, HSF1, LCORL, LCOR, IRF6, IRF1, IRF3, IRF5, IRF4, IRF8, IRF2, IRF7, IRF9, MBD3, BAZ2B, MBD4, SETDB2, MBD1, MECP2, SETDB1, MBD2, BAZ2A, SMAD7, SMAD5, SMAD9, SMAD6, SMAD4, SMAD3, SMAD1, SMAD2, ZZZ3, RCOR1, CDC5L, MYBL2, DNAJC2, TADA2A, RCOR3, MYB, TERF2, DMTF1, DNAJC1, NCOR1, TERF1, MIER3, MYSM1, SNAPC4, RCOR2, TADA2B, MYBL1, TERF1P2, NCOR2, CCDC79, SMARCC1, SMARCC2, TTF1, C11orf9, NFYA, NFYC, NFYB, NRF1, NR4A3, NR4A1, NR4A2, ESR1, NR0B2, NR0B1, PREB, EAF2, SPZ1, TP63, TP73, TP53, PAX6, PAX7, PAX2, PAX4, PAX8, PAX1, PAX3, PAX5, PAX9, SUB1, POU2F2, POU1F1, POU4F3, POU6F2, POU2F3, POU2F1, POU4F2, POU4F1, POU6F1, POU3F2, POU3F1, POU3F4, POU3F3, POU5F1, POU5F1B, PPARD, PPARG, PPARA, PGR, PROX1, PROX2, NR2E1, NR5A2, NR2C1, NR5A1, NR6A1, ESRRA, NR2C2, RFX3, RFX2, RFX4, RFX1, RFX5, RFX7, RFX6, RFX8, NFATC3, NFKB2, NFATC4, NFATC2, NFAT5, RELB, NFKB1, NFATC1, REL, RELA, RORA, RORC, NR1D2, RORB, RUNX3, RUNX1, SP100, SP140, GMEB2, SP110, AIRE, GMEB1, DEAF1, SP140L, LOC729991-MEF2B, MEF2A, SRF, MEF2D, MEF2B, STAT1, STAT5A, STAT4, STAT6, STAT3, STAT2, STAT5B, TBX21, TBX5, TBX15, TBX18, TBX2, TBX4, TBX22, TBX3, TBR1, TBX19, TBX6, EOMES, T, TBX20, TBX10, MGA, TBX1, TEAD3, TEAD2, TEAD1, TEAD4, CREBL2, NFE2L3, CREB3L3, FOSL2, NFE2L1, CREM, DBP, CREB3, HLF, BACH2, ATF2, NFE2L2, ATF6, CREB1, ATF1, NFE2, FOSB, ATF4, NRL, JUND, JDP2, CREB3L4, BATF, BACH1, CREB3L1, NFIL3, TEF, BATF2, ATF5, FOS, JUNB, DDIT3, FOSL1, JUN, MAF, CREB3L2, MAFA, MAFF, MAFG, MAFK, MAFB, ATF6B, CRX, OTX1, OTX2, THAP3, THAP10, THAP1, PRKRIR, THAP8, THAP9, THAP11, THAP2, THAP6, THAP4, THAP5, THAP7, NR1H4, NR2E3, RARB, HNF4A, VDR, ESRRB, THRA, NR1D1, RARA, ESR2, NR1I3, NR1I2, THRB, NR3C2, HNF4G, RARG, RXRA, ESRRG, RXRB, TSC22D1, TSC22D3, TSC22D4, TSC22D2, TULP3, TULP2, TULP1, TULP4, TUB, ZBTB33, ZBTB32, ZBTB11, MYNN, ZBTB25, PATZ1, ZBTB16, ZBTB24, BCL6, ZBTB47, ZBTB17, ZBTB45, GZF1, ZBTB1, ZBTB46, ZBTB8A, ZBTB7B, BCL6B, ZBTB49, ZBTB43, HIC2, ZBTB26, ZNF131, ZNF295, ZBTB4, ZBTB34, ZBTB38, HIC1, ZBTB41, ZBTB7A, ZNF238, ZBTB42, ZBTB2, ZBTB20, ZBTB40, ZBTB7C, ZBTB37, ZBTB3, ZBTB6, ZBTB44, ZFP161, ZBTB12, ZBTB48, ZBTB10, ZBED4, ZBED3, ZBED2, C11orf95, ZBED1, IKZF5, ZNF821, ZNF451, ZNF195, ZFX, ZNF263, ZNF200, HIVEP2, WIZ, ZNF582, SNAI2, ZFP64, IKZF2, ZIC2, ZNF800, PRDM1, PRDM6, ZFP112, ZNF275, ZNF76, ZFAT, KLF6, ZFY, ZXDC, GLI2, ZNF532, ZNF37A, ZNF510, ZNF506, ZNF324, ZNF671, ZNF416, ZNF586, ZNF446, ZNF8, ZNF264, REST, MECOM, ZNF213, ZNF343, ZNF302, ZNF268, ZNF10, HIVEP1, ZNF184, MZF1, SALL4, ZNF516, KLF8, KLF5, ZNF629, ZNF423, CTCF, ZNF500, ZNF174, SALL1, MAZ, ZNF419, OVOL3, ZNF175, ZNF14, ZNF574, ZNF85, SP4, ZKSCAN1, GLI3, GLIS3, KLF3, PRDM4, GLI1, PRDM13, ZNF142, PRDM2, ZNF684, ZNF541, KLF7, PLAGL1, ZNF430, KLF12, KLF9, ZNF410, BCL11A, EGR1, ZFP30, TSHZ3, ZNF549, ZSCAN18, ZNF211, ZNF639, ZSCAN20, GTF3A, ZNF205, ZNF644, EGR2, IKZF4, CTCFL, ZNF831, SNAI1, ZNF576, ZNF45, TRERF1, ZNF391, RREB1, ZNF133, OVOL2, ZNF436, PLAGL2, GLIS2, ZNF384, ZNF484, HIVEP3, BCL11B, KLF2, ZNF780B, FEZF1, KLF16, ZSCAN10, ZNF557, ZNF337, PRDM12, ZNF317, ZNF426, ZNF331, ZNF236, ZNF341, ZNF227, ZNF141, ZNF304, ZSCAN5A, ZNF132, ZNF20, EGR4, ZNF670, VEZF1, KLF4, ZFP37, ZNF189, ZNF193, ZNF280D, PRDM5, ZNF740, ZIC5, ZSCAN29, ZNF710, ZNF434, ZNF287, ZIM3, PRDM15, ZFP14, ZNF787, ZNF473, ZNF614, PRDM16, ZNF697, ZNF687, OSR1, ZNF514, ZNF660, ZNF300, RBAK, ZNF92, ZNF157, ZNF182, ZNF41, ZNF711, PRDM14, ZNF7, ZNF214, ZNF215, SALL3, ZNF827, ZNF547, ZNF773, ZNF776, ZNF256, ZSCAN1, ZNF837, PRDM8, ZNF117, ZIC1, FEZF2, ZNF599, ZNF18, KLF10, ZKSCAN2, ZNF689, ZIC3, ZNF19, ZSCAN12, ZNF276, ZNF283, ZNF221, ZNF225, ZNF230, ZNF222, ZNF234, ZNF233, ZNF235, ZNF362, ZNF208, ZNF714, ZNF394, ZNF333, ZNF382, IKZF3, ZNF577, ZNF653, ZNF75A, GFI1, ZNF281, ZNF496, ZNF2, ZNF513, ZNF148, KLF15, ZNF691, ZNF589, PRDM9, ZNF12, SP8, OSR2, ZNF367, ZNF22, GFI1B, ZNF219, SALL2, ZNF319, ZNF202, ZNF143, ZNF3, ZSCAN21, ZNF606, SP2, ZNF91, ZNF23, ZNF226, ZNF229, ZNF180, ZNF668, ZNF646, ZNF641, ZNF610, ZNF528, ZNF701, ZNF526, ZNF146, ZNF444, ZNF83, ZNF558, ZNF232, E4F1, ZNF597, INSM2, ZNF30, ZNF507, ZNF354A, ZEB2, ZNF32, KLF13, ZFPM2, ZNF764, ZNF768, ZNF35, ZNF778, ZNF212, ZNF282, PRDM10, SP7, SCRT1, ZNF16, ZNF296, ZNF160, ZNF415, ZNF672, ZNF692, ZNF439, ZNF440, ZNF581, ZNF524, ZNF562, ZNF561, ZNF584, ZNF274, ZIK1, ZNF540, ZNF570, KLF17, ZNF217, ZNF57, ZNF556, ZNF554, KLF11, HINFP, ZNF24, ZNF596, OVOL1, SP3, ZNF621, ZNF680, BNC2, ZNF483, ZNF449, INSM1, ZNF417, ZNF791, ZNF80, GLIS1, ZNF497, KLF14, ZNF266, ZIC4, ZNF408, ZNF519, ZNF25, ZNF77, ZNF169, ZNF613, ZNF683, ZNF135, ZSCAN2, ZNF575, ZNF491, ZNF620, ZNF619, ZNF354C, ZNF114, ZNF366, ZNF454, ZNF543, ZNF354B, ZNF223, ZNF713, ZNF852, ZNF552, ZFP42, ZNF664, EGR3, ZFPM1, ZNF784, ZNF648, FIZ1, ZNF771, TSHZ1, ZNF48, ZNF816, ZNF571, ZSCAN4, ZNF594, ZFP3, ZNF443, ZNF792, ZNF572, ZNF707, ZNF746, ZNF322A, ZNF467, ZNF678, ZFP41, HKR1, PLAG1, ZNF329, ZNF101, ZNF716, ZNF708, ZSCAN22, ZNF662, ZNF320, ZNF623, ZNF530, ZNF285, ZFP1, WT1, ZFP90, ZNF479, ZNF445, ZNF74, SP1, SNAI3, ZNF696, IKZF1, ZNF267, ZNF566, ZNF224, ZNF529, ZNF284, ZNF749, ZNF17, ZNF555, ZNF75D, ZNF501, ZNF197, ZNF396, ZFP91, ZNF732, ZNF397, ZSCAN30, ZNF546, ZNF286A, ZKSCAN4, ZNF70, ZNF643, ZNF642, ZSCAN23, ZNF490, ZNF626, ZNF793, ZNF383, ZNF669, ZNF559, ZNF177, ZNF548, MTF1, ZNF322B, ZNF563, ZNF292, ZNF567, SP6, ZNF573, ZNF527, ZNF33A, ZNF600, ZKSCAN3, ZNF676, ZNF699, ZNF250, ZNF79, ZNF681, ZNF766, ZNF107, ZNF471, ZNF836, ZNF493, ZNF167, ZNF565, ZNF34, ZNF781, ZNF140, ZNF774, ZNF658, ZNF765, ZNF124, ZNF569, ZNF777, ZNF775, ZNF799, ZNF782, ZNF846, ZNF136, ZKSCAN5, ZNF502, ZFP62, ZNF33B, ZNF512B, ZNF431, ZNF418, ZNF700, ZNF239, ZSCAN16, ZFP28, ZNF705A, ZNF585A, ZNF138, ZNF429, ZNF470, ZNF100, ZNF398, ZNF498, ZNF441, ZNF420, ZNF763, ZNF679, ZNF682, ZNF772, ZNF257, ZNF785, ZSCAN5B, ZNF165, ZNF655, ZNF98, ZNF786, ZNF517, ZNF675, ZNF860, ZNF628, ZNF665, ZNF624, ZNF841, ZNF615, ZNF350, ZNF432, ZNF433, ZNF460, ZNF81, ZNF780A, ZNF461, ZNF181, LOC100287841, ZNF44, ZNF790, ZNF677, ZNF823, ZNF311, ZNF347, ZNF71, ZNF121, ZNF335, ZNF560, ZNF273, ZNF84, ZNF667, ZNF649, ZNF248, ZNF544, ZNF770, ZNF737, ZNF251, ZNF607, ZNF334, ZXDA, ZNF485, ZIM2, PEG3, ZNF192, ZNF442, ZNF813, ZNF26, ZNF69, ZNF583, ZNF568, ZXDB, ZNF480, ZNF587, ZNF808, ZNF43, ZNF28, ZNF627, ZNF789, ZNF536, ZNF534, ZNF652, ZNF521, ZNF358, ZFP2, SP5, ZNF814, ZNF551, ZNF805, ZSCAN5C, ZNF468, ZNF616, ZFP57, ZNF155, ZNF783, ZNF425, ZNF580, ZNF611, ZNF254, ZNF625, ZNF134, ZNF845, ZNF99, ZNF253, ZNF90, ZNF93, ZNF486, REPIN1, LOC100131539, ZNF705D, LOC100132396, ZNF705G, SCRT2, ZNF407, SP9, ZNF579, ZNF880, ZNF630, ZNF844, ZNF469, ZNF717, ZNF865, ZNF492, ZNF688, YY2, ZNF878, ZNF879, ZNF736, ZNF323, ZNF709, ZNF512, ZNF585B, ZNF154, ZNF324B, ZNF564, ZFP82, GLI4, ZNF674, ZNF345, ZNF550, KLF1, YY1, MYST2, ST18, L3MBTL4, MYT1L, MYT1, L3MBTL1, MTA3, GATA1, TRPS1, GATA3, GATA5, GATA4, GATA6, GATAD2B, GATAD1, GATA2, MTA1, ZGLP1, MTA2, RERE, C16orf5, LITAF, PIAS1, PIAS2, PIAS4, ZMIZ1, ZMIZ2, PIAS3, RNF138, NFX1, NFXL1, or any combinations thereof.

In some embodiments, cells are manipulated (e.g., converted or differentiated) from one cell type to another. In some embodiments, a pancreatic cell is manipulated into a beta islet cell. In some embodiments, a fibroblast is manipulated into an iPS cell. In some embodiments, a preadipocyte is manipulated into a brown fat cell. Other exemplary cells include, e.g., muscle cells, neural cells, leukocytes, and lymphocytes.

In some embodiments, the cell is a diseased or mutant-bearing cell. Such cells can be manipulated to treat the disease, e.g., to correct a mutation, or to alter the phenotyope of the cell, e.g., to inhibit the growth of a cancer cell. For example, a cell is associated with one or more diseases or conditions described herein.

In some embodiments, the manipulated cell is a normal cell.

In some embodiments, the manipulated cell is a stem cell or progenitor cell (e.g., iPS, embryonic, hematopoietic, adipose, germline, lung, or neural stem or progenitor cells). In some embodiments, the manipulated cell can be a cell from any of the three germ layers (i.e. mesodermal, endodermal or ectodermal. In some embodiments, the manipulated cell can be from an extraembryonic tissue, for example, from the placenta.

In some embodiments, the cell being manipulated is selected from fibroblasts, monocytic-precursors, B cells, exocrine cells, pancreatic progenitors, endocrine progenitors, hepatoblasts, myoblasts, or preadipocytes. In some embodiments, the cell is manipulated (e.g., converted or differentiated) into muscle cells, erythroid-megakaryocytic cells, eosinophils, iPS cells, macrophages, T cells, islet beta-cells, neurons, cardiomyocytes, blood cells, endocrine progenitors, exocrine progenitors, ductal cells, acinar cells, alpha cells, beta cells, delta cells, PP cells, hepatocytes, cholangiocytes, angioblast, mesoangioblast or brown adipocytes.

In some embodiments, the cell is a muscle cell, erythroid-megakaryocytic cell, eosinophil, iPS cell, macrophage, T cell, islet beta-cell, neuron, cardiomyocyte, blood cell, endocrine progenitor, exocrine progenitor, ductal cell, acinar cell, alpha cell, beta cell, delta cell, PP cell, hepatocyte, cholangiocyte, or white or brown adipocyte.

In some embodiments, the cell is a precursor cell, a pluripotent cell, a totipotent cell, an adult stem cell, an inner cell mass cell, an embryonic stem cell, or an iPS cell.

In some embodiments, the manipulated cell is a cancer cell. In some embodiments, the cancer cell can be a lung cancer cell, a breast cancer cell, a skin cancer cell, a brain cancer cell, a pancreatic cancer cell, a hematopoietic cancer cell, a liver cancer cell, a kidney cancer cell, an ovarian cancer cell, a prostate cancer cell, a skin cancer cell.

In some embodiments, the cell is a muscle cell, erythroid-megakaryocytic cell, eosinophil, iPS cell, macrophage, T cell, islet beta-cell, neuron, cardiomyocyte, blood cell, endocrine progenitor, exocrine progenitor, ductal cell, acinar cell, alpha cell, beta cell, delta cell, PP cell, hepatocyte, cholangiocyte, or white or brown adipocyte.

Administration of DNA-PK Inhibitors and Gene-Editing System to a Cell(s)

Administering to a cell(s) a genome editing system and a DNA-PK inhibitor can be performed by any method known in the art. The administering can be in vitro, ex vivo or in vivo. The administering to a cell(s) a genome editing system and a DNA-PK inhibitor can occur simultaneously or sequentially. In some embodiments, the administering results in the DNA-PK inhibitor and the genome editing system components to enter the cell membrane. In some embodiments, the administering results in the DNA-PK inhibitor and the genome editing system components to enter into the cell nucleus. In some embodiments, the administering includes incubating the cell in the presence of the DNA-PK inhibitor and genome editing system.

The gene editing system can be administered to a cell(s) by any method known in the art. For example, any nucleic acid or protein delivery methods known in the art can be used. The gene editing system is administered (e.g., delivered) to a cell by way of a nucleic acid encoding the gene editing system components. The gene editing system can be administered to a cell by either viral vectors or non-viral vectors. In some embodiments, viral vectors are used. The viral vectors can be retroviral (e.g. murine leukemia, HIV, or lentiviral) or DNA viruses (e.g. adenovirus, herpes simplex, and adeno-associated). In some embodiments, transfection methods (e.g. non-viral delivery methods) are used to introduce the genome editing system into a cell. Transfection methods include contacting the cell with DEAE-Dextran, calcium phosphate, liposomes or electroporation of a plasmid into a cell. Additional methods of non-viral delivery include electroporation, lipofection, microinjection, biolistics, virosomes, liposomes, immunoliposomes, polycation or lipid: nucleic acid conjugates, naked DNA, naked RNA, artificial virions, and agent-enhanced uptake of DNA. Sonoporation using, e.g., the Sonitron 2000 system (Rich-Mar) can also be used for delivery of nucleic acids. In some embodiments, one or more nucleic acids are delivered as mRNA. In some embodiments, capped mRNAs are used to increase translational efficiency and/or mRNA stability. In some embodiments, ARCA (anti-reverse cap analog) caps or variants thereof are used. See U.S. Pat. Nos. 7,074,596 and 8,153,773.

In embodiments, the endonuclease (e.g. Cas, Cpf1 and the like) and the gRNA, are transcribed from DNA.

In embodiments, the endonuclease (e.g. Cas, Cpf1 and the like) is transcribed from DNA and the gRNA is provided as RNA.

In embodiments, the endonuclease (e.g. Cas, Cpf1 and the like) and the gRNA are provided as RNA.

In embodiments, the endonuclease (e.g. Cas, Cpf1 and the like) is provided as a protein and the gRNA is provided as DNA.

In embodiments, the endonuclease (e.g. Cas, Cpf1 and the like) is provided as protein and the gRNA is provided as RNA.

Additional nucleic acid delivery systems include those provided by Amaxa Biosystems (Cologne, Germany), Maxcyte, Inc. (Rockville, Maryland), BTX Molecular Delivery Systems (Holliston, MA) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™ and Lipofectamine™ RNAiMAX). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995);

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) Nature Biotechnology 27(7):643) Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

In some embodiments, the transfection can be transient in which the transfected genome editing system containing plasmid enters the nucleus but does not become incorporated into the genome of the cell during replication. The transfection can be stable in which the transfected plasmid will become integrated into a genomic region of the cell.

In some embodiments in which transient expression is used, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94: 1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol Cell. Biol. 4:2072-2081 (1984); Hermonat & Muzyczka, PNAS 81:6466-6470 (1984); and Samulski et al., J. Virol 63:03822-3828 (1989).

In some embodiments, the administering to a cell(s) of a DNA-PK inhibitor is performed by culturing an isolated cell(s) in the presence of the DNA-PK inhibitor and any suitable medium that allows for the DNA-PK inhibitor to enter the cell membrane and/or the cell nucleus.

In some embodiments, the DNA-PK inhibitors are administered to a cell (s) in vitro, in vivo or ex vivo. In some embodiment, the DNA-PK inhibitor is contacted with a cell(s) for about 5 hours, 10 hours, 15 hours, 20 hours, 21 hours, 22 hours, 23 hours, 24 hours, 25 hours, 30 hours, 35 hours, 40 hours, 45 hours, 50 hours, 55 hours, 60 hours, 65 hours, 70 hours, 85 hours, 90 hours, 100 hours, 125 hours, 150 hours, 200 hours, or for any period of time in between. In some embodiments, the DNA-PK inhibitor is contacted with a cell(s) for about 1.5 weeks, 2.0 weeks, 2.5 weeks, 3.0 weeks, 3.5 weeks, 4 weeks, or any period of time in between. The DNA-PK inhibitor may be re-administered with cell culture medium changes. The DNA-PK inhibitor can be contacted with the cell either before, during or after introduction of genome editing system components.

In some embodiments, the DNA-PK inhibitor is administered to a cell(s) at a concentration of about 0.1 µM, 0.25 µM, 0.5 µM, 0.75 µM, 1.0 µM, 1.25 µM, 1.50 µM, 1.75 µM, 2.0 µM, 2.5 µM, 3.0 µM, 3.5 µM, 4.0 µM, 4.5 µM, 5.0 µM, 5.5 µM, 6.0 µM, 6.5 µM, 7.0 µM, 7.5 µM, 8.0 µM, 8.5 µM, 9.0 µM, 9.5 µM, 10 µM, 10.5 µM, 11.0 µM, 11.5 µM, 12 µM, or any concentrations in between. The DNA-PK inhibitor concentration can be modified during the course of administration.

In some embodiments, the gene-editing components are delivered into a cell(s) by one or more vectors or in the form of RNA, mRNA or in the case of the endonuclease component as purified protein or mRNA (e.g. Cas9 protein). The one or more vectors can include viral vectors, plasmids or ssDNAs. Viral vectors can include retroviral, lentiviral, adenoviral, adeno-associated, and herpes simplex viral vectors, or any combinations thereof. In some embodiments, the gene-editing components are delivered via RNA or synthetic RNA.

In some embodiments, administration of the DNA-PK inhibitors to a cell along with a gene-editing system results in increased amounts of homologous directed repair gene-editing outcome in comparison to a baseline condition in which the cell is not administered a DNA-PK inhibitor. In some embodiments, administration of the DNA-PK inhibitors to a cell(s) along with a gene-editing system results in suppression of indels (from NHEJ) either on-target or off-target. In some embodiments, administration of the DNA-PK inhibitors to a cell(s) along with a gene-editing system results in increased or decreased expression of a gene of interest. Administration of the DNA-PK inhibitors to a cell(s) along with a gene-editing system can result in the expression of a gene not endogenous to a cell. In some embodiments, administration of the DNA-PK inhibitors to a cell(s) along with a gene-editing system results in the complete or partial removal, or a modification of a gene from a cell(s). In some embodiments, administration of the DNA-PK inhibitors to a cell(s) along with gene-editing system result(s) in the complete or partial removal, or a modification of an intron and/or an exon in a cell(s). In some embodiments, administration of the DNA-PK inhibitors to a cell(s) along with gene-editing system result(s) in the complete or partial removal, or a modification of a non-coding region in a cell(s). In some embodiments, administration of the DNA-PK inhibitors to a cell along with gene-editing system result(s) in simultaneous or sequential, complete or partial removal, or a modification of a coding and/or non-coding genetic region in a cell(s). In some embodiments, administration of the DNA-PK inhibitors to a cell(s) along with gene-editing system results in simultaneous or sequential, complete or partial removal, or a modification of a coding and/or non-coding genetic region in a cell(s), including extrachromosomal DNA or RNA. The Extrachromosomal DNA can be mitochondrial DNA, chloroplast DNA, extrachromosomal circular DNA, or viral extra chromosomal DNA.

In some embodiments, administration of DNA-PK inhibitors to a cell along with genome editing system results in increased expression or decreased expression of a gene of interest. In some embodiments, the increase or decrease in expression of a gene of interest can be about or between, 2.5%, 5%, 10%, 20%, 30%, 40%, 50%, 60%, 70%, 80%, 90% in comparison to a baseline condition in which the cell is not administered a DNA-PK inhibitor. In some embodiments, the increase or decrease of a gene of interest can be about or between, 0.5-fold, 1.0-fold, 1.5-fold, 2.0-fold, 2.5-fold, 3.0-fold, 3.5-fold, 4-fold, 4.5-fold, 5-fold or 10-fold in comparison to the baseline expression level in which the cell is not administered a DNA-PK inhibitor.

In some embodiments, administration of DNA-PK inhibitors to a cell along with a genome editing system results in an increase in genome editing. In some embodiments, the increase in genome editing can be about or between 2.5%, 5%, 10%, 20%, 30%, 40%, 50%, 60%, 70%, 80%, 90% in comparison to a baseline condition in which the cell is not administered a DNA-PK inhibitor. In some embodiments, the increase in genome editing can be about or between 0.5-fold, 1.0-fold, 1.5-fold, 2.0-fold, 2.5-fold, 3.0-fold, 3.5-fold, 4-fold, 4.5-fold, 5-fold or 10-fold in comparison to the baseline expression level in which the cell is not administered a DNA-PK inhibitor.

In some embodiments, administration of a DNA-PK inhibitor and a gene editing system to a cell population results in greater cell survival in comparison to a baseline condition in which a cell population only administered a gene editing system and is not administered a DNA-PK inhibitor. In some embodiments, the DNA-PK inhibitor that results in greater cell survival is a compound of Formula (I), (II), (III-A-1), (III-A-2), (III-B-1), (III-B-2), (IV), (V-A) and (V-B).

In some embodiments, the cell is synchronized at the S or G2 cell cycle phase, either before, after or during administration of the DNA-PK inhibitor. In some embodiments, the cell is synchronized at the S or G2 cell cycle phase, either before, after or during introduction of the gene-editing components. Synchronization of the cell at the S or G2 cell cycle phase can be achieved by any method known in the art. As a non-limiting example, agents that can be used to synchronize a cell at the S or G2 cell cycle phase include aphidicolin, dyroxyurea, lovastatin, mimosine, nocodazole, thymidine, or any combinations thereof (See, Lin et al. Elife. 2014 Dec. 15; 32014). In some embodiments, the agents for cell synchronization can be administered at any time during the gene-editing process.

In some embodiments, the DNA-PK inhibitor and/or the genome editing system can be included in a container, pack, or dispenser together with instructions for use. In some embodiments, the DNA-PK inhibitor agent and/or the genome editing system included in a container, pack or dispenser together with instructions for use is a kit.

In some embodiments, the DNA-PK inhibitors and/or the genome editing system are included in a kit with instructions for use. The kit can contain any genome editing system, and/or DNA-PK inhibitor and instructions for use. In some embodiments the DNA-PK inhibitor is any of compounds represented by Structural Formula (I). In some embodiments, the genome editing system is a selected from a meganuclease based system, a zinc finger nuclease (ZFN) based system, a Transcription Activator-Like Effector-based Nuclease (TALEN) system, a CRISPR-based system, or a NgAgo-based system. The genome editing system can be provided in the kit in any form, for example as a plasmid, vector, DNA, or RNA construct.

In some embodiments, the DNA-PK inhibitor and/or a genome editing system is administered in vivo. The DNA-PK inhibitor and the gene-editing system is formulated to be compatible with its intended route of administration. Examples of routes of administration are described above.

In some embodiments, the formulation can also contain more than one active compound as necessary for the particular indication being treated, for example, those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In some embodiments, the DNA-PK inhibitor agent and/or the genome editing system are administered in combination therapy, i.e., combined with other agents, e.g., therapeutic agents, that are useful for treating pathological conditions or disorders, such as various forms of cancer and inflammatory diseases. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

Genome Editing Screening Methods

Any method known in the art can be used to screen cells for genome-editing efficiency, including the efficiency of NHEJ and/or HDR. For example, screening methods can include PCR based amplification of targeted regions followed by sequencing or deep sequencing of the amplified regions to confirm genome editing. PCR genotyping permits the quantification and ranking of compounds in stimulating HDR. Other screening methods can include next-generation sequencing. See, for example Bell et al., "A high-throughput screening strategy for detecting CRISPR-Cas9 induced mutations using next-generation sequencing," BMC Genomics, 15:1002 (2014).

PCR primers can be engineered to selectively amplify both unmodified and modified genetic regions, resulting in amplicons of different lengths depending on the genetic modification status. The amplicons can then be resolved on a gel, and the HDR efficiency estimated by densitometry using a Bio-Imager. Alternatively, a new PCR technology, the rapid digital droplet PCR (DDPCR) can be used to simultaneously measure HDR and NHEJ events in genome-edited samples. See, for example, Miyaoka et al., "Systematic quantification of HDR and NHEJ reveals effectors of locus, nuclease, and cell type on genome-editing," *Scientific Reports*, 6, 2016. Other methods that can be used for screening cells for genomic modifications including, Sanger sequencing, deep sequencing, and RT-PCR.

In some embodiments, a traffic light reporter (TLR) construct is used for screening cells. TLR screening includes a reporter cell that is engineered to express a fluorescent marker upon targeted genome editing. Following appropriate targeting, the fluorescent marker is expressed by the cell. Quantification of the appropriately targeted cells can be performed by any method known in the art, for example, flow-cytometric analysis. See, for example, Certo et al. 2011, "Tracking genome engineering outcome at individual DNA breakpoints," *Nature Methods*, 8, pages 671-676 (2011).

Preparation of Compounds of the Invention

As used herein, all abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C.: American Chemical Society, 1997. The following definitions describe terms and abbreviations used herein:

BPin pinacol boronate ester
Brine a saturated NaCl solution in water
DCM dichloromethane
DIAD diisopropylazodicarboxylate
DIEA diisopropylethylamine
DMA dimethylacetamide
DMF dimethylformamide
DMSO dimethylsulfoxide
DTT dithiothreitol
ESMS electrospray mass spectrometry
Et$_2$O ethyl ether
EtOAc ethyl acetate
EtOH ethyl alcohol
HEPES 4-(2-hydroxyethyl)-1-piperazineethanesulfonic acid
HPLC high performance liquid chromatography
IPA isopropanol
LAH lithium aluminum hydride
LC-MS liquid chromatography-mass spectrometry
LDA lithium diisoproylethylamide
Me methyl
MeOH methanol
MsCl methanesulfonyl chloride
MTBE methyl t-butyl ether
NMP N-methylpyrrolidine
Pd$_2$(dba)$_3$ tris(dibenzylideneacetone)dipalladium(0)
Pd(dppf)Cl$_2$ 1,1'bis(diphenylphosphino)-ferrocene dichloro-palladium
PG protecting group
Ph phenyl
(rac)-BINAP racemic 2,2'-bis(diphenylphosphino)-1,1'-binaphthyl
RockPhos di-tert-butyl(2',4',6'-triisopropyl-3,6-dimethoxy-[1,1'-biphenyl]-2-yl)phosphine
RT or rt room temperature
SFC supercritical fluid chromatography
SPhos 2-dicyclohexylphosphino-2',6'-dimethoxybiphenyl
TBAI tetrabutylammonium iodide
tBu tertiary butyl
THF tetrahydrofuran
TEA triethylamine
TMEDA tetramethylethylenediamine
VPhos [3-(2-dicyclohexylphosphanylphenyl)-2,4-dimethoxy-phenyl]sulfonyloxysodium General Synthetic Procedures In general, the compounds of the invention may be prepared by methods described herein or by other methods known to those skilled in the art, for example, US2013/0281431 and PCT/US2014/024767 filed Mar. 12, 2014. Specific exemplary preparations of the compounds of the invention are described in the Exemplification section below.

In one embodiment, the methods of preparing compounds represented by Formula (I) or pharmaceutically acceptable salts thereof employ the step of reacting Compound (X-1) with Compound (Y-1) under suitable conditions to form a compound represented by formula (I) or a pharmaceutically acceptable salt thereof:

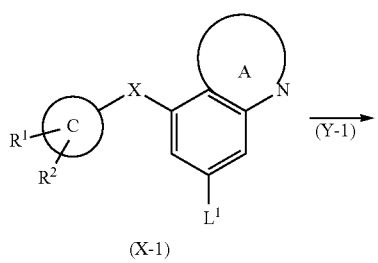

(X-1)

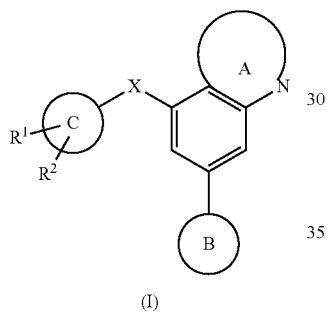

(I)

The variables of Formula (I) are each and independently as described above for the Compounds of the Invention. $L^1$ of Compound (X-1) is a leaving group such as a halogen (e.g., —F, —Cl, —Br, or —I), toluenesulfonate, methanesulfonate or trifluoromethanesulfonate, and the other variables of Compound (X-1) are each and independently as described above for Formula (I). In a specific embodiment, $L^1$ is —Br, toluenesulfonate methanesulfonate or trifluoromethanesulfonate. Compound (Y-1) is

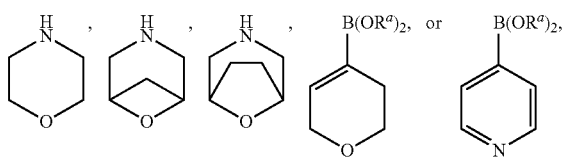

wherein $R^a$ is —H or two $R^a$, together with the oxygen atom to which they are attached, form a dioxolane ring optionally substituted with one or more $C_{1-2}$ alkyl. In a specific embodiment, two $R^a$, together with the oxygen atom to which they are attached and with the boron atom, form 4,4,5,5-tetramethyl-1,3,2-dioxaborolane. Any suitable conditions for effectuating cross-couplings, such as $Csp_2$-$Csp_2$ couplings, known in the art can be used. Specific exemplary conditions are described below in the Exemplification.

In another embodiment, the compounds of Formula (I) or pharmaceutically acceptable salts thereof, wherein $R^1$ is —NHC(O)$R^4$, —NHC(O)O$R^4$, —NHC(O)NH$R^4$, —NHS(O)$_2R^4$, —NH$R^4$, or —O$R^4$, and the other variables of formula (I) are each and independently as described above, are prepared by employing the step of reacting Compound (X-2) with Compound (Y-2) under suitable conditions:

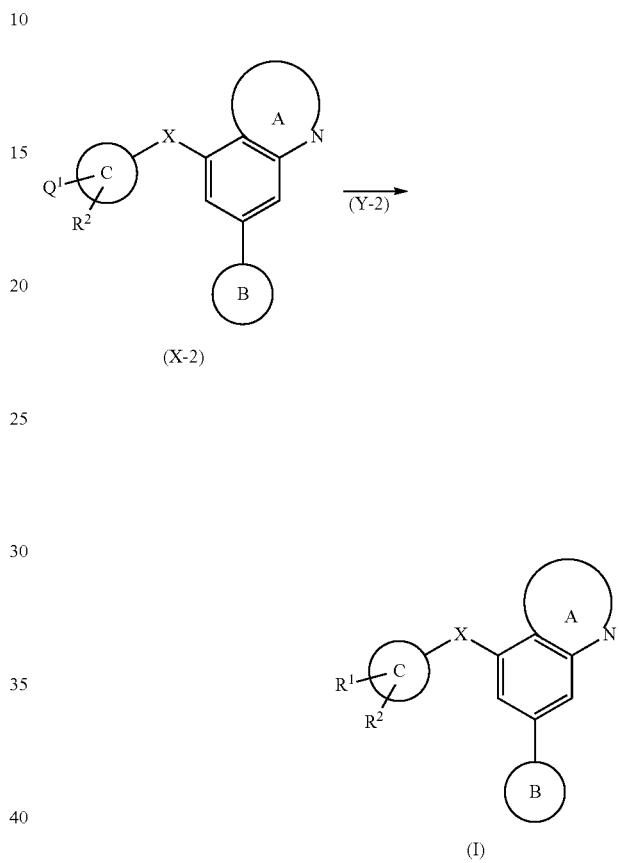

$Q^1$ of Compound (X-2) is —NH$_2$ or —OH, and the other variables of Compound (X-2) are each and independently as described above for Formula (I). Compound (Y-2) is $R^4$—C(O)-$L^2$, $R^4$—O—C(O)-$L^2$, NH$R^4$—C(O)-$L^2$, $R^4$S(O)$_2$-$L^2$, $R^4$-$L^2$, $R^4$C(O)O$R^b$, or $R^4$—N═C═O, wherein each $R^4$ independently is as described for Formula (I); $L^2$ is a halogen (e.g., —F, —Cl, —Br, or —I), toluenesulfonate, methanesulfonate, or trifluoromethanesulfonate; and $R^b$ is $C_{1-4}$ alkyl, such as methyl or ethyl. In a specific embodiment, $L^2$ is —Br, toluenesulfonate, methanesulfonate, or trifluoromethanesulfonate. Any suitable conditions effectuating the reaction known in the art can be used. Specific exemplary conditions are described below in the Exemplification.

In another embodiment, the compounds of Formula (I) or pharmaceutically acceptable salts thereof, wherein X is —NH— or —O—, and the other variables of formula (I) are each and independently as described above, are prepared by the methods employing:

(i) reacting Compound (X-3) with Compound (Y-3) to form a compound represented by formula (I) or a pharmaceutically acceptable salt thereof:

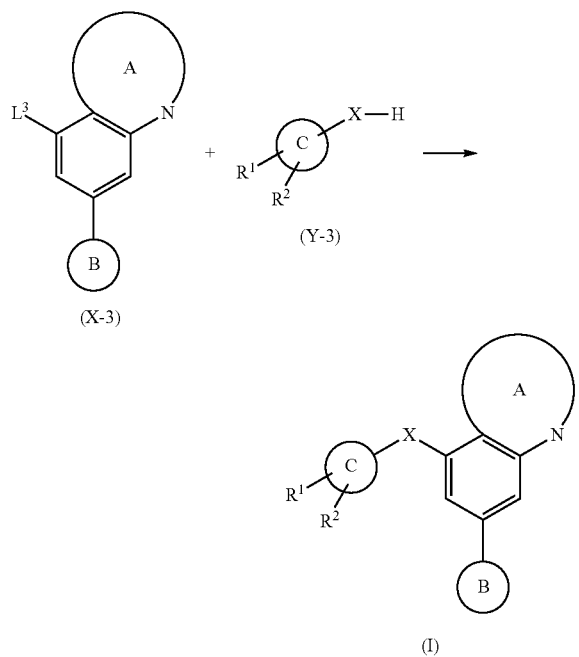

(X-3)   (Y-3)

→

(I)

or
(ii) reacting Compound (X-4) with Compound (Y-4) to form a compound represented by formula (I) or a pharmaceutically acceptable salt thereof:

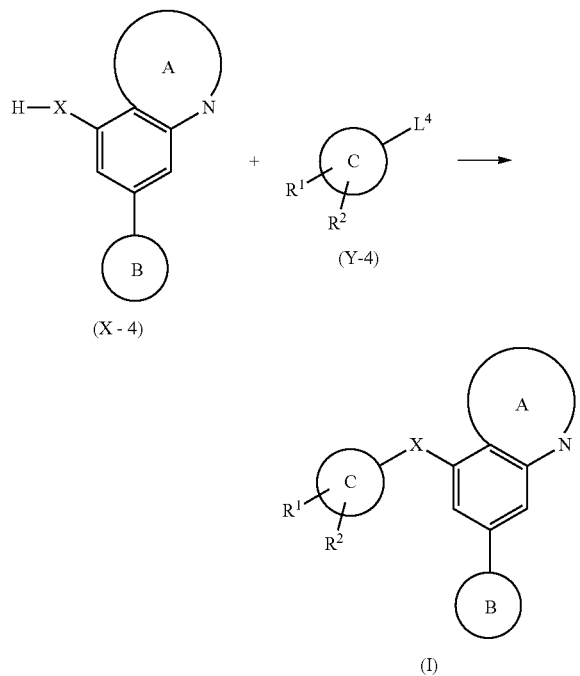

(X-4)   (Y-4)

→

(I)

$L^3$ of Compound (X-3) is a halogen (e.g., —Br, —Cl, or —I). $L^4$ of Compound (Y-4) is a halogen (e.g., —Br, —Cl, or —I), toluenesulfonate, methanesulfonate, or trifluoromethanesulfonate. Each X for Compounds (Y-3) and (X-4) is independently —NH— or —O—. The remaining variables of each of Compounds (X-3), (X-4), (Y-3), and (Y-4) are each and independently as described above for Formula (I). In a specific embodiment, $L^3$ of Compound (X-3) is —Br. In another specific embodiment, $L^4$ of Compound (Y-4) is —Br, toluenesulfonate, methanesulfonate, or trifluoromethanesulfonate. Any suitable conditions for nucleophilic substitutions known in the art can be used. Specific exemplary conditions are described below in the Exemplification.

In another embodiment, the methods of the invention employ the step of reacting Compound (X-5) with $R^5OH$ or ROH to form a compound represented by formula (I) or a pharmaceutically acceptable salt thereof, wherein $R^1$ is —C(O)NHR$^4$, —C(O)OR$^4$, —NHC(O)R$^4$, —NHC(O)OR$^4$, —NHC(O)NHR$^4$, —NHS(O)$_2$R$^4$, —NHR$^4$, —C$_{1-4}$ alkyl-NHR$^4$, or —OR$^4$, or R$^7$; R$^4$ is 5-10 membered heteroaryl substituted with at least one —OR$^5$; R$^7$ is 5-10-membered heteroaryl substituted with at least one —OR; and R, R$^5$, and the other variables of formula (I) are each and independently as described above for Formula (I), provided that both R and R$^5$ are not hydrogen:

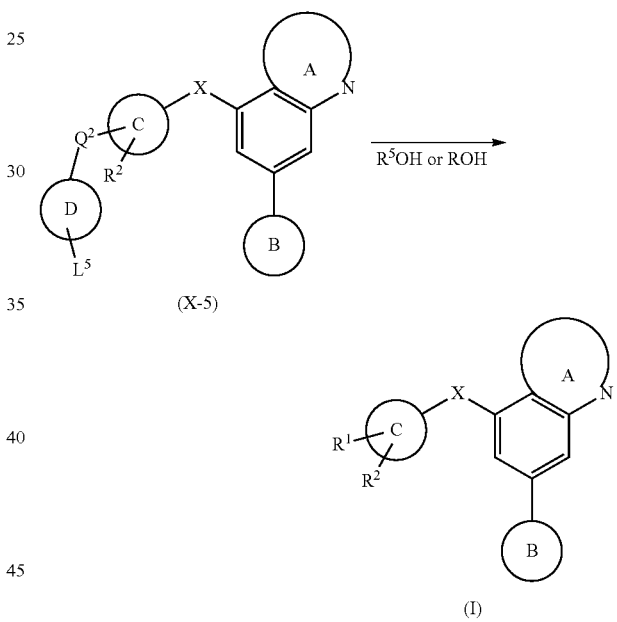

(X-5)   $\xrightarrow{R^5OH \text{ or } ROH}$   (I)

$Q^2$ of Compound (A-5) is a bond, —C(O)NH—, —C(O)O—, —NHC(O)—, —NHC(O)O—, —NHC(O)NH—, —NHS(O)$_2$—, —NH—, —C$_{1-4}$ alkyl-NH—, or —O—. Ring D of Compound (A-5) is 5-10-membered heteroaryl. $L^5$ is a halogen (e.g., —Br, —Cl, —F, or —I). R of ROH, R$^5$ of R$^5$OH, and the remaining variables of Compound (X-5) are each and independently as described above for Formula (I). In a specific embodiment, $L^5$ is —Br. Any suitable conditions for nucleophilic aromatic substitutions known in the art can be used. Specific exemplary conditions are described below in the Exemplification.

In another embodiment, the compounds of Formula (I) or pharmaceutically acceptable salts thereof, wherein X is —O—, and the other variables of formula (I) are each and independently as described above, are prepared by the methods employing:

reacting Compound (X-6) with Compound (Y-6) to form a compound represented by formula (I) or a pharmaceutically acceptable salt thereof:

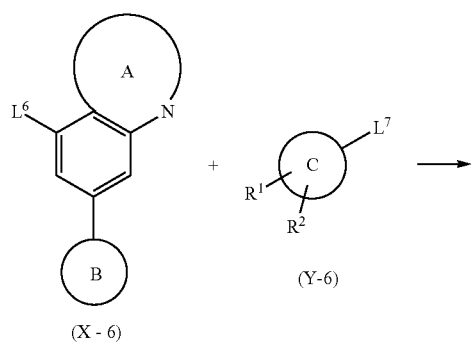

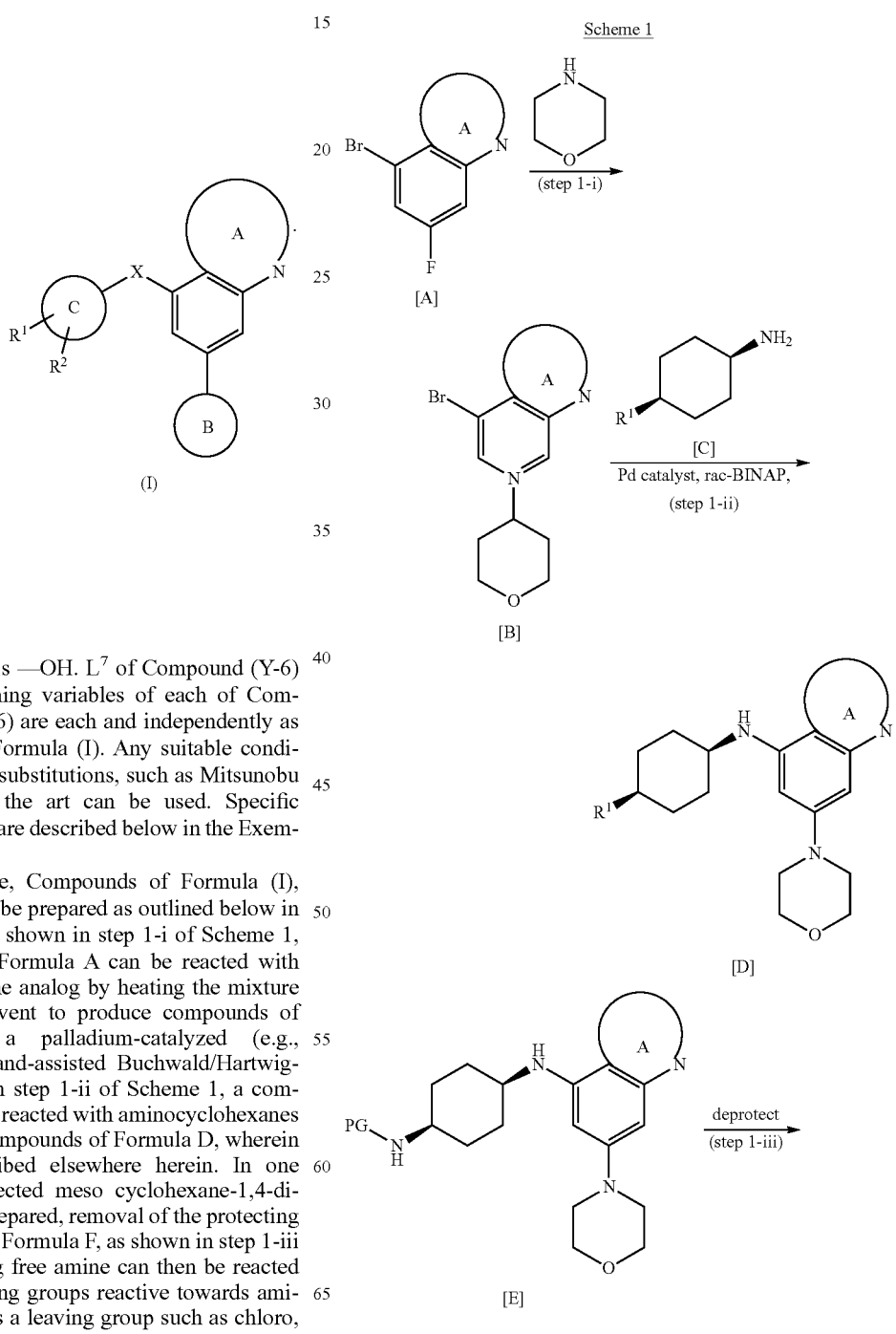

$L^6$ of Compound (X-6) is —OH. $L^7$ of Compound (Y-6) is —OH. The remaining variables of each of Compounds (X-6) and (Y-6) are each and independently as described above for Formula (I). Any suitable conditions for nucleophilic substitutions, such as Mitsunobu reactions, known in the art can be used. Specific exemplary conditions are described below in the Exemplification.

In one specific example, Compounds of Formula (I), wherein X is —NH—, can be prepared as outlined below in Scheme 1. Accordingly, as shown in step 1-i of Scheme 1, heteroaryl compounds of Formula A can be reacted with morpholine or a morpholine analog by heating the mixture in a polar, non-protic solvent to produce compounds of Formula B. Utilizing a palladium-catalyzed (e.g., $Pd_2(dba)_3$), phosphine ligand-assisted Buchwald/Hartwig-type coupling, as shown in step 1-ii of Scheme 1, a compound of Formula B can be reacted with aminocyclohexanes of formula C to produce compounds of Formula D, wherein $R^1$ and $R^2$ are as described elsewhere herein. In one example, when monoprotected meso cyclohexane-1,4-diamines of Formula E are prepared, removal of the protecting group forms compounds of Formula F, as shown in step 1-iii of Scheme 1. The resulting free amine can then be reacted with various moieties having groups reactive towards amines (e.g., $R^{1a}$-L, where L is a leaving group such as chloro, bromo, iodo, toluenesulfonate, methanesulfonate, or trifluoromethanesulfonate; or where L is a reactive carbonyl-containing moiety such as an active ester or an isocyanato group) to produce a compound of formula G, as shown in step 1-iv of Scheme 1. Compounds of Formula (I), wherein X is —S— can be prepared in a similar manner as outlined in Scheme 1, employing a thiol counterpart of Compound (C) under suitable conditions.

Example 1. General Preparation of the Compounds of Formula G

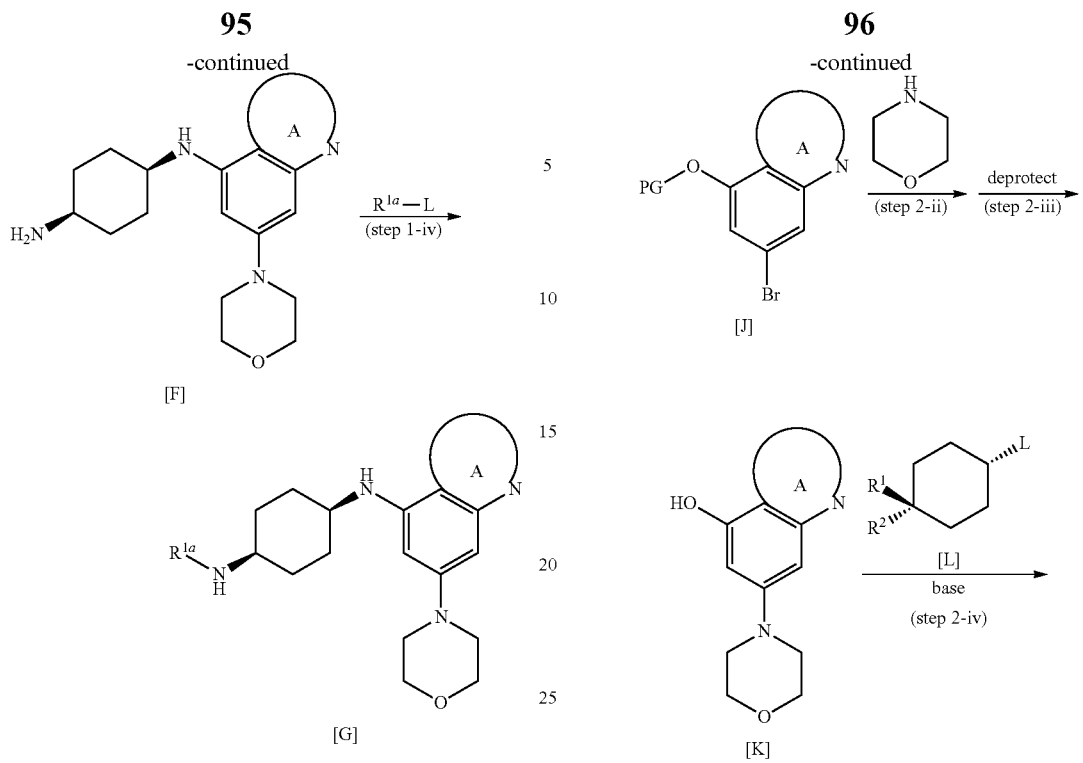

In another example, Compounds of Formula (I), wherein X is —O— can be prepared as outlined below in Schemes 2a and 2b. Accordingly, as shown in step 2-i of Scheme 2a, the hydroxyl group of heteroaryl compounds of Formula H can be protected to produce compounds of Formula J, which can then be reacted with morpholine or a morpholine analog by heating the mixture in a polar, non-protic solvent to produce compounds of Formula K after removal of the protecting group, as shown in steps 2-ii and 2-iii of Scheme 2a. Subsequently, as shown in step 2-iv of Scheme 2a, a compound of Formula K can be reacted with a compound of Formula L under conditions sufficient to affect the SN2 displacement of its leaving group (e.g., where L is a leaving group such as chloro, bromo, iodo, toluenesulfonate, methanesulfonate, or trifluoromethanesulfonate) to produce a compound of Formula M or Formula M, depending on whether $R^1$ or $R^2$ is hydrogen. In those instances when $R^1$ or $R^2$ are protected nitrogen or oxygen moieties, compounds of the invention can be produced by removal of the protecting group and subsequent synthetic manipulation of the resulting free amine/alcohol.

Example 2. General Preparation of the Compounds of Formula M, N, R, and S

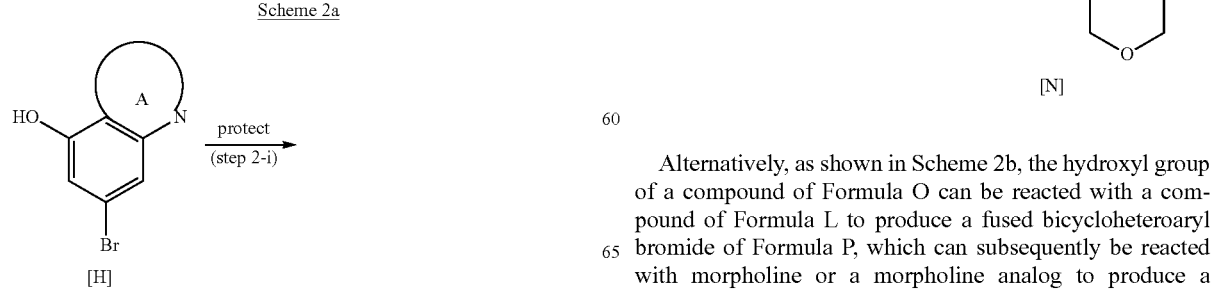

Alternatively, as shown in Scheme 2b, the hydroxyl group of a compound of Formula O can be reacted with a compound of Formula L to produce a fused bicycloheteroaryl bromide of Formula P, which can subsequently be reacted with morpholine or a morpholine analog to produce a compound of Formula M or Formula N.

Scheme 2b

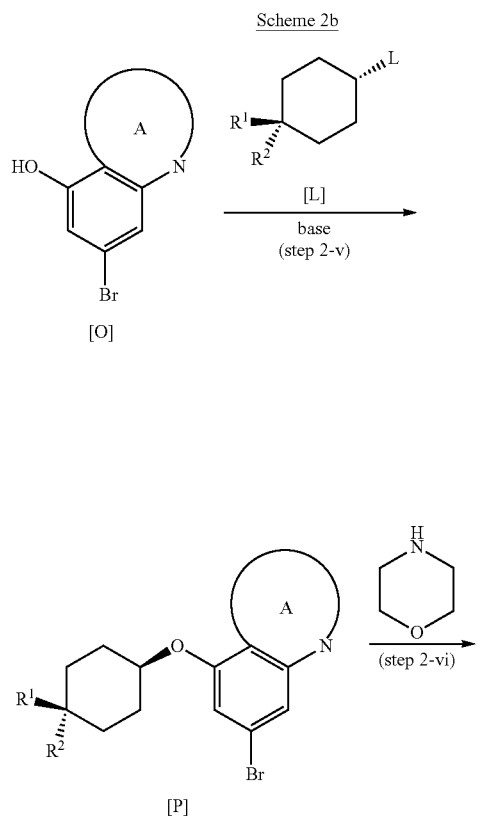

Scheme 2c

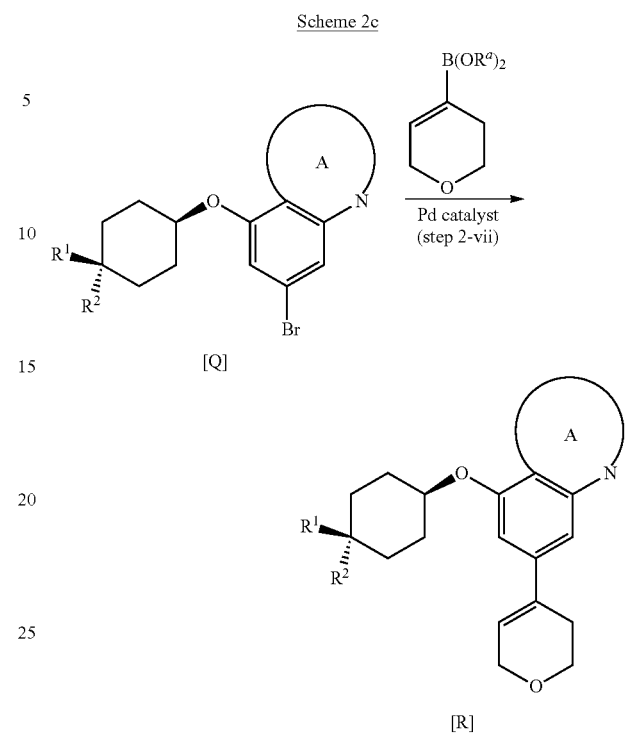

Alternatively, as shown in Scheme 2c, compounds of the invention in which Ring B is a dihydropyran ring can be prepared by reacting compounds of Formula Q with dialkyl (3,6-dihydro-2H-pyran-4-yl)boronates to produce compounds of Formula R. The reaction can be made under a Pd catalyst, such as Pd(dppf) in a basic condition (e.g, a metal carbonate, such as $Na_2CO_3$). $R^a$ in Scheme 2c is —H or two $R^a$, together with the oxygen atom to which they are attached, form a dioxolane ring optionally substituted with one or more $C_{1-2}$ alkyl. In a specific embodiment, two $R^a$, together with the oxygen atom to which they are attached and with the boron atom, form 4,4,5,5-tetramethyl-1,3,2-dioxaborolane.

In another example, Compounds of Formula (I), wherein X is —$CH_2$— can be prepared as outlined below in Schemes 3A and 3B. For example, Compound (3A-10) where Ring C is a $C_{4-6}$ cycloalkyl and X is —$CH_2$— can be prepared as shown in Scheme 3A. In step (i), a nucleophilic aromatic substitution of the F group of Compound (3A-1) with the cyanide group of Compound (3A-2) generates Compound (3A-2). Treatment of Compound (3A-2) with methanolic HCl forms ester Compound (3A-3), which reacts in Step (iii) with a morpholine under Buchwald conditions to form Compound (3A-4). Reduction of ester Compound (3A-4) with a suitable reducing agent, such as lithium aluminum hydride, yields primary alcohol Compound (3A-5). Chlorination of alcohol Compound (3A-5) with a suitable chlorinating agent, such as $POCl_3$, followed by a reaction with atriphenylphosphine forms a Wittig salt, Compound (3A-7). Deprotonation of Compound (3A-7) with a base, such as KO'Bu generaters Compound (3A-8). A reaction of Compound (3A-8) with an appropriately substituted cyclohexanone yields alkene Compound (3A-9). Alkene Compound (3A-9) is then reduced under suitable hydrogenation conditions, such as Pd/C with $H_2$ gas.

Scheme 3A

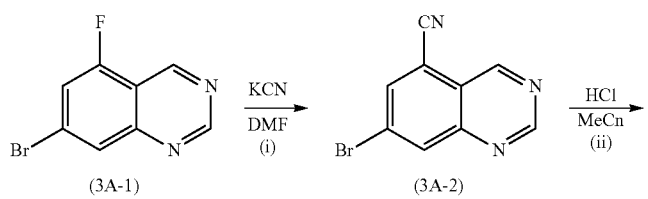

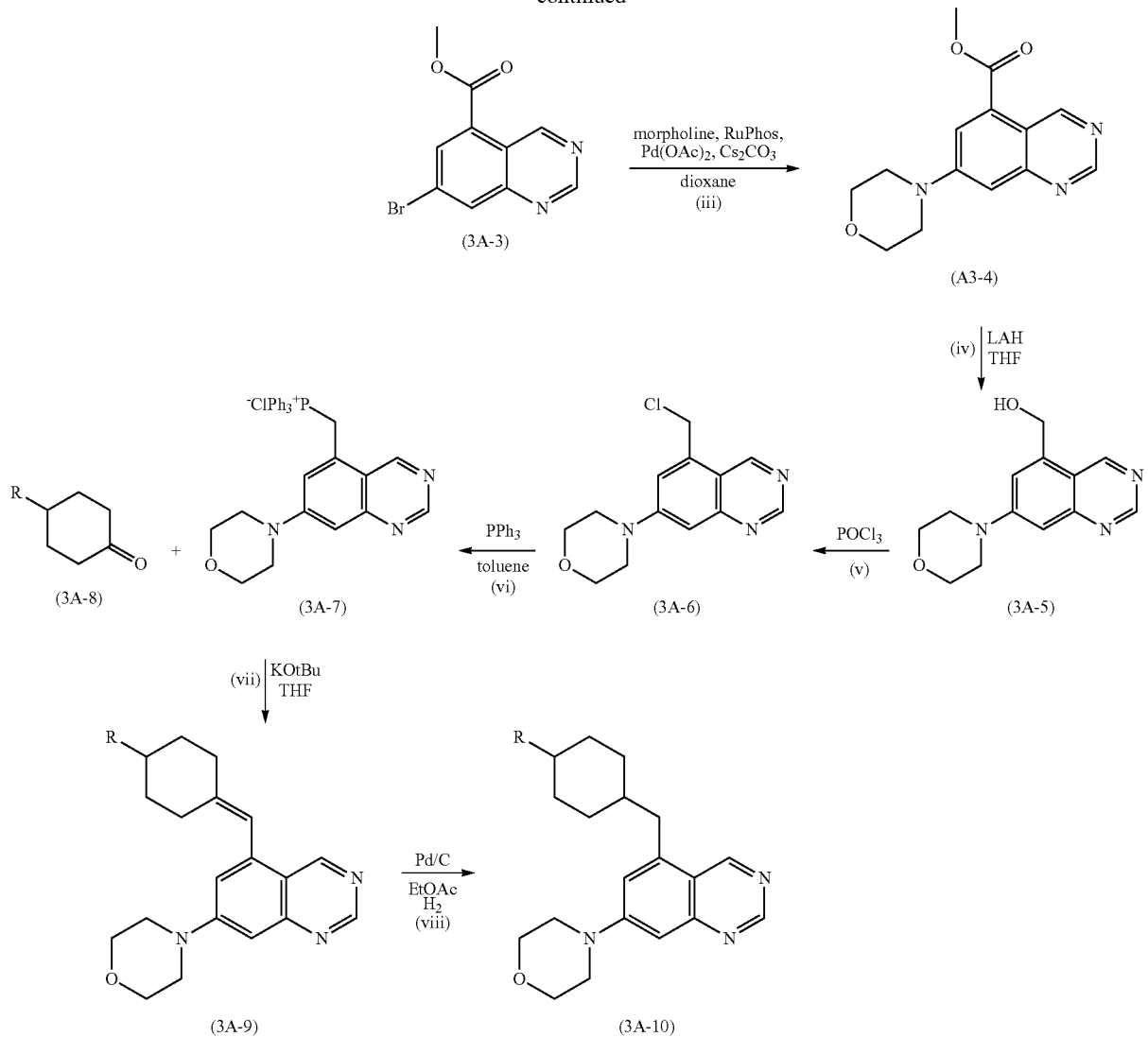
In another example, Compound (3B-4) where Ring C is an aromatic ring system (either phenyl or heteroaryl) and X is —CH₂— can be prepared as shown in Scheme 3B. Specific conditions for Scheme 3B can be found in the prior art, for example, *J. Org. Chem.* 2014, 79, 4285-4292.
Scheme 3B
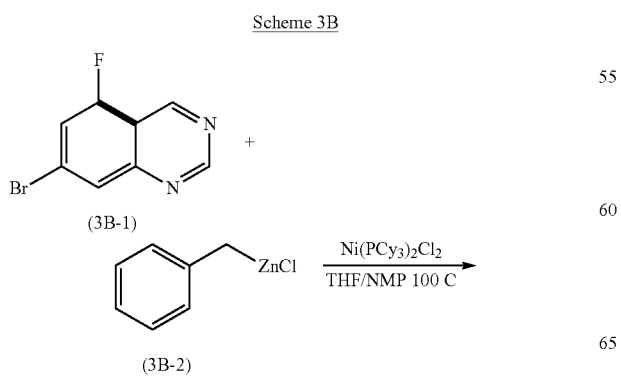
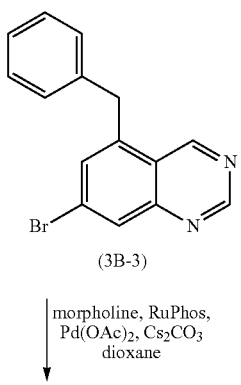
-continued -continued

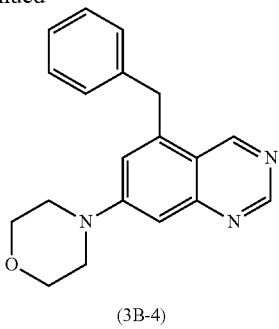

(3B-4)

Alternatively, the compounds of Table 2 can also be used for preparing other compounds of Formula (I), as illustrated below in the Exemplification.

EXEMPLIFICATION

Analytical Characterizations

As used herein, the term "Rt(min)" refers to the HPLC retention time, in minutes, associated with the compound. Unless otherwise indicated, the HPLC methods utilized to obtain the reported retention times are as described below:

HPLC Method A
  Instrument: Waters Acquity UPLC, Waters 3100 Mass Spec
  Column: Waters CSH C18 1.7 um 2.1×50 mm
  Temp: 25° C.
  Solvent A: Water+0.1% TFA
  Solvent B: Acetonitrile+0.1% TFA
  Detection: DAD 220-400 nm
  Gradient:

| | |
|---|---|
| 0 min | 95% A, 5% B |
| 0.6 min | 5% A, 95% B |
| 0.7 min | 5% A, 95% B |
| 1.4 min | 95% A, 5% B |

Flow rate: 0.600 mL/min
HPLC Method B
  Instrument: Waters Autopure
  Column: Waters Sunfire C18 5 μm, 4.6×100 mm
  Temp: Ambient temperature
  Solvent A: Water+0.1% TFA
  Solvent B: Acetonitrile+0.1% TFA
  Detection: Mass spec—Waters 3100, DAD (220-400 nm)
  Gradient:
    0 min—98% A, 2% B
    3.8 min—2% A, 98% B
    4.9 min—2% A, 98% B
    5.0 min—98% A, 2% B
  Flow rate: 1.50 mL/min
HPLC Method C
  Instrument: Waters Acquity UPLC, Waters 3100 Mass Spec
  Column: Waters CSH C18 1.7 um 2.1×50 mm
  Temp: 25° C.
  Solvent A: Water+0.1% TFA
  Solvent B: Acetonitrile+0.1% TFA
  Detection: DAD 220-400 nm
  Gradient:

| | |
|---|---|
| 0 min | 90% A, 10% B |
| 0.6 min | 40% A, 60% B |
| 0.7 min | 90% A, 10% B |
| 1.4 min | 90% A, 10% B |

Flow rate: 0.600 mL/min
HPLC Method D
  Instrument: Waters Acquity UPLC, Waters 3100 Mass Spec
  Column: Waters UPLC BEH C8 1.7 um 2.1×50 mm
  Temp: 25 C
  Solvent A: 95/5 Water (50 mM Ammonium Formate, pH9)/Acetonitrile
  Solvent B: Acetonitrile
  Detection: DAD 220-400 nm
  Gradient:

| | |
|---|---|
| 0 min | 95% A, 5% B |
| 0.6 min | 5% A, 95% B |
| 0.7 min | 5% A, 95% B |
| 1.4 min | 95% A, 5% B |

Flow rate: 0.600 mL/min.

Example 1: Preparation of Compounds

Preparation of Compound 1: 2-methyl-N-[4-(7-morpholinoquinazolin-5-yl)oxycyclohexyl]-6,7-dihydrofuro[3,2-d]pyrimidin-4-amine 4-[(2-chlorofuro[3,2-d]pyrimidin-4-yl)amino]cyclohexanol (1-A)

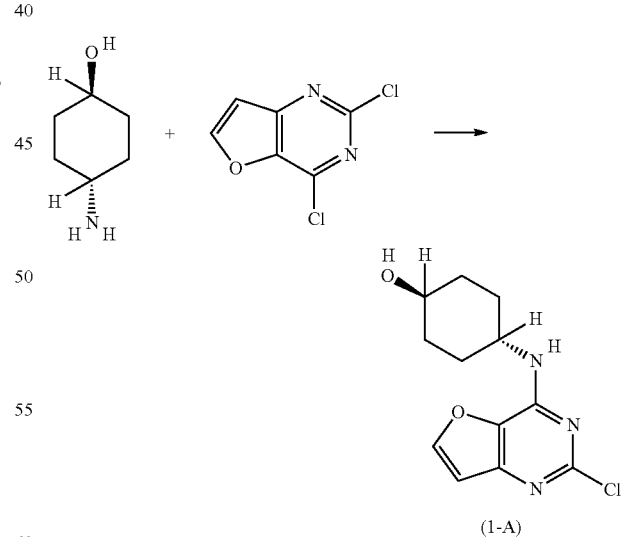

(1-A)

In a round bottom flask fitted with a condenser, a mixture of 4-aminocyclohexan-1-ol (1.219 g, 10.58 mmol), 2,4-dichlorofuro[3,2-d]pyrimidine (2.000 g, 10.58 mmol), Hunig's base (2.735 g, 3.686 mL, 21.16 mmol), and iPrOH (26.38 mL) was heated to 100° C. for 16 h. The solvent was removed, and the crude residue was partitioned between EtOAc and saturated aqueous NH4Cl. The layers were separated, and the aqueous further extracted with EtOAc (2×). The combined organics were dried (Na$_2$SO$_4$), filtered and concentrated to furnish an orange solid. 1H NMR (CDCl$_3$) shows clean desired 4-[(2-chlorofuro[3,2-d]pyrimidin-4-yl)amino]cyclohexanol (2.659 g, 9.932 mmol, 93.89%) along with residual EtOAc. Dried under vacuum overnight and carried forward as is. 1H NMR (400 MHz, CDCl$_3$) δ 7.73 (d, J=1.7 Hz, 1H), 6.78 (d, J=2.1 Hz, 1H), 5.09 (s, 1H), 4.20-4.08 (m, 1H), 3.78-3.61 (m, 1H), 2.19 (d, J=11.5 Hz, 2H), 2.05 (d, J=10.8 Hz, 2H), 1.66-1.45 (m, 4H), 1.45-1.30 (m, 2H). ESI-MS m/z calc. 267.07745, found 268.15 (M+1)+; Retention time: 0.56 minutes.

4-[(2-methylfuro[3,2-d]pyrimidin-4-yl)amino]cyclohexanol (1-B)

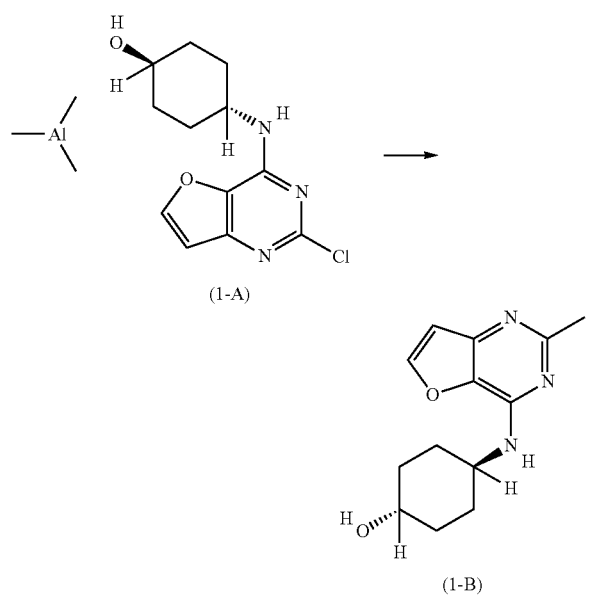

(1-A)

(1-B)

In an oven-dried microwave tube under N$_2$, dissolved Compound (1-A) in anhydrous THF (8.0 mL). Degassed the reaction by bubbling N$_2$ through the solution for 5 minutes. Added Pd(PPh$_3$)$_4$ (215.9 mg, 0.1868 mmol) and degassed for a further two minutes. Trimethylaluminum (2.107 g, 2.802 mL of 2 M, 5.603 mmol) was added cautiously, and the reaction mixture was heated in a 125° C. bath of aluminum beads for 16 h. The reaction mixture was poured carefully into saturated aqueous NH$_4$Cl. The layers were separated, and the aqueous further extracted with EtOAc (2×) and CH$_2$Cl$_2$ (2×). The combined organics were washed with brine, dried (Na$_2$SO$_4$), filtered and concentrated to an orange semi-solid. The crude residue was purified by silica gel chromatography (12 g Isco gold column, linear gradient 0→30% MeOH/CH$_2$Cl$_2$) to provide the desired product (180.75 mg, 0.7309 mmol, 78.27%). 1H NMR (400 MHz, CDCl$_3$) δ 7.67 (d, J=2.1 Hz, 1H), 6.75 (d, J=2.2 Hz, 1H), 4.91 (d, J=7.8 Hz, 1H), 4.15 (tdt, J=12.2, 8.1, 4.0 Hz, 1H), 3.70 (ddd, J=14.7, 10.3, 4.1 Hz, 1H), 2.57 (s, 3H), 2.19 (d, J=12.7 Hz, 2H), 2.11-1.98 (m, 2H), 1.67 (s, 1H), 1.52 (ddd, J=23.4, 13.0, 3.4 Hz, 2H), 1.35 (ddd, J=24.1, 12.9, 3.3 Hz, 2H). ESI-MS m/z calc. 247.13208, found 248.25 (M+1)+; Retention time: 0.46 minutes.

4-[(2-methyl-6,7-dihydrofuro[3,2-d]pyrimidin-4-yl)amino]cyclohexanol (1-C)

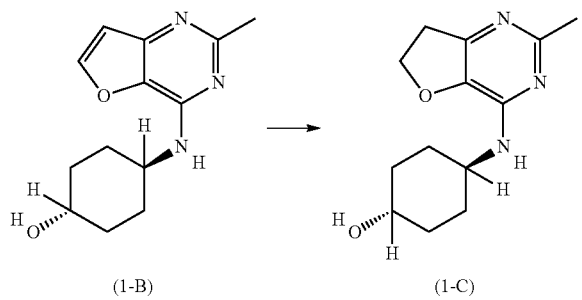

(1-B)    (1-C)

To a flask containing Pd(OH)$_2$ (3.424 g, 4.877 mmol) was added Compound (1-B) (2.68 g, 9.754 mmol) in EtOH (270.9 mL) and HCl (11 mL of 2 M, 22.00 mmol). The resultant reaction mixture was shaken under 50 psi H2 on the Parr shaker for 2 h 10 min. The reaction mixture was filtered through celite and concentrated. The material was dry-loaded onto Celite and purified by silica gel chromatography (80 g Isco gold column, linear gradient 0% hexanes→30% MeOH/CH$_2$Cl$_2$). Relevant fractions were combined and concentrated to provide 4-[(2-methyl-6,7-dihydrofuro[3,2-d]pyrimidin-4-yl)amino]cyclohexanol (2.15 g, 8.624 mmol, 88.40%). 1H NMR (400 MHz, MeOH-D4) δ 4.85-4.79 (t, J=9.2 Hz, 2H), 4.24-4.12 (m, 1H), 3.63-3.51 (m, 1H), 3.42 (t, J=9.2 Hz, 2H), 2.56 (s, 3H), 2.11-1.85 (m, 4H), 1.44 (dq, J=22.9, 10.4 Hz, 4H). ESI-MS m/z calc. 249.14772, found 250.19 (M+1)+; Retention time: 0.46 minutes.

[4-[(2-methyl-6,7-dihydrofuro[3,2-d]pyrimidin-4-yl)amino]cyclohexyl]methanesulfonate (1-D)

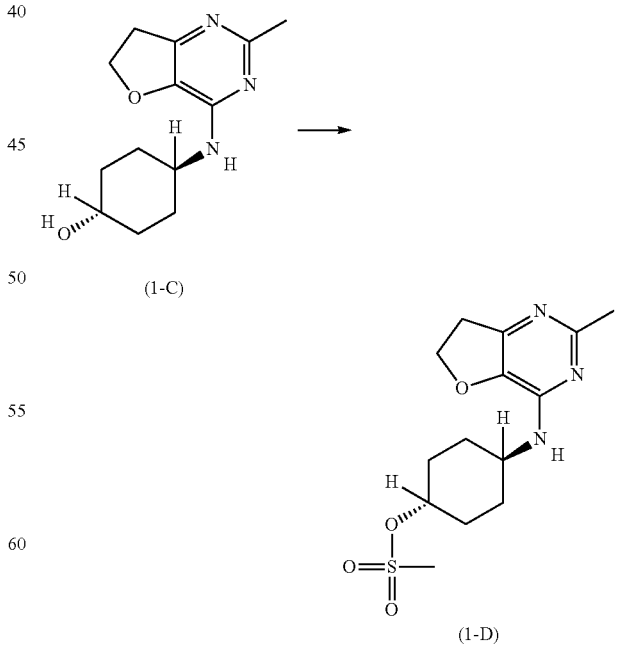

(1-C)

(1-D)

To a room temperature suspension of 4-[(2-methyl-6,7-dihydrofuro[3,2-d]pyrimidin-4-yl)amino]cyclohexanol (2.15 g, 8.624 mmol) and Et₃N (2.793 g, 3.847 mL, 27.60 mmol) in CH₂Cl₂ (223.6 mL) was added MsCl (1.087 g, 734.5 μL, 9.486 mmol). Continued stirring at room temperature for 30 min. The reaction was poured into sat NaHCO₃. The layers were separated, and the aqueous phase was further extracted with CH2Cl2 (2×150 mL). The combined organics were washed with brine, dried (Na₂SO₄), filtered and concentrated. The crude residue was purified by silica gel chromatography (120 g Isco gold column, linear gradient 0%→10% MeOH/CH₂Cl₂). [4-[(2-methyl-6,7-dihydrofuro[3,2-d]pyrimidin-4-yl)amino]cyclohexyl] methanesulfonate (2.3269 g, 7.107 mmol, 82.43%) was obtained. 1H NMR (300 MHz, CDCl3) δ 4.74-4.62 (m, 1H), 4.57 (t, J=9.1 Hz, 2H), 4.34 (d, J=8.1 Hz, 1H), 4.11-3.95 (m, 1H), 3.18 (t, J=9.0 Hz, 2H), 3.03 (s, 3H), 2.46 (s, 3H), 2.20 (d, J=10.4 Hz, 4H), 1.78 (dd, J=22.4, 10.3 Hz, 2H), 1.34 (dd, J=22.4, 10.8 Hz, 2H). ESI-MS m/z calc. 327.12527, found 328.16 (M+1)+; Retention time: 0.52 minutes.

2-methyl-N-[4-(7-morpholinoquinazolin-5-yl)oxycyclohexyl]-6,7-dihydrofuro[3,2-d]pyrimidin-4-amine

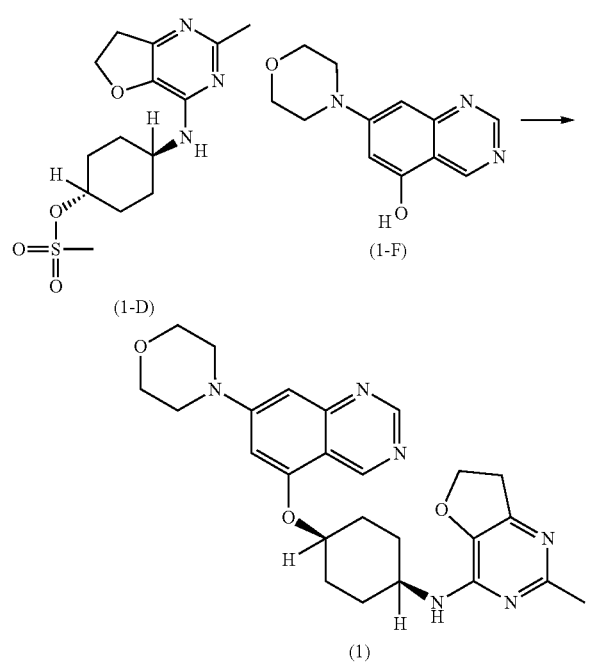

A suspension of 7-morpholinoquinazolin-5-ol (17.4 mg, 0.07524 mmol, Compound (1-F): please see the preparation for Compound 7 below), [4-[(2-methyl-6,7-dihydrofuro[3,2-d]pyrimidin-4-yl)amino]cyclohexyl] methanesulfonate (49.3 mg, 0.1506 mmol) and Cs₂CO₃ (73.6 mg, 0.2259 mmol) in anhydrous dioxane (1.0 mL) was heated to 110° C. for 72 h. The reaction mixture was poured into H₂O and extracted with CH₂Cl₂. The combined organics were dried (Na₂SO₄), filtered and concentrated. The crude residue was purified by silica gel chromatography (12 g Isco gold column, linear gradient 0→10% MeOH/CH₂Cl₂) to provide the desired product, though it contained residual impurities. The material was and further purified by reverse phase Isco [50 g C18 Aq column; 0→50% CH₃CN/H₂O (TFA modifier)]. Relevant fractions were combined and concentrated. The residue was dissolved in CH₂Cl₂ and passed through a Stratospheres SPE cartridge to provide 2-methyl-N-[4-(7-morpholinoquinazolin-5-yl)oxycyclohexyl]-6,7-dihydrofuro[3,2-d]pyrimidin-4-amine (12.2 mg, 0.02374 mmol, 31.55%). 1H NMR (400 MHz, CDCl3) δ 9.43 (s, 1H), 9.09 (s, 1H), 6.78 (s, 1H), 6.58 (d, J=1.5 Hz, 1H), 4.75 (s, 1H), 4.59 (t, J=9.0 Hz, 2H), 4.52 (d, J=8.1 Hz, 1H), 4.24-4.11 (m, 1H), 3.94-3.83 (m, 4H), 3.42-3.31 (m, 4H), 3.19 (t, J=9.0 Hz, 2H), 2.48 (s, 3H), 2.21 (d, J=13.1 Hz, 2H), 1.99 (dd, J=12.6, 3.6 Hz, 2H), 1.90-1.72 (m, 4H). ESI-MS m/z calc. 462.23795, found 463.26 (M+1)+; Retention time: 0.5 minutes.

Preparation of Compound 2: 5-[4-[(2-methyl-6,7-dihydrofuro[3,2-d]pyrimidin-4-yl)amino]cyclohexoxy]-7-morpholino-quinazoline-4-carbonitrile

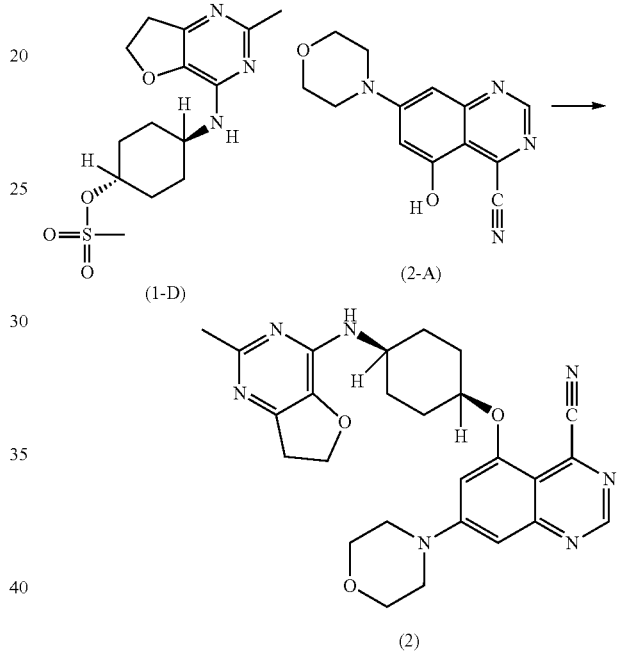

A suspension of 5-hydroxy-7-morpholino-quinazoline-4-carbonitrile (31 mg, 0.1210 mmol, Compound (2-A): see the preparation of Compound 11 below), [4-[(2-methyl-6,7-dihydrofuro[3,2-d]pyrimidin-4-yl)amino]cyclohexyl] methanesulfonate (80 mg, 0.2444 mmol) and Cs₂CO₃ (160 mg, 0.4911 mmol) in anhydrous dioxane (1.5 mL) was heated to 115° C. for 72 h. The reaction mixture was filtered through Celite, and the filtrate concentrated. The crude residue was dissolved in minimal in DMSO and purified by reverse phase Isco [150 g C18 Aq column; 0→50% CH₃CN/H₂O (TFA modifier)]. Relevant fractions were combined and concentrated. The residue was dissolved in CH₂Cl₂ and passed through a Stratospheres SPE cartridge to provide the product, through purity is only ~75%. Repurified by normal phase Isco (40 g Isco gold column, linear gradient 0%→10% MeOH/CH₂Cl₂) to obtain 5-[4-[(2-methyl-6,7-dihydrofuro[3,2-d]pyrimidin-4-yl)amino]cyclohexoxy]-7-morpholino-quinazoline-4-carbonitrile (3.1 mg, 0.005881 mmol, 4.861%) with 92.5% purity by weight. 1H NMR (300 MHz, CDCl₃) δ 9.08 (s, 1H), 6.83 (d, J=2.1 Hz, 1H), 6.67 (d, J=2.0 Hz, 1H), 4.84 (s, 1H), 4.64 (dd, J=8.6, 4.2 Hz, 1H), 4.62-4.52 (m, 2H), 4.27-4.17 (m, 1H), 3.94-3.85 (m, 4H), 3.51-3.40 (m, 4H), 3.18 (t, J=9.1 Hz, 2H), 2.49 (s, 3H), 2.33-2.22

(m, 2H), 2.07-1.86 (m, 6H). ESI-MS m/z calc. 487.2332, found 488.34 (M+1)+; Retention time: 0.63 minutes.

Preparation of Compound 3: 2-methyl-N-[4-(7-morpholinoquinazolin-5-yl)oxycyclohexyl]pyrimidin-4-amine Preparation of Compound 4: 5-[4-[(2-methylpyrimidin-4-yl)amino]cyclohexoxy]-7-morpholino-quinazoline-4-carbonitrile

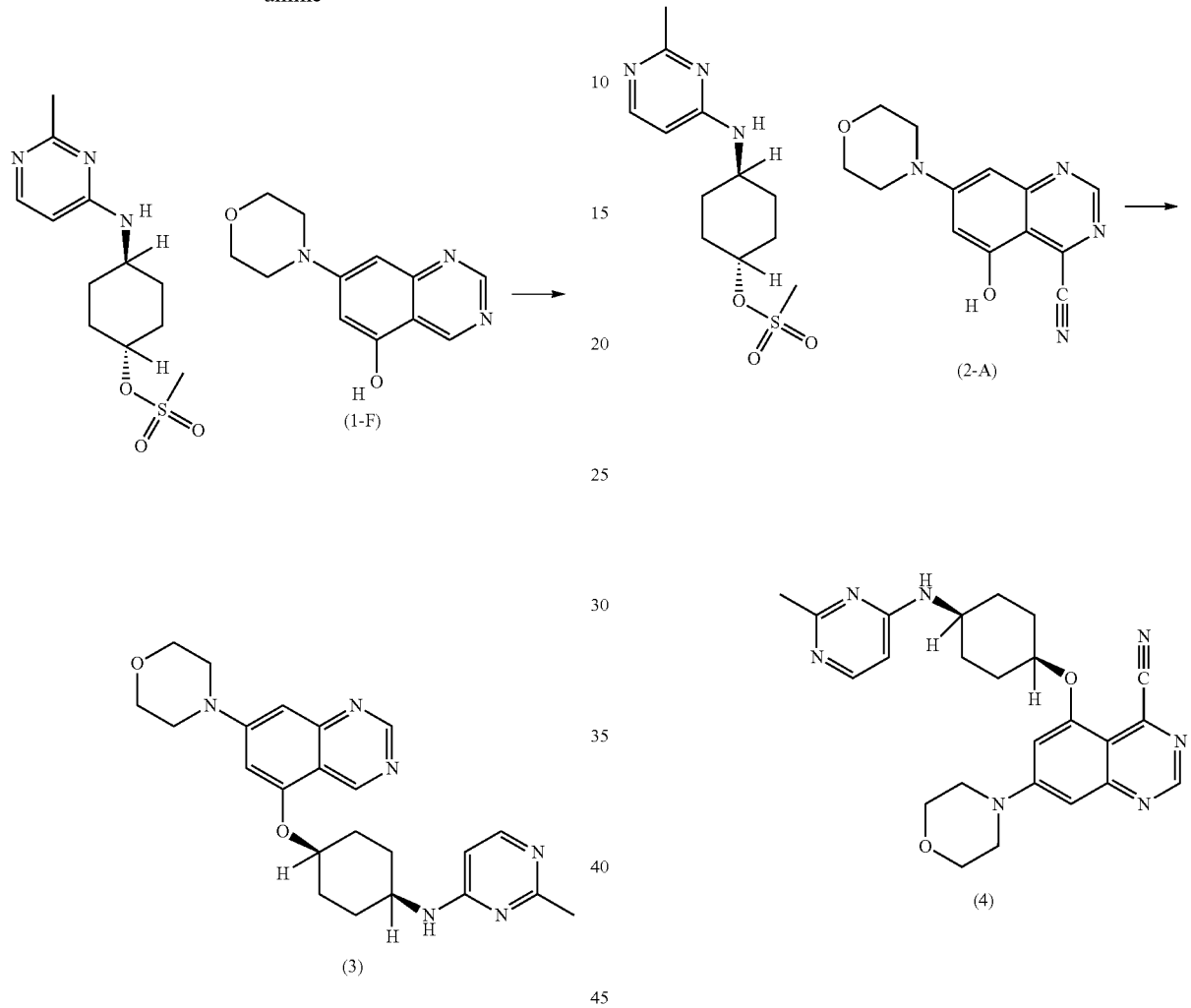

A suspension of 7-morpholinoquinazolin-5-ol (Trifluoroacetic Acid (1)) (68.78 mg, 0.1992 mmol), [4-[(2-methylpyrimidin-4-yl)amino]cyclohexyl]methanesulfonate (142.1 mg, 0.4980 mmol), and $Cs_2CO_3$ (324.5 mg, 0.9960 mmol) in anhydrous dioxane (3.3 mL) was heated to 110° C. for 24 h. The reaction mixture was poured into $H_2O$ and extracted with $CH_2Cl_2$. The combined organics were dried ($Na_2SO_4$), filtered and concentrated. The crude residue was purified by silica gel chromatography (40 g Isco gold column, linear gradient 0→100% $CH_2Cl_2$ to 20% MeOH/$CH_2Cl_2$) to provide the product (11.5 mg, 0.02653 mmol, 13.32%). 1H NMR (300 MHz, Chloroform-d) δ 9.45 (s, 1H), 9.12 (s, 1H), 8.12 (d, J=5.9 Hz, 1H), 6.86-6.77 (m, 1H), 6.60 (d, J=2.2 Hz, 1H), 6.18 (d, J=5.9 Hz, 1H), 4.87 (s, 1H), 4.79 (d, J=3.5 Hz, 1H), 4.02-3.80 (m, 5H), 3.48-3.30 (m, 4H), 2.52 (s, 3H), 2.32-2.20 (m, 2H), 2.07-1.95 (m, 2H), 1.94-1.76 (m, 4H). ESI-MS m/z calc. 420.2274, found 421.42 (M+1)+; Retention time: 0.55 minutes.

A suspension of 5-hydroxy-7-morpholino-quinazoline-4-carbonitrile (trifluoroacetic acid salt) (95.42 mg, 0.2577 mmol), [4-[(2-methylpyrimidin-4-yl)amino]cyclohexyl] methanesulfonate (220.6 mg, 0.7731 mmol), and $Cs_2CO_3$ (420 mg, 1.289 mmol) in anhydrous DMF (2.6 mL) was heated to 80° C. for 112 h. The reaction mixture was filtered through a glass frit, rinsing with $CH_2Cl_2$. The filtrate was evaporated, and the crude residue was purified by silica gel chromatography (40 g Isco gold column, linear gradient 0→100% $CH_2Cl_2$ to 20% MeOH/$CH_2Cl_2$) to provide the product (41.8 mg, 0.09101 mmol, 35.32%). 1H NMR (300 MHz, Chloroform-d) δ 9.08 (s, 1H), 8.06 (d, J=5.9 Hz, 1H), 6.83 (d, J=2.3 Hz, 1H), 6.71-6.63 (m, 1H), 6.14 (d, J=6.0 Hz, 1H), 4.93 (s, 1H), 4.85 (s, 1H), 4.06-3.79 (m, 5H), 3.49 (s, 3H), 3.48-3.40 (m, 4H), 2.49 (s, 3H), 2.34-2.21 (m, 2H), 2.13-1.85 (m, 6H). ESI-MS m/z calc. 445.22263, found 446.35 (M+1)+; Retention time: 0.61 minutes.

Preparation of Compound 5: N-[4-(4-methoxy-7-morpholino-quinazolin-5-yl)oxycyclohexyl]-2-methyl-6,7-dihydrofuro[3,2-d]pyrimidin-4-amine Preparation of Compound 6: N-[4-(4-methoxy-7-morpholino-quinazolin-5-yl)oxycyclohexyl]-2-methyl-pyrimidin-4-amine

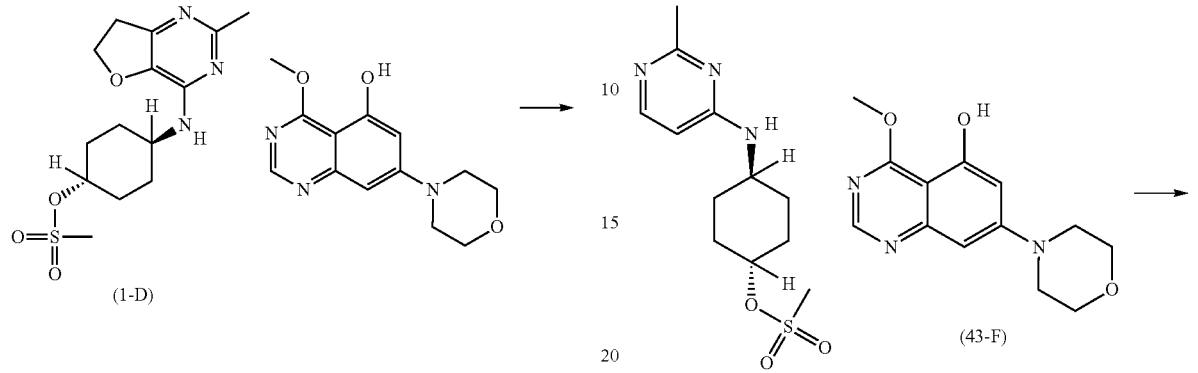

A suspension of 4-methoxy-7-morpholino-quinazolin-5-ol (Trifluoroacetic Acid (1)) (73.78 mg, 0.1966 mmol), [4-[(2-methyl-6,7-dihydrofuro[3,2-d]pyrimidin-4-yl)amino]cyclohexyl] methanesulfonate (161 mg, 0.4918 mmol) and $Cs_2CO_3$ (321 mg, 0.9852 mmol) in anhydrous DMF (1.3 mL) was heated to 90° C. for 24 h. The reaction mixture was filtered through a cotton plug, rinsing with $CH_2Cl_2$. The filtrate was evaporated, and the crude residue was purified by silica gel chromatography (40 g Isco gold column, linear gradient 0→100% $CH_2Cl_2$ to 20% MeOH/$CH_2Cl_2$) to provide the product (39.9 mg, 0.07938 mmol, 40.38%). 1H NMR (300 MHz, Chloroform-d) δ 8.58 (s, 1H), 6.80 (d, J=2.4 Hz, 1H), 6.56 (d, J=2.4 Hz, 1H), 4.68 (s, 1H), 4.58 (t, J=9.1 Hz, 2H), 4.46 (d, J=8.3 Hz, 1H), 4.13 (s, 3H), 3.93-3.82 (m, 4H), 3.38-3.27 (m, 4H), 3.19 (t, J=9.1 Hz, 2H), 2.49 (s, 3H), 2.25-2.13 (m, 2H), 1.99-1.74 (m, 6H). ESI-MS m/z calc. 492.2485, found 493.34 (M+1)+; Retention time: 0.58 minutes A suspension of 4-methoxy-7-morpholino-quinazolin-5-ol (Trifluoroacetic Acid (1)) (73.78 mg, 0.1966 mmol), [4-[(2-methylpyrimidin-4-yl)amino]cyclohexyl]methanesulfonate (140 mg, 0.4906 mmol), and $Cs_2CO_3$ (330 mg, 1.013 mmol) in anhydrous DMF (1.3 mL) was heated to 90° C. for 24 h. The reaction mixture was filtered through a cotton plug, rinsing with $CH_2Cl_2$. The filtrate was evaporated, and the crude residue was purified by silica gel chromatography (40 g Isco gold column, linear gradient 0→100% $CH_2Cl_2$ to 20% MeOH/$CH_2Cl_2$) to provide the product (20.3 mg, 0.04416 mmol, 22.46%). 1H NMR (300 MHz, Chloroform-d) δ 8.58 (s, 1H), 8.12 (d, J=5.9 Hz, 1H), 6.81 (d, J=2.4 Hz, 1H), 6.55 (d, J=2.1 Hz, 1H), 6.17 (d, J=5.9 Hz, 1H), 4.86 (s, 1H), 4.69 (s, 1H), 4.12 (s, 3H), 3.94-3.84 (m, 4H), 3.70 (d, J=12.4 Hz, 1H), 3.41-3.25 (m, 4H), 2.49 (s, 3H), 2.21 (d, J=11.0 Hz, 2H), 1.98-1.73 (m, 6H). ESI-MS m/z calc. 450.23795, found 451.35 (M+1)+; Retention time: 0.57 minutes.

Preparation of Compound 7: 4-[5-[(4-methoxyphenyl)methoxy]quinazolin-7-yl]morpholine

Preparation of Compound (1-F): 7-morpholinoquinazolin-5-ol

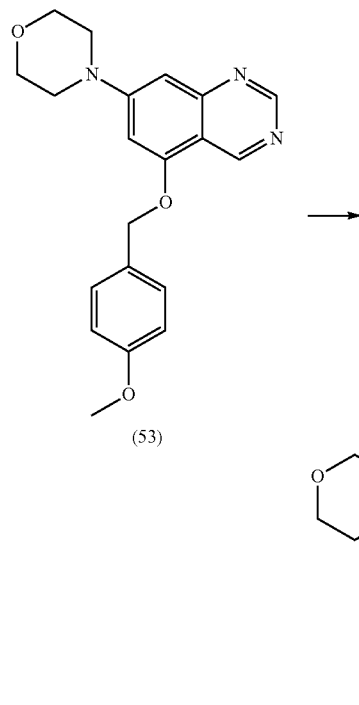

To a solution of 4-[5-[(4-methoxyphenyl)methoxy]quinazolin-7-yl]morpholine (1.38 g, 3.927 mmol) in CH$_2$Cl$_2$ (40 mL) was added TFA (12.36 g, 8.351 mL, 108.4 mmol). The resultant deep red-orange mixture was stirred at 50° C. for 4 h, then room temperature overnight. The solvent was evaporated under gentle heat/N2 stream. The crude residue was carried directly onto the next step. M+ 1: 232.32. Retention Time: 0.5

Preparation of [4-(1,3-dioxoisoindolin-2-yl)cyclohexyl] methanesulfonate

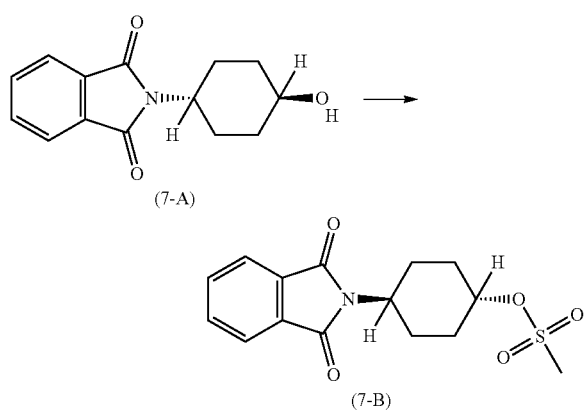

A 0° C. suspension of 2-(4-hydroxycyclohexyl)isoindoline-1,3-dione (1.0 g, 4.077 mmol) in Et3N (1.238 g, 1.705 mL, 12.23 mmol) and CH2Cl2 (6.683 mL) was treated with MsCl (607.1 mg, 410.2 µL, 5.300 mmol) (exothermic, rxn warms up—placed in RT water bath). Continued stirring while warming to RT overnight. The reaction was diluted with EtOAc and poured into H2O. The layers were separated, and the aqueous phase was further extracted with EtOAc (2×50 mL). The combined organics were washed with brine, dried (Na2SO4), filtered and concentrated to a fluffy white solid. 1H NMR shows clean desired product, no purification required; product weighs 1.277 g.

Preparation of Compound 7: 2-[4-(7-morpholinoquinazolin-5-yl)oxycyclohexyl]isoindoline-1,3-dione

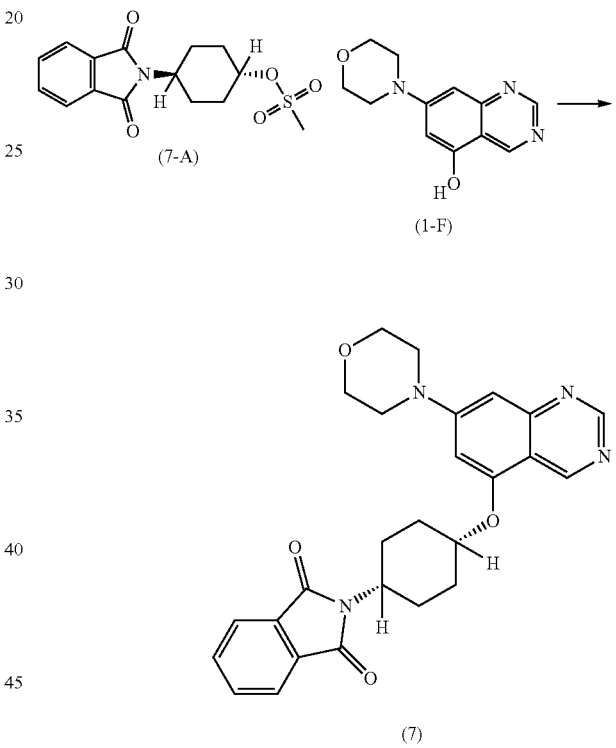

A suspension of 7-morpholinoquinazolin-5-ol (Trifluoroacetic Acid (1)) (324.7 mg, 0.9405 mmol), [4-(1,3-dioxoisoindolin-2-yl)cyclohexyl] methanesulfonate (760.2 mg, 2.351 mmol), and Cs2CO3 (1.535 g, 4.712 mmol) in anhydrous DMF (5.705 mL) was heated to 90° C. for 24 h. The reaction mixture was filtered through a plug of Celite, rinsing with CH2Cl2. The filtrate was evaporated, and the crude residue was dry-loaded onto Celite and purified by silica gel chromatography (40 g Isco gold column, linear gradient 0→30% MeOH/CH2Cl2) to provide the product (206.5 mg, 0.4414 mmol, 46.93%) as an tan solid. 1H NMR (300 MHz, Chloroform-d) δ 9.80 (d, J=0.6 Hz, 1H), 9.15 (s, 1H), 7.89-7.78 (m, 2H), 7.78-7.65 (m, 2H), 6.80 (dd, J=2.3, 0.6 Hz, 1H), 6.61 (d, J=2.0 Hz, 1H), 4.86 (s, 1H), 4.30 (tt, J=12.5, 4.1 Hz, 1H), 3.96-3.82 (m, 4H), 3.47-3.30 (m, 4H), 2.83 (qd, J=12.8, 3.4 Hz, 2H), 2.35 (d, J=15.0 Hz, 2H), 1.84-1.62 (m, 4H). ESI-MS m/z calc. 458.1954, found 459.31 (M+1)+; Retention time: 0.66 minutes.

Preparation of Compound 8: N-methyl-2-[[4-(7-morpholinoquinazolin-5-yl)oxycyclohexyl]amino]pyrimidine-4-carboxamide Preparation of 4-(7-morpholinoquinazolin-5-yl)oxycyclohexanamine: Compound (8-A)

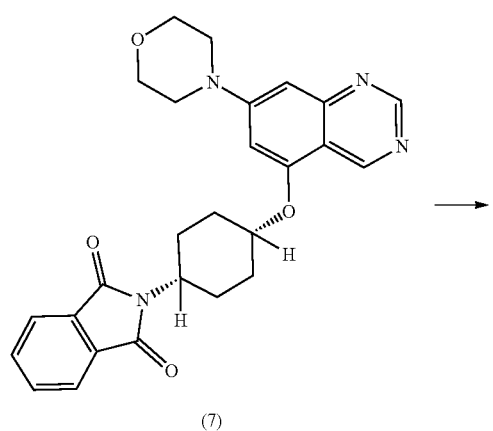

(7)

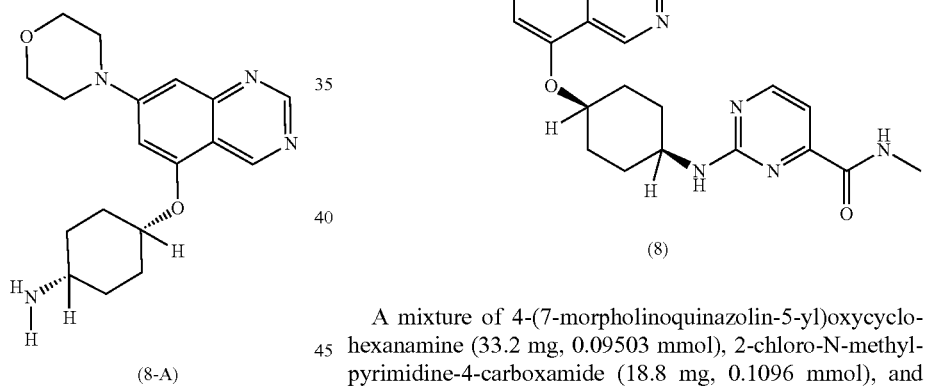

(8-A)

To a stirred solution of 2-[4-(7-morpholinoquinazolin-5-yl)oxycyclohexyl]isoindoline-1,3-dione (1.477 g, 3.221 mmol) in MeOH (110 mL) was added hydrazine (2.0 mL, 63.72 mmol). The resultant reaction was sealed and stirred at room temperature for 20 h. The reaction mixture was concentrated. To the crude residue was added CH2Cl2 and the suspension was filtered through a medium porosity glass frit (solid was rinsed several times with CH2Cl2 and collected in to the same flask). The filtrate was concentrated to provide 4-(7-morpholinoquinazolin-5-yl)oxycyclohexanamine (1.0133 g, 3.085 mmol, 95.78%). The entire batch was dried under vacuum at 50 C for 4 days. 4-(7-morpholinoquinazolin-5-yl)oxycyclohexanamine (1.0133 g, 3.085 mmol, 95.78%) was obtained. 1H NMR (300 MHz, Chloroform-d) δ 9.47 (s, 1H), 9.11 (s, 1H), 6.86-6.72 (m, 1H), 6.58 (d, J=1.7 Hz, 1H), 4.72 (s, 1H), 4.02-3.83 (m, 4H), 3.47-3.29 (m, 4H), 2.95-2.79 (m, 1H), 2.21 (d, J=14.0 Hz, 2H), 1.90-1.69 (m, 6H). ESI-MS m/z calc. 328.1899, found 0.52 (M+1)+; Retention time: 329.39 minutes.

Preparation of N-methyl-2-[[4-(7-morpholinoquinazolin-5-yl)oxycyclohexyl]amino]pyrimidine-4-carboxamide (Compound 8)

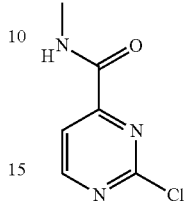 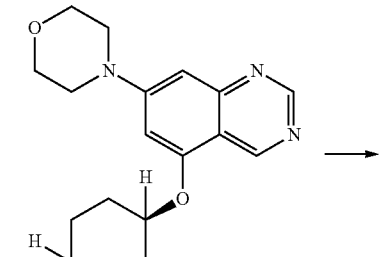

(8-A)

A mixture of 4-(7-morpholinoquinazolin-5-yl)oxycyclohexanamine (33.2 mg, 0.09503 mmol), 2-chloro-N-methylpyrimidine-4-carboxamide (18.8 mg, 0.1096 mmol), and Na2CO3 (190 μL of 2 M, 0.3800 mmol) in water (156 μL) was heated to reflux (100° C.) in a sealed microwave tube. The resultant mixture was allowed to stir overnight. The crude suspension was cooled, frozen, and dried down on the lyophilizer. The residue was dry-loaded onto celite and purified by reverse phase Isco [150 g C18 Aq column; 0→50% CH3CN/H2O (TFA modifier)]. Relevant fractions were combined and concentrated. The sample was dissolved in minimal CH2Cl2 and passed through a Stratospheres PL-HCO3 MP Resin cartridge. The filtrate was concentrated and dried in vacuo to provide N-methyl-2-[[4-(7-morpholinoquinazolin-5-yl)oxycyclohexyl]amino]pyrimidine-4-carboxamide (32.4 mg, 0.06920 mmol, 72.82%). 1H NMR (300 MHz, Chloroform-d) δ 9.45 (s, 1H), 9.10 (s, 1H), 8.49 (d, J=4.8 Hz, 1H), 7.76 (d, J=4.5 Hz, 1H), 7.32 (d, J=4.9 Hz, 1H), 6.79 (d, J=2.2 Hz, 1H), 6.59 (d, J=2.2 Hz, 1H), 5.18 (d, J=7.6 Hz, 1H), 4.86-4.70 (m, 1H), 4.15-3.96 (m, 1H), 3.96-3.78 (m, 4H), 3.49-3.33 (m, 4H), 3.00 (d, J=5.2 Hz, 3H), 2.32-2.14 (m, 2H), 2.10-1.96 (m, 2H), 1.96-1.74 (m, 4H). ESI-MS m/z calc. 463.2332, found 464.35 (M+1)+; Retention time: 0.58 minutes.

115

Preparation of Compound (9): 2-[[4-(4-methoxy-7-morpholino-quinazolin-5-yl)oxycyclohexyl]amino]-N-methyl-pyrimidine-4-carboxamide Preparation of 4-methoxy-7-morpholino-quinazolin-5-ol: Compound (9-A)

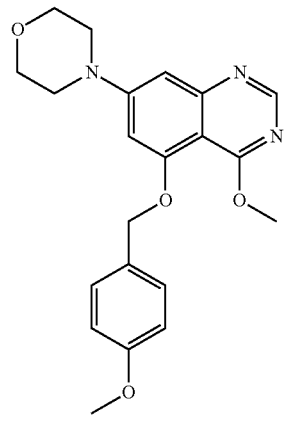

(53)

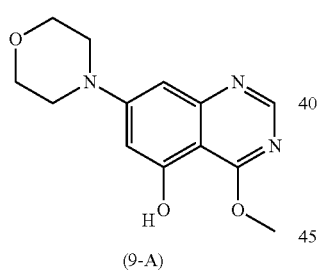

(9-A)

To a solution of 4-[4-methoxy-5-[(4-methoxyphenyl)methoxy]quinazolin-7-yl]morpholine (100 mg, 0.2622 mmol) in CH2Cl2 (2.667 mL) was added TFA (1.794 g, 1.212 mL, 15.73 mmol). The reaction was sealed and heated thermally to 50° C. for 16 h. The solvent was removed under N2 stream/gentle heat. The crude residue was directly carried forward to the next reaction. Mass+1: 262.34. Retention Time: 0.55

116

Preparation of [4-(tert-butoxycarbonylamino)cyclohexyl] methanesulfonate: Compound (9-B)

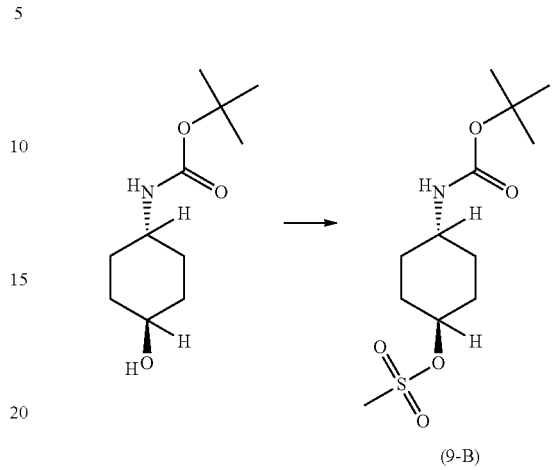

(9-B)

A solution of tert-butyl N-(4-hydroxycyclohexyl)carbamate (8.2 g, 38.09 mmol) in DCM (100 mL) was added DIEA (14 mL, 80.38 mmol) and MsCl (3.2 mL, 41.34 mmol). The mixture was stirred for 0.5 h and diluted with DCM, washed with H2O, dried over Na2SO4, filtered though a layer of silica gel Pad, concentrated. Recovered off white solid. 1H NMR (300 MHz, Chloroform-d) δ 4.64 (tt, J=10.8, 4.1 Hz, 1H), 4.40 (s, 1H), 3.48 (s, 1H), 3.02 (s, 3H), 2.25-1.99 (m, 4H), 1.80-1.59 (m, 2H), 1.45 (s, 9H), 1.36-1.13 (m, 2H).

Preparation of tert-butyl N-[4-(4-methoxy-7-morpholino-quinazolin-5-yl)oxycyclohexyl]carbamate: Compound (9-C)

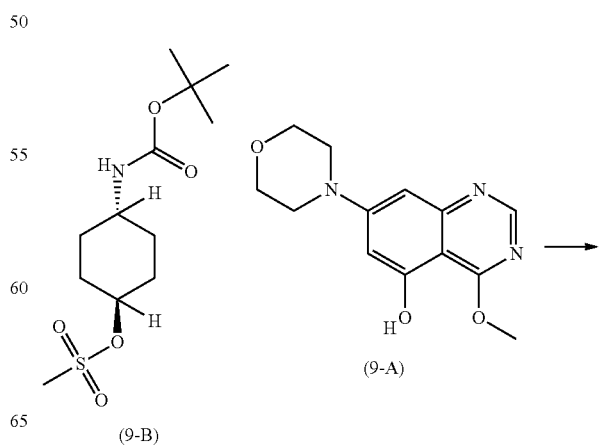

(9-B)   (9-A)

-continued

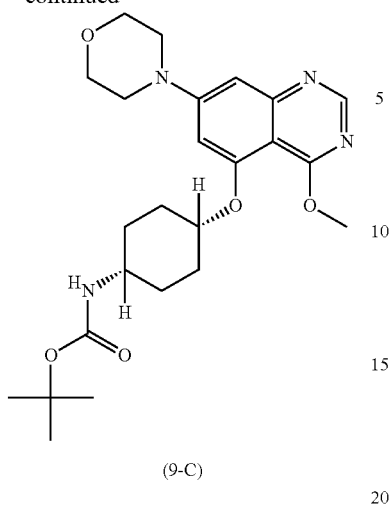

(9-C)

A suspension of 4-methoxy-7-morpholino-quinazolin-5-ol (Trifluoroacetic Acid (1)) (98.4 mg, 0.2622 mmol), [4-(tert-butoxycarbonylamino)cyclohexyl]methanesulfonate (154 mg, 0.5249 mmol), and Cs2CO3 (427 mg, 1.311 mmol) in anhydrous DMF (1.75 mL) was heated to 90° C. for 24 h. The reaction mixture was filtered through a cotton plug, rinsing with CH2Cl2. The filtrate was evaporated, and the crude residue was purified by silica gel chromatography (40 g Isco gold column, linear gradient 0→20% MeOH/CH2Cl2) to provide tert-butyl N-[4-(4-methoxy-7-morpholino-quinazolin-5-yl)oxycyclohexyl]carbamate. The crude material was carried forward to Boc deprotection as is. ESI-MS m/z calc. 458.25293, found 459.45 (M+1)+; Retention time: 0.67 minutes.

-continued (9-F)

To a solution of tert-butyl N-[4-(4-methoxy-7-morpholino-quinazolin-5-yl)oxycyclohexyl]carbamate (120.2 mg, 0.2622 mmol) in CH2Cl2 (2.622 mL) was added TFA (896.9 mg, 606.0 µL, 7.866 mmol). The resultant solution was stirred overnight at room temperature. The reaction mixture was concentrated, and the crude residue was purified by reverse phase Isco [50 g C18 Aq column; 0→40% CH3CN/H2O (TFA modifier)]. Relevant fractions were combined, concentrated, and dried by toluene azeotrope (2×) and vacuum to provide 4-(4-methoxy-7-morpholino-quinazolin-5-yl)oxycyclohexanamine (Trifluoroacetic Acid (1)) (50 mg, 0.1058 mmol, 40.36%) (Yield over 3 steps). ESI-MS m/z calc. 358.2005, found 359.36 (M+1)+; Retention time: 0.53 minutes.

Preparation of 4-(4-methoxy-7-morpholino-quinazolin-5-yl)oxycyclohexanamine: Compound (9-F)

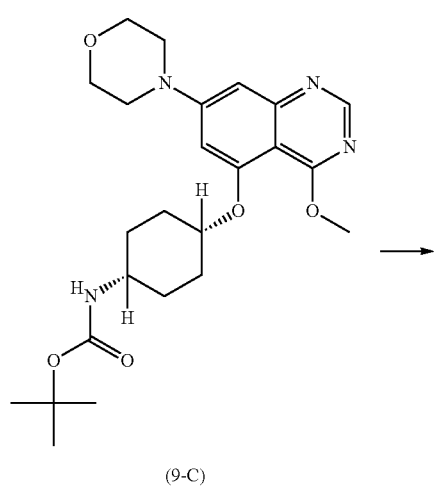

(9-C)

Preparation of 2-[[4-(4-methoxy-7-morpholino-quinazolin-5-yl)oxycyclohexyl]amino]-N-methyl-pyrimidine-4-carboxamide: Compound (9)

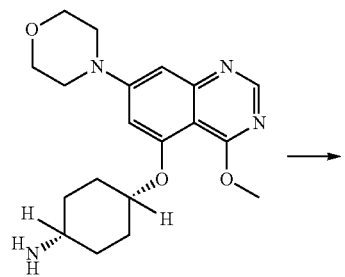

(9-F)

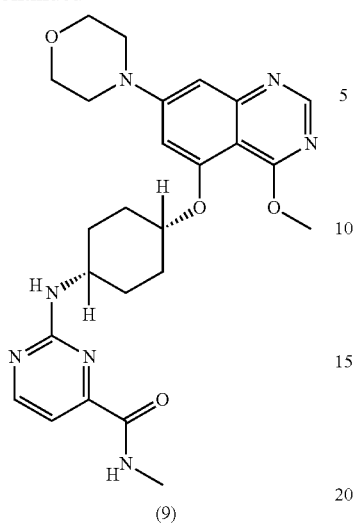

(9)

Preparation of Compound (10): tert-butyl N-[4-(2-methyl-7-morpholino-quinazolin-5-yl)oxycyclohexyl]carbamate

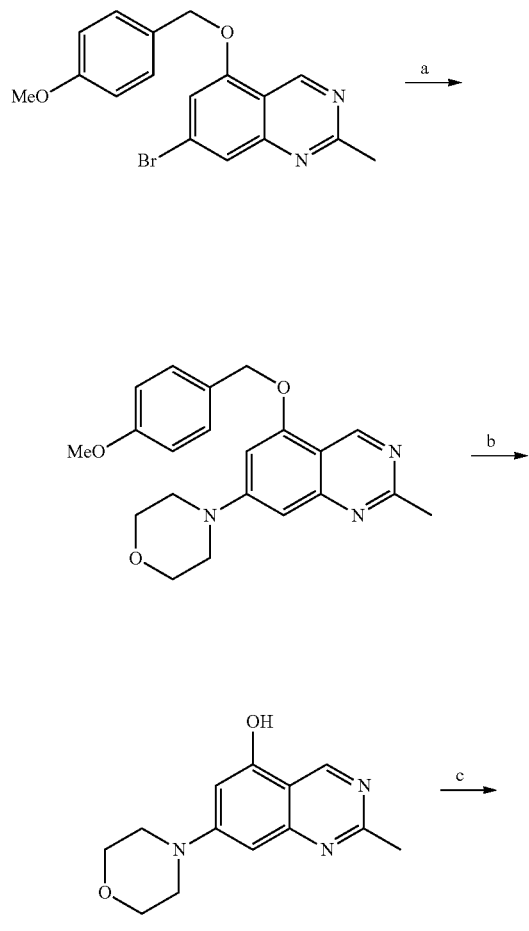

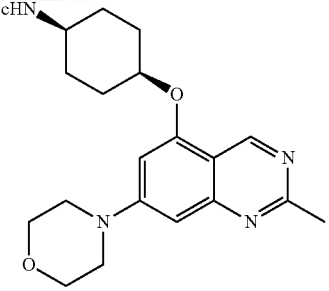

Reagents and conditions: (a) morpholine, DIEA, iPrOH; (b) TFA, DCM; (c) [4-(tert-butoxycarbonylamino)cyclohexyl] methanesulfonate, CsCO3, DMF Step a A mixture of 7-bromo-5-[(4-methoxyphenyl)methoxy]-2-methyl-quinazoline (80 mg, 0.22 mmol), morpholine (23 mg, 0.27 mmol), cesium carbonate (145 mg, 0.45 mmol), Pd(OAc)$_2$ (5.0 mg, 0.023 mmol) and rac-BINAP (28 mg, 0.045 mmol) in 1,4-dioxane (2 mL) was bubbled with N2 and stirred at 90° C. for 1 h. The reaction mixture was diluted with DCM, filtered though a layer of Celite, evaporated. The crude was purified by silica gel chromatography eluting with a gradient of 0-5% MeOH/DCM. This was afforded 4-[5-[(4-methoxyphenyl)methoxy]-2-methyl-quinazolin-7-yl]morpholine (50 mg, 61%). ESI-MS m/z calc. 365.1, found 366.14 (M+1)$^+$; Retention time: 0.58 minutes.

Step b

To a solution of 4-[5-[(4-methoxyphenyl)methoxy]-2-methyl-quinazolin-7-yl]morpholine (180 mg, 0.49 mmol) in DCM (10 mL) was added TFA (1 mL, 12.9 mmol), and the resultant reaction was stirred at room temperature for 1 h. The mixture was concentrated in vacuo. The crude was purified by 12 g silica gel cartridge eluting with a gradient of 04% MeOH/DCM and afforded 2-methyl-7-morpholino-quinazolin-5-ol (85 mg, 70%). $^1$H NMR (400 MHz, CDCl$_3$) δ 9.37 (s, 1H), 6.67 (d, J=2.1 Hz, 1H), 6.52 (d, J=2.1 Hz, 1H), 3.82 (dd, J=5.8, 4.0 Hz, 4H), 3.35-3.23 (m, 4H), 2.80 (s, 3H).

Step c

To a mixture of 2-methyl-7-morpholino-quinazolin-5-ol (30 mg, 0.12 mmol), cesium carbonate (200 mg, 0.62 mmol) in DMF (1 mL) at 70° C. was added [4-(tert-butoxycarbonylamino)cyclohexyl] methanesulfonate (100 mg, 0.34 mmol). The resultant reaction mixture was stirred for 1 h at 70° C. To the mixture was added another portion of [4-(tert-butoxy-carbonylamino)-cyclohexyl]methanesulfonate (100 mg, 0.34 mmol), and stirring was continued at 70° C. for 18 h. The mixture was diluted with DCM, filtered though a layer of Celite, concentrated in vacuo. The crude was purified by silica gel chromatography eluting with a gradient of 0-10% MeOH/DCM and recovered tert-butyl N-[4-(2-methyl-7-morpholino-quinazolin-5-yl)oxycyclohexyl]carbamate (2.0 mg, 3.6%) (Compound 10). $^1$H NMR (400 MHz, Chloroform-d) δ 9.32 (s, 1H), 6.80 (s, 1H), 6.50 (d, J=2.0 Hz, 1H), 4.71 (s, 1H), 4.56 (s, 1H), 3.89 (t, J=4.9 Hz, 4H), 3.63 (s, 1H), 3.42 (t, J=4.9 Hz, 4H), 2.84 (s, 3H), 2.17 (d, J=13.4 Hz, 2H), 1.97-1.60 (m, 6H), 1.47 (s, 9H). ESI-MS m/z calc. 442.26, found 443.2 (M+1)$^+$; Retention time: 0.6 minutes.

Preparation of Compound 11: N-methyl-2-[[4-[(7-morpholino-4-oxo-3H-quinazolin-5-yl)oxy]cyclohexyl]amino]pyrimidine-4-carboxamide

Preparation of 5-hydroxy-7-morpholino-quinazoline-4-carbonitrile (Compound (2-A))

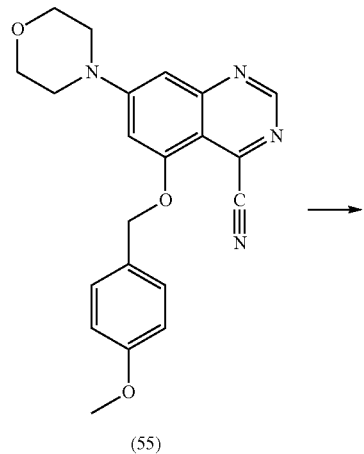

(55)

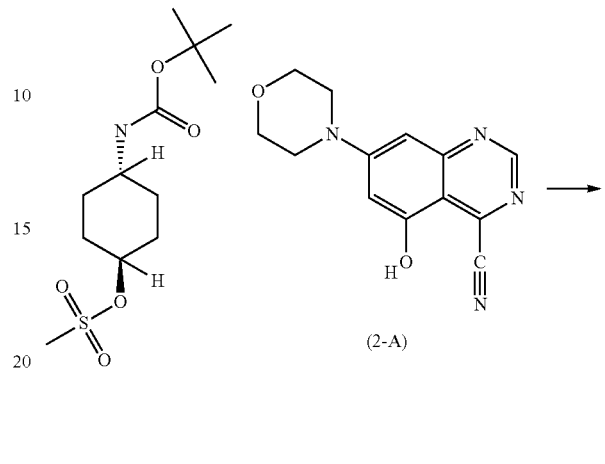

(2-A)

To a solution of 5-[(4-methoxyphenyl)methoxy]-7-morpholino-quinazoline-4-carbonitrile (160 mg, 0.4251 mmol) in CH2Cl2 (4.25 mL) was added TFA (1.800 g, 1.216 mL, 15.79 mmol) (solutions turns from yellow to red). The reaction mixture was stirred overnight at room temperature, after which LCMS shows only a major peak corresponding to [M+1] of the desired product. The solvent was removed under gentle heat/N2 stream, and the crude residue was carried directly into the next step without further manipulation. ESI-MS m/z calc. 256.09604, found 257.3 (M+1)+; Retention time: 0.62 minutes.

Preparation of tert-butyl N-[4-(4-cyano-7-morpholino-quinazolin-5-yl)oxycyclohexyl]carbamate (Compound (11-A))

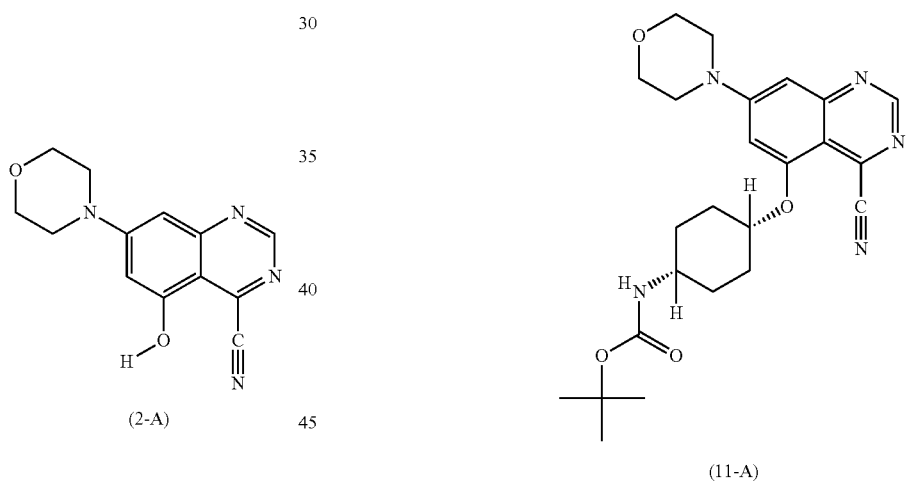

(11-A)

A suspension of 5-hydroxy-7-morpholino-quinazoline-4-carbonitrile (Trifluoroacetic Acid (1)) (157.4 mg, 0.4251 mmol), [4-(tert-butoxycarbonylamino)cyclohexyl] methanesulfonate (312 mg, 1.063 mmol) and Cs2CO3 (694 mg, 2.130 mmol) in anhydrous DMF (2.75 mL) was heated to 90° C. for 24 h. The reaction mixture was vacuum-filtered through a celite plug, rinsing with CH2Cl2. The filtrate was evaporated, and the crude residue was purified by silica gel chromatography (40 g Isco gold column, linear gradient 0→100% CH2Cl2 to 20% MeOH/CH2Cl2) to provide C24H31N5O4 (192.8 mg, 0.4251 mmol, 100.0%). This crude material was carried forward into the next step. ESI-MS m/z calc. 453.2376, found 454.41 (M+1)+; Retention time: 0.83 minutes.

Preparation of 5-(4-aminocyclohexoxy)-7-morpholino-quinazoline-4-carbonitrile (Compound (11-B))

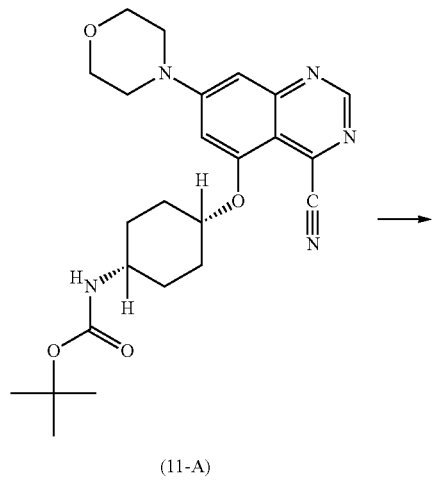

(11-A)

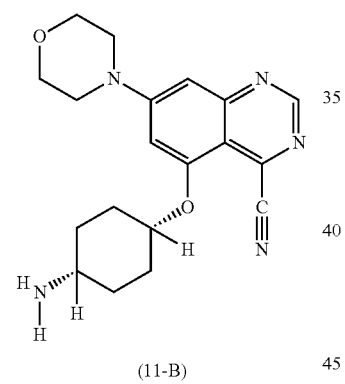

(11-B)

To a solution of tert-butyl N-[4-(4-cyano-7-morpholino-quinazolin-5-yl)oxycyclohexyl]carbamate (192.8 mg, 0.4251 mmol) in CH2Cl2 (10 mL) was added TFA (1.454 g, 982.4 μL, 12.75 mmol). The resultant solution was stirred at room temperature for 4 h.

The reaction mixture was concentrated, and the crude residue was purified by reverse phase Isco [50 g C18 Aq column; 0→40% CH3CN/H2O (TFA modifier)]. Relevant fractions were combined, concentrated, and dried by toluene azeotrope (2×) and vacuum to provide 5-(4-aminocyclohexoxy)-7-morpholino-quinazoline-4-carbonitrile (Trifluoroacetic Acid (1)) (47.8 mg, 0.1023 mmol, 24.06%) (Yield over 3 steps). ESI-MS m/z calc. 353.18518, found 354.41 (M+1)+; Retention time: 0.57 minutes.

Preparation of N-methyl-2-[[4-[(7-morpholino-4-oxo-3H-quinazolin-5-yl)oxy]cyclohexyl]amino]pyrimidine-4-carboxamide (Compound (11))

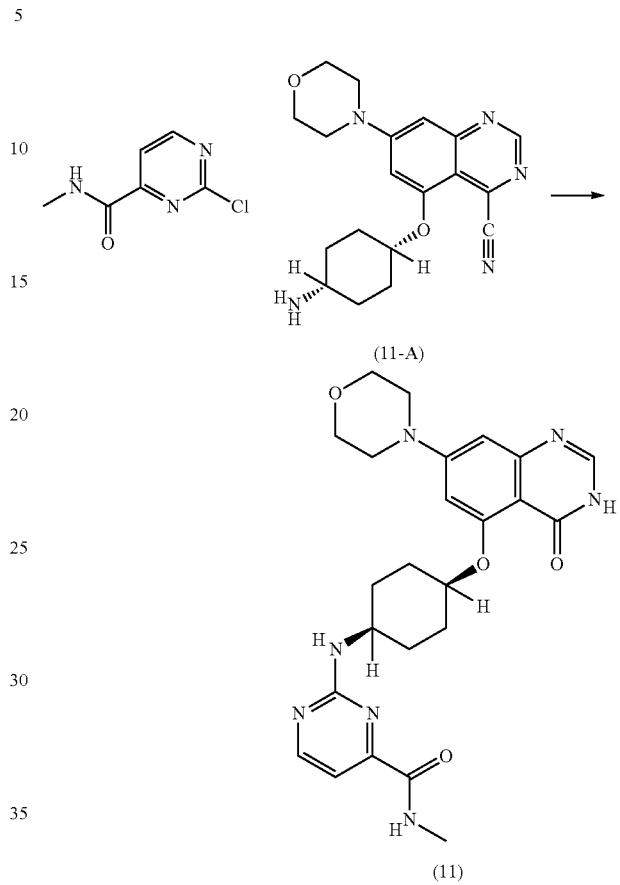

A mixture of 5-(4-aminocyclohexoxy)-7-morpholino-quinazoline-4-carbonitrile (Trifluoroacetic Acid (1)) (47.8 mg, 0.1023 mmol), 2-chloro-N-methyl-pyrimidine-4-carboxamide (23 mg, 0.1340 mmol), and Na2CO3 (256.2 μL of 2 M, 0.5124 mmol) in water (506.7 μL) was heated to 110° C. in a sealed microwave tube and stirred for 16 h. LCMS shows conversion to a major peak, though it corresponds to [M+1] 480.42. It appeared that N-methyl-2-[[4-[(7-morpholino-4-oxo-3H-quinazolin-5-yl)oxy]cyclohexyl]amino]pyrimidine-4-carboxamide (or its tautomer) was formed during the reaction. The crude suspension was cooled to room temperature. To aid dissolution, 1:1 MeOH/H2O (~1 mL) and ~6-8 drops TFA were added. The resultant solution was directly loaded onto reverse phase Isco [50 g C18 Aq column; 0→50% CH3CN/H2O (TFA modifier)]. Fractions corresponding to [M+1] 480.42 product were collected and concentrated under reduced pressure. The sample was dissolved in minimal 1:1 CH2Cl2/MeOH and passed through a Stratospheres PL-HCO3 MP Resin cartridge. The filtrate was concentrated, leaving behind a white solid film. 1H NMR (CDCl3) of the material was consistent with N-methyl-2-[[4-[(7-morpholino-4-oxo-3H-quinazolin-5-yl)oxy]cyclohexyl]amino]pyrimidine-4-carboxamide (or its tautomer). 1H NMR (300 MHz, Chloroform-d) δ 8.46 (d, J=4.9 Hz, 1H), 8.02 (s, 1H), 7.87 (dd, J=5.4, 4.5 Hz, 1H), 7.29 (d, J=4.8 Hz, 1H), 6.70 (d, J=2.4 Hz, 1H), 6.48 (d, J=2.5 Hz, 1H), 5.76-5.31 (m, 1H), 4.72 (s, 1H), 3.99 (dt, J=8.1, 4.0 Hz, 1H), 3.92-3.74 (m, 4H), 3.42-3.22 (m, 4H), 2.98 (d, J=5.1 Hz, 3H), 2.32-2.12 (m, 2H), 2.12-1.84 (m, 4H), 1.77 (td, J=13.2, 11.9, 3.2 Hz, 2H). ESI-MS m/z calc. 479.2281, found 480.33 (M+1)+; Retention time: 0.57 minutes.

Preparation of Compound 12: 2-methyl-N-[4-(2-methyl-7-morpholino-quinazolin-5-yl)oxycyclohexyl]-pyrimidin-4-amine

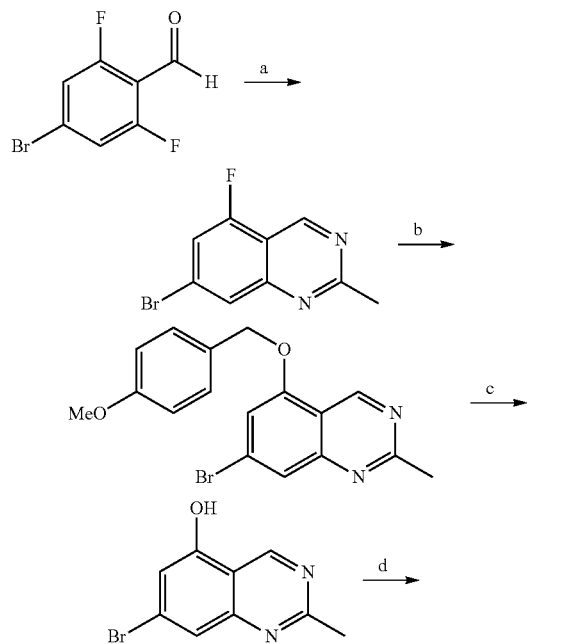

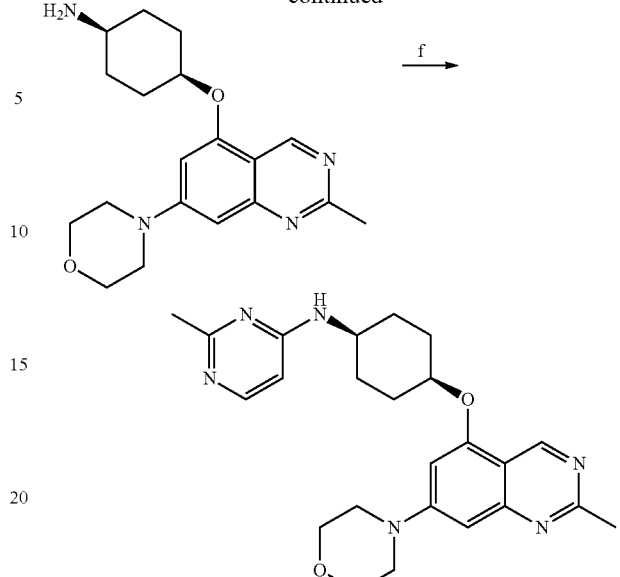

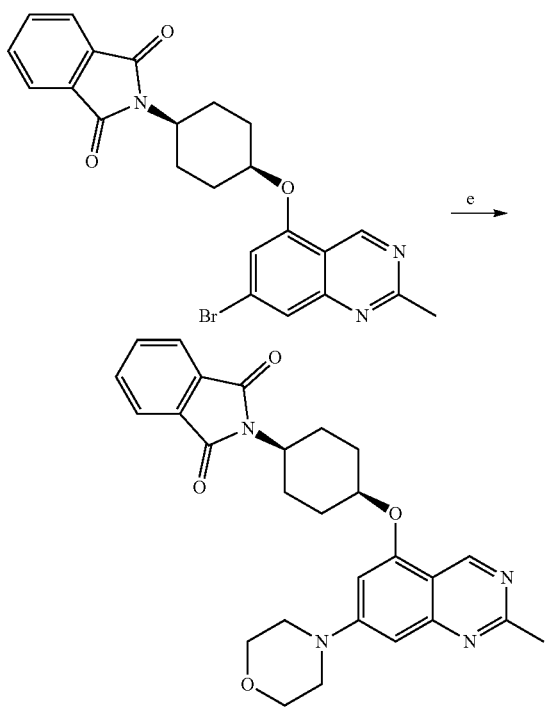

Reagents and conditions: (a) acetamidine(HCl), K₂CO₃ and MS 4A, butyronitrile, 130° C., 22 h, (b) NaH, PMB—OH, DMF; (c) TFA, DCM; (d) 2-(4-hydroxycyclohexyl) isoindoline-1,3-dione, PPh₃, DIAD, THF; (e) morpholine, Pd(OAc)₂, rac-BINAP, CsCO₃, dioxane; (f) NH₂NH₂, MeOH; (g) 4-chloro-2-methyl-pyrimidine, t-butylxPhospalladcycle, NaOtBu, tBuOH.

Step a:

A mixture of 4-bromo-2,6-difluoro-benzaldehyde (4 g, 18.1 mmol), acetamidine (Hydrochloric Acid (1)) (2.4 g, 25.4 mmol), K₂CO₃ (3.5 g, 25 mmol) and MS 4A (2.8 g, powder) in butyronitrile (20.00 mL) was stirred at 130° C. for 20 h. After cooling to room temperature, the mixture was diluted with EtOAc (20 mL), filtered though a layer of celite, concentrated under vacuum. The crude was purified from 120 g silica gel cartridge eluting with a gradient 0-30% EtOAc/heptane. This affords 7-bromo-5-fluoro-2-methyl-quinazoline (1.35 g, 31%). ¹H NMR (400 MHz. Chloroform-d) δ 9.47 (s, 1H), 7.89 (dt, J=1.9, 1.0 Hz, 1H), 7.31 (dd, J=8.7, 1.6 Hz, 1H), 2.84 (s, 3H).

Step b:

To a solution of (4-methoxyphenyl)methanol (886 mg, 0.8 mL, 6.4 mmol) in DMF (20.00 mL) was added NaH (260 mg, 6.4 mmol), and the resultan mixture was stirred for 30 min. To the mixture was added 7-bromo-5-fluoro-2-methyl-quinazoline (800 mg, 3.3 mmol), and stirring was continued for 1 h. The reaction mixture was diluted with EtOAc, washed with H₂O, dried over Na₂SO₄, concentrated. The crude was purified from 40 g silica gel cartridge eluting with a gradient 0-60% EtOAc/heptane. This afford 7-bromo-5-[(4-methoxyphenyl)methoxy]-2-methyl-quinazoline (900 mg, 75.5%). ¹H NMR (400 MHz, Chloroform-d) δ 9.58 (d, J=0.8 Hz, 1H), 7.74-7.65 (m, 1H), 7.43-7.37 (m, 2H), 7.06 (d, J=1.5 Hz, 1H), 6.99-6.92 (m, 2H), 5.17 (s, 2H), 3.85 (s, 3H), 2.86 (s, 3H).

Step c:

To a solution of 7-bromo-5-[(4-methoxyphenyl)methoxy]-2-methyl-quinazoline (1.2 g, 3.3 mmol) in DCM (10 mL) was added TFA (2.0 mL, 26 mmol), and the resultant reaction mixture was stirred for 30 min. The reaction mixture was concentrated and purified from 40 g silica gel cartridge eluting with a gradient 0-100% EtOAc/heptane to afford 7-bromo-2-methyl-quinazolin-5-ol (450 mg, 56%). ¹H NMR (400 MHz, CDCl₃) δ 9.60 (d, J=0.9 Hz, 1H), 7.56 (dt, J=1.8, 0.9 Hz, 1H), 7.01 (t, J=1.3 Hz, 1H), 2.83 (d, J=0.9 Hz, 3H).

Step d:

A solution of 7-bromo-2-methyl-quinazolin-5-ol (200 mg, 0.83 mmol), 2-(4-hydroxycyclohexyl)isoindoline-1,3-dione (210 mg, 0.85 mmol) and PPh₃ (330 mg, 1.25 mmol) in THF (10 mL) was slowly added DIAD (253 mg, 250 µL, 1.25 mmol). The resultant reaction mixture was stirred for 1 h. The mixture was concentrated under vacuum, purified from 12 g silica gel cartridge eluting with a gradient 0-70% EtOAc/heptane to afford 2-[4-(7-bromo-2-methyl-quinazolin-5-yl)oxycyclohexyl]isoindoline-1,3-dione (280 mg, 71%). ¹H NMR (400 MHz, CDCl3) δ 10.01 (t, J=1.1 Hz, 1H), 7.91-7.80 (m, 2H), 7.75-7.68 (m, 2H), 7.03 (d, J=1.6 Hz, 1H), 6.36 (s, 2H), 5.06-4.93 (m, 2H), 4.33 (tt, J=12.5, 4.2 Hz, 1H), 2.94-2.84 (m, 2H), 2.83-2.78 (m, 2H), 2.37 (s, 3H), 1.87-1.7 (m, 4H).

Step e:

A mixture of 2-[4-(7-bromo-2-methyl-quinazolin-5-yl)oxycyclohexyl]isoindoline-1,3-dione (280 mg, 0.60 mmol), morpholine (100 µL, 1.1 mmol), cesium carbonate (400 mg, 1.2 mmol), rac-BINAP (40 mg, 0.06 mmol) and PdOAc₂ (7 mg, 0.03 mmol) in dioxane (5 mL) was bubbled with N2 for 5 min. The reaction mixture was sealed and stirred overnight at 100° C. After cooling to room temperature, the mixture was diluted with DCM, filtered though a layer of Celite, and concentrated. The crude was purified from silica gel chromatography with a gradient 0-3% MeOH/DCM to afford 2-[4-(2-methyl-7-morpholino-quinazolin-5-yl)oxycyclohexyl]isoindoline-1,3-dione (125 mg, 44%) ¹H NMR (400 MHz, CDCl3) δ 9.7 (s, 1H), 7.88-7.75 (m, 2H), 7.72-7.65 (m, 2H), 6.8 (d, J=1.6 Hz, 1H), 6.55 (s, 2H), 5.03-4.83 (m, 1H), 4.35-4.25 (m, 1H), 3.92-3.83 (m, 4H), 3.42-3.31 (m, 4H), 2.7-2.9 (m, 2H), 2.45-2.3 (m, 2H), 2.37 (s, 3H), 1.80 (m, 4H).

Step f:

To a solution of 2-[4-(2-methyl-7-morpholino-quinazolin-5-yl)oxycyclohexyl]isoindoline-1,3-dione (120 mg, 0.25 mmol) in MeOH (5 mL) was added hydrazine (Water (1)) (250 mg, 280 µL, 5 mmol), and the resultant reaction mixture was stirred at 70° C. for 1 h. The reaction mixture was cooled to room temperature, concentrated in vacuo, and purified from silica gel chromatography (12 g cartridge) eluting with a gradient 0-10% (7M NH₃ in MeOH/DCM). This afford 4-(2-methyl-7-morpholino-quinazolin-5-yl)oxy-cyclohexanamine (66 mg, 76%). ¹H NMR (400 MHz, CDCl₃) δ 9.39 (d, J=0.6 Hz, 1H), 6.72 (d, J=2.0 Hz, 1H), 6.51 (d, J=2.1, 1H), 4.72-4.60 (m, 1H), 3.94-3.81 (m, 4H), 3.43-3.30 (m, 4H), 2.80 (s, 3H), 2.26-2.12 (m, 2H), 1.86-1.54 (m, 6H).

Step g:

A mixture of 4-(2-methyl-7-morpholino-quinazolin-5-yl)oxycyclohexanamine (66 mg, 0.19 mmol), 4-chloro-2-methyl-pyrimidine (42 mg, 0.32 mmol), t-butyl xPhos palladiumcycle (13 mg, 0.02 mmol) in t-BuOH (2 mL) was added sodium tert-butoxide (200 µL of 2 M solution in THF, 0.4 mmol) and stirred overnight at room temperature. The reaction mixture was diluted with DCM, filtered though layer of Celite, concentrated. The crude was purified from silica gel chromatography (4 g cartridge) eluting with a gradient 0-6% MeOH/DCM and afford 2-methyl-N-[4-(2-methyl-7-morpholino-quinazolin-5-yl)oxycyclohexyl]-pyrimidin-4-amine (20.9 mg, 23.7%). ¹H NMR (400 MHz, CDCl3) δ 9.27 (s, 1H), 8.01 (d, J=5.8 Hz, 1H), 6.65 (d, J=2.0 Hz, 1H), 6.44 (d, J=2.1 Hz, 1H), 6.19-6.05 (m, 1H), 4.87 (s, 1H), 4.66 (s, 1H), 3.80 (t, J=4.9 Hz, 5H), 3.29 (dd, J=6.8, 3.1 Hz, 4H), 2.71 (d, J=1.9 Hz, 3H), 2.43 (d, J=1.8 Hz, 4H), 2.14 (d, J=13.8 Hz, 2H), 2.01-1.68 (m, 6H). ESI-MS m/z calc. 434.24, found 435.28 (M+1)⁺; Retention time: 0.50 minutes.

Preparation of Compound 13: N-methyl-2-[[4-(4-methyl-7-morpholino-quinazolin-5-yl)oxycyclohexyl]amino]pyrimidine-4-carboxamide

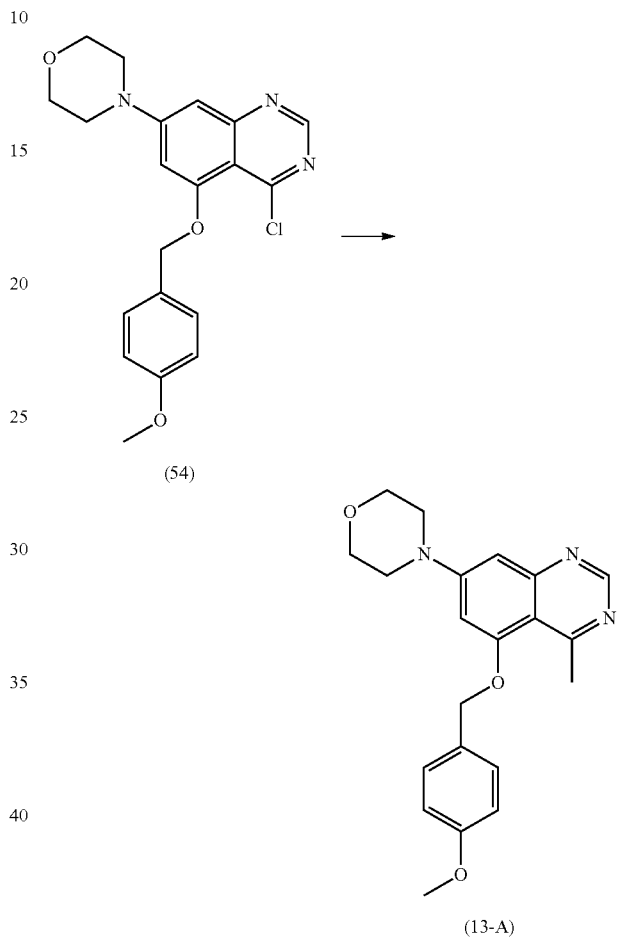

Preparation of 4-[5-[(4-methoxyphenyl)methoxy]-4-methyl-quinazolin-7-yl]morpholine (Compound (13-A))

4-[4-chloro-5-[(4-methoxyphenyl)methoxy]quinazolin-7-yl]morpholine (100 mg, 0.2592 mmol) was dissolved in THF (1.3 mL) under N2 and cooled to 0° C. PdCl2(dppf)-CH2Cl2 (10.6 mg, 0.01298 mmol) was added, followed by MeMgBr (110 µL of 3 M solution in diethyl ether, 0.3300 mmol) dropwise. The ice bath was removed, and the resultant reaction mixture was stirred at room temperature under N2 overnight. This step was repeated on larger scale, this time using 2-2.5 equivalents of MeMgBr. The products from the two batches were combined and poured into H2O. The layers were separated, and the aqueous further extracted with CH2Cl2 (2×20 mL). The combined organics were washed with brine, dried (Na2SO4), filtered and concentrated to a bright orange-yellow solid. The crude residue was purified by silica gel chromatography (40 g Isco gold column, linear gradient 0→10% MeOH/CH2Cl2) to provide 4-[5-[(4-methoxyphenyl)methoxy]-4-methyl-quinazolin-7-yl]morpholine (245.0 mg, 0.6705 mmol, 43.12%). 1H NMR (300 MHz, Chloroform-d) δ 8.85 (s, 1H), 7.46-7.35 (m, 2H), 7.01-6.92 (m, 2H), 6.84 (d, J=2.4 Hz, 1H), 6.63 (d, J=2.4 Hz, 1H), 5.12 (s, 2H), 3.93-3.86 (m, 4H), 3.84 (s, 3H), 3.44-3.32 (m, 4H), 2.90 (s, 3H). ESI-MS m/z calc. 365.17395, found 366.39 (M+1)+; Retention time: 0.64 minutes.

Preparation of 4-methyl-7-morpholino-quinazolin-5-ol (Compound (13-B))

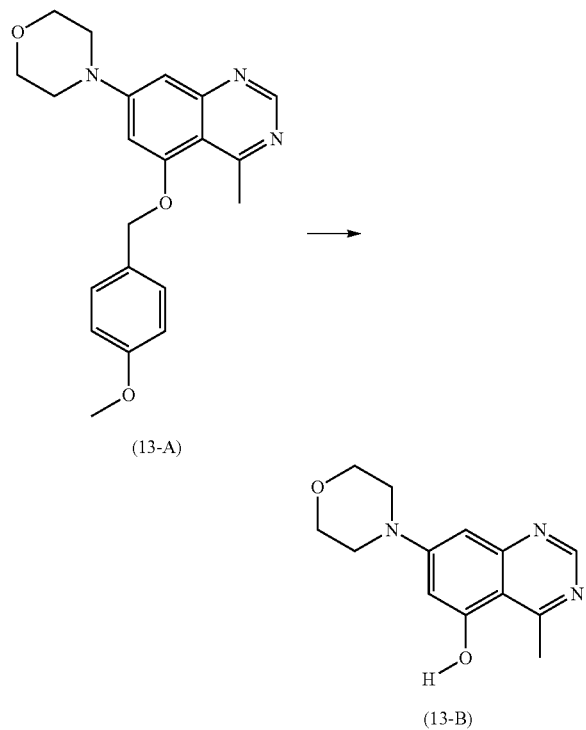

To a solution of 4-[5-[(4-methoxyphenyl)methoxy]-4-methyl-quinazolin-7-yl]morpholine (245.0 mg, 0.6705 mmol) in CH2Cl2 (6.534 mL) was added TFA (2.0 mL, 25.96 mmol). The reaction was stirred at room temperature for 16 h. The solvent was removed under N2 stream/gentle heat. The crude residue was directly carried forward to the next reaction. Mass+1: 246.41. Retention Time: 0.54

Preparation of 2-[4-(4-methyl-7-morpholino-quinazolin-5-yl)oxycyclohexyl]isoindoline-J, 3-dione (Compound (13-C))

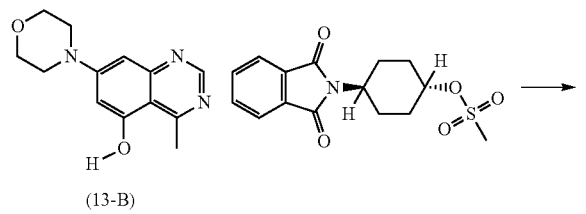

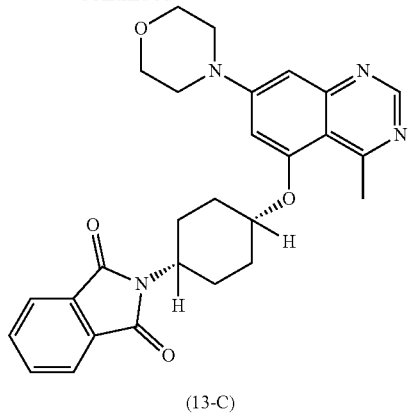

A suspension of 4-methyl-7-morpholino-quinazolin-5-ol (trifluoroacetic acid salt) (240.9 mg, 0.6705 mmol), [4-(1,3-dioxoisoindolin-2-yl)cyclohexyl]methanesulfonate (542 mg, 1.676 mmol), and Cs2CO3 (1.10 g, 3.376 mmol) in anhydrous DMF (4.2 mL) was heated to 90° C. for 5 h. LCMS shows partial progress. Added another 1.5 eq of mesylate and heated to 110° C. for 16 h. The reaction mixture was filtered through a plug of Celite, rinsing with CH2Cl2. The filtrate was evaporated, and the crude residue was dry-loaded onto Celite and purified by silica gel chromatography (40 g Isco gold column, linear gradient 0→20% MeOH/CH2Cl2) to provide 2-[4-(4-methyl-7-morpholino-quinazolin-5-yl)oxycyclohexyl]isoindoline-1,3-dione (127.9 mg, 0.2707 mmol, 40.37%). 1H NMR (300 MHz, Chloroform-d) δ 8.89 (s, 1H), 7.91-7.77 (m, 2H), 7.77-7.65 (m, 2H), 6.82 (d, J=2.3 Hz, 1H), 6.61-6.49 (m, 1H), 4.89-4.74 (m, 1H), 4.29 (tt, J=12.4, 3.9 Hz, 1H), 4.00-3.79 (m, 4H), 3.44-3.31 (m, 4H), 3.27 (s, 3H), 2.77 (qd, J=13.2, 12.7, 3.0 Hz, 2H), 2.51-2.30 (m, 2H), 1.84-1.68 (m, 4H). ESI-MS m/z calc. 472.21106, found 473.4 (M+1)+; Retention time: 0.66 minutes.

Preparation of 4-(4-methyl-7-morpholino-quinazolin-5-yl)oxycyclohexanamine (Compound (13-D))

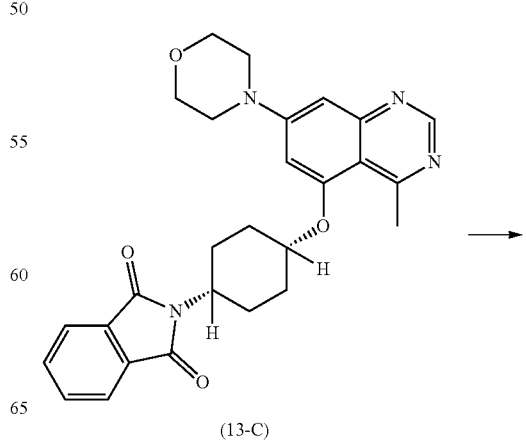

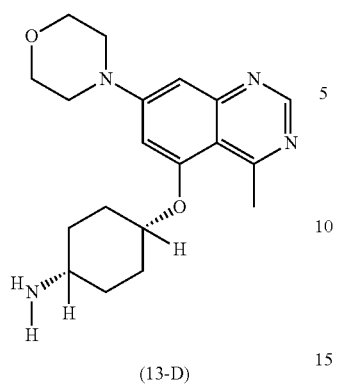

(13-D)

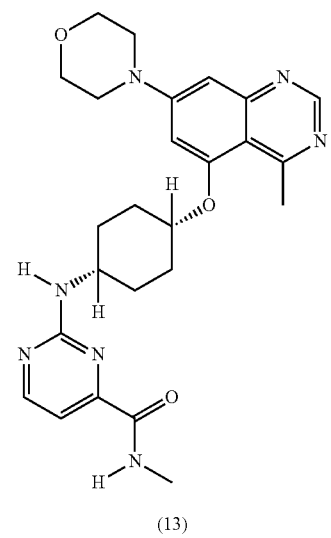

(13)

To a stirred solution of 2-[4-(4-methyl-7-morpholino-quinazolin-5-yl)oxycyclohexyl]isoindoline-1,3-dione (127.9 mg, 0.2707 mmol) in MeOH (10 mL) was added hydrazine (172 μL, 5.480 mmol). The resultant reaction was sealed and stirred at room temperature for 20 h (LCMS shows complete). The reaction mixture was concentrated. To the crude residue was added $CH_2Cl_2$. The suspension was filtered through a medium porosity glass frit (solid was rinsed several times with CH2Cl2 and collected in to the same flask). The filtrate was concentrated, and the crude residue was purified by reverse phase Isco [50 g C18 Aq column; 0→50% CH3CN/H2O (TFA modifier)]. Relevant fractions were combined and concentrated under reduced pressure to provide the product (Trifluoroacetic Acid (1)) (21.9 mg, 0.04798 mmol, 17.72%). The TFA salt was taken directly into the next reaction. Mass+1: 343.39. Retention Time: 0.52

A mixture of 4-(4-methyl-7-morpholino-quinazolin-5-yl)oxycyclohexanamine (Trifluoroacetic Acid (1)) (21.9 mg, 0.04798 mmol), 2-chloro-N-methyl-pyrimidine-4-carboxamide (12.35 mg, 0.07197 mmol), and Na2CO3 (120 μL of 2 M, 0.2400 mmol) in water (250 μL) was heated to reflux (100° C.) in a sealed microwave tube. The resultant mixture was allowed to stir 72 h. The crude suspension was treated with MeOH and a few drops of TFA, and the resultant solution was purified by reverse phase Isco [50 g C18 Aq column; 0→50% CH3CN/H2O (TFA modifier)]. Relevant fractions were combined and concentrated. The sample was dissolved in minimal 1:1 MeOH/CH2Cl2 and passed through a Stratospheres PL-HCO3 MP Resin cartridge. The filtrate was concentrated to provide the product (5.8 mg, 0.01154 mmol, 24.05%) as a pale yellow solid. 1H NMR (300 MHz, Chloroform-d) δ 8.87 (s, 1H), 8.49 (d, J=4.8 Hz, 1H), 7.75 (d, J=4.9 Hz, 1H), 7.34 (d, J=4.8 Hz, 1H), 6.82 (d, J=2.4 Hz, 1H), 6.56 (d, J=2.4 Hz, 1H), 5.18 (d, J=7.4 Hz, 1H), 4.79-4.69 (m, 1H), 4.03 (ddt, J=13.1, 7.8, 4.4 Hz, 1H), 3.89 (dd, J=5.7, 4.1 Hz, 4H), 3.42-3.27 (m, 4H), 3.05 (s, 3H), 3.01 (d, J=5.1 Hz, 3H), 2.31-2.16 (m, 2H), 2.13-2.00 (m, 2H), 2.00-1.75 (m, 4H). ESI-MS m/z calc. 477.24884, found 478.44 (M+1)+; Retention time: 0.59 minutes.

Preparation of N-methyl-2-[[4-(4-methyl-7-morpholino-quinazolin-5-yl)oxycyclohexyl]amino]pyrimidine-4-carboxamide (Compound (13))

Preparation of Compound 14: 6-(4-methylpiperazin-1-yl)-N-[4-(7-morpholinoquinazolin-5-yl)oxycyclohexyl]pyrimidin-4-amine Preparation of 4-chloro-6-(4-methylpiperazin-1-yl)pyrimidine (Compound (14-A))

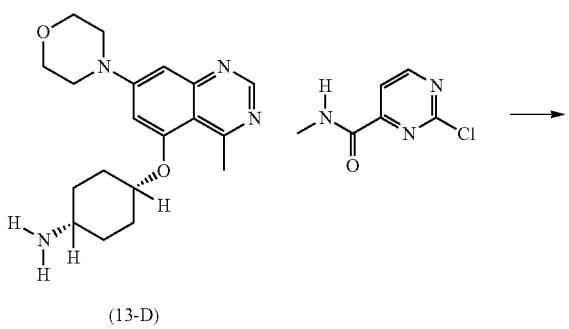

(13-D)

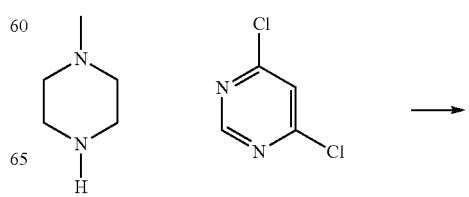

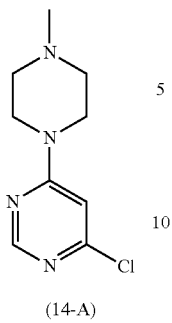

(14-A)

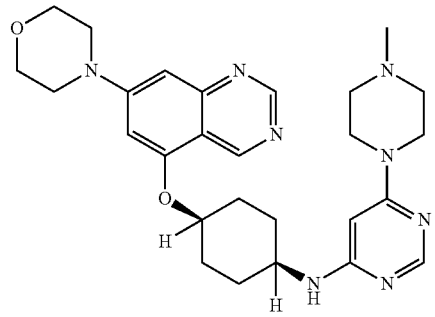

(14)

To a 0° C. solution of 4,6-dichloropyrimidine (2.0 g, 13.42 mmol) and Et3N (1.494 g, 2.058 mL, 14.76 mmol) in EtOH (40 mL) was added 1-methylpiperazine (1.344 g, 1.490 mL, 13.42 mmol). The resultant solution was warmed to room temperature, then stirred for 5 h. The reaction was concentrated in vacuo and partitioned between EtOAc and 1N NaOH. The layers were separated, and the aqueous phase was further extracted with EtOAc (2×30 mL). The combined organics were washed with brine, dried (Na2SO4), filtered and concentrated. The crude residue was dissolved in hexanes/EtOAc and allowed to stand for 5 days, during which an off-white material precipitated (not product). Filtered off the solid and concentrated the filtrate to obtain the product. 1H NMR (CDCl3) shows clean desired 4-chloro-6-(4-methylpiperazin-1-yl)pyrimidine (2.126 g, 9.896 mmol, 73.75%) 1H NMR (400 MHz, CDCl3) δ 8.37 (d, J=0.7 Hz, 1H), 6.49 (d, J=0.8 Hz, 1H), 3.67 (s, 4H), 2.56-2.41 (m, 4H), 2.34 (s, 3H). ESI-MS m/z calc. 212.08287, found 213.14 (M+1)+; Retention time: 0.39 minutes.

A suspension of 4-(7-morpholinoquinazolin-5-yl)oxycyclohexanamine (40 mg, 0.1218 mmol), 4-chloro-6-(4-methylpiperazin-1-yl)pyrimidine (28.5 mg, 0.1340 mmol), 4-chloro-6-(4-methylpiperazin-1-yl)pyrimidine (28.5 mg, 0.1340 mmol) and NaOtBu (35 mg, 0.3642 mmol) in tBuOH (800 µL) was treated with t-BuXPhos Palladacycle (8 mg, 0.01165 mmol). The reaction was sealed and heated to 100° C. in an aluminum bead bath for 2 h. The solvent was removed under N2 stream, and The crude residue was purified by silica gel chromatography (40 g Isco gold column, linear gradient 0%→10% MeOH/CH2Cl2 [+0.1% Et3N]). Relevant fractions were combined and concentrated to obtain the product (42.1 mg, 0.07509 mmol, 61.65%). 1H NMR (300 MHz, Chloroform-d) δ 9.42 (s, 1H), 9.08 (s, 1H), 8.18 (d, J=0.8 Hz, 1H), 6.77 (d, J=2.0 Hz, 1H), 6.56 (d, J=2.2 Hz, 1H), 5.44 (d, J=1.0 Hz, 1H), 4.85-4.62 (m, 2H), 3.97-3.74 (m, 5H), 3.60-3.55 (m, 4H), 3.45-3.27 (m, 4H), 2.52-2.46 (m, 4H), 2.33 (d, J=2.5 Hz, 3H), 2.26-2.15 (m, 2H), 2.05-1.91 (m, 2H), 1.91-1.64 (m, 4H). ESI-MS m/z calc. 504.2961, found 505.44 (M+1)+; Retention time: 0.53 minutes.

Preparation of 6-(4-methylpiperazin-1-yl)-N-[4-(7-morpholinoquinazolin-5-yl)oxycyclohexyl]pyrimidin-4-amine (Compound (14))

Preparation of Compound 15: N-[4-(7-morpholinoquinazolin-5-yl)oxycyclohexyl]pyrimidine-4-carboxamide

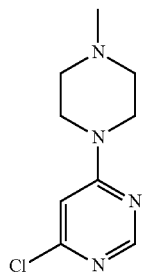

(14-A)

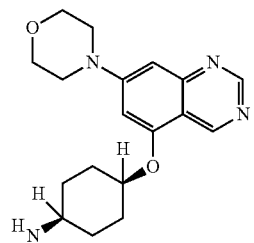

(8-A)

→

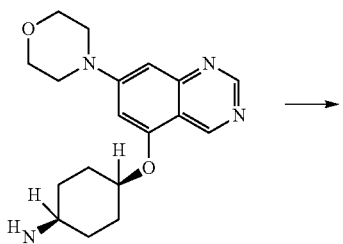

(8-A)

→

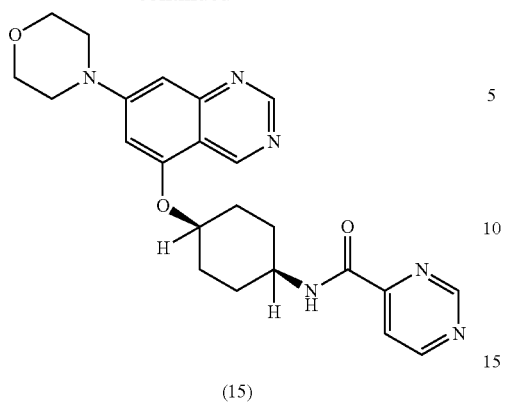

(15)

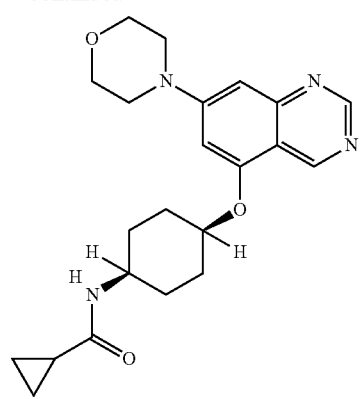

(16)

To a suspension of 4-(7-morpholinoquinazolin-5-yl)oxycyclohexanamine (40 mg, 0.1218 mmol), pyrimidine-4-carboxylic acid (23 mg, 0.1853 mmol), and Et3N (102 μL, 0.7318 mmol) in 1,4-dioxane (1.2 mL) was added T3P (235 μL of 50% w/v solution in ethyl acetate, 0.3693 mmol) dropwise. The resultant solution was heated to 50° C. for 20 h. The solvent was removed under a stream of N2, and the crude residue was purified by silica gel chromatography [12 g Isco gold column; linear gradient 0→10% MeOH/CH2Cl2 (+0.5% Et3N)], but material still contained impurities. The material was dissolved/suspended in 2 mL DMSO and purified by C18 preparatory HPLC (water/acetonitrile with TFA modifier). Relevant fractions were dried-down, and the residue was dissolved in 1:1 MeOH/CH2Cl2 and passed through a Stratospheres PL-HCO3 MP Resin cartridge. The filtrate was concentrated to provide N-[4-(7-morpholinoquinazolin-5-yl)oxycyclohexyl]pyrimidine-4-carboxamide (20.9 mg, 0.04714 mmol, 38.70%). 1H NMR (300 MHz, Chloroform-d) δ 9.47 (s, 1H), 9.26 (d, J=1.4 Hz, 1H), 9.10 (s, 1H), 8.97 (d, J=5.0 Hz, 1H), 8.12 (dd, J=5.1, 1.5 Hz, 1H), 8.02 (d, J=8.2 Hz, 1H), 6.82-6.75 (m, 1H), 6.58 (d, J=2.2 Hz, 1H), 4.83-4.73 (m, 1H), 4.20-4.07 (m, 1H), 3.95-3.82 (m, 4H), 3.43-3.31 (m, 4H), 2.33-2.17 (m, 2H), 2.06-1.82 (m, 6H). ESI-MS m/z calc. 434.20663, found 435.35 (M+1)+; Retention time: 2.48 minutes.

Preparation of Compounds 16: N-[4-(7-morpholinoquinazolin-5-yl)oxycyclohexyl]cyclopropanecarboxamide To a solution of 4-(7-morpholinoquinazolin-5-yl)oxycyclohexanamine (40 mg, 0.1218 mmol) in CH3CN (1.0 mL) was added K2CO3 (20.21 mg, 0.1462 mmol) followed by cyclopropanecarbonyl chloride (12.73 mg, 11.05 μL, 0.1218 mmol) dropwise. The resultant red-orange reaction mixture was stirred at room temperature for 1 h. The reaction mixture was concentrated. The crude residue was dissolved/suspended in 1:1 MeOH/H2O, filtered through Celite, and submitted for C18 preparatory HPLC (water/acetonitrile with TFA modifier). The relevant fractions were dried down, and the residue was dissolved in 1:1 MeOH/CH2Cl2 and passed through a Stratospheres PL-HCO3 MP Resin cartridge. The filtrate was concentrated to provide N-[4-(7-morpholinoquinazolin-5-yl)oxycyclohexyl]cyclopropanecarboxamide (7.2 mg, 0.01780 mmol, 14.61%). 1H NMR (300 MHz, Chloroform-d) δ 9.43 (s, 1H), 9.09 (s, 1H), 6.78 (d, J=2.3 Hz, 1H), 6.56 (d, J=2.2 Hz, 1H), 5.73-5.54 (m, 1H), 4.74 (t, J=3.9 Hz, 1H), 3.97 (ddd, J=14.9, 6.4, 4.1 Hz, 1H), 3.92-3.81 (m, 4H), 3.45-3.30 (m, 4H), 2.19 (dd, J=12.1, 2.7 Hz, 2H), 1.95-1.59 (m, 6H), 1.34 (tt, J=7.7, 4.6 Hz, 1H), 1.03-0.91 (m, 2H), 0.79-0.68 (m, 2H). ESI-MS m/z calc. 396.21616, found 397.44 (M+1)+; Retention time: 0.58 minutes.

Preparation of Compounds 17: N-[4-(7-morpholinoquinazolin-5-yl)oxycyclohexyl]furo[3,2-d]pyrimidin-4-amine

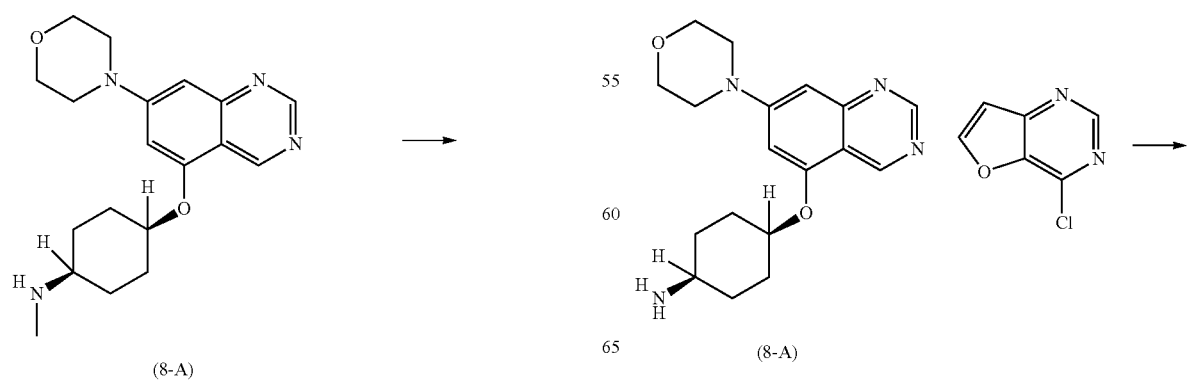

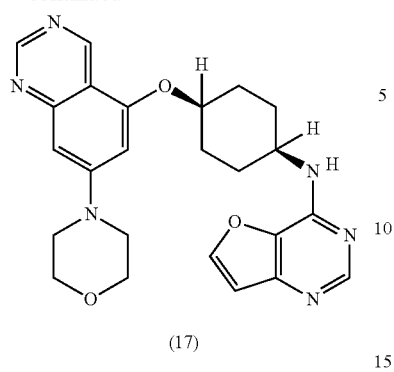

(17)

A suspension of 4-(7-morpholinoquinazolin-5-yl)oxycyclohexanamine (40 mg, 0.1218 mmol), 4-chlorofuro[3,2-d]pyrimidine (21 mg, 0.1359 mmol), and sodium tert-butoxide (35 mg, 0.3642 mmol) was degassed by bubbling N2 through the mixture for 10 min. t-BuXPhos Palladacycle (8 mg, 0.01165 mmol) was added, and the reaction was heated to 100° C. for 16 h. The reaction mixture was concentrated, dissolved/suspended in 2 mL DMSO, filtered through Celite, and purified by C18 preparatory HPLC (water/acetonitrile with TFA modifier). The relevant fractions were dried down, and the residue was dissolved in 1:1 MeOH/CH2Cl2 and passed through a Stratospheres PL-HCO3 MP Resin cartridge. The filtrate was concentrated to provide N-[4-(7-morpholinoquinazolin-5-yl)oxycyclohexyl]furo[3,2-d]pyrimidin-4-amine (10.5 mg, 0.02116 mmol, 17.38%). 1H NMR (300 MHz, Chloroform-d) δ 9.49 (s, 1H), 9.12 (s, 1H), 8.51 (s, 1H), 7.76 (d, J=2.2 Hz, 1H), 6.87 (d, J=2.2 Hz, 1H), 6.82 (dd, J=2.2, 0.5 Hz, 1H), 6.62 (d, J=2.3 Hz, 1H), 5.17 (d, J=7.9 Hz, 1H), 4.83 (d, J=2.9 Hz, 1H), 4.45-4.29 (m, 1H), 3.94-3.90 (m, 4H), 3.45-3.39 (m, 4H), 2.30 (d, J=9.4 Hz, 2H), 2.15-2.06 (m, 2H), 1.99-1.86 (m, 4H). ESI-MS m/z calc. 446.20663, found 447.12 (M+1)+; Retention time: 0.55 minutes.

Preparation of Compounds 18: 2-(4-methylpiperazin-1-yl)-N-[4-(7-morpholinoquinazolin-5-yl)oxycyclohexyl]pyrimidin-4-amine Preparation of 2-chloro-N-[4-(7-morpholinoquinazolin-5-yl)oxycyclohexyl]pyrimidin-4-amine

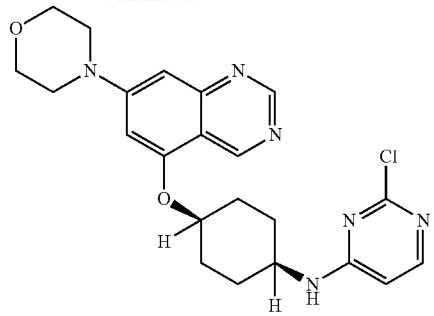

A mixture of 4-(7-morpholinoquinazolin-5-yl)oxycyclohexanamine (110 mg, 0.3349 mmol), 2,4-dichloropyrimidine (55 mg, 0.3692 mmol), and Na2CO3 (670 μL of 2 M, 1.340 mmol) in water (450 μL) was heated to reflux in a sealed microwave tube for 16 h at which time material had clustered into a large ball (solidifies upon cooling). The supernatant was removed via pipette, and the solid was broken up with a spatula and washed with several portions of water. The solid was dissolved in CH2Cl2 and the solution was dried (Na2SO4), filtered, and concentrated to a brownish-orange foam. The crude residue was purified by silica gel chromatography (40 g Isco gold column, linear gradient 0%→20% MeOH/CH2Cl2) to provide 2-chloro-N-[4-(7-morpholinoquinazolin-5-yl)oxycyclohexyl]pyrimidin-4-amine (41.2 mg, 0.09344 mmol, 27.89%). 1H NMR (300 MHz, Chloroform-d) δ 9.41 (s, 1H), 9.08 (s, 1H), 7.99 (d, J=5.7 Hz, 1H), 6.79 (d, (J=2.1 Hz, 1H), 6.57 (d, J=2.2 Hz, 1H), 6.25 (d, J=5.9 Hz, 1H), 5.24 (d, J=33.6 Hz, 1H), 4.76 (d, J=6.5 Hz, 1H), 4.15-3.77 (m, 5H), 3.45-3.29 (m, 4H), 2.34-2.15 (m, 2H), 2.07-1.93 (m, 2H), 1.93-1.70 (m, 6H).

Preparation of 2-(4-methylpiperazin-1-yl)-N-[4-(7-morpholinoquinazolin-5-yl)oxycyclohexyl]pyrimidin-4-amine

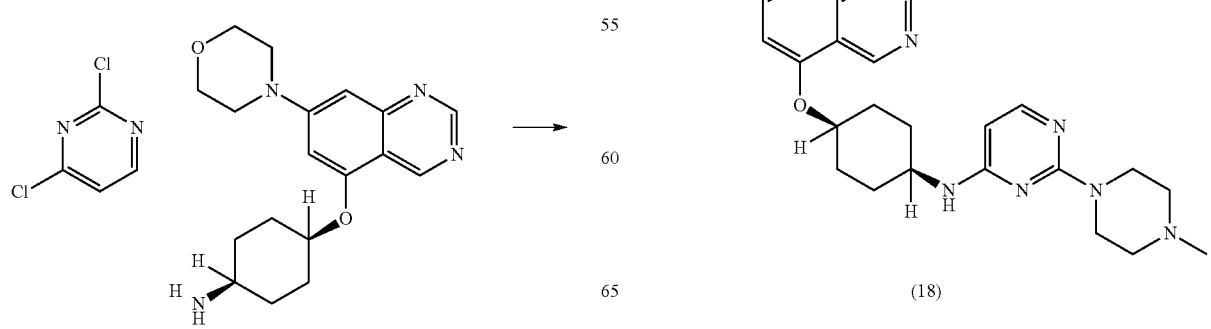

(18)

A mixture of 2-chloro-N-[4-(7-morpholinoquinazolin-5-yl)oxycyclohexyl]pyrimidin-4-amine (41.2 mg, 0.09344 mmol), 1-methylpiperazine (25 μL, 0.2254 mmol), and Hunig's base (40 μL, 0.2296 mmol) in iPrOH (700 μL) was heated to 170° C. in the microwave for 1 h. The i-PrOH was removed in vacuo. The crude residue was dissolved in CH2Cl2 and poured into saturated aqueous NH4Cl. The layers were separated, and the aqueous further extracted with CH2Cl2. The combined organics were washed with 1N NaOH and brine, dried (Na2SO4), filtered and concentrated. The crude residue was purified by Isco (40 g Gold column; 0→60% MeOH/CH2Cl2) to provided 2-(4-methylpiperazin-1-yl)-N-[4-(7-morpholinoquinazolin-5-yl)oxycyclohexyl]pyrimidin-4-amine (21.6 mg, 0.04152 mmol, 44.44%). The resulting product was dissolved in CH3CN, refluxed, and reconcentrated several times to remove residual solvents. 1H NMR (300 MHz, Chloroform-d) δ 9.43 (s, 1H), 9.09 (s, 1H), 7.89 (d, J=5.8 Hz, 1H), 6.85-6.72 (m, 1H), 6.57 (d, J=2.2 Hz, 1H), 5.68 (d, J=5.9 Hz, 1H), 4.74 (s, 1H), 4.60 (d, J=7.9 Hz, 1H), 3.95-3.70 (m, 9H), 3.44-3.32 (m, 4H), 2.49-2.39 (m, 4H), 2.32 (s, 3H), 2.27-2.14 (m, 2H), 2.05-1.92 (m, 2H), 1.92-1.76 (m, 4H). ESI-MS m/z calc. 504.2961, found 505.49 (M+1)+; Retention time: 0.53 minutes.

Preparation of Compound 19: N-methyl-2-[4-(2-methyl-7-morpholino-quinazolin-5-yl)oxycyclohexyl]-pyrimidin-4-carboxylamideas Compound 19 was prepares as shown in the synthetic scheme above for Compound 12, but employing the following procedure for step g:

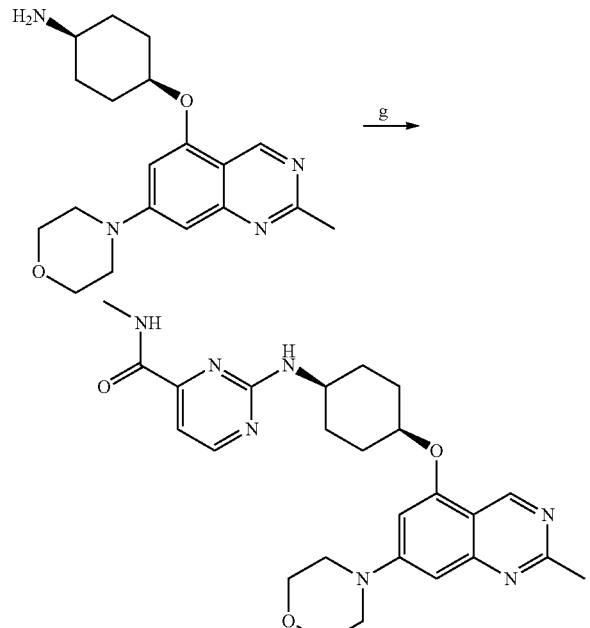

g) 2-chloro-N-methyl-pyrimidine-4-carboxamide, sodium t-butoxide, t-BuXPhos palladacycle, t-BuOH To a mixture of 4-(2-methyl-7-morpholino-quinazolin-5-yl)oxycyclohexanamine (80 mg, 0.23 mmol), chloro-N-methyl-pyrimidine-4-carboxamide (68 mg, 0.4 mmol), and t-butyl xPhos palladacycle 20 mg, 0.03 mmol) in t-BuOH (2 mL) was added sodium t-butoxide (250 μL of 2 M, 0.50 mmol), and the resultant mixture was stirred overnight at 50° C. The reaction mixture was diluted with DCM, filtered though a layer of Celite, and evaporated. The crude was purified by silica gel chromatography with a gradient 0-10% MeOH/DCM to afford the desired product. The product was purified by C18 preparatory HPLC (water/acetonitrile with TFA modifier). The relevant fractions were dried down, and the residue was passed though a PL-HCO3 MP SPE to furnish N-methyl-2-[4-(2-methyl-7-morpholino-quinazolin-5-yl)oxycyclohexyl]-pyrimidin-4-carboxylamideas (13.3 mg, 11.3%). $^1$H NMR (400 MHz, CDCl3) δ 9.17 (s, 1H), 8.28 (d, J=4.9 Hz, 1H), 7.56 (s, 1H), 7.12 (dd, J=4.8, 0.7 Hz, 1H), 6.52 (d, J=2.0 Hz, 1H), 6.32 (d, J=2.0 Hz, 1H), 4.94 (d, J=8.0 Hz, 1H), 4.54 (d, J=4.3 Hz, 1H), 3.82 (dp, J=13.9, 4.2 Hz, 1H), 3.67 (dd, J=5.9, 3.8 Hz, 4H), 3.21-3.12 (m, 4H), 2.80 (d, J=5.0 Hz, 3H), 2.59 (s, 3H), 2.12-1.95 (m, 2H), 1.88-1.75 (m, 2H), 1.73-1.51 (m, 4H). ESI-MS m/z calc. 477.25, found 478.3 (M+1)+; Retention time: 0.53 minutes.

Preparation of Compound 20: 2-methoxy-N-((1s,4s)-4-((7-morpholinoquinazolin-5-yl)oxy)cyclohexyl)acetamide

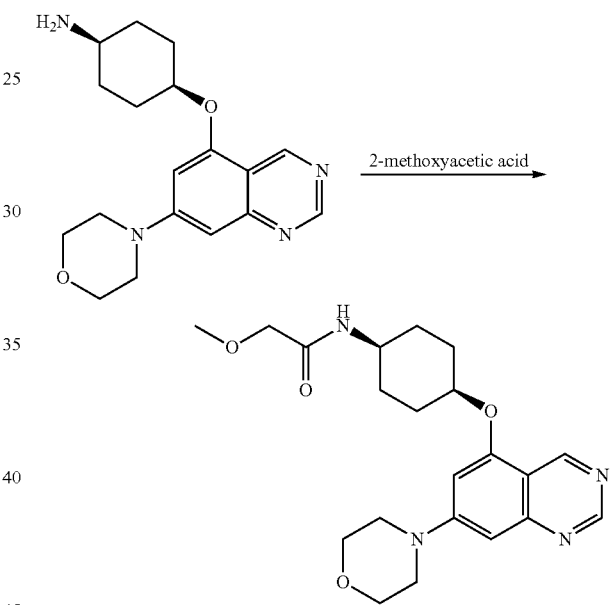

1-hydroxybenzotriazole monohydrate (16 mg, 0.118 mmol), 3-(ethyliminomethyleneamino)-N,N-dimethyl-propan-1-amine (Hydrochloric Acid (1)) (35 mg, 0.183 mmol), and 2-methoxyacetic acid (8.8 μL, 0.115 mmol) were combined in DMF (0.2 mL) under nitrogen at room temperature. The resultant mixture was stirred for 40 minutes. 4-(7-morpholinoquinazolin-5-yl)oxycyclohexanamine (25 mg, 0.0761 mmol) was added and stirring was continued for 30 minutes. Saturated sodium bicarbonate was added, and the mixture was extracted with EtOAc (2x). The combined organics were washed with water (2x), brine, dried over sodium sulfate, and concentrated under reduced pressure. The resulting residue was purified by chromatography over 4 g silica gel using a 0-10% methanol/DCM gradient. 2-methoxy-N-((1s,4s)-4-((7-morpholinoquinazolin-5-yl)oxy)cyclohexyl)acetamide (10 mg), was obtained (33% yield). 1H NMR (400 MHz, CDCl$_3$) δ 9.45 (s, 1H), 9.09 (s, 1H), 6.79 (d, J=2.0 Hz, 1H), 6.57 (d, J=2.1 Hz, 1H), 6.52 (d, J=8.4 Hz, 1H), 4.75 (p, J=3.2 Hz, 1H), 4.06-3.93 (m, 1H), 3.94-3.84 (m, 6H), 3.45 (s, 3H), 3.42-3.33 (m, 4H), 2.26-2.14 (m, 2H), 1.93-1.61 (m, 6H). ESI-MS m/z=401.32 (M+1)+.

Preparation of 3-methyl-5-[4-[(2-methylpyrimidin-4-yl)amino]cyclohexoxy]-7-morpholino-quinazolin-4-one: Compound 21
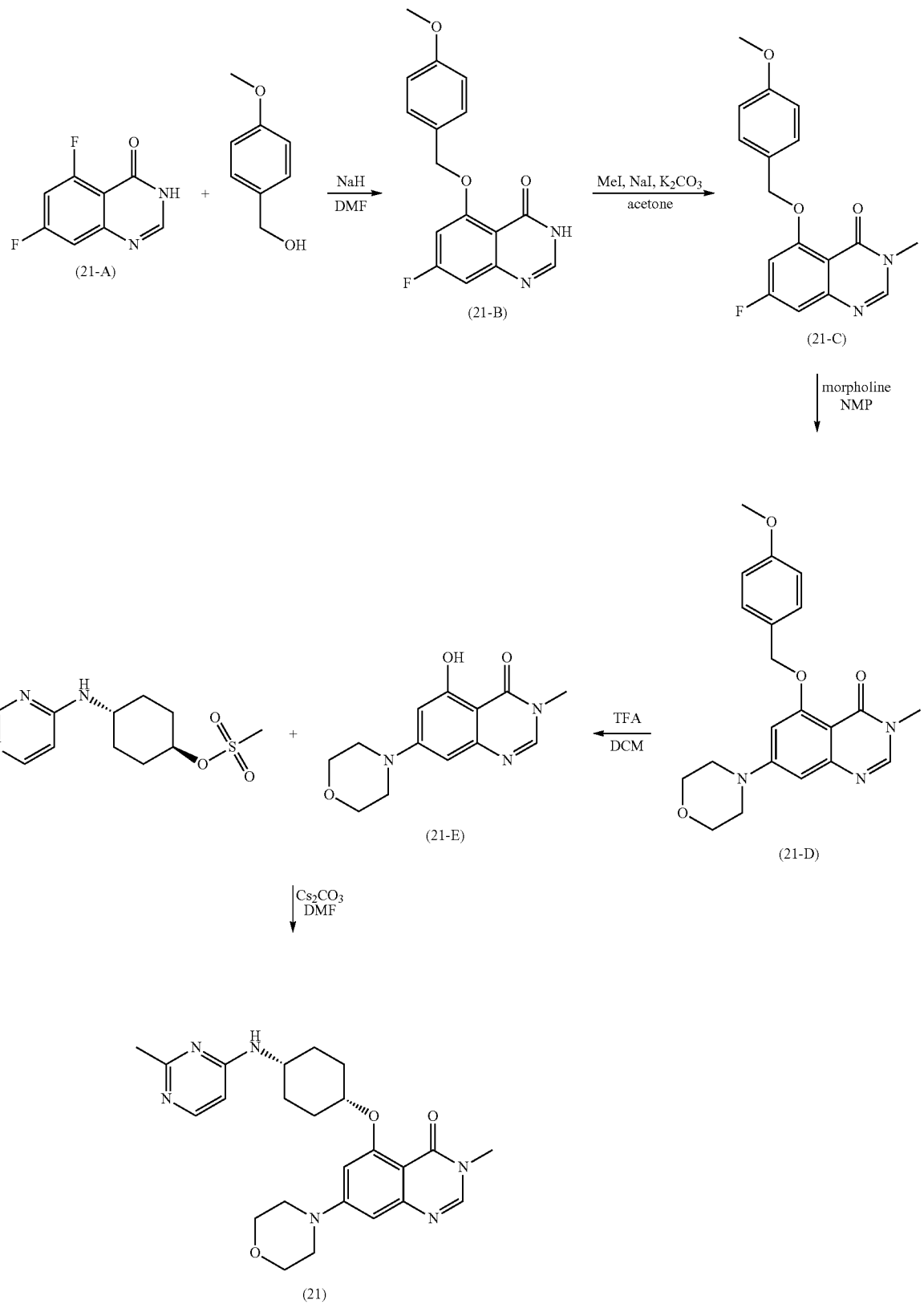

Preparation of 7-fluoro-5-[(4-methoxyphenyl)methoxy]-3H-quinazolin-4-one: Compound (21-B)

To a solution of (4-methoxyphenyl)methanol (10.69 g, 77.39 mmol) in DMF (200 mL) at 0° C. was added NaH (6.89 g, 172.3 mmol) in portions over 5 minutes, then warmed to room temperature over 30 minutes. The reaction was cooled to 0° C., and 5,7-difluoro-3H-quinazolin-4-one (23.78 g, 114.9 mmol) was added in portions over 5 minutes. The reaction was stirred at this temperature for 30 minutes, then warmed to room temperature overnight. The reaction was deemed incomplete, so 0.96 mL alcohol and 680 mg of NaH was added and the reaction stirred at room temperature for 30 minutes. The reaction was still deemed incomplete, so another 0.96 mL alcohol and 680 mg of NaH was added and the reaction stirred at room temperature overnight. The reaction was diluted with water and the pH was adjusted to 5 with acetic acid. The resulting solid was filtered and washed with water and Et$_2$O, then dried under vacuum to yield 7-fluoro-5-[(4-methoxyphenyl)methoxy]-3H-quinazolin-4-one (23.45 g, 100% yield). $^1$H-NMR (400 MHz, DMSO) δ 8.00 (s, 1H), 7.54-7.46 (m, 2H), 7.00-6.83 (m, 4H), 5.16 (s, 2H), 3.76 (s, 3H).

Preparation of 7-fluoro-5-[(4-methoxyphenyl)methoxy]-3-methyl-quinazolin-4-one: Compound (21-C)

A Biotage 10 mL microwave vial equipped with a magnetic stir bar was charged with 7-fluoro-5-[(4-methoxyphenyl)methoxy]-3H-quinazolin-4-one (406 mg, 1.352 mmol), MeI (193.9 mg, 85.04 µL, 1.366 mmol), NaI (20.00 mg, 0.1334 mmol), and K$_2$CO$_3$ (935.9 mg, 6.772 mmol) in acetone (10 mL). The vial was sealed with a Teflon septum cap and heated to 100° C. in the microwave for 15 minutes. The reaction was filtered and concentrated in vacuo. The residue was purified by on a reverse phase C18-derivatized silica gel column using 10-50% CH$_3$CN (0.1% TFA) in H$_2$O (0.1% TFA). The product fractions were combined, neutralized by addition of NaHCO$_3$ (sat), and extracted with EtOAc. The organic extracts were combined and washed with brine, dried over MgSO$_4$, filtered, and concentrated to yield 7-fluoro-5-[(4-methoxyphenyl)methoxy]-3-methyl-quinazolin-4-one (227 mg, 53.4% yield). ESI-MS m/z calc. 314.10666, found 315.09 (M+1)$^+$.

Preparation of 5-[(4-methoxyphenyl)methoxy]-3-methyl-7-morpholino-quinazolin-4-one: Compound (21-D)

A solution of 7-fluoro-5-[(4-methoxyphenyl)methoxy]-3-methyl-quinazolin-4-one (80 mg, 0.25 mmol) and morpholine (430 µL, 4.9 mmol) in anhydrous NMP (1 mL) was heated at 120° C. for 18 hours. The reaction was cooled to room temperature and diluted with water. The precipitate was filtered and washed with water, then dried under vacuum to yield 5-[(4-methoxyphenyl)methoxy]-3-methyl-7-morpholino-quinazolin-4-one (60 mg, 64% yield). ESI-MS m/z calc. 381.16885, found 382.21 (M+1)$^+$.

Preparation of 3-methyl-5-[4-[(2-methylpyrimidin-4-yl)amino]cyclohexoxy]-7-morpholino-quinazolin-4-one: Compound (21-E)

A solution of 5-[(4-methoxyphenyl)methoxy]-3-methyl-7-morpholino-quinazolin-4-one (60 mg, 0.16 mmol) and TFA (0.5 mL, 6.5 mmol) in DCM (1 mL) was stirred at room temperature overnight. The solvent was removed in vacuo to yield 5-hydroxy-3-methyl-7-morpholino-quinazolin-4-one. ESI-MS m/z calc. 261.11133, found 262.07 (M+1)$^+$.

Preparation of 3-methyl-5-[4-[(2-methylpyrimidin-4-yl)amino]cyclohexoxy]-7-morpholino-quinazolin-4-one: Compound (21)

A microwave vial equipped with a magnetic stir bar was charged with 5-hydroxy-3-methyl-7-morpholino-quinazolin-4-one (60.9 mg, 0.2331 mmol), [4-[(2-methylpyrimidin-4-yl)amino]cyclohexyl] methanesulfonate (200 mg, 0.7009 mmol), and Cs$_2$CO$_3$ (380 mg, 1.17 mmol) in DMF (3 mL). The vial was sealed with a disposable Teflon septum cap and heated in the microwave at 120° C. for 10 minutes. Added 50 mg of [4-[(2-methylpyrimidin-4-yl)amino]cyclohexyl] methanesulfonate and heated in the microwave at 120° C. for 10 minutes. The reaction was heated in the microwave at 120° C. for an additional 5 minutes. The reaction was filtered and purified on a reverse phase C18-derivatized SiO$_2$ column using 10-50% CH$_3$CN (0.1% TFA) in H$_2$O (0.1% TFA). The product fractions were combined and neutralized with NaHCO$_3$ (sat) and then extracted with EtOAc. The organic extracts were combined and washed with brine, dried over MgSO$_4$, filtered, and concentrated to yield 3-methyl-5-[4-[(2-methylpyrimidin-4-yl)amino]cyclohexoxy]-7-morpholino-quinazolin-4-one (32.6 mg, 30.8% yield). $^1$H-NMR (300 MHz, CDCl$_3$) δ 8.08 (d, J=5.9 Hz, 1H), 7.93 (s, 1H), 6.65 (d, J=2.3 Hz, 1H), 6.48 (d, J=2.2 Hz, 1H), 6.18 (d, J=6.1 Hz, 1H), 5.22 (s, 1H), 4.72 (s, 1H), 3.97-3.81 (m, 4H), 3.53 (d, J=10.6 Hz, 3H), 3.40-3.25 (m, 4H), 2.52 (s, 3H), 2.23 (d, J=12.9 Hz, 2H), 2.05-1.70 (m, 7H). ESI-MS m/z calc. 450.23795, found 451.33 (M+1)$^+$.

Preparation of Compound 22: ethyl ((1s,4s)-4-((7-morpholinoquinazolin-5-yl)oxy)cyclohexyl)carbamate

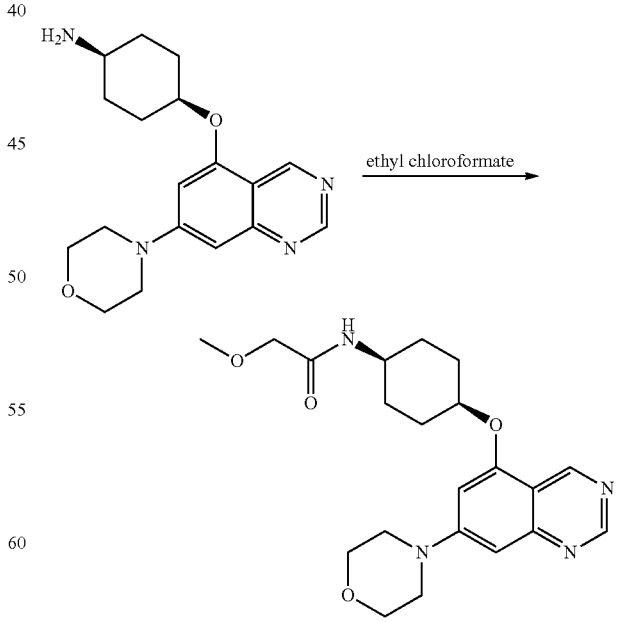

To an ice-cold solution of 4-(7-morpholinoquinazolin-5-yl)oxycyclohexanamine (25 mg, 0.076 mmol) and TEA (32 µL, 0.230 mmol) in DCM (800 µL) was added ethyl chloroformate (10.9 μL, 0.114 mmol). Allowed to stir for 30 min. The reaction was diluted with DCM and saturated sodium bicarbonate (aq) was added. The mixture was run through phase separator and the organics were concentrated under reduced pressure. Chromatographed over 4 g silica gel column using 0-10% MeOH/DCM as eluent and further purified by C18 preparatory HPLC (water/acetonitrile with TFA modifier). The relevant fractions were dried down, and the residue was passed though a PL-HCO3 MP SPE to furnish ethyl ((1s,4s)-4-((7-morpholinoquinazolin-5-yl)oxy) cyclohexyl)carbamate (2.3 mg, 7% yield) was obtained. 1H NMR (400 MHz, CDCl3) δ 9.41 (s, 1H), 9.09 (s, 1H), 6.85-6.72 (m, 1H), 6.56 (d, J=2.0 Hz, 1H), 4.78-4.56 (m, 2H), 4.12 (q, J=7.1 Hz, 2H), 3.96-3.82 (m, 4H), 3.66 (d, J=9.7 Hz, 1H), 3.46-3.31 (m, 4H), 2.25-2.08 (m, 2H), 1.90 (dt, J=12.5, 4.1 Hz, 2H), 1.84-1.61 (m, 4H), 1.25 (t, J=7.1 Hz, 3H). ESI-MS m/z=401.32 (M+1)+.

Preparation of Compound 23: 1-methyl-N-((1s,4s)-4-((7-morpholinoquinazolin-5-yl)oxy)cyclohexyl) cyclopropane-1-carboxamide

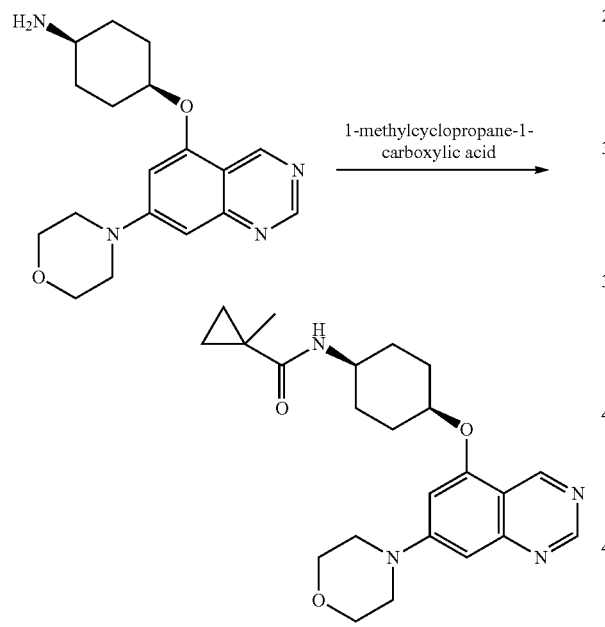

1-hydroxybenzotriazole monohydrate (16 mg, 0.118 mmol), 3 (ethyliminomethyleneamino)-N,N-dimethyl-propan-1-amine (Hydrochloric Acid (1)) (35 mg, 0.183 mmol), and 1-methylcyclopropane-1-carboxylic acid (12 mg, 0.1199 mmol) were combined in DMF (0.2 mL) under nitrogen at room temperature and allowed to stir for 40 min. 4-(7-morpholinoquinazolin-5-yl)oxycyclohexanamine (25 mg, 0.0761 mmol) was added and stirring was continued a further 30 minutes. Saturated sodium bicarbonate was added, and the mixture was extracted with EtOAc (2×). The combined organics were washed with water (2×), brine, dried over sodium sulfate, and concentrated under reduced pressure. The resulting residue was purified by chromatography over 4 g silica gel using a 0-10% methanol/DCM gradient. 1-methyl-N-((1s,4s)-4-((7-morpholinoquinazolin-5-yl)oxy)cyclohexyl)cyclopropane-1-carboxamide (13 mg, 40% yield) was. 1H NMR (400 MHz, CDCl3) δ 9.46 (s, 1H), 9.09 (s, 1H), 6.85-6.74 (m, 1H), 6.56 (d, J=2.1 Hz, 1H), 5.67 (d, J=8.1 Hz, 1H), 4.74 (t, J=3.2 Hz, 1H), 4.04-3.80 (m, 5H), 3.47-3.32 (m, 4H), 2.28-2.14 (m, 2H), 1.96-1.83 (m, 2H), 1.83-1.51 (m, 4H), 1.35 (s, 3H), 1.19 (q, J=3.8 Hz, 2H), 0.65-0.53 (m, 2H). ESI-MS m/z=411.31 (M+1)+.

Preparation of Compound 24: 1-methyl-N-((1s,4s)-4-((7-morpholinoquinazolin-5-yl)oxy)cyclohexyl) cyclopropane-1-carboxamide

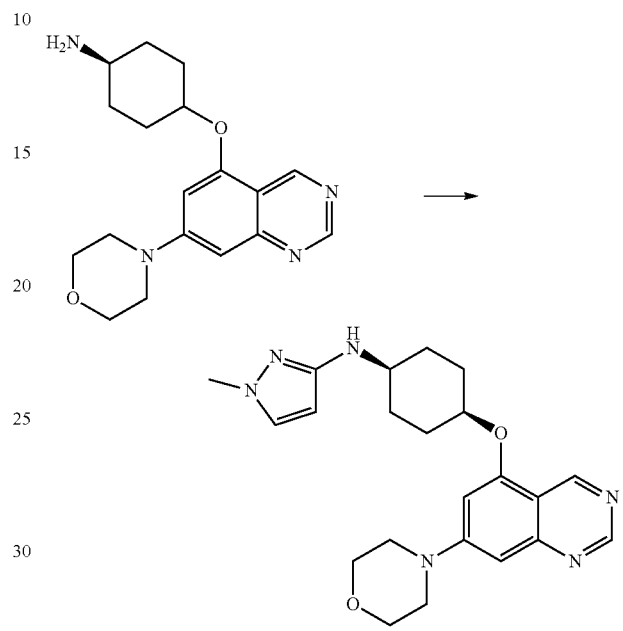

In a 2 mL microwave tube, a mixture of 4-(7-morpholino-quinazolin-5-yl)oxycyclohexanamine (27 mg, 0.082 mmol), 3-bromo-1-methyl-pyrazole (9.5 μL, 0.0999 mmol), allyl (chloro)palladium (0.8 mg, 0.004 mmol), di-tert-butyl(2',4',6'-triisopropyl-3,6-dimethoxy-[1,1'-biphenyl]-2-yl)phosphane (4 mg, 0.008 mmol), and sodium 2-methylpropan-2-olate (83 μL of 2 M in tetrahydrofuran, 0.166 mmol) in tBuOH (400 μL) was heated to 90° C. and allowed to stir overnight. The reaction was diluted with DCM and filtered through celite and the filtrate was concentrated under reduced pressure. The residue was chromatographed over 12 g silica gel using 0-10% MeOH/DCM as eluent to yield 1-methyl-N-((1s,4s)-4-((7-morpholinoquinazolin-5-yl)oxy) cyclohexyl)-1H-pyrazol-3-amine (12.5 mg, 36%). 1H NMR (400 MHz, CDCl3) δ 9.43 (d, J=1.5 Hz, 1H), 9.09 (d, J=1.6 Hz, 1H), 7.10 (d, J=2.2 Hz, 1H), 6.78 (d, J=2.1 Hz, 1H), 6.57 (d, J=1.9 Hz, 1H), 5.53 (t, J=2.0 Hz, 1H), 4.76-4.66 (m, 1H), 3.88 (dt, J=5.0, 3.0 Hz, 4H), 3.72 (d, J=1.5 Hz, 3H), 3.49-3.33 (m, 5H), 2.18 (dd, J=13.8, 4.1 Hz, 3H), 1.99 (dt, J=11.7, 3.7 Hz, 2H), 1.89-1.63 (m, 4H). ESI-MS m/z=409.33 (M+1)+.

Preparation of Compound 25: N-methyl-2-[[4-(3-methyl-7-morpholino-4-oxo-quinazolin-5-yl)oxycyclohexyl]amino]pyrimidine-4-carboxamide

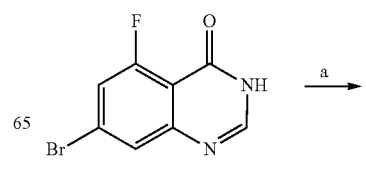

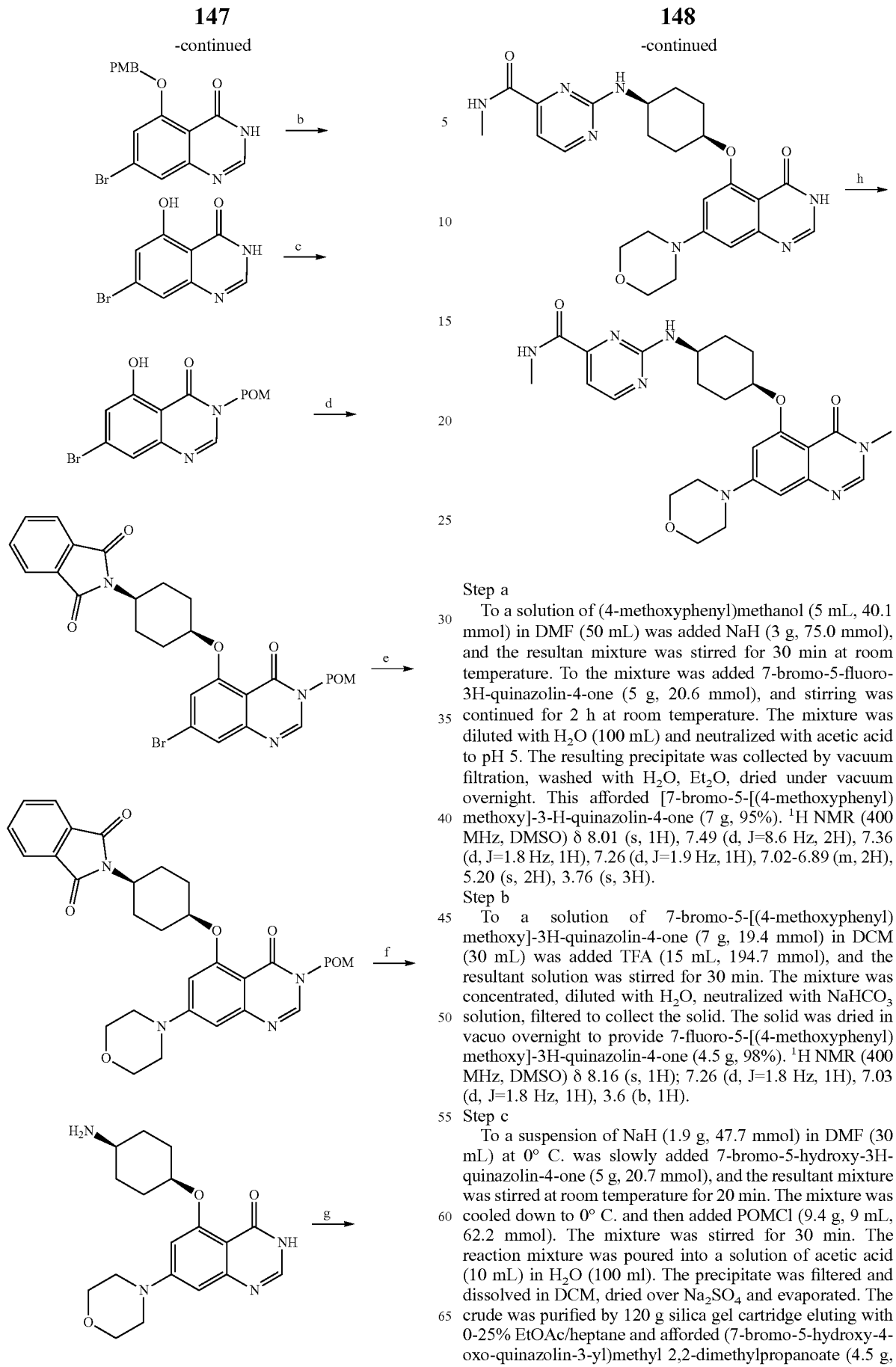

Step a

To a solution of (4-methoxyphenyl)methanol (5 mL, 40.1 mmol) in DMF (50 mL) was added NaH (3 g, 75.0 mmol), and the resultan mixture was stirred for 30 min at room temperature. To the mixture was added 7-bromo-5-fluoro-3H-quinazolin-4-one (5 g, 20.6 mmol), and stirring was continued for 2 h at room temperature. The mixture was diluted with H$_2$O (100 mL) and neutralized with acetic acid to pH 5. The resulting precipitate was collected by vacuum filtration, washed with H$_2$O, Et$_2$O, dried under vacuum overnight. This afforded [7-bromo-5-[(4-methoxyphenyl)methoxy]-3-H-quinazolin-4-one (7 g, 95%). $^1$H NMR (400 MHz, DMSO) δ 8.01 (s, 1H), 7.49 (d, J=8.6 Hz, 2H), 7.36 (d, J=1.8 Hz, 1H), 7.26 (d, J=1.9 Hz, 1H), 7.02-6.89 (m, 2H), 5.20 (s, 2H), 3.76 (s, 3H).

Step b

To a solution of 7-bromo-5-[(4-methoxyphenyl)methoxy]-3H-quinazolin-4-one (7 g, 19.4 mmol) in DCM (30 mL) was added TFA (15 mL, 194.7 mmol), and the resultant solution was stirred for 30 min. The mixture was concentrated, diluted with H$_2$O, neutralized with NaHCO$_3$ solution, filtered to collect the solid. The solid was dried in vacuo overnight to provide 7-fluoro-5-[(4-methoxyphenyl)methoxy]-3H-quinazolin-4-one (4.5 g, 98%). $^1$H NMR (400 MHz, DMSO) δ 8.16 (s, 1H); 7.26 (d, J=1.8 Hz, 1H), 7.03 (d, J=1.8 Hz, 1H), 3.6 (b, 1H).

Step c

To a suspension of NaH (1.9 g, 47.7 mmol) in DMF (30 mL) at 0° C. was slowly added 7-bromo-5-hydroxy-3H-quinazolin-4-one (5 g, 20.7 mmol), and the resultant mixture was stirred at room temperature for 20 min. The mixture was cooled down to 0° C. and then added POMCl (9.4 g, 9 mL, 62.2 mmol). The mixture was stirred for 30 min. The reaction mixture was poured into a solution of acetic acid (10 mL) in H$_2$O (100 ml). The precipitate was filtered and dissolved in DCM, dried over Na$_2$SO$_4$ and evaporated. The crude was purified by 120 g silica gel cartridge eluting with 0-25% EtOAc/heptane and afforded (7-bromo-5-hydroxy-4-oxo-quinazolin-3-yl)methyl 2,2-dimethylpropanoate (4.5 g, 61%) $^1$H NMR (400 MHz, CDCl$_3$) δ 11.35 (d, J=1.1 Hz, 1H), 8.21 (d, J=1.1 Hz, 1H), 7.39 (t, J=1.4 Hz, 1H), 7.15 (t, J=1.5 Hz, 1H), 5.90 (d, J=1.1 Hz, 2H), 1.23 (d, J=1.2 Hz, 9H).

Step d

To a mixture of (7-bromo-5-hydroxy-4-oxo-quinazolin-3-yl)methyl 2,2-dimethylpropanoate (3.5 g, 9.85 mmol), PPh$_3$ (4.1 g, 15.8 mmol) and 2-(4-hydroxycyclohexyl)isoindoline-1,3-dione (2.8 g, 11.4 mmol) in THF (35 mL) was added DIAD dropwise (3.2 g, 3.1 mL, 15.8 mmol). The mixture was stirred at room temperature for 1 h. The mixture was concentrated, purified by silica gel chromatography column eluting with EtOAc/heptane. This afforded [7-bromo-5-[4-(1,3-dioxoisoindolin-2-yl)cyclohexoxy]-4-oxo-quinazolin-3-yl]methyl 2,2-dimethylpropanoate (4.2 g, 73%). $^1$H NMR (400 MHz, CDCl$_3$) δ 8.22 (d, J=1.4 Hz, 1H), 7.73 (tt, J=5.2, 3.7 Hz, 2H), 7.65-7.57 (m, 2H), 7.40 (t, J=1.7 Hz, 1H), 7.00 (d, J=1.7 Hz, 1H), 5.90 (d, J=1.4 Hz, 2H), 4.65 (s, 1H), 4.16 (tt, J=12.9, 3.9 Hz, 1H), 2.80 (dt, J=15.5, 12.0 Hz, 2H), 2.29 (d, J=14.5 Hz, 2H), 1.74-1.52 (m, 5H), 1.16 (d, J=1.5 Hz, 9H).

Step e

A mixture of [7-bromo-5-[4-(1,3-dioxoisoindolin-2-yl)cyclohexoxy]-4-oxo-quinazolin-3-yl]methyl 2,2-dimethylpropanoate (500 mg, 0.86 mmol), morpholine (83 mg, 85 μL, 1.0 mmol), cesium carbonate (566 mg, 1.7 mmol), rac-BINAP (107 mg, 0.17 mmol) and in 1,4-dioxane (5.0 mL) was bubbled with N2 for 5 min. The mixture was heated in the microwave for 15 min at 150° C. The mixture was cooled to room temperature, diluted with DCM, filtered though a layer of Celite, and concentrated. The crude residue was purified by silica gel chromatography eluting with 0-20% DCM/EtOAc to afford [5-[4-(1,3-dioxoisoindolin-2-yl)cyclohexoxy]-7-morpholino-4-oxo-quinazolin-3-yl]methyl 2,2-dimethylpropanoate (56 mg, 11%). ESI-MS m/z calc. 588.26, found 589.3 (M+1)+; Retention time: 0.78 minutes.

Step f

To a solution of [5-[4-(1,3-dioxoisoindolin-2-yl)cyclohexoxy]-7-morpholino-4-oxo-quinazolin-3-yl]methyl 2,2-dimethylpropanoate (56 mg, 0.1 mmol) in MeOH (5 mL) was added NH$_2$NH$_2$ (100 μL, 3.2 mmol), and the resultant reaction solution was stirred at 70° C. for 90 min. After cooling down to room temperature, the mixture was concentrated and purified by 4 g silica gel cartridge eluting with 0-10% (7N NH$_3$/MeOH)/DCM to afford 5-(4-amino-cyclohexoxy)-7-morpholino-3H-quinazolin-4-one desired (30 mg, 91%). $^1$H NMR (400 MHz, CDCl$_3$) δ 7.93 (s, 1H), 6.64 (d, J=2.2 Hz, 1H), 6.41 (d, J=2.3 Hz, 1H), 3.86 (t, J=4.9 Hz, 4H), 3.31 (t, J=5.0 Hz, 4H), 3.11 (td, J=8.9, 7.1, 3.4 Hz, 1H), 2.12 (d, J=13.6 Hz, 2H), 2.03-1.91 (m, 2H), 1.82 (d, J=10.8 Hz, 2H), 1.58 (t, J=13.2 Hz, 2H).

Step g

A mixture of 5-(4-aminocyclohexoxy)-7-morpholino-3H-quinazolin-4-one (30 mg, 0.14 mmol), 2-chloro-N-methyl-pyrimidine-4-carboxamide (30 mg, 0.17 mmol) and K$_2$CO$_3$ (100 mg, 0.72 mmol) in H$_2$O (2 mL) was stirred at 100° C. for 18 h. The mixture was extracted with DCM, dried over Na$_2$SO$_4$, concentrated and purified by silica gel chromatography eluting with 0-10% MeOH/DCM. This afforded N-methyl-2-[[4-[(7-morpholino-4-oxo-3H-quinazolin-5-yl)oxy]cyclohexyl]amino]pyrimidine-4-carboxamid (15 mg, 35.9%). $^1$H NMR (400 MHz, CDCl$_3$) δ 8.48 (d, J=4.9 Hz, 1H), 8.05 (s, 1H), 7.97-7.78 (m, 2H), 7.31 (d, J=4.9 Hz, 1H), 6.73 (d, J=2.3 Hz, 1H), 6.49 (d, J=2.4 Hz, 1H), 4.04 (s, 1H), 3.93-3.81 (m, 4H), 3.50 (s, 1H), 3.43-3.29 (m, 4H), 3.00 (d, J=5.1 Hz, 3H), 2.29-2.17 (m, 2H), 2.11-1.97 (m, 2H), 1.92 (dq, J=12.7, 4.2 Hz, 2H), 1.85-1.70 (m, 2H).

Step h

A mixture of N-methyl-2-[[4-[(7-morpholino-4-oxo-3H-quinazolin-5-yl)oxy]cyclohexyl]amino]-pyrimidine-4-carboxamide (15 mg, 0.031 mmol), K$_2$CO$_3$ (80 mg, 0.58 mmol) in DMF (1 mL) was added MeI (50 μL, 0.80 mmol) and stirred at 70° C. for 30 min. The solvent was evaporated and the crude was purified by 4 g silica gel cartridge eluting with 0-10% MeOH/DCM. The product recovered was impure. The product was submitted for SFC separation to afford N-methyl-2-[[4-(3-methyl-7-morpholino-4-oxo-quinazolin-5-yl)oxycyclohexyl]amino]pyrimidine-4-carboxamide (2 mg, 16.3%). $^1$H NMR (400 MHz, CDCl$_3$) δ 8.47 (d, J=4.8 Hz, 1H), 7.91 (s, 1H), 7.76 (s, 1H), 7.28 (d, J=4.9 Hz, 1H), 6.63 (d, J=2.4 Hz, 1H), 6.47 (d, J=2.4 Hz, 1H), 5.32 (s, 1H), 4.67 (s, 1H), 3.99 (d, J=9.4 Hz, 1H), 3.92-3.80 (m, 4H), 3.50 (s, 3H), 3.37-3.23 (m, 4H), 3.01 (d, J=5.1 Hz, 3H), 2.27-2.15 (m, 2H), 2.07-1.95 (m, 2H), 1.90 (dd, J=13.0, 4.2 Hz, 2H), 1.79 (t, J=12.8 Hz, 2H). ESI-MS m/z calc. 493.24374, found 494.37 (M+1)+; Retention time: 0.6 minute.

Preparation of Compound 26: 1-methyl-N-((1s,4s)-4-((7-morpholinoquinazolin-5-yl)oxy)cyclohexyl)-1H-imidazole-4-carboxamide

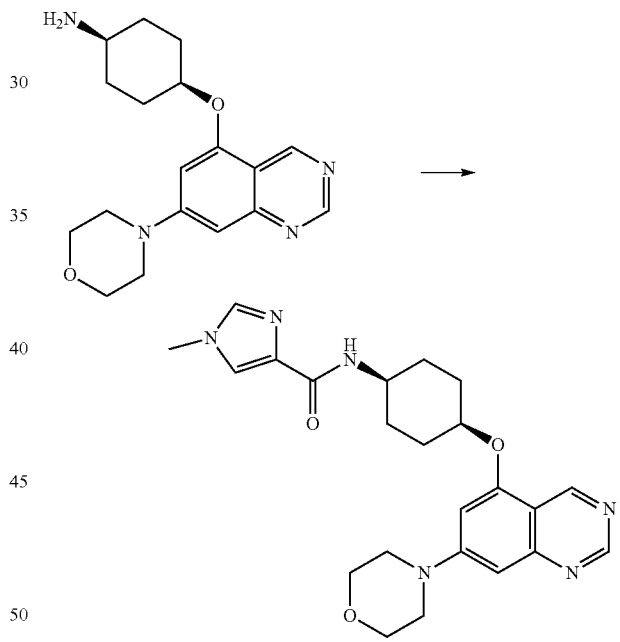

1-hydroxybenzotriazole monohydrate (16 mg, 0.118 mmol), 3-(ethyliminomethyleneamino)-N,N-dimethyl-propan-1-amine (Hydrochloric Acid (1)) (35 mg, 0.183 mmol), and 1-methyl-1H-imidazole-4-carboxylic acid (15 mg, 0.119 mmol) were combined in DMF (0.2 mL) under nitrogen at room temperature and allowed to stir for 40 min. 4-(7-morpholinoquinazolin-5-yl)oxycyclohexanamine (25 mg, 0.0761 mmol) was added, and stirring was continued a further 30 min. Saturated sodium bicarbonate was added, an the mixture was extracted with EtOAc (2×). The combined organics were washed with water (2×), brine, dried over sodium sulfate, and concentrated under reduced pressure. The resulting residue was purified by chromatography over 4 g silica gel using a 0-10% methanol/DCM gradient to yield 1-methyl-N-((1s,4s)-4-((7-morpholinoquinazolin-5-yl)oxy)

cyclohexyl)-1H-imidazole-4-carboxamide (6 mg, 17%). 1H NMR (400 MHz, CDCl₃) δ 9.44 (s, 1H), 9.10 (s, 1H), 7.51 (d, J=1.3 Hz, 1H), 7.40-7.34 (m, 1H), 7.09 (d, J=8.4 Hz, 1H), 6.78 (d, J=1.9 Hz, 1H), 6.57 (d, J=2.0 Hz, 1H), 4.74 (d, J=3.9 Hz, 1H), 4.11 (tq, J=9.9, 6.2, 5.3 Hz, 1H), 3.89 (dd, J=5.9, 3.9 Hz, 4H), 3.73 (s, 3H), 3.43-3.33 (m, 4H), 2.29-2.17 (m, 2H), 2.04-1.73 (m, 6H). ESI-MS m/z=433.05 (M+1)+.

Preparation of Compound 27

Preparation of 2-(1,4-dioxaspiro[4.5]decan-8-yloxy) pyrimidine: Compound (27-A)

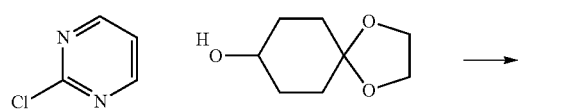

(27-A)

To a suspension of NaH (370.1 mg, 9.254 mmol) (60% in mineral oil) in DMA (2 ml), cooled with ice bath was added a solution of 1,4-dioxaspiro[4.5]decan-8-ol (1 g, 6.321 mmol) in DMA (10 mL) and imidazole (43 mg). After stirring at rt for 30 min, 2-chloropyrimidine (868.7 mg, 7.585 mmol) was added and the mixture was stirred for 30 min at rt for 2 h, then 60° C. for 1 h. The reaction was then diluted with EtOAc, washed with H2O, dried over Na2SO4 and concentrated. Purified by silica gel chromatography (40 g silica gel, EtOAc/heptane 0-50%) to yield 2-(1,4-dioxaspiro[4.5]decan-8-yloxy)pyrimidine (3.20 g, 6.230 mmol, 98.59%) that was carried on to the next reaction as is. 1H NMR (300 MHz, Chloroform-d) δ 8.43 (d, J=4.8 Hz, 2H), 6.83 (t, J=4.8 Hz, 1H), 5.06 (tt, J=6.5, 4.2 Hz, 1H), 4.06-3.75 (m, 4H), 1.98-1.77 (m, 6H), 1.64-1.55 (m, 2H). ESI-MS m/z calc. 236.11609, found 237.22 (M+1)+; Retention time: 0.72 minutes.

Preparation of 4-pyrimidin-2-yloxycyclohexanone: Compound (27-B)

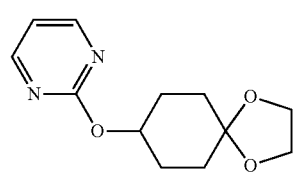

(27-A)

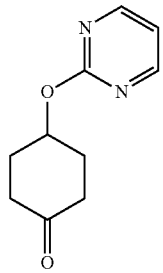

(27-B)

To a solution of 2-(1,4-dioxaspiro[4.5]decan-8-yloxy)pyrimidine (1.10 g, 4.656 mmol) in dioxane (6 mL) was added HCl (7.883 mL of 6 M, 47.30 mmol). After stirring for 2 days, the reaction mixture was evaporated, neutralized with aq saturated NaHCO₃, extracted with DCM (3×), dried with MgSO4, filtered and purified by silica gel chromatography (12 g silica gel, EtOAc/heptane 0-100%) to yield 4-pyrimidin-2-yloxycyclohexanone (800 mg, 4.162 mmol, 89.39%). 1H NMR (300 MHz, Chloroform-d) δ 8.56 (d, J=4.8 Hz, 2H), 6.98 (t, J=4.8 Hz, 1H), 5.47 (tt, J=6.4, 3.3 Hz, 1H), 2.88-2.62 (m, 2H), 2.51-2.28 (m, 5H), 2.30-2.11 (m, 2H). ESI-MS m/z calc. 192.08987, found 193.07 (M+1)+; Retention time: 0.6 minutes.

Preparation of Compounds (27-C), (27-D), and (27-E)

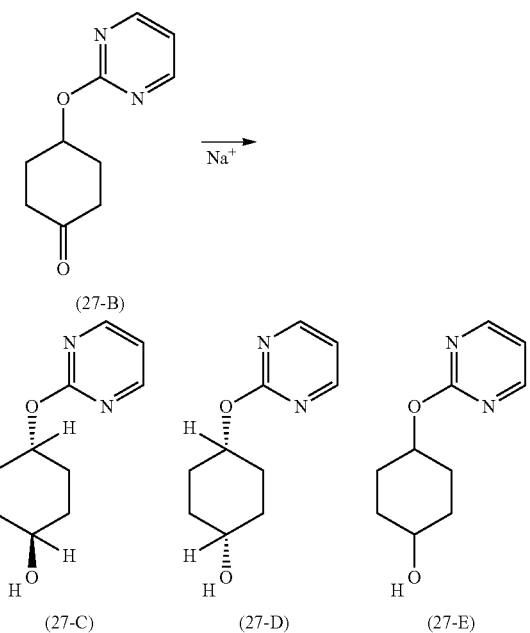

To A solution of Compound (27-B) (383 mg, 1.993 mmol) in MeOH (2 mL) was added Sodium borohydride (151 mg, 3.991 mmol). Moderate gas evolution observed with small raise in temperature. The reaction was allowed to stir for 1 hr, then it was quenched with HCl (6N 0.70 mL) and allowed to stir until gas evolution ceased. The mixture was basified to pH-8 with 1N NaOH and extracted with EtOAc (20 mL). The organics were dried over sodium sulfate and concentrated under reduced pressure. 248 mg of 4-pyrimidin-2-yloxycyclohexanol obtained. 12 mg of the sample was purified via HPLC prep chromatography (10-90% CH3CN/Water gradient) to separate cis/trans isomers. Trans-4-pyrimidin-2-yloxycyclohexanol: 1H NMR (300 MHz, Chloroform-d) δ 8.54 (d, J=4.8 Hz, 2H), 6.95 (t, J=4.8 Hz, 1H), 5.05 (tt, J=9.4, 4.0 Hz, 1H), 3.91-3.75 (m, 1H), 2.26-1.99 (m, 4H), 1.76-1.41 (m, 4H). Cis-4-pyrimidin-2-yloxycyclohexanol: 1H NMR (300 MHz, Chloroform-d) δ 8.62 (d, J=4.9 Hz, 2H), 7.04 (t, J=4.9 Hz, 1H), 5.21 (tt, J=5.3, 2.6 Hz, 1H), 4.56 (s, 1H), 3.85 (p, J=5.9 Hz, 1H), 2.17-2.02 (m, 2H), 1.88-1.67 (m, 6H).

Preparation of 7-morpholinoquinazolin-5-ol: Compound (1-F)

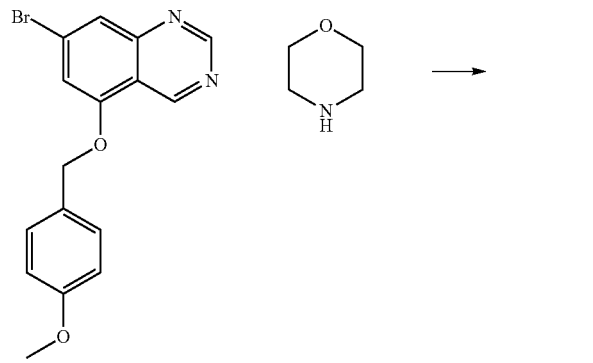

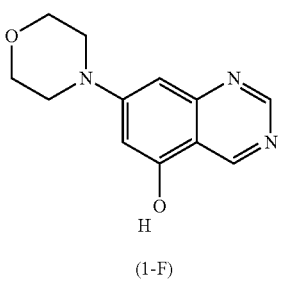

(1-F)

A suspension of 7-bromo-5-[(4-methoxyphenyl)methoxy]quinazoline (300 mg, 0.8691 mmol), Pd(OAc)2 (18 mg, 0.08017 mmol), and RuPhos (81.10 mg, 0.1738 mmol) in 1,4-dioxane (5 mL) in a 20 ml microwave vial was bubbled with N2. Morpholine (113.6 mg, 113.7 µL, 1.304 mmol) was added, followed by sodium tert-butoxide (250.5 mg, 2.607 mmol). The vial was sealed and heated at 100° C. for 19 h. Aqueous NH4Cl was added, and the mixture was extracted with EtOAc (6×). The combined organic phase was dried over MgSO4, filtered, and concentrated. The crude product was further purified twice by silica gel chromatography (4 g+12 g silica gel, MeOH/DCM 0-10%) to yield 7-morpholinoquinazolin-5-ol (147 mg, 0.6357 mmol, 73.14%). 1H NMR (300 MHz, DMSO-d6) δ 10.86 (s, 1H), 9.23 (s, 1H), 8.93 (s, 1H), 6.72 (d, J=2.1 Hz, 1H), 6.66 (d, J=2.2 Hz, 1H), 3.76 (t, J=4.9 Hz, 4H), 3.33 (dd, J=6.2, 3.4 Hz, 4H). ESI-MS m/z calc. 231.10078, found 232.22 (M+1)+; Retention time: 0.49 minutes.

Preparation of trans-(4-pyrimidin-2-yloxycyclohexyl)methanesulfonate: Compound (27-F)

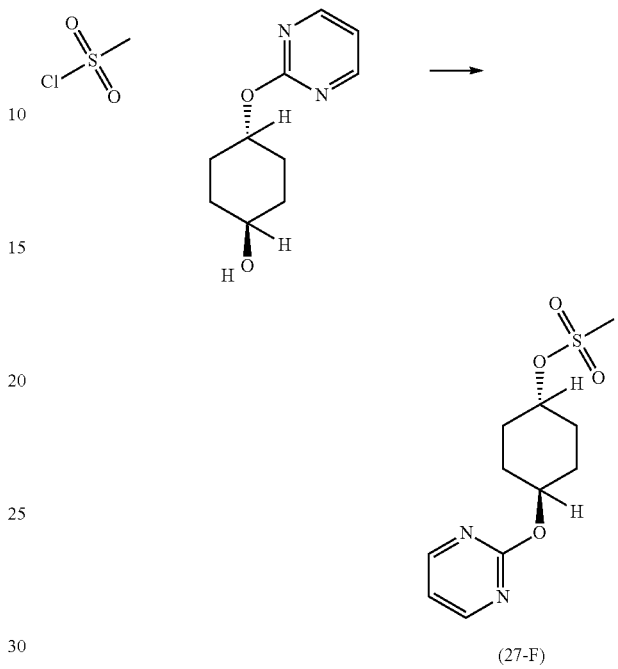

(27-F)

A solution of trans-4-pyrimidin-2-yloxycyclohexanol (80 mg, 0.4119 mmol) (from FC1), TEA (125.1 mg, 172.3 µL, 1.236 mmol) in DCM (5 mL) was treated with methanesulfonyl chloride (70.77 mg, 47.82 µL, 0.6178 mmol) for 1 h. The reaction mixture was evaporated, and the residue was purified by flash chromatography (4 g silica gel, EtOAc/DCM 0-30%) to yield trans-(4-pyrimidin-2-yloxycyclohexyl) methanesulfonate (74 mg, 0.2717 mmol, 65.95%). 1H NMR (300 MHz, Chloroform-d) δ 8.43 (d, J=4.8 Hz, 2H), 6.86 (t, J=4.8 Hz, 1H), 5.05 (tt, J=6.6, 3.4 Hz, 1H), 4.78 (tt, J=7.0, 3.2 Hz, 1H), 2.17-1.93 (m, 5H), 1.82 (tdd, J=13.0, 5.7, 3.5 Hz, 4H). ESI-MS m/z calc. 272.08307, found 273.12 (M+1)+; Retention time: 0.76 minutes.

Preparation of 4-[5-cis-(4-pyrimidin-2-yloxycyclohexoxy)quinazolin-7-yl]morpholine: Compound (27)

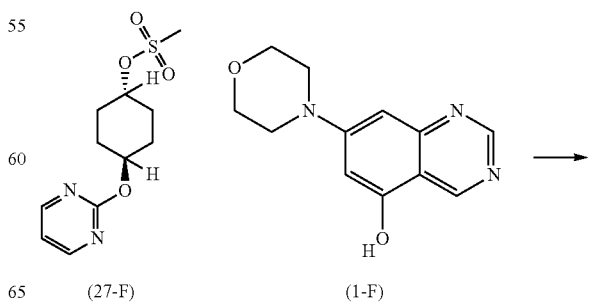

(27-F)     (1-F)

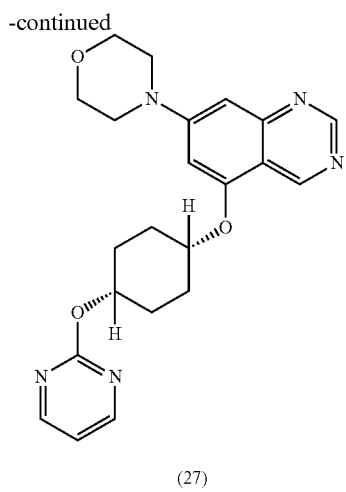

(27)

A mixture of trans-(4-pyrimidin-2-yloxycyclohexyl) methanesulfonate (58.7 mg, 0.2156 mmol), 7-morpholinoquinazolin-5-ol (40 mg, 0.1730 mmol), and Cs2CO3 (67.64 mg, 0.2076 mmol) in Dioxane (1 mL) and DMF (1 ml) was sealed in a 5 mL microwave tube and heated to 110° C. for 15 h. The reaction mixture was concentrated under reduced pressure. The residue was dissolved in DCM/MeOH 9:1 and filtered through celite. The filtrate was evaporated and purified by silica gel chromatography (2×4 g silica gel, MeOH/DCM 0-5%) to yield 4-[5-cis-(4-pyrimidin-2-yloxycyclohexoxy)quinazolin-7-yl]morpholine (45 mg, 0.0994 mmol, 57.45%). 1H NMR (300 MHz, Chloroform-d) δ 9.45 (s, 1H), 9.10 (s, 1H), 8.53 (d, J=4.8 Hz, 2H), 6.93 (t, J=4.8 Hz, 1H), 6.85-6.72 (m, 1H), 6.60 (d, J=2.1 Hz, 1H), 5.20 (dq, J=7.6, 3.7 Hz, 1H), 4.67 (dt, J=6.3, 3.1 Hz, 1H), 3.99-3.79 (m, 4H), 3.51-3.15 (m, 4H), 2.38-2.06 (m, 4H), 2.11-1.78 (m, 4H). ESI-MS m/z calc. 407.19574, found 408.35 (M+1)+; Retention time: 0.63 minutes.

Preparation of Compound 28: 4-[5-trans-(4-pyrimidin-2-yloxycyclohexoxy)quinazolin-7-yl]morpholine Preparation of cis-(4-pyrimidin-2-yloxycyclohexyl) methanesulfonate: Compound (27-F)

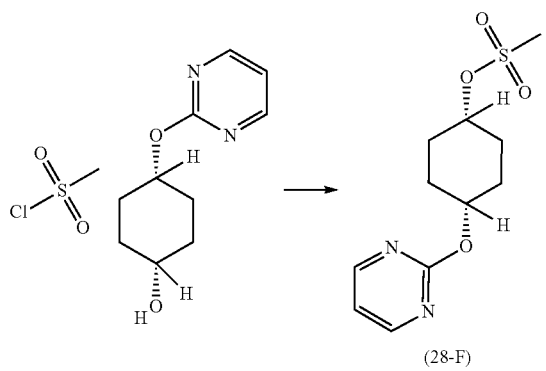

(28-F)

To a solution of cis-4-pyrimidin-2-yloxycyclohexanol (160 mg, 0.8238 mmol) (FC2) and TEA (250.0 mg, 344.4 µL, 2.471 mmol) in DCM (1078 mL) was added methane sulfonyl chloride (140.7 mg, 95.07 µL, 1.228 mmol). The mixture was stirred at rt for 1 h, concentrated, and chromatographed over 12 g silica gel using 0→70% EtOAc/heptane as eluant to yield cis-(4-pyrimidin-2-yloxycyclohexyl) methanesulfonate (142 mg, 0.5214 mmol, 63.31%). 1H NMR (300 MHz, Chloroform-d) δ 8.51 (d, J=4.8 Hz, 2H), 6.93 (t, J=4.8 Hz, 1H), 5.15 (tt, J=7.9, 3.1 Hz, 1H), 4.97-4.70 (m, 1H), 3.04 (s, 3H), 2.38-2.04 (m, 4H), 1.95-1.68 (m, 4H). ESI-MS m/z calc. 272.08307, found 273.16 (M+1)+; Retention time: 0.74 minutes.

Preparation of 4-[5-(4-pyrimidin-2-yloxycyclohexoxy)quinazolin-7-yl]morpholine: Compound (27)

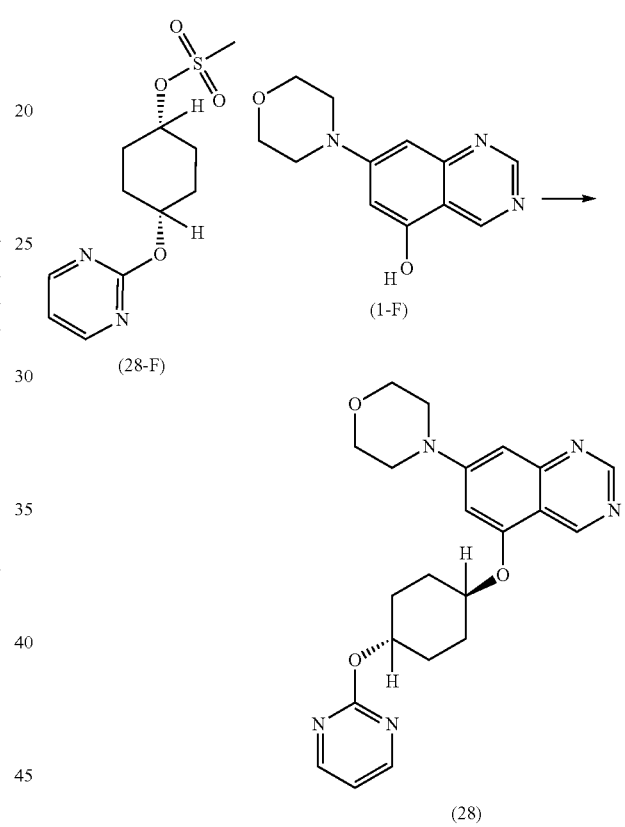

(28)

A mixture of cis-(4-pyrimidin-2-yloxycyclohexyl) methanesulfonate (43 mg, 0.1579 mmol), 7-morpholinoquinazolin-5-ol (40 mg, 0.1730 mmol), and Cs2CO3 (67.64 mg, 0.2076 mmol) in dioxane (1 mL) and DMF (1 ml) was sealed in a 5 mL microwave tube and heated to 110° C. for 15 h. The reaction mixture was concentrated under reduced pressure. The residue was dissolved in DCM/MeOH 9:1, filtered through celite. The filtrate was evaporated and purified by silica gel chromatography (2×4 g silica gel, MeOH/DCM 0-5%) to yield 4-[5-trans-(4-pyrimidin-2-yloxycyclohexoxy)quinazolin-7-yl]morpholine (14.5 mg, 0.03203 mmol, 18.51%). 1H NMR (300 MHz, Chloroform-d) δ 9.43 (s, 1H), 9.10 (s, 1H), 8.54 (d, J=4.8 Hz, 2H), 6.95 (t, J=4.8 Hz, 1H), 6.80 (dd, J=2.1, 0.8 Hz, 1H), 6.62 (d, J=2.0 Hz, 1H), 5.29-5.24 (m, 1H), 4.80-4.59 (m, 1H), 4.11-3.77 (m, 4H), 3.58-3.30 (m, 4H), 2.33-2.20 (m, 4H), 2.04-1.70 (m, 4H). ESI-MS m/z calc. 407.19574, found 408.39 (M+1)+; Retention time: 0.62 minutes.

Preparation of Compounds 29 and 35

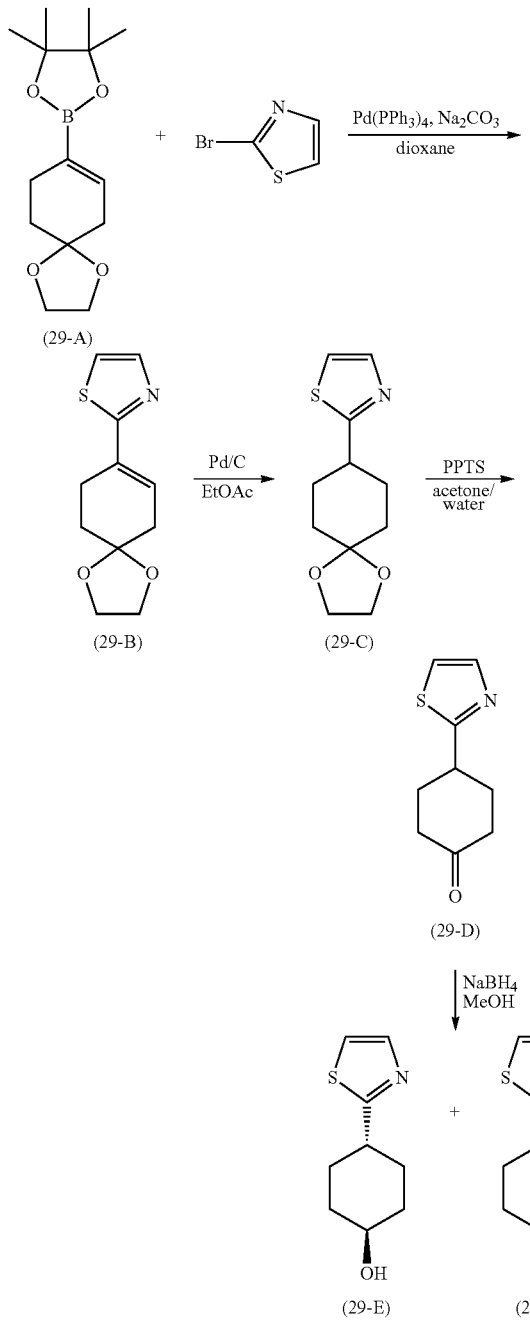

Preparation of 2-(1,4-dioxaspiro[4.5]dec-7-en-8-yl)thiazole: Compound (29-B)

A mixture of 2-(1,4-dioxaspiro[4.5]dec-7-en-8-yl)-4,4,5,5-tetramethyl-1,3,2-dioxaborolane (2.0 g, 7.5 mmol), 2-bromothiazole (1.27 g, 7.74 mmol), Pd(PPh$_3$)$_4$ (436 mg, 0.377 mmol), and Na$_2$CO$_3$ (7.60 mL of 2M solution, 15.2 mmol) in dioxane (40 mL) was evacuated and back-filled with nitrogen (repeated 2 times), then heated to 90° C. for 6 hours. The reaction was cooled to room temperature and diluted with water, then extracted with EtOAc. The organic extracts were combined and washed with brine, dried over MgSO$_4$, filtered, and concentrated. The residue was purified by flash chromatography using EtOAc and heptane to yield 2-(1,4-dioxaspiro[4.5]dec-7-en-8-yl)thiazole (889 mg, 53.0% yield). $^1$H-NMR (300 MHz, CDCl$_3$) δ 7.75 (d, J=3.3 Hz, 1H), 7.19 (d, J=3.3 Hz, 1H), 6.63-6.52 (m, 1H), 4.04 (s, 4H), 3.00-2.74 (m, 2H), 2.69-2.38 (m, 2H), 1.94 (t, J=6.6 Hz, 2H).

Preparation of 2-(1,4-dioxaspiro[4.5]decan-8-yl)thiazole: Compound (29-C)

A mixture of 2-(1,4-dioxaspiro[4.5]dec-7-en-8-yl)thiazole (889 mg, 3.98 mmol) and 10% palladium on activated carbon (425 mg, 0.399 mmol) in EtOAc (15 mL) was stirred at room temperature under 1 atm of hydrogen overnight. The reaction was filtered through Celite and concentrated in vacuo to yield 2-(1,4-dioxaspiro[4.5]decan-8-yl)thiazole (860 mg, 93.9% yield). $^1$H-NMR (300 MHz, CDCl$_3$) δ 7.70 (d, J=3.3 Hz, 1H), 7.22 (d, J=3.3 Hz, 1H), 3.99 (s, 4H), 3.11 (tt, J=11.1, 3.8 Hz, 1H), 2.28-2.12 (m, 2H), 1.99-1.83 (m, 4H), 1.72 (td, J=13.3, 4.3 Hz, 2H). ESI-MS m/z calc. 225.08235, found 226.05 (M+1)$^+$.

Preparation of 4-thiazol-2-ylcyclohexanone: Compound (29-D)

A solution of 2-(1,4-dioxaspiro[4.5]decan-8-yl)thiazole (860 mg, 3.82 mmol) and pyridinium p-toluenesulfonate (1.93 g, 7.68 mmol) in acetone (19 mL) and water (19 mL) was heated to reflux overnight. The acetone was removed in vacuo. The aqueous layer was extracted with EtOAc. The organic extracts were combined and washed with brine, dried over MgSO$_4$, filtered, and concentrated to yield 4-thiazol-2-ylcyclohexanone (641.5 mg, 90% yield). $^1$H-NMR (300 MHz, CDCl$_3$) δ 7.74 (d, J=3.3 Hz, 1H), 7.28 (d, J=0.8 Hz, 1H), 3.53 (tt, J=10.4, 3.4 Hz, 1H), 2.66-2.40 (m, 6H), 2.27-2.05 (m, 2H). ESI-MS m/z calc. 181.05614, found 182.02 (M+1)$^+$.

Preparation of Compounds (29-E) and (29-F)

To a solution of 4-thiazol-2-ylcyclohexanone (564 mg, 3.11 mmol) in MeOH (15 mL) at 0° C. was added NaBH$_4$ (244 mg, 6.32 mmol). The reaction was warmed to room temperature over 1 hour. The solvent was removed in vacuo. The reaction was diluted with water and then extracted with EtOAc. The organic extracts were combined and washed with brine, dried over MgSO$_4$, filtered, and concentrated to yield 4-thiazol-2-ylcyclohexanol (492 mg, 82.4% yield). $^1$H-NMR (300 MHz, CDCl$_3$) δ 7.68 (t, J=3.2 Hz, 1H), 7.20 (dd, J=5.3, 3.3 Hz, 1H), 4.11-4.01 (m, 1H), 3.70 (tt, J=10.6, 4.3 Hz, 1H), 3.16-2.90 (m, 1H), 2.29-2.16 (m, 2H), 2.16-2.05 (m, 2H), 1.73-1.56 (m, 2H), 1.54-1.35 (m, 2H). ESI-MS m/z calc. 183.07178, found 184.0 (M+1)$^+$.

A mixture of trans- and cis-4-thiazol-2-ylcyclohexanol (492 mg, 2.68 mmol) was purified by SFC using CO$_2$ and EtOH (0.2% Et$_2$NH) to give trans-4-thiazol-2-ylcyclohexanol (381 mg, 2.08 mmol)$^1$H-NMR (300 MHz, CDCl$_3$) δ 7.70 (d, J=3.3 Hz, 1H), 7.21 (d, J=3.3 Hz, 1H), 3.72 (tt, J=10.6, 4.3 Hz, 1H), 3.02 (tt, J=11.9, 3.7 Hz, 1H), 2.33-2.19 (m, 2H), 2.19-2.05 (m, 2H), 1.77-1.37 (m, 4H) and cis-4-thiazol-2-ylcyclohexanol (65.7 mg, 0.359 mmol) $^1$H-NMR (400 MHz, CDCl$_3$) δ 7.70 (d, J=3.3 Hz, 1H), 7.22 (dt, J=7.2, 3.6 Hz, 1H), 4.08 (s, 1H), 3.11 (tt, J=10.2, 3.9 Hz, 1H), 2.19-2.01 (m, 2H), 2.01-1.92 (m, 2H), 1.92-1.81 (m, 2H), 1.81-1.70 (m, 2H).

Preparation of Compound (29)

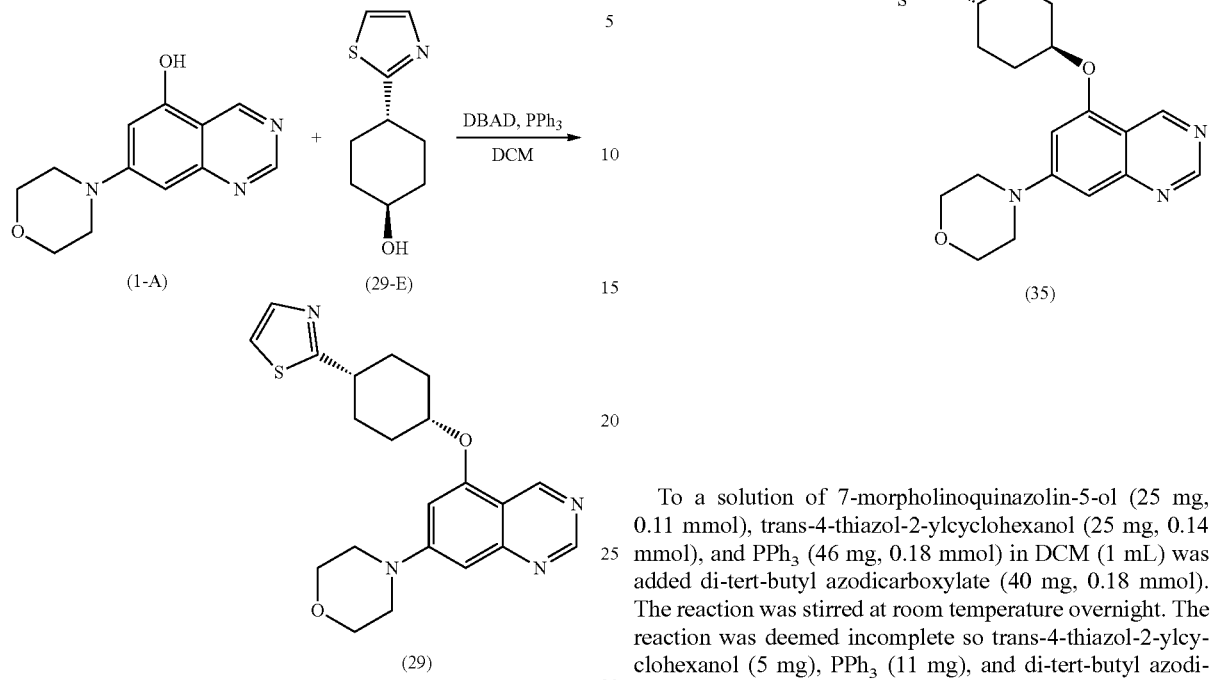

To a solution of 7-morpholinoquinazolin-5-ol (25 mg, 0.11 mmol), cis-4-thiazol-2-ylcyclohexanol (30 mg, 0.16 mmol), and PPh$_3$ (52 mg, 0.20 mmol) in DCM (1 mL) was added di-tert-butyl azodicarboxylate (45 mg, 0.20 mmol). The reaction was stirred at room temperature overnight. The reaction was concentrated in vacuo and the residue was purified on a reverse phase C18-derivatized SiO2 column using 5-50% CH$_3$CN (0.1% TFA) in H$_2$O (0.1% TFA). The product fractions were combined and neutralized with NaHCO$_3$ (sat) and then extracted with EtOAc. The organic extracts were combined and washed with brine, dried over MgSO4, filtered, and concentrated to yield 4-[5-(trans-4-thiazol-2-ylcyclohexoxy)quinazolin-7-yl]morpholine (17.2 mg, 38.5%). $^1$H-NMR (300 MHz, CDCl$_3$) δ 9.42 (s, 1H), 9.09 (s, 1H), 7.74 (d, J=3.3 Hz, 1H), 7.26 (d, J=3.3 Hz, 1H), 6.83 (d, J=1.8 Hz, 1H), 6.63 (d, J=2.0 Hz, 1H), 4.63-4.42 (m, 1H), 4.01-3.84 (m, 4H), 3.49-3.31 (m, 4H), 3.30-3.10 (m, 1H), 2.39 (d, J=9.6 Hz, 4H), 2.04-1.58 (m, 4H). ESI-MS m/z calc. 396.162, found 397.32 (M+1)$^+$.

Preparation of Compound (35)

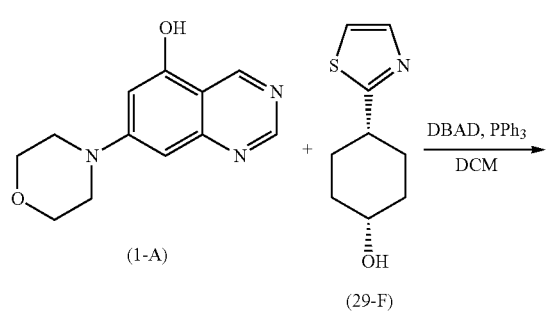

To a solution of 7-morpholinoquinazolin-5-ol (25 mg, 0.11 mmol), trans-4-thiazol-2-ylcyclohexanol (25 mg, 0.14 mmol), and PPh$_3$ (46 mg, 0.18 mmol) in DCM (1 mL) was added di-tert-butyl azodicarboxylate (40 mg, 0.18 mmol). The reaction was stirred at room temperature overnight. The reaction was deemed incomplete so trans-4-thiazol-2-ylcyclohexanol (5 mg), PPh$_3$ (11 mg), and di-tert-butyl azodicarboxylate (10 mg) were added and the reaction stirred at room temperature for 2 hours. The reaction was concentrated in vacuo and the residue was purified on a reverse phase C18-derivatized SiO2 column using 5-40% CH$_3$CN (0.1% TFA) in H$_2$O (0.1% TFA). The product fractions were combined and neutralized with NaHCO$_3$ (sat) and then extracted with EtOAc. The organic extracts were combined and washed with brine, dried over MgSO4, filtered, and concentrated to yield 4-(5-((cis-4-(thiazol-2-yl)cyclohexyl)oxy)quinazolin-7-yl)morpholine (14.8 mg, 33.2% yield). $^1$H-NMR (300 MHz, CDCl$_3$) δ 9.47 (s, 1H), 9.09 (s, 1H), 7.74 (d, J=3.3 Hz, 1H), 7.27 (d, J=3.3 Hz, 1H), 6.84 (d, J=1.6 Hz, 1H), 6.61 (d, J=1.9 Hz, 1H), 4.87 (s, 1H), 3.96-3.84 (m, 4H), 3.51-3.38 (m, 4H), 3.31-3.16 (m, 1H), 2.42-2.27 (m, 2H), 2.22-2.05 (m, 4H), 1.96-1.82 (m, 2H). ESI-MS m/z calc. 396.162, found 397.26 (M+1)$^+$.

Preparation of Compounds 30 and 38

Preparation of Compounds (30-A) and (30-B)

Compounds (30-A) and (30-B) were prepared in a similar manner as that for Compounds (29-E) and (29-F). A mixture of trans- and cis-4-(2-methylpyrimidin-4-yl)cyclohexanol (465 mg, 2.42 mmol) was purified by SFC using CO$_2$ and EtOH (0.2% Et$_2$NH) to give trans-4-(2-methylpyrimidin-4-yl)cyclohexanol (331 mg, 1.69 mmol) $^1$H-NMR (300 MHz, CDCl$_3$) δ 8.53 (d, J=5.2 Hz, 1H), 6.98 (d, J=5.2 Hz, 1H), 3.82-3.62 (m, 1H), 2.72 (s, 3H), 2.62 (tt, J=12.0, 3.5 Hz, 1H), 2.23-2.09 (m, 2H), 2.09-1.96 (m, 2H), 1.70-1.35 (m, 4H) and cis-4-(2-methylpyrimidin-4-yl)cyclohexanol (71 mg, 0.35 mmol) $^1$H-NMR (300 MHz, CDCl$_3$) δ 8.55 (d, J=5.3 Hz, 1H), 7.05 (d, J=5.3 Hz, 1H), 4.22-4.08 (m, 1H), 2.80-2.59 (m, 4H), 2.08-1.61 (m, 8H).

Preparation of Compound 30: 4-[5-[cis-4-(2-methylpyrimidin-4-yl)cyclohexoxy]quinazolin-7-yl]morpholine

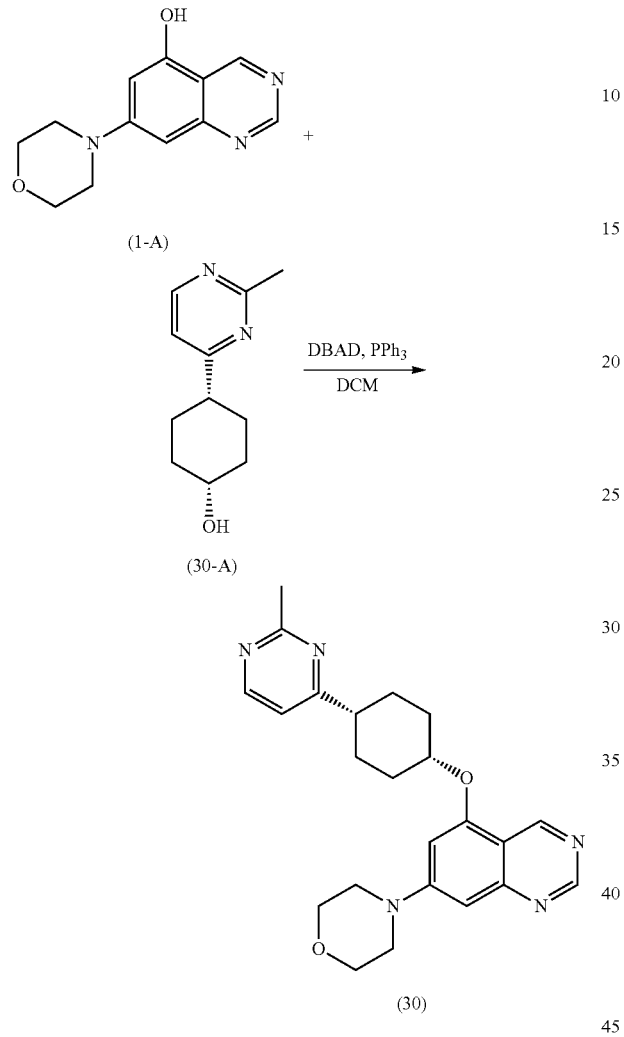

To a solution of 7-morpholinoquinazolin-5-ol (27.5 mg, 0.12 mmol), trans-4-(2-methylpyrimidin-4-yl)cyclohexanol (35 mg, 0.18 mmol), and PPh$_3$ (56 mg, 0.21 mmol) in DCM (1 mL) was added di-tert-butyl azodicarboxylate (49 mg, 0.21 mmol). The reaction was stirred at room temperature overnight. The reaction was concentrated in vacuo and the residue was purified on a reverse phase C18-derivatized SiO2 column using 5-40% CH$_3$CN (0.1% TFA) in H$_2$O (0.1% TFA). The product fractions were combined and neutralized with NaHCO$_3$ (sat) and then extracted with EtOAc. The organic extracts were combined and washed with brine, dried over MgSO4, filtered, and concentrated to yield 4-[5-[cis-4-(2-methylpyrimidin-4-yl)cyclohexoxy] quinazolin-7-yl]morpholine (18.5 mg, 36.5% yield). $^1$H-NMR (300 MHz, CDCl$_3$) δ 9.51 (s, 1H), 9.10 (s, 1H), 8.59 (d, J=5.2 Hz, 1H), 7.06 (d, J=5.2 Hz, 1H), 6.84 (d, J=1.7 Hz, 1H), 6.61 (d, J=1.9 Hz, 1H), 4.96-4.82 (m, 1H), 4.03-3.82 (m, 4H), 3.51-3.30 (m, 4H), 2.90-2.77 (m, 1H), 2.75 (s, 3H), 2.44-2.28 (m, 2H), 2.19-1.75 (m, 6H). ESI-MS m/z calc. 405.21646, found 406.36 (M+1)$^+$.

Preparation of Compound 38: 4-[5-[trans-4-(2-methylpyrimidin-4-yl)cyclohexoxy]quinazolin-7-yl]morpholine

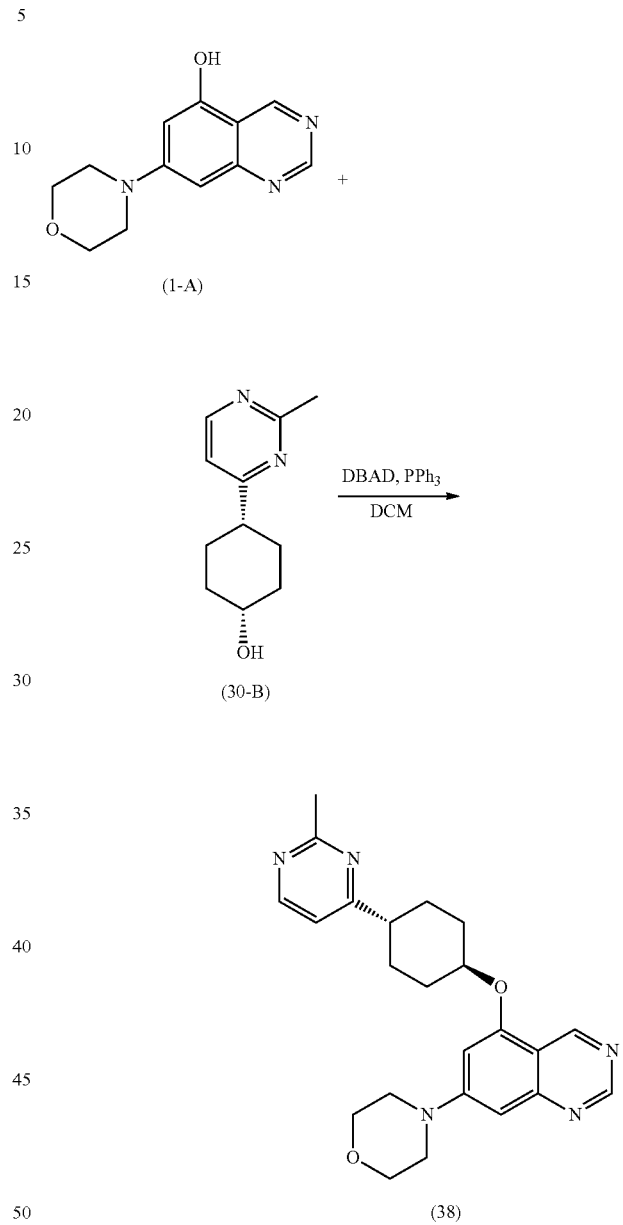

To a solution of 7-morpholinoquinazolin-5-ol (25 mg, 0.11 mmol), cis-4-(2-methylpyrimidin-4-yl)cyclohexanol (33 mg, 0.16 mmol), and PPh$_3$ (52 mg, 0.20 mmol) in DCM (1 mL) was added di-tert-butyl azodicarboxylate (45 mg, 0.20 mmol). The reaction was stirred at room temperature for 2 days. The reaction was concentrated in vacuo and the residue was purified by silica gel chromatography using EtOAc to yield 4-[5-[trans-4-(2-methylpyrimidin-4-yl)cyclohexoxy]quinazolin-7-yl]morpholine (17 mg, 0.041 mmol, 37% yield). $^1$H-NMR (300 MHz, CDCl$_3$) δ 9.41 (s, 1H), 9.08 (s, 1H), 8.57 (d, J=5.2 Hz, 1H), 7.02 (d, J=5.1 Hz, 1H), 6.83 (d, J=1.7 Hz, 1H), 6.64 (d, J=2.0 Hz, 1H), 4.63-4.41 (m, 1H), 4.05-3.83 (m, 4H), 3.53-3.29 (m, 4H), 2.86-2.76 (m, 1H), 2.75 (s, 3H), 2.51-2.33 (m, 2H), 2.25-2.10 (m, 2H), 1.96-1.62 (m, 6H). ESI-MS m/z calc. 405.21646, found 406.29 (M+1)$^+$.

Preparation of Compound 31: ethyl 4-(7-morpholinoquinazolin-5-yl)oxycyclohexanecarboxylate

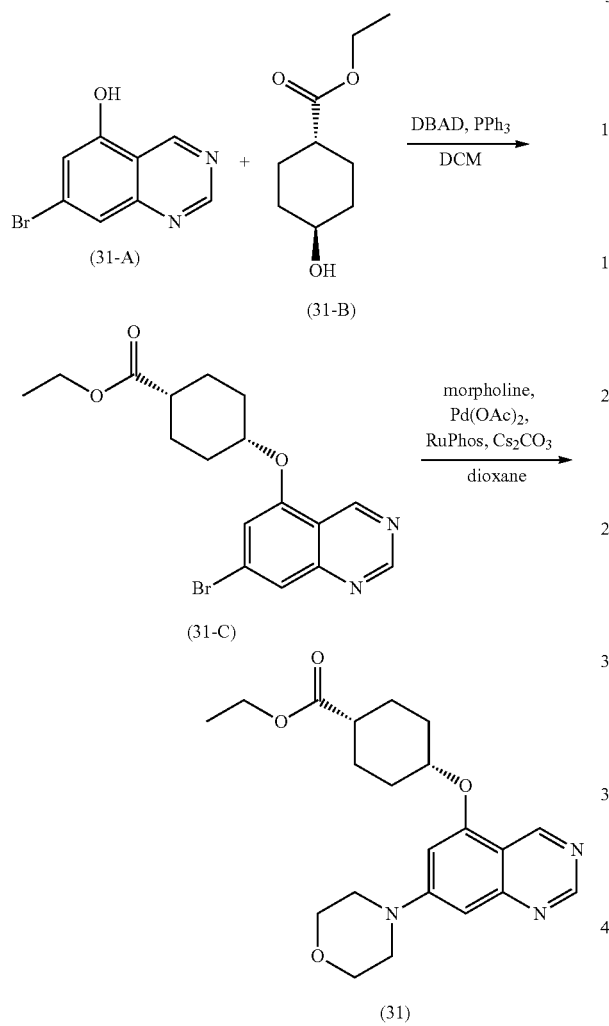

Preparation of Compound (31-C)

To a solution of 7-bromoquinazolin-5-ol (500 mg, 2.22 mmol), ethyl 4-hydroxycyclohexanecarboxylate (516 mg, 3.00 mmol), and PPh$_3$ (937 mg, 3.57 mmol) in DCM (20 mL) was added di-tert-butyl azodicarboxylate (819 mg, 3.56 mmol). The reaction was stirred at room temperature for 2 days. The reaction was concentrated in vacuo and the residue was purified by silica gel chromatography using EtOAc and heptane to yield cis-ethyl 4-(7-bromoquinazolin-5-yl)oxycyclohexanecarboxylate (585 mg, 69.4% yield). $^1$H-NMR (300 MHz, CDCl$_3$) δ 9.74 (s, 1H), 9.32 (s, 1H), 7.79 (s, 1H), 7.05 (d, J=1.4 Hz, 1H), 4.82-4.72 (m, 1H), 4.19 (q, J=7.1 Hz, 2H), 2.58-2.43 (m, 1H), 2.28-2.12 (m, 2H), 2.12-1.74 (m, 6H), 1.30 (t, J=7.1 Hz, 3H). ESI-MS m/z calc. 378.0579, found 379.1 (M+1)$^+$.

Preparation of Compound (31)

A Biotage 0.5-2 mL microwave vial equipped with a magnetic stir bar was charged with ethyl 4-(7-bromoquinazolin-5-yl)oxycyclohexanecarboxylate (100 mg, 0.264 mmol), Pd(OAc)$_2$ (6 mg, 0.03 mmol), and RuPhos (25 mg, 0.054 mmol) in dioxane (1.6 mL) and nitrogen was bubbled through the reaction for 10 minutes. Morpholine (36 µL, 0.41 mmol) and Cs$_2$CO$_3$ (258 mg, 0.792 mmol) were added, and the vial was sealed with a disposable Teflon septum cap. The vial was heated to 100° C. for 4.5 hours. The reaction was cooled to room temperature and diluted with water, then extracted with EtOAc. The organic extracts were combined and washed with brine, dried over MgSO$_4$, filtered, and concentrated. The residue was purified by flash chromatography using EtOAc to yield ethyl 4-(7-morpholinoquinazolin-5-yl)oxycyclohexanecarboxylate (90 mg, 85% yield). $^1$H-NMR (300 MHz, CDCl$_3$) δ 9.46 (s, 1H), 9.10 (s, 1H), 6.81 (d, J=1.7 Hz, 1H), 6.57 (d, J=1.9 Hz, 1H), 4.83-4.66 (m, 1H), 4.19 (q, J=7.1 Hz, 2H), 4.01-3.83 (m, 4H), 3.51-3.29 (m, 4H), 2.48 (tt, J=10.3, 3.9 Hz, 1H), 2.30-2.12 (m, 2H), 2.12-1.65 (m, 6H), 1.30 (t, J=7.1 Hz, 3H). ESI-MS m/z calc. 385.20016, found 386.28 (M+1)$^+$.

Preparation of Compound 32: cis-N-cyclopropyl-4-((7-morpholinoquinazolin-5-yl)oxy)cyclohexanecarboxamide

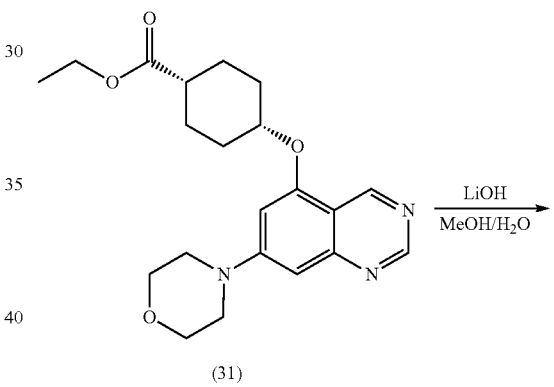

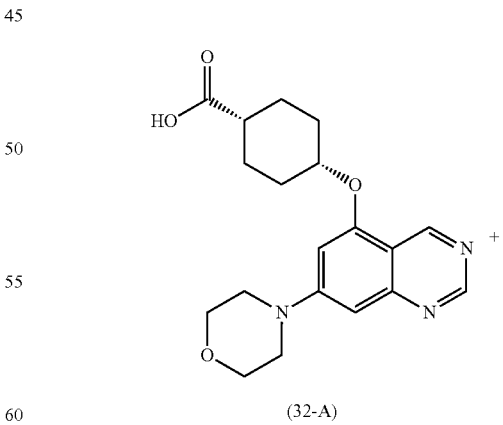

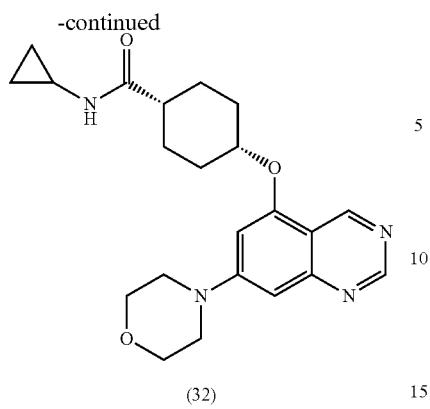

(32)

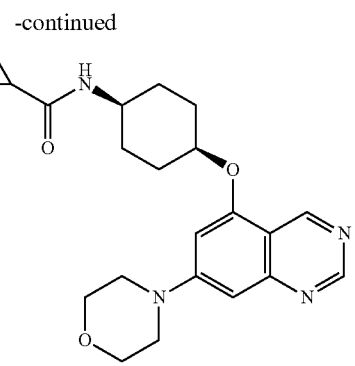

Preparation of Compound (32-A)

A solution of ethyl 4-(7-morpholinoquinazolin-5-yl)oxy-cyclohexanecarboxylate (210 mg, 0.545 mmol: Compound (31)) and LiOH (20 mg, 0.835 mmol) in MeOH (3 mL) and water (500 µL) was stirred at 65° C. for 1.5 hours. The reaction was cooled to room temperature and the pH was adjusted to 1 with 6M HCl. The solvent was removed to yield 4-(7-morpholinoquinazolin-5-yl)oxycyclohexanecarboxylic acid hydrochloride.

Preparation of Compound (32)

To a solution of 4-(7-morpholinoquinazolin-5-yl)oxycyclohexanecarboxylic acid hydrochloride (46.4 mg, 0.118 mmol), cyclopropanamine (10 µL, 0.14 mmol), and HATU (49 mg, 0.13 mmol) in THF (2 mL) was added DIPEA (82 µL, 0.47 mmol). The reaction was stirred at room temperature for 40 minutes. The reaction was concentrated in vacuo, and the residue was purified on a reverse phase C18-derivatized SiO2 column using 5-30% $CH_3CN$ (0.1% TFA) in $H_2O$ (0.1% TFA). The product fractions were combined and neutralized with $NaHCO_3$ (sat) and then extracted with EtOAc. The organic extracts were combined and washed with brine, dried over $MgSO_4$, filtered, and concentrated to yield cis-N-cyclopropyl-4-((7-morpholinoquinazolin-5-yl)oxy)cyclohexanecarboxamide (27 mg, 56% yield). $^1$H-NMR (300 MHz, $CDCl_3$) δ 9.47 (s, 1H), 9.11 (s, 1H), 6.81 (d, J=1.7 Hz, 1H), 6.56 (d, J=1.8 Hz, 1H), 5.65 (s, 1H), 4.87-4.72 (m, 1H), 4.02-3.83 (m, 4H), 3.48-3.35 (m, 4H), 2.82-2.68 (m, 1H), 2.37-2.17 (m, 3H), 2.02-1.68 (m, 8H), 0.90-0.75 (m, 2H), 0.59-0.41 (m, 2H). ESI-MS m/z calc. 396.21616, found 397.31 (M+1)$^+$.

Preparation of Compound 33: 2,2-dimethyl-N-((1s,4s)-4-((7-morpholinoquinazolin-5-yl)oxy)cyclohexyl)cyclopropane-1-carboxamide 1-hydroxybenzotriazole monohydrate (23 mg, 0.170 mmol), 3-(ethyliminomethyleneamino)-N,N-dimethyl-propan-1-amine (Hydrochloric Acid (1) (49 mg, 0.256 mmol), and 2,2-dimethylcyclopropanecarboxylic acid (18 mg, 0.158 mmol) were combined in DMF (280 µL) under nitrogen at room temperature and allowed to stir for 40 min. 4-(7-morpholinoquinazolin-5-yl)oxycyclohexanamine (35 mg, 0.107 mmol) was added and allowed to stir overnight. Saturated sodium bicarbonate was added and extracted with EtOAc (2×). The combined organics were washed with water (2×), brine, dried over sodium sulfate, and concentrated under reduced pressure. The residue was chromatographed over 4 g silica gel column using 0-10% MeOH/DCM as eluent and further purified by C18 preparatory HPLC (water/acetonitrile with TFA modifier). The relevant fractions were dried down, and the residue was passed though a PL-HCO3 MP SPE to furnish 2,2-dimethyl-N-((1s,4s)-4-((7-morpholinoquinazolin-5-yl)oxy)cyclohexyl)cyclopropane-1-carboxamide (11.5 mg, 25% yield). 1H NMR (300 MHz, CDCl3) δ 9.45 (s, 1H), 9.09 (s, 1H), 6.78 (d, J=1.9 Hz, 1H), 6.57 (d, J=2.0 Hz, 1H), 5.57 (d, J=8.2 Hz, 1H), 4.74 (q, J=3.2 Hz, 1H), 4.05-3.84 (m, 5H), 3.46-3.31 (m, 4H), 2.19 (dq, J=9.9, 3.3 Hz, 2H), 1.97-1.55 (m, 6H), 1.26 (dd, J=8.0, 5.3 Hz, 1H), 1.17 (s, 3H), 1.15 (s, 3H), 1.09 (t, J=4.8 Hz, 1H), 0.73 (dd, J=8.0, 4.3 Hz, 1H). ESI-MS m/z=425.33 (M+1)+.

Preparation of Compound 34: N-((1s,4s)-4-((7-morpholinoquinazolin-5-yl)oxy)cyclohexyl)oxetane-3-carboxamide

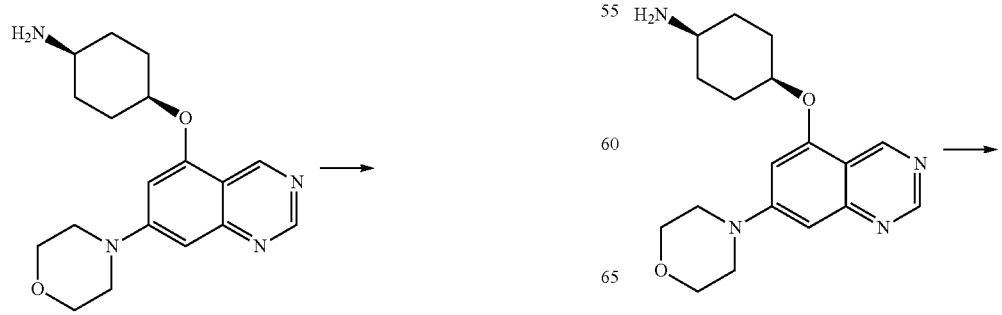

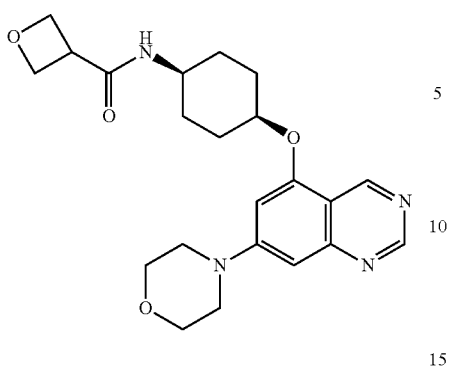

1-hydroxybenzotriazole monohydrate (18 mg, 0.133 mmol), 3-(ethyliminomethyleneamino)-N,N-dimethyl-propan-1-amine (Hydrochloric Acid (1) (38 mg, 0.198 mmol), and oxetane-3-carboxylic acid (13 mg, 0.127 mmol) and triethylamine (15 µL, 0.1076 mmol) were combined in DMF (1 mL) under nitrogen at room temperature and allowed to stir for 40 min. 4-(7-morpholinoquinazolin-5-yl)oxycyclohexanamine (27 mg, 0.0822 mmol) was added, and the reaction was allowed to stir overnight. Saturated sodium bicarbonate was added and extracted with EtOAc (2×). The combined organics were washed with water (2×), brine, dried over sodium sulfate, and concentrated under reduced pressure. The resulting residue was purified by chromatography over 4 g silica gel using a 0-10% methanol/DCM gradient to yield N-((1s,4s)-4-((7-morpholinoquinazolin-5-yl)oxy)cyclohexyl)oxetane-3-carboxamide (4 mg, 11% yield). 1H NMR (300 MHz, CDCl3) δ 9.42 (s, 1H), 9.08 (d, J=2.2 Hz, 1H), 6.79 (d, J=1.9 Hz, 1H), 6.57 (d, J=2.1 Hz, 1H), 5.51 (d, J=8.1 Hz, 1H), 4.95-4.72 (m, 5H), 4.10-3.84 (m, 5H), 3.70 (tt, J=8.3, 6.7 Hz, 1H), 3.39 (dd, J=5.8, 4.0 Hz, 5H), 2.30-2.15 (m, 3H), 1.98-1.58 (m, 4H). ESI-MS m/z=413.46 (M+1)+.

Preparation of Compound 36: N-[4-(2,4-dimethyl-7-morpholino-quinazolin-5-yl)oxycyclohexyl]-2-methyl-pyrimidin-4-amine

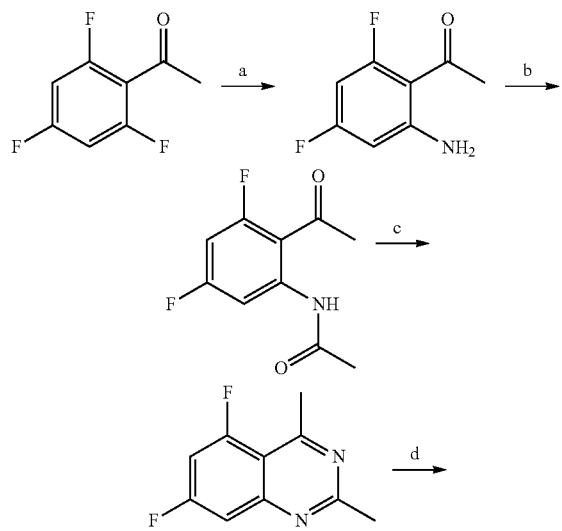

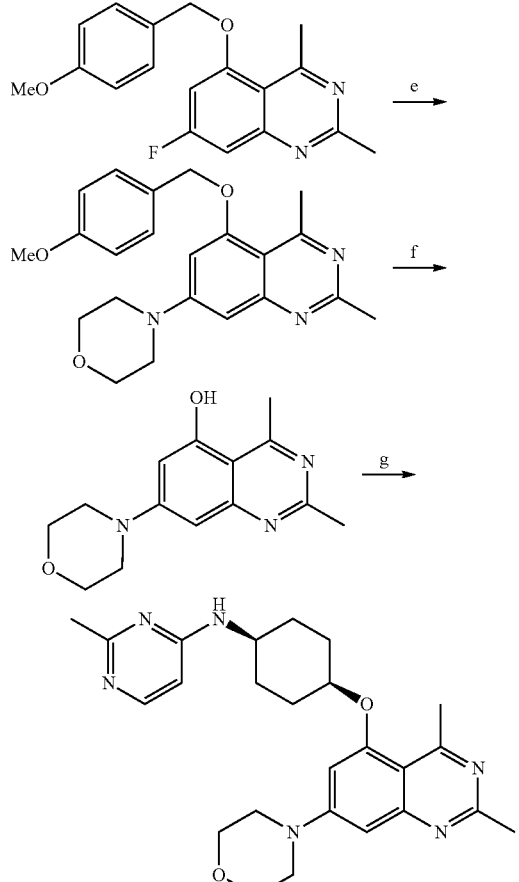

Reagents and conditions: (a) NH₃, 90° C., 22 h; (b) AcCl, DIEA, DCM; (c) NH₃, EtOH; (d) NaH, PMB—OH, DMF; (e) morpholine, DIEA, iPrOH; (f) TFA, DCM; (g) [4-[(2-methylpyrimidin-4-yl)amino]cyclohexyl] methanesulfonate, CsCO₃, DMF Step a A mixture of 1-(2,4,6-trifluorophenyl)ethanone (7 g, 40.2 mmol) and ammonium (40 g, 665 mmol, 30% w/w) was stirred at 90° C. for 22 h in a sealed pressure bottle. After cooling to room temperature, the mixture was extracted with DCM, dried over Na₂SO₄, concentrated and purified by 120 g silica gel cartridge eluting with 0-30% EtOAc/heptane. This afforded 1-(2-amino-4,6-difluoro-phenyl)ethanone (5.1 g, 74%). ¹H NMR (400 MHz, CDCl3) δ 6.66-6.27 (m, 2H), 6.19-6.11 (m, 2H), 2.59 (dd, J=8.4, 1.4 Hz, 3H).

Step b

To a solution of 1-(2-amino-4,6-difluoro-phenyl)ethanone (3.1 g, 18.1 mmol) in DCM (30 mL) was added DIEA (3.8 mL, 21.8 mmol) and AcCl (2 mL, 28.1 mmol) at 0° C. The mixture was stirred for 1 h and concentrated. The residue was diluted with DCM, washed with sat. NaHCO3 solution and concentrated in vacuo. The white residue was carried to next step. This afforded N-(2-acetyl-3,5-difluoro-phenyl)acetamide (3.8 g, 17.8 mmol, 98.4%). ¹H NMR (300 MHz, CDCl₃) δ 11.66 (s, 1H), 8.39 (ddd, J=11.7, 2.6, 1.6 Hz, 1H), 6.60 (ddd, J=12.2, 8.2, 2.6 Hz, 1H), 2.67 (d, J=8.5 Hz, 3H), 2.24 (s, 3H).

Step c

A mixture of N-(2-acetyl-3,5-difluoro-phenyl)acetamide (1.7 g, 8 mmol) and 2M of NH₃ in EtOH (80 mL of 2 M, 160 mmol) was stirred at 90° C. for 18 h. The mixture was concentrated in vacuo and purified by 40 g silica gel cartridge with 0-30% EtOAc/hex. This afforded 5,7-difluoro-2,4-dimethyl-quinazoline (1.2 g, 77%). $^1$H NMR (300 MHz, CDCl3) δ 7.40 (ddt, J=9.3, 2.3, 1.2 Hz, 1H), 7.03 (ddd, J=11.2, 8.9, 2.4 Hz, 1H), 3.01 (dd, J=6.0, 0.9 Hz, 3H), 2.83 (s, 3H).

Step d

To a solution of (4-methoxyphenyl)methanol (270 μL, 2.0 mmol) in DMF (5 mL) was added NaH (110 mg, 2.75 mmol), and the resultant mixture was stirred for 10 min. To the mixture was added to a solution of 5,7-difluoro-2,4-dimethyl-quinazoline (350 mg, 1.8 mmol) in DMF (5 mL), and stirred was continued for an additional 30 min. The mixture was quenched by H$_2$O, extracted with DCM, dried over Na$_2$SO$_4$, concentrated. The crude was purified by 40 g silica gel cartridge eluting with a gradient of 0-40% EtOAc/heptane and afforded 7-fluoro-5-[(4-methoxyphenyl)methoxy]-2,4-dimethyl-quinazoline (300 mg, 37%). $^1$H NMR (300 MHz, CDCl$_3$) δ 7.51-7.36 (m, 2H), 7.17 (dd, J=9.4, 2.3 Hz, 1H), 7.07-6.91 (m, 2H), 6.76 (dd, J=10.9, 2.4 Hz, 1H), 5.15 (s, 2H), 3.87 (s, 3H), 2.97 (s, 3H), 2.81 (s, 3H).

Step e

A mixture of 7-fluoro-5-[(4-methoxyphenyl)methoxy]-2,4-dimethyl-quinazoline (300 mg, 0.96 mmol), morpholine (300 μL, 3.4 mmol) and DIEA (300 μL, 1.7 mmol) in iPrOH (3 mL) was microwaved at 160° C. for 20 min. The mixture was microwaved for 30 min at 180° C. and then 60 min at 190° C. The mixture was concentrated, purified by silica gel chromatography eluting with a gradient of 0-70% EtOAc/heptane and afforded 4-[5-[(4-methoxyphenyl)methoxy]-2,4-dimethyl-quinazolin-7-yl]morpholine (60 mg, 0.158 mmol, 16.5%). $^1$H NMR (300 MHz, CDCl$_3$) δ 7.49-7.37 (m, 2H), 7.03-6.90 (m, 2H), 6.77 (d, J=2.3 Hz, 1H), 6.58 (d, J=2.3 Hz, 1H), 5.11 (s, 2H), 3.99-3.81 (m, 7H), 3.46-3.32 (m, 4H), 2.88 (s, 3H), 2.73 (s, 3H). ESI-MS m/z calc. 379.1896, found 380.1 (M+1)+; Retention time: 0.6 minutes.

Step f

To a solution of 4-[5-[(4-methoxyphenyl)methoxy]-2,4-dimethyl-quinazolin-7-yl]morpholine (60 mg, 0.16 mmol) in DCM (10 mL) was added TFA (1 mL, 13 mmol), and the resultant solution was stirred for 1 h. The mixture was concentrated and purified by 4 g silica gel cartridge eluting with 0-5% MeOH/DCM to afford 2,4-dimethyl-7-morpholino-quinazolin-5-ol (37 mg, 90%). $^1$H NMR (300 MHz, DMSO) δ 6.69 (s, 2H), 5.76 (s, 1H), 3.74 (t, J=4.9 Hz, 4H), 3.36 (s, 4H), 2.93 (s, 3H), 2.58 (s, 3H).

Step g

A mixture of 2,4-dimethyl-7-morpholino-quinazolin-5-ol (34 mg, 0.13 mmol), [4-[(2-methylpyrimidin-4-yl)amino]cyclohexyl] methanesulfonate (55 mg, 0.19 mmol) and cesium carbonate (70 mg, 0.21 mmol) in DMF (1 mL) was stirred at 90° C. for 20 h. The mixture was diluted with DCM, filtered thought a layer of Celite, and concentrated. The crude was purified by Silica gel chromatography eluting with 0-10% MeOH/DCM and afforded N-[4-(2,4-dimethyl-7-morpholino-quinazolin-5-yl)oxycyclohexyl]-2-methyl-pyrimidin-4-amine (6.1 mg, 0.013 mmol, 9.9%). $^1$H NMR (300 MHz, CDCl$_3$) δ 8.13 (d, J=6.0 Hz, 1H), 6.76 (d, J=2.2 Hz, 1H), 6.50 (d, J=2.1 Hz, 1H), 6.18 (d, J=6.0 Hz, 1H), 4.93 (d, J=7.9 Hz, 1H), 4.73 (d, J=4.2 Hz, 1H), 3.96-3.85 (m, 4H), 3.42-3.28 (m, 4H), 3.01 (s, 3H), 2.73 (s, 3H), 2.51 (s, 3H), 2.32-2.19 (m, 2H), 2.08-1.73 (m, 9H). ESI-MS m/z calc. 448.25867, found 449.32 (M+1)+; Retention time: 0.5 minutes Preparation of 4-(7-morpholinoquinazolin-5-yl)oxy-N-(2-pyridyl)cyclohexanecarboxamide: Compound 37

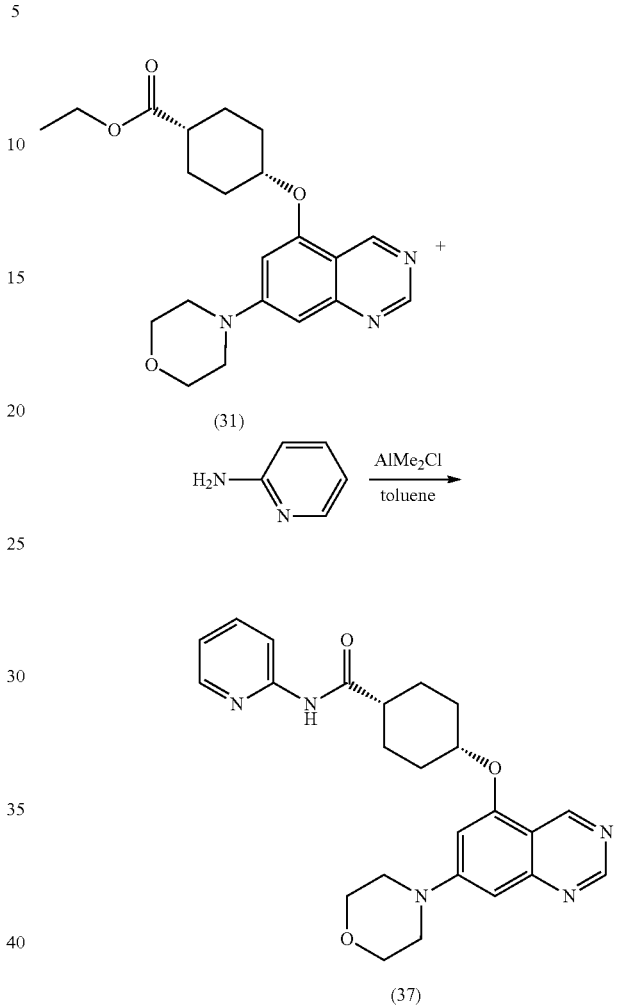

To a solution of ethyl 4-(7-morpholinoquinazolin-5-yl)oxycyclohexanecarboxylate (30 mg, 0.078 mmol: Compound (30)) and pyridin-2-amine (15 mg, 0.16 mmol) in toluene (0.5 mL) under nitrogen was added AlMe$_2$Cl (155 μL of 1.0 M, 0.155 mmol) dropwise. After complete addition, the reaction was heated to 80° C. for 30 minutes. The reaction was cooled to room temperature and concentrated in vacuo. The residue was purified by MPLC on a C18 reverse phase SiO$_2$ column using 5-40% CH$_3$CN (0.1% TFA) in H$_2$O (0.1% TFA). The product fractions were combined and neutralized with NaHCO$_3$ (sat) and then extracted with EtOAc. The organic extracts were combined and washed with brine, dried over MgSO$_4$, filtered, and concentrated to yield 4-(7-morpholinoquinazolin-5-yl)oxy-N-(2-pyridyl)cyclohexanecarboxamide (21.8 mg, 63.3% yield). $^1$H-NMR (300 MHz, CDCl$_3$) δ 9.49 (s, 1H), 9.11 (s, 1H), 8.28 (d, J=7.7 Hz, 2H), 8.16 (s, 1H), 7.84-7.68 (m, 1H), 7.15-7.02 (m, 1H), 6.83 (d, J=1.7 Hz, 1H), 6.59 (d, J=1.9 Hz, 1H), 4.88-4.76 (m, 1H), 4.05-3.81 (m, 4H), 3.40 (dd, J=14.8, 10.0 Hz, 4H), 2.59-2.42 (m, 1H), 2.42-2.25 (m, 2H), 2.25-2.04 (m, 2H), 2.04-1.71 (m, 4H). ESI-MS m/z calc. 433.2114, found 434.33 (M+1)+.

Preparation of Compound 39: N-[4-(7-bromoquinazolin-5-yl)oxycyclohexyl]-2-methyl-pyrimidin-4-amine

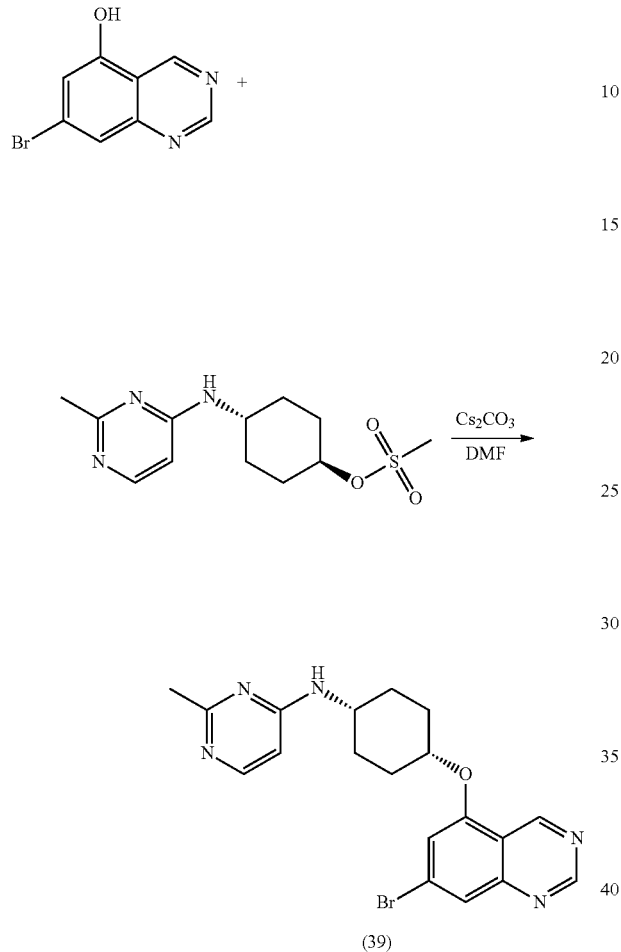

(39)

A microwave vial equipped with a magnetic stir bar was charged with 7-bromoquinazolin-5-ol (31.3 mg, 0.139 mmol), [4-[(2-methylpyrimidin-4-yl)amino]cyclohexyl] methanesulfonate (120 mg, 0.421 mmol), and $Cs_2CO_3$ (136 mg, 0.417 mmol) in DMF (0.5 mL). The vial was sealed and heated in the microwave at 120° C. for 10 minutes. The reaction was deemed incomplete so the reaction was heated in the microwave at 120° C. for 10 minutes and then at 140° C. for 10 minutes. The reaction was filtered and purified on a reverse phase C18-derivatized SiO2 column. The product was neutralized by dissolving in ethyl acetate and washing with saturated aqueous NaHCO3. The layers were separated, and the aqueous extracted with EtOAc. The combined organic extracts and washed with brine, dried over MgSO4, filtered, and concentrated to yield N-[4-(7-bromoquinazolin-5-yl)oxycyclohexyl]-2-methyl-pyrimidin-4-amine (19.3 mg, 32.4% yield). $^1$H-NMR (300 MHz, $CDCl_3$) δ 9.72 (s, 1H), 9.33 (s, 1H), 8.12 (d, J=6.1 Hz, 1H), 7.81 (d, J=0.7 Hz, 1H), 7.08 (d, J=1.3 Hz, 1H), 6.22 (d, J=6.0 Hz, 1H), 5.04 (s, 1H), 4.90-4.75 (m, 1H), 3.90 (s, 1H), 2.54 (s, 3H), 2.36-2.18 (m, 2H), 2.14-1.59 (m, 6H). ESI-MS m/z calc. 413.0851, found 414.17 (M+1)$^+$.

Preparation of Compound 40: N-methyl-4-(7-morpholinoquinazolin-5-yl)oxy-cyclohexanecarboxamide

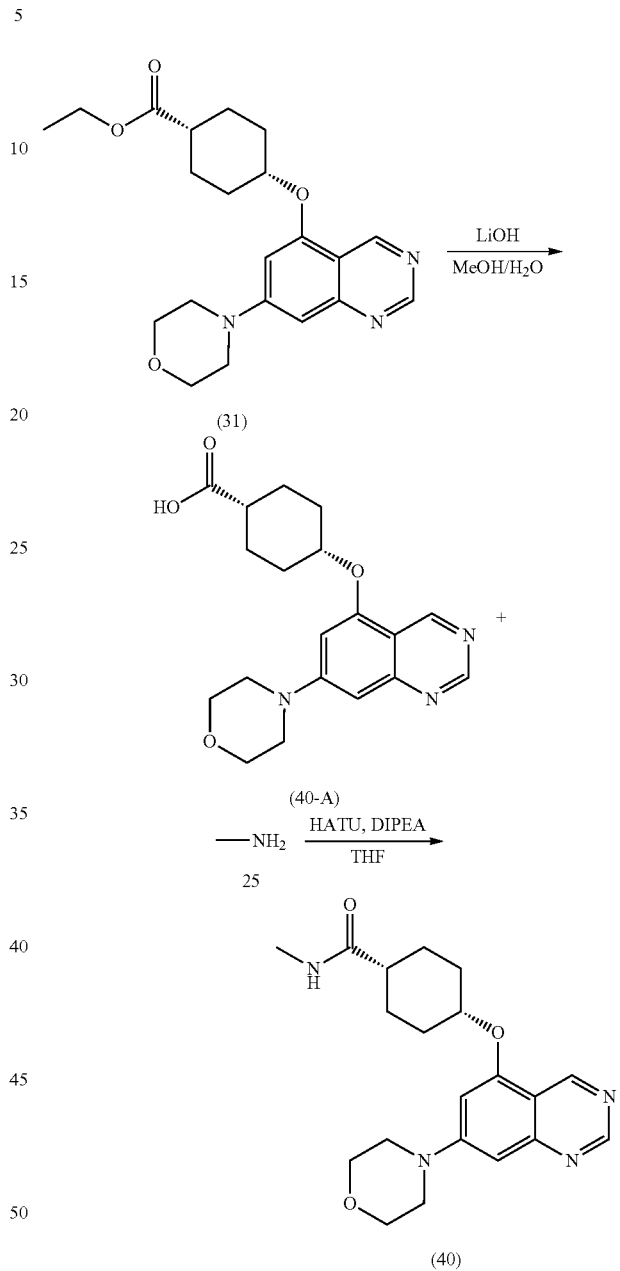

(40)

To a solution of 4-(7-morpholinoquinazolin-5-yl)oxycyclohexanecarboxylic acid hydrochloride (46.4 mg, 0.118 mmol), methylamine (100 µL of 2M, 0.200 mmol), and HATU (55 mg, 0.14 mmol) in THF (1 mL) and DMF (1 mL) was added DIPEA (95 µL, 0.55 mmol). The reaction was stirred at room temperature for 1 hour. The reaction was concentrated in vacuo and the residue was purified by C18 preparatory HPLC (water/acetonitrile with TFA modifier). The relevant fractions were dried down and neutralized with $NaHCO_3$ (sat) and then extracted with EtOAc. The organic extracts were combined and washed with brine, dried over $MgSO_4$, filtered, and concentrated to yield N-methyl-4-(7-morpholinoquinazolin-5-yl)oxy-cyclohexanecarboxamide (30 mg, 63% yield). $^1$H-NMR (300 MHz, CDCl$_3$) δ 9.47 (s, 1H), 9.09 (s, 1H), 6.83 (d, J=1.7 Hz, 1H), 6.57 (d, J=1.9 Hz, 1H), 5.67-5.49 (m, 1H), 4.83-4.75 (m, 1H), 3.95-3.85 (m, 4H), 3.48-3.36 (m, 4H), 2.87 (d, J=4.8 Hz, 3H), 2.38-2.24 (m, 3H), 2.11-1.84 (m, 4H), 1.83-1.67 (m, 2H). ESI-MS m/z calc. 370.2005, found 371.38 (M+1)$^+$.

Preparation of Compound 41: N-(3-methoxypropyl)-4-(7-morpholinoquinazolin-5-yl)oxy-cyclohexanecarboxamide

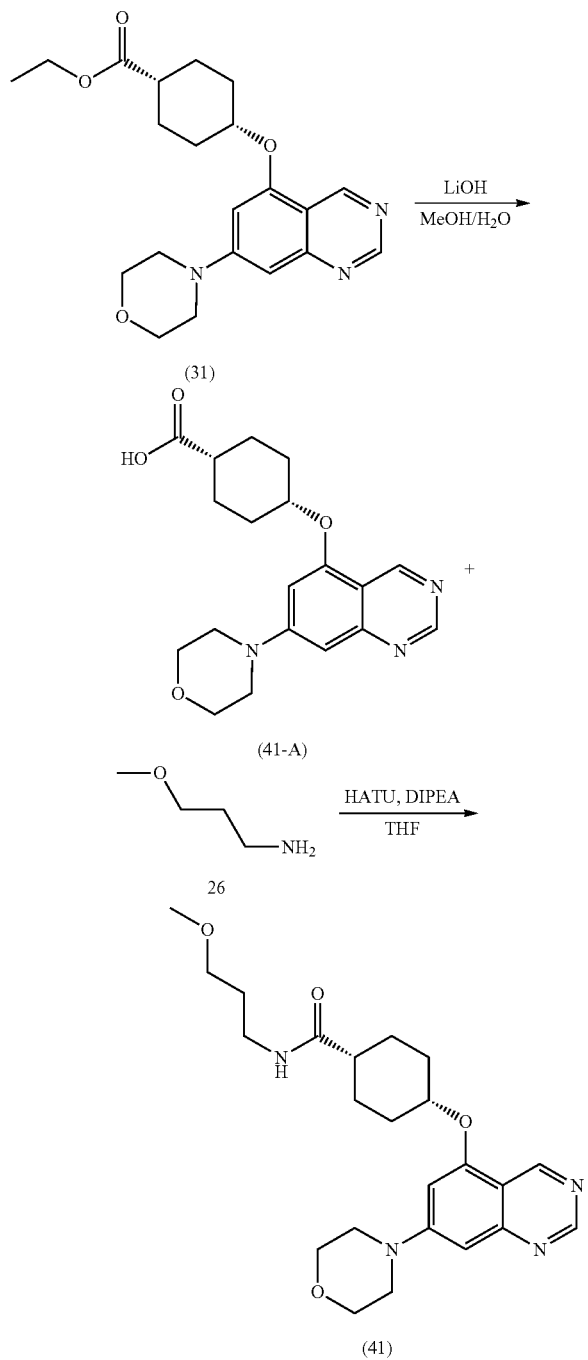

To a solution of 4-(7-morpholinoquinazolin-5-yl)oxycyclohexanecarboxylic acid hydrochloride (46 mg, 0.13 mmol), 3-methoxypropan-1-amine (13 mg, 0.15 mmol), and HATU (55 mg, 0.14 mmol) in THF (1 mL) was added DIPEA (95 µL, 0.55 mmol). The reaction was stirred at room temperature for 1 hour. The reaction was concentrated in vacuo and the residue was purified by MPLC on a C18 reverse phase SiO$_2$ column using 5-50% CH$_3$CN (0.1% TFA) in H$_2$O (0.1% TFA). The product fractions were combined and neutralized with NaHCO$_3$ (sat) and then extracted with EtOAc. The organic extracts were combined and washed with brine, dried over MgSO$_4$, filtered, and concentrated to yield N-(3-methoxypropyl)-4-(7-morpholinoquinazolin-5-yl)oxy-cyclohexanecarboxamide (39.4 mg, 69.3% yield). $^1$H-NMR (300 MHz, CDCl$_3$) δ 9.47 (s, 1H), 9.10 (s, 1H), 6.81 (d, J=1.7 Hz, 1H), 6.57 (d, J=1.9 Hz, 1H), 6.38-6.21 (m, 1H), 4.83-4.72 (m, 1H), 3.98-3.84 (m, 4H), 3.53 (t, J=5.6 Hz, 2H), 3.49-3.29 (m, 9H), 2.40-2.19 (m, 3H), 2.12-1.63 (m, 8H). ESI-MS m/z calc. 428.24237.

Preparation of Compound 42: 2-[[4-(2,4-dimethyl-7-morpholino-quinazolin-5-yl)oxycyclohexyl]amino]-N-methyl-pyrimidine-4-carboxamide

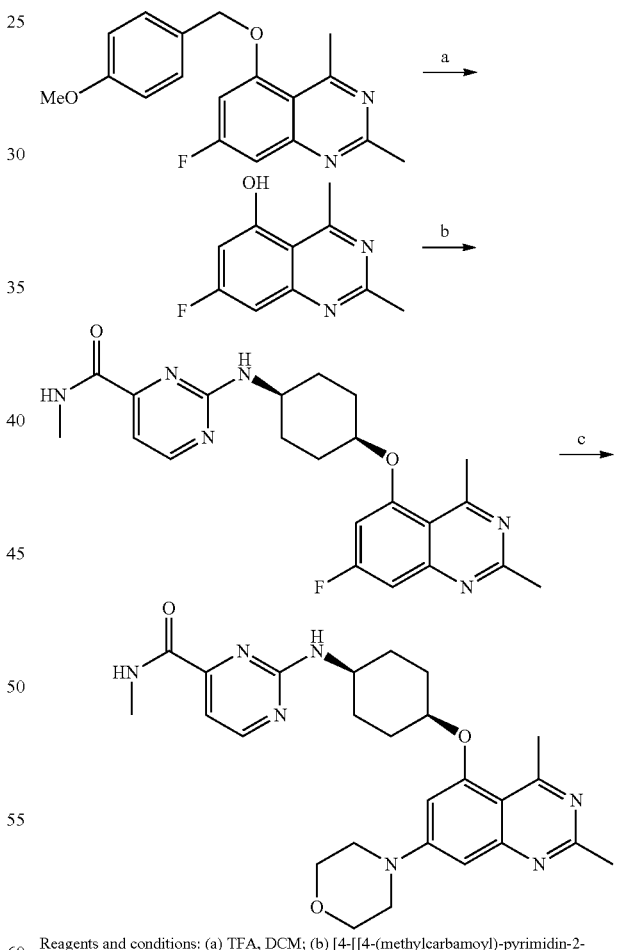

Reagents and conditions: (a) TFA, DCM; (b) [4-[[4-(methylcarbamoyl)-pyrimidin-2-yl]amino]cyclohexyl] methanesulfonate, CsCO3, DMF; (c) morpholine, DIEA, iPrOH Step a To a solution of 7-fluoro-5-[(4-methoxyphenyl)methoxy]-2,4-dimethyl-quinazoline (130 mg, 0.41 mmol) in DCM (1 mL) was added TFA (0.5 mL, 6.5 mmol), and stirring was continued at room temperature for 1 h. The mixture was concentrated and purified on a 12 g silica gel cartridge eluting with 0-4% MeOH/DCM to afford 7-fluoro-2,4-dimethyl-quinazolin-5-ol (70 mg, 87%) $^1$H NMR (300 MHz, CDCl$_3$) δ 7.00 (ddd, J=28.8, 9.8, 2.4 Hz, 2H), 3.17 (s, 3H), 2.87 (s, 3H).

Step b

A mixture of 7-fluoro-2,4-dimethyl-quinazolin-5-ol (45 mg, 0.23 mmol), [4-[[4-(methylcarbamoyl)-pyrimidin-2-yl]amino]cyclohexyl] methanesulfonate (120 mg, 0.36 mmol) and cesium carbonate (200 mg, 0.61 mmol) in DMF (1 mL) was stirred at 90° C. for 20 h. The mixture was diluted with DCM, filtered though a layer of celite, concentrated and purified by 4 g silica gel cartridge using 0-5% MeOH/DCM to afford 2-[[4-(7-fluoro-2,4-dimethyl-quinazolin-5-yl)oxy-cyclohexyl]amino]-N-methyl-pyrimidine-4-carboxamide (10 mg, 10%). ESI-MS m/z calc. 424.2, found 425.3 (M+1)+; Retention time: 0.55 minutes.

Step c

A mixture of 2-[[4-(7-fluoro-2,4-dimethyl-quinazolin-5-yl)oxycyclohexyl]amino]-N-methyl-pyrimidine-4-carboxamide (10 mg, 0.023 mmol), morpholine (200 µL, 2.3 mmol) and DIEA (400 µL, 2.3 mmol) in iPrOH (0.5 mL) was stirred at 90° C. for 3 days. The mixture was concentrated and purified by C18 preparatory HPLC (water/acetonitrile with TFA modifier). The relevant fractions were dried down, and the residue was passed though a PL-HCO3 MP SPE to furnish 2-[[4-(2,4-dimethyl-7-morpholino-quinazolin-5-yl)oxycyclohexyl]amino]-N-methyl-pyrimidine-4-carboxamide (3.2 mg, 25%). $^1$H NMR (300 MHz, CDCl3) δ 8.52 (d, J=4.9 Hz, 1H), 7.78 (s, 1H), 7.36 (d, J=4.9 Hz, 1H), 6.78 (d, J=2.2 Hz, 1H), 6.55-6.47 (m, 1H), 5.19 (s, 1H), 4.75 (s, 1H), 4.15-4.00 (m, OH), 3.90 (dd, J=6.0, 3.8 Hz, 4H), 3.43-3.32 (m, 4H), 3.11-2.98 (m, 6H), 2.80 (s, OH), 2.33-2.18 (m, 2H), 2.13-1.77 (m, 6H). ESI-MS m/z calc. 491.2645, found 492.3 (M+1)+; Retention time: 0.54 minutes.

Preparation of Compound 43: 2-methoxy-N-[4-(4-methoxy-7-morpholino-quinazolin-5-yl)oxycyclohexyl]acetamide Preparation of Compound (43-A)

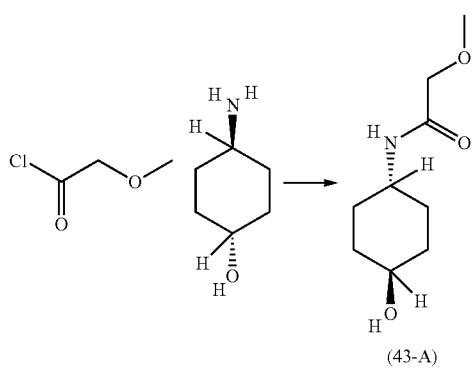

To a 0° C. solution of 4-aminocyclohexan-1-ol (5.01 g, 42.19 mmol) in DCM (50 mL) was added DIEA (14.7 mL, 84.39 mmol) followed by 2-methoxyacetyl chloride (4.4 mL, 47.31 mmol) dropwise. The reaction was stirred for 5 min then the ice bath was removed and the reaction was stirred overnight at RT. The reaction mixture was then transferred to a separtory funnel, organic layer was washed with 1N HCl, the aqeuous layer extracted with EtOAc, the organic layers were combined, dried over Na2SO4, filtered and concentrated to a brownish solid to yield 2.4 g of crude product. This crude product was dissolved in DCM and injected onto an 80 g ISCO column, ELSD detector, 0-7% MeOH/DCM. Desired fractions were combined and concentrated under vacuum to yield N-(4-hydroxycyclohexyl)-2-methoxy-acetamide (800 mg). 1H NMR (400 MHz, Chloroform-d) δ 6.32 (s, 1H), 3.86 (s, 2H), 3.79 (ddd, J=11.7, 8.1, 3.9 Hz, 1H), 3.62 (tt, J=10.5, 3.9 Hz, 1H), 3.41 (d, J=0.6 Hz, 3H), 2.00 (dtd, J=11.8, 7.7, 7.1, 3.5 Hz, 4H), 1.47-1.35 (m, 2H), 1.31-1.17 (m, 2H).

Preparation of Compound (43-B)

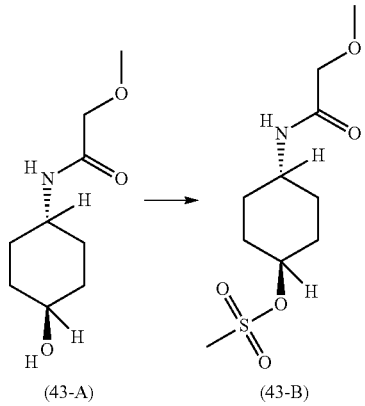

To a solution of N-(4-hydroxycyclohexyl)-2-methoxyacetamide (800 mg, 4.144 mmol) in DCM (9.467 mL) was added DIEA (1.130 g, 1.523 mL, 8.744 mmol) and MsCl (515.0 mg, 348.0 µL, 4.496 mmol). The mixture was stirred for 0.5 h and diluted with DCM, washed with H2O, dried over Na2SO4, filtered though a thin pad of silica gel, the silica pad was washed with DCM, and concentrated. [4-[(2-methoxyacetyl)amino]cyclohexyl] methanesulfonate was obtained as an off white solid (1.09 g, 99.1% yield). 1H NMR (300 MHz, Chloroform-d) δ 6.36 (d, J=8.1 Hz, 1H), 4.65 (m, 1H), 3.87 (m, 3H), 3.41 (s, 3H), 3.02 (s, 3H), 2.22-2.01 (m, 4H), 1.81-1.64 (m, 2H), 1.40-1.24 (m, 2H).

Preparation of Compound (43)

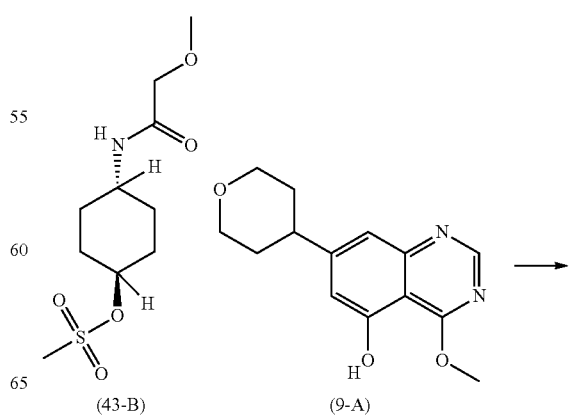

-continued

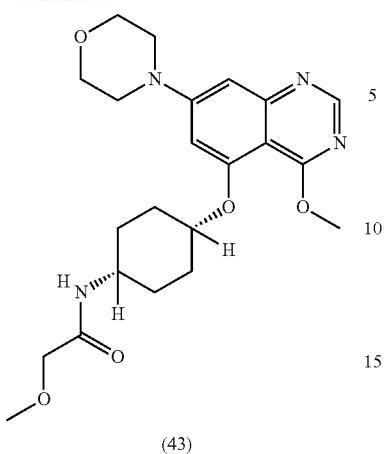

(43)

A mixture of [4-[(2-methoxyacetyl)amino]cyclohexyl] methanesulfonate (75 mg, 0.2827 mmol), 4-methoxy-7-morpholino-quinazolin-5-ol (trifluoroacetic acid salt: Compound (9-A)) (54 mg, 50% purity, 0.07194 mmol), and Cs2CO3 (251 mg, 0.7704 mmol) in DMF was sealed in a 5 mL microwave tube and heated to 100° C. Removed from heat and stirred at RT overnight, the the reaction mixture was filtered, concentrated, and dissolved in DCM and injected onto a 4 g ISCO column and eluted with 0-10% MeOH/DCM. Desired fractions were collected, combined, and concentrated to yield 22 mg of impure product. This material was dissolved in MeOH and purified on a C18 column to yield 24 mg yellow oil. This material was dissolved in DCM and passed through a Stratospheres carbonate cartridge to yield a clear solution that was concentrated under vacuum and dried overnight under high vacuum to yield 2-methoxy-N-[4-(4-methoxy-7-morpholino-quinazolin-5-yl)oxycyclohexyl]acetamide (14 mg, 43.8% yield). 1H NMR (300 MHz, DMSO-d6) δ 8.48 (s, 1H), 7.54 (d, J=7.5 Hz, 1H), 6.78 (d, J=2.2 Hz, 1H), 6.68 (d, J=2.1 Hz, 1H), 4.84 (m, 1H), 4.04 (s, 3H), 3.79 (s, 2H), 3.75 (m, 5H), 3.35 (m, 4H), 3.30 (s, 3H), 2.01 (m, 2H), 1.84-1.53 (m, 6H).

Preparation of Compound 44: 2-[[4-[4-(dimethylamino)-7-morpholino-quinazolin-5-yl]oxycyclohexyl]amino]-N-methyl-pyrimidine-4-carboxamide Preparation of 2-[(4-hydroxycyclohexyl)amino]-N-methyl-pyrimidine-4-carboxamide: Compound (44-A)

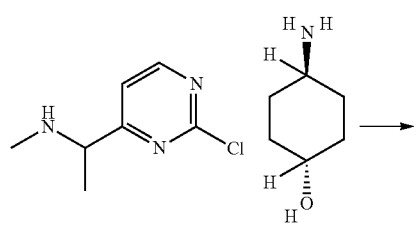

-continued

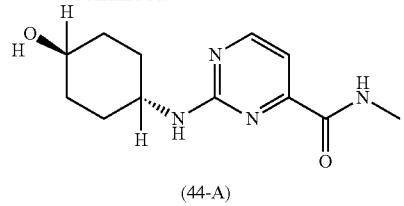

(44-A)

A mixture of 2-chloro-N-methyl-pyrimidine-4-carboxamide (4.5 g, 26.23 mmol), 4-aminocyclohexan-1-ol (3 g, 26.05 mmol) in iPrOH (25.00 mL) was added DIEA (6 mL, 34.45 mmol) and reflux overnight, then concentrated to yield 4.2 g (96%) of 2-[(4-hydroxycyclohexyl)amino]-N-methyl-pyrimidine-4-carboxamide. 1H NMR (300 MHz, CDCl3) ? 8.48 (d, J=4.9 Hz, 1H), 7.75 (s, 1H), 7.34 (d, J=4.9 Hz, 1H), 3.80 (dtt, J=39.2, 9.9, 3.8 Hz, 2H), 3.51 (s, 1H), 3.03 (d, J=5.1 Hz, 3H), 2.29-0 2.00 (m, 4H), 1.65-1.22 (m, 4H).

Preparation of 4-(dimethylamino)-7-morpholino-quinazolin-5-ol: Compound (44-B)

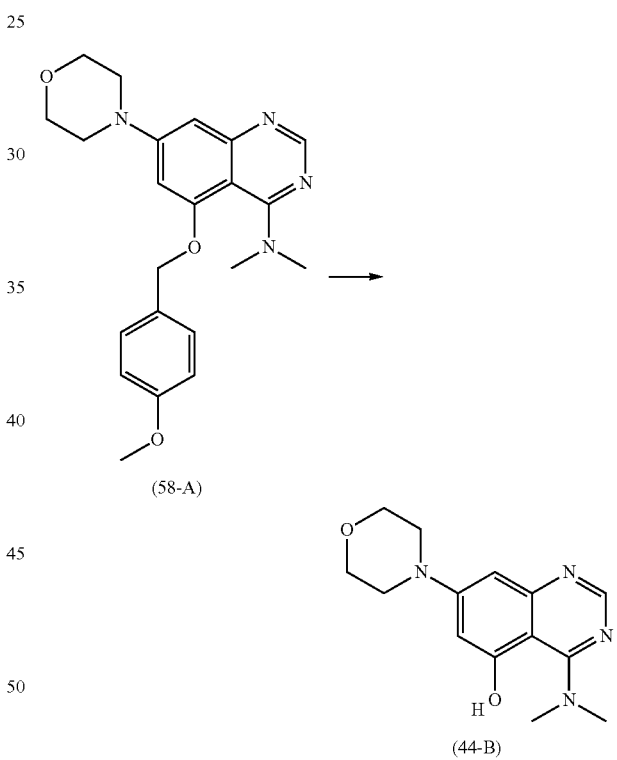

A solution of 5-[(4-methoxyphenyl)methoxy]-N,N-dimethyl-7-morpholino-quinazolin-4-amine (370 mg, 0.8911 mmol) in DCM (4.456 mL) and TFA (5 mL, 64.90 mmol) was stirred at 50° C. for 3 h. The reaction was then concentrated to dryness, treated with saturated aqueous sodium bicarbonate, and extracted 3×EtOAc. The combined organics were concentrated to dryness, dissolved in minimal EtOAc and dropped into heptane. The resulting tan precipitate was filtered and dried to give 4-(dimethylamino)-7-morpholino-quinazolin-5-ol as a tan solid (240 mg, 0.8749 mmol, 98.20%) that was used without further purification. ESI-MS m/z calc. 274.14297, found 275.0 (M+1)+; Retention time: 0.55 minutes.

Preparation of [4-[[4-(methylcarbamoyl)pyrimidin-2-yl]amino]cyclohexyl]methanesulfonate: Compound (44-C)

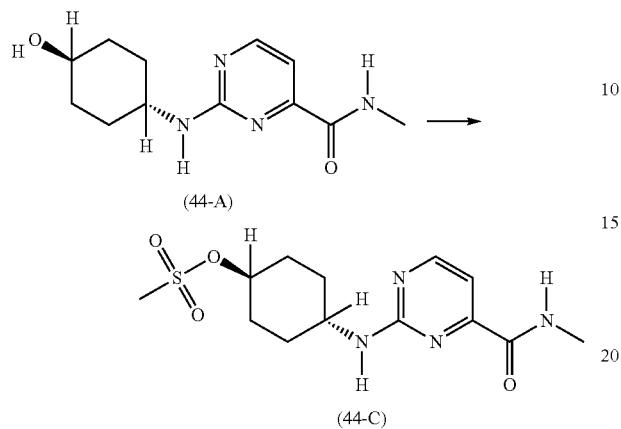

A solution of 2-[(4-hydroxycyclohexyl)amino]-N-methyl-pyrimidine-4-carboxamide (4.3 g, 17.18 mmol) in DCM (50 mL) was added DIEA (15 mL, 86.12 mmol) and MsCl (2.8 mL, 36.18 mmol). The solution was stirred for 3 h then concentrated and purified from 80 g silica gel cartridge with 0-100% EtOAc/hex to provide [4-[[4-(methylcarbamoyl)pyrimidin-2-yl]amino]cyclohexyl]methanesulfonate (5.2 g, 15.83 mmol, 92.17%). 1H NMR (300 MHz, CDCl3) δ 8.49 (d, J=4.9 Hz, 1H), 7.73 (s, 1H), 7.36 (d, J=4.9 Hz, 1H), 5.15 (s, 1H), 4.73 (tt, J=10.3, 3.8 Hz, 1H), 3.92 (dtd, J=10.7, 7.5, 3.7 Hz, 1H), 3.11-2.98 (m, 6H), 2.23 (dq, J=12.7, 3.1, 2.5 Hz, 4H), 1.92-1.63 (m, 4H).

Preparation of 2-[[4-[4-(dimethylamino)-7-morpholino-quinazolin-5-yl]oxycyclohexyl]amino]-N-methyl-pyrimidine-4-carboxamide: Compound (44)

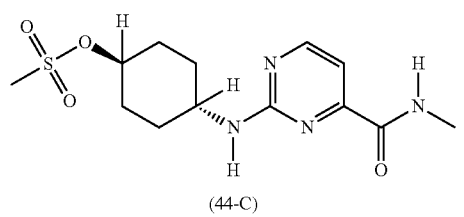

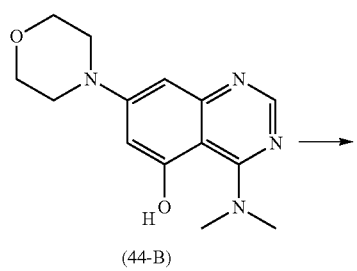

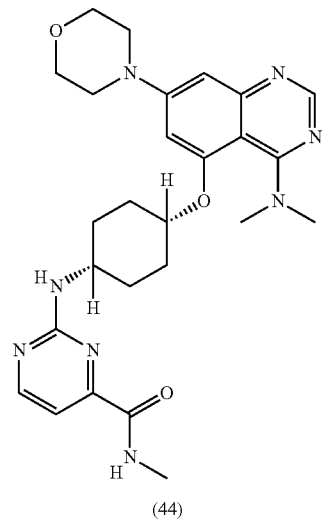

4-(dimethylamino)-7-morpholino-quinazolin-5-ol (75 mg, 0.2734 mmol), [4-[[4-(methylcarbamoyl)pyrimidin-2-yl]amino]cyclohexyl] methanesulfonate (125.7 mg, 0.3828 mmol), and cesium carbonate (267.2 mg, 0.8202 mmol) in DMF (1.367 mL) were stirred overnight in a sealed tube at 100° C. Added another 0.7 eq. of mesylate and stirred at 100° C. for an additional 3 h. The reaction was then diluted with water and extracted 3×EtOAc. The combined organics were concentrated to dryness and purified via flash chromatography eluting with 0-20% MeOH in DCM. Pure fractions were combined, concentrated, and lyophilized to yield 2-[[4-[4-(dimethylamino)-7-morpholino-quinazolin-5-yl]oxycyclohexyl]amino]-N-methyl-pyrimidine-4-carboxamide (19.7 mg, 0.03694 mmol, 13.51%). 1H NMR (300 MHz, CDCl3) δ 8.49 (d, J=4.9 Hz, 1H), 8.42 (s, 1H), 7.76 (d, J=4.8 Hz, 1H), 7.34 (d, J=4.9 Hz, 1H), 6.78 (d, J=2.3 Hz, 1H), 6.54 (d, J=2.3 Hz, 1H), 5.13 (s, 1H), 4.55 (s, 1H), 4.06-3.78 (m, 5H), 3.31 (dd, J=14.5, 9.7 Hz, 4H), 3.15 (s, 6H), 3.02 (d, J=5.1 Hz, 3H), 2.12-2.00 (m, 2H), 1.81 (dd, J=30.2, 11.2 Hz, 6H). ESI-MS m/z calc. 506.2754, found 507.0 (M+1)+; Retention time: 0.64 minutes.

Preparation of Compound 51: 5-[(4-methoxyphenyl)methoxy]-7-morpholino-3H-quinazolin-4-one

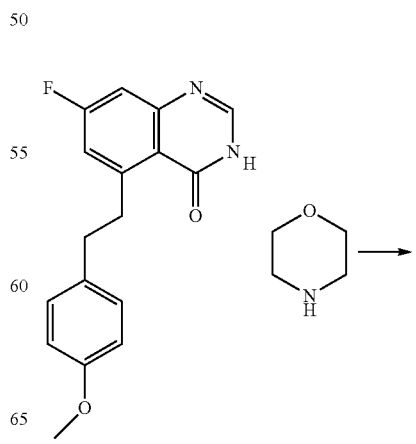

182

Preparation of Compound 52: 4-[5-[(4-methoxyphenyl)methoxy]quinazolin-7-yl]morpholine

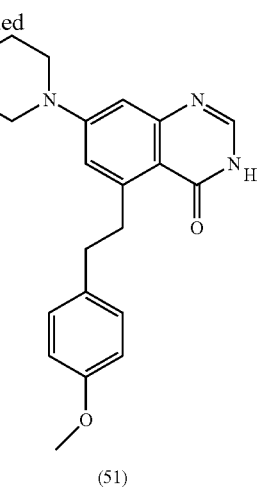

(51)

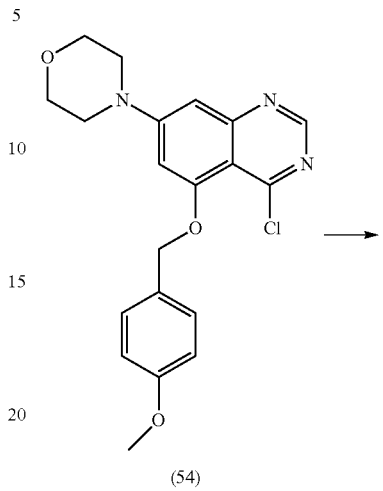

(54)

To a mixture of 7-bromo-5-[(4-methoxyphenyl)methoxy]-3H-quinazolin-4-one (1.38 g, 3.821 mmol), tBu-toxide (Sodium Ion (1)) (1.11 g, 11.55 mmol), Pd(OAc)$_2$ (43 mg, 0.1915 mmol), and RuPhos (176 mg, 0.3772 mmol) was added a solution of morpholine (467 µL, 5.355 mmol) in 1,4-dioxane (16.8 mL) (added 14 mL first, then another 2.8 mL because the mixture did not stir well). The resultant mixture was heated at 100° C. overnight. The mixture was cooled to room temperature and partitioned between DCM and saturated aqueous NH$_4$Cl. The layers were separated, and the water and floating solids were washed with with DCM. The organic layers were combined, and the aqueous layer was filtered. All organic layers were combined and dried over Na$_2$SO$_4$, filtered, and concentrated to yield 1.3 g of product. This material was dissolved in DCM and MeOH and purified by flash column chromatography (40 gram column equilibrated with DCM, Eluted with MeOH/DCM 0-10% over 20 min.) to yield 240 mg white solid. The solid material from the filters and the aqueous layers were dissolved in MeOH/DCM, combined and concentrated, redissolved in DCM/MeOH mixture, and 14 g of celite were added. This mixture was concentrated to near dryness, dryload onto 40 g ISCO column, and eluted as above to yield product as a white solid (370 mg). The first fractions from this column were concentrated to yield additional product (480 mg) as an off-white solid. The pure materials were combined to yield 1.1 grams of 5-[(4-methoxyphenyl)methoxy]-7-morpholino-3H-quinazolin-4-one. 1H NMR (400 MHz, DMSO-d6) δ 11.45 (s, 1H), 7.83 (d, J=3.1 Hz, 1H), 7.57-7.45 (m, 2H), 6.99-6.87 (m, 2H), 6.60 (dd, J=39.0, 2.3 Hz, 2H), 5.13 (s, 2H), 3.75 (m, 7H), 3.31 (m, 4H).

(52)

To a solution of 4-[4-chloro-5-[(4-methoxyphenyl)methoxy]quinazolin-7-yl]morpholine (8.0 g, 20.73 mmol) in CH2Cl2 (470 mL) was added NaCl (360 mL). The resultant biphasic mixture was heated to reflux (55° C. aluminum bead bath), and NH$_{40}$H (100 mL of 30% w/v, 856.0 mmol), and zinc (45.0 g, 688.0 mmol) were added. Heating was continued for 2.5 h. The mixture was filtered through celite, and the filter pad was washed with CH2Cl2 and H2O. The filtrate was separated into aqueous and organic layers. The aqueous was further extracted with CH2Cl2 (2×), washed with brine, dried (Na$_2$SO4), filtered, and concentrated. The crude residue was dry-loaded onto Celite and purified by silica gel chromatography (220 g Isco column, linear gradient 0%→10% MeOH/CH$_2$Cl$_2$) to provide 4-[5-[(4-methoxyphenyl)methoxy]quinazolin-7-yl]morpholine (3.96 g, 10.14 mmol, 48.92%), ~90-95% pure. 1H NMR (400 MHz, CDCl$_3$) δ 9.42 (s, 1H), 9.09 (s, 1H), 7.41 (d, J=8.5 Hz, 2H), 7.01-6.92 (m, 2H), 6.79 (d, J=1.8 Hz, 1H), 6.64 (d, J=2.0 Hz, 1H), 5.16 (s, 2H), 3.95-3.86 (m, 4H), 3.84 (s, 3H), 3.44-3.31 (m, 4H). ESI-MS m/z calc. 351.1583, found 352.39 (M+1)+; Retention time: 0.63 minutes.

Preparation of 4-[4-methoxy-5-[(4-methoxyphenyl)methoxy]quinazolin-7-yl]morpholine: Compound 53

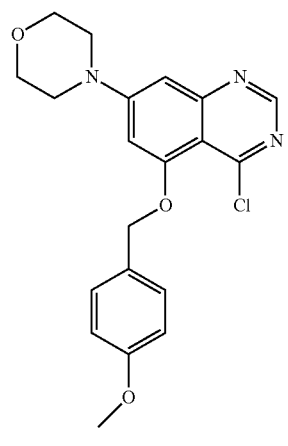

(54)

Preparation of Compound 54: 4-[4-chloro-5-[(4-methoxyphenyl)methoxy]quinazolin-7-yl]morpholine

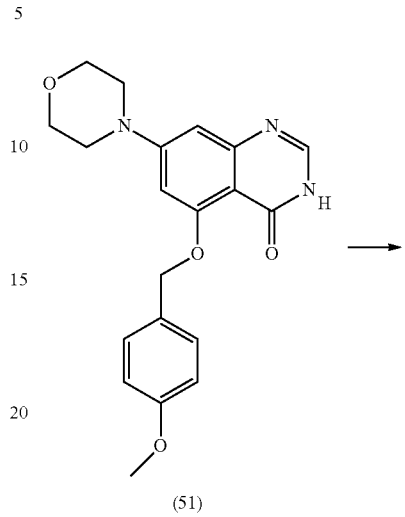

(51)

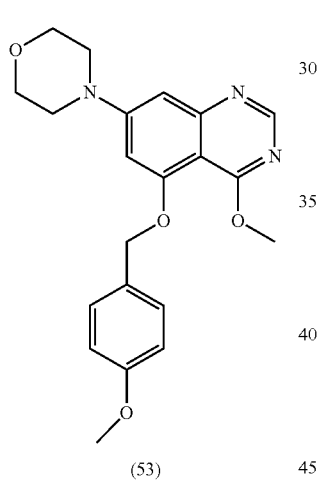

(53)

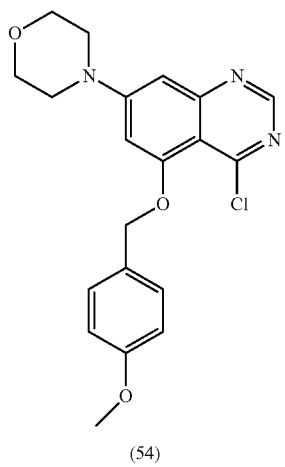

(54)

4-[4-chloro-5-[(4-methoxyphenyl)methoxy]quinazolin-7-yl]morpholine (450 mg, 1.166 mmol), methanol (0.236 mL, 5.826 mmol), K2CO3 (322 mg, 2.330 mmol), and DMF (5.0 mL) were combined in a microwave vessel and heated in the microwave to 150° C. for 30 minutes, resulting in partial conversion as deemed by LCMS. Heated again in the microwave to 175° C. for 1 h. The reaction mixture was filtered through a glass frit, and the solvent was evaporated. The crude residue was purified by silica gel chromatography (12 g Isco gold column, linear gradient 0%→10% MeOH/CH2Cl2) to provide 4-[4-methoxy-5-[(4-methoxyphenyl)methoxy]quinazolin-7-yl]morpholine (206 mg, 0.5347 mmol, 45.86%). 1H NMR (300 MHz, Chloroform-d) δ 8.61 (s, 1H), 7.55-7.43 (m, 2H), 7.04-6.93 (m, 2H), 6.84 (d, J=2.4 Hz, 1H), 6.61 (d, J=2.4 Hz, 1H), 5.16 (s, 2H), 4.13 (s, 3H), 3.95-3.88 (m, 4H), 3.86 (s, 3H), 3.42-3.30 (m, 4H). ESI-MS m/z calc. 381.16885, found 382.32 (M+1)+; Retention time: 0.65 minutes.

To a suspension of 5-[(4-methoxyphenyl)methoxy]-7-morpholino-3H-quinazolin-4-one (Compound (51): 18.60 g, 47.08 mmol) in toluene (250 mL) was added N,N-diisopropylethylamine (41.00 mL, 235.4 mmol) followed by POCl3 (17.55 mL, 188.3 mmol). The reaction was heated at 80° C. for 3 hrs. The reaction was diluted with CH2Cl2 and poured into saturated aqueous NaHCO3. The layers were separated, and the aqueous further extracted with CH2Cl2. The combined organic layer was dried (Na2SO4), filtered, and concentrated to an orange amorphous solid. The crude residue was dry-loaded onto Celite and purified by silica gel chromatography (40 g Isco gold column, linear gradient 0%→15% MeOH/CH2Cl2) to provide 4-[4-chloro-5-[(4-methoxyphenyl)methoxy]quinazolin-7-yl]morpholine (11.977 g, 31.04 mmol, 65.92%). 1H NMR (300 MHz, Chloroform-d) δ 8.71 (s, 1H), 7.51-7.40 (m, 2H), 7.01-6.89 (m, 2H), 6.84 (d, J=2.4 Hz, 1H), 6.66 (d, J=2.4 Hz, 1H), 5.16 (s, 2H), 3.93-3.85 (m, 4H), 3.83 (s, 3H), 3.43-3.34 (m, 4H). ESI-MS m/z calc. 385.11932, found 386.32 (M+1)+; Retention time: 0.77 minutes.

Preparation of Compound 55: 5-[(4-methoxyphenyl)methoxy]-7-morpholino-quinazoline-4-carbonitrile

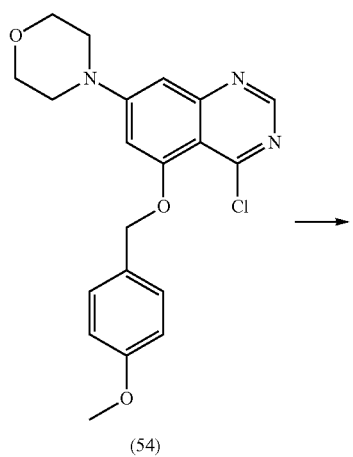

(54)

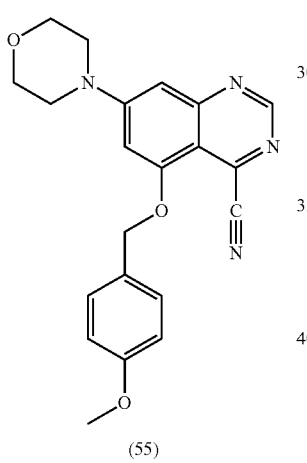

(55)

A mixture of 4-[4-chloro-5-[(4-methoxyphenyl)methoxy]quinazolin-7-yl]morpholine (400 mg, 1.037 mmol), KCN (204 mg, 3.133 mmol), sodium p-toluenesulfonate (132 mg, 0.6798 mmol), and DMF (7.2 mL) was sealed and heated to 80° C. for 16 h. The reaction mixture was partitioned between H2O and CH2Cl2. The layers were separated, and the aqueous further extracted with CH2Cl2 (2×20 mL). The combined organics were washed twice with water and once with brine, dried (Na2SO4), filtered and concentrated. The crude residue was purified by silica gel chromatography (12 g Isco gold column, linear gradient 0%→10% MeOH/CH2Cl2) to provide 5-[(4-methoxyphenyl)methoxy]-7-morpholino-quinazoline-4-carbonitrile (263.5 mg, 0.7000 mmol, 67.51%). Dried under heat/vacuum to remove residual DMF. 1H NMR (300 MHz, Chloroform-d) δ 9.08 (s, 1H), 7.53-7.43 (m, 2H), 6.98-6.91 (m, 2H), 6.81 (d, J=2.3 Hz, 1H), 6.69 (d, J=2.3 Hz, 1H), 5.29 (s, 2H), 3.95-3.85 (m, 4H), 3.82 (s, 3H), 3.48-3.36 (m, 4H). ESI-MS m/z calc. 376.15353, found 377.32 (M+1)+; Retention time: 0.81 minutes.

Preparation of Compound 56: 4-[4-cyclopropyl-5-[(4-methoxyphenyl)methoxy]quinazolin-7-yl]morpholine

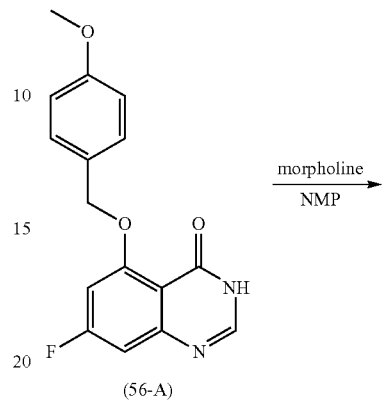

(56-A)

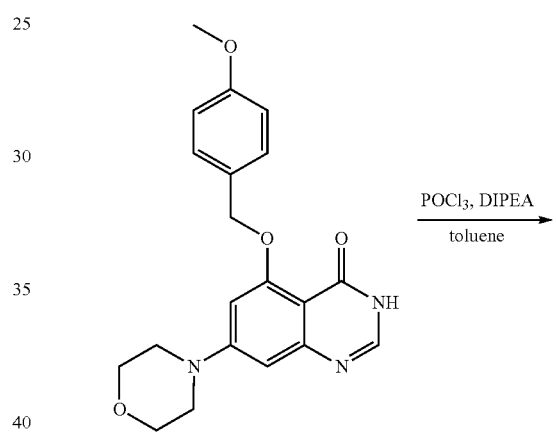

(56-B)

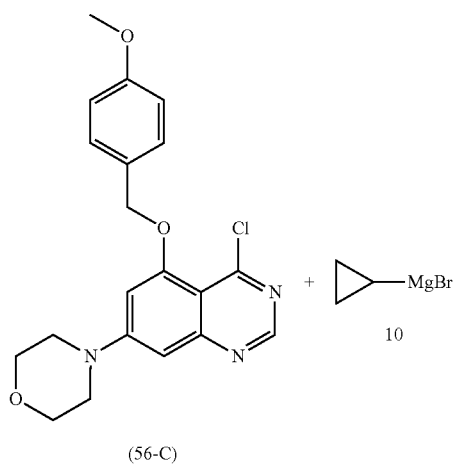

(56-C)

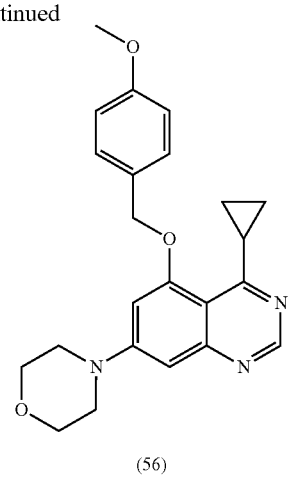

(56)

Preparation of Compound (56-B)

A solution of 7-fluoro-5-[(4-methoxyphenyl)methoxy]-3H-quinazolin-4-one (5.63 g, 18.8 mmol) and morpholine (33 mL, 380 mmol) in anhydrous NMP (60 mL) was heated to 120° C. overnight. The reaction was cooled to room temperature and diluted with water. The precipitate was filtered and dried under vacuum at 55° C. to yield 5-[(4-methoxyphenyl)methoxy]-7-morpholino-3H-quinazolin-4-one (3.26 g, 47.3% yield). $^1$H-NMR (300 MHz, DMSO) δ 11.46 (s, 1H), 7.83 (s, 1H), 7.51 (d, J=8.7 Hz, 2H), 6.95 (d, J=8.7 Hz, 2H), 6.60 (dd, J=29.8, 2.1 Hz, 2H), 5.14 (s, 2H), 3.90-3.58 (m, 7H), 3.31 (s, 4H).

Preparation of Compound (56-C)

To a suspension of 5-[(4-methoxyphenyl)methoxy]-7-morpholino-3H-quinazolin-4-one (2.0 g, 5.4 mmol) in toluene (25 mL) was added DIPEA (5.69 mL, 32.7 mmol) followed by POCl$_3$ (2.54 mL, 27.3 mmol). The reaction was heated to 80° C. for 3.5 hours. The reaction was cooled to room temperature, diluted with water, and extracted with EtOAc/DCM. The combined organic extracts were washed with brine, dried over MgSO4, filtered, and concentrated. The residue was purified by flash chromatography using EtOAc and heptanes to yield 4-[4-chloro-5-[(4-methoxyphenyl)methoxy]quinazolin-7-yl]morpholine (1.46 g, 69.5% yield). $^1$H-NMR (300 MHz, CDCl$_3$) δ 8.73 (s, 1H), 7.52-7.41 (m, 2H), 7.04-6.91 (m, 2H), 6.87 (d, J=2.3 Hz, 1H), 6.68 (d, J=2.3 Hz, 1H), 6.68 (d, J=2.3 Hz, 1H), 5.19 (s, 2H), 3.98-3.87 (m, 4H), 3.86 (s, 3H), 3.48-3.35 (m, 4H).

Preparation of Compound (56)

To a mixture of 4-[4-chloro-5-[(4-methoxyphenyl)methoxy]quinazolin-7-yl]morpholine (200 mg, 0.520 mmol) and Fe(acac)$_3$ (55 mg, 0.16 mmol) in THF (5 mL) and NMP (0.25 mL) under nitrogen was added (cyclopropyl)magnesium bromide (1.20 mL of 0.5 M, 0.6000 mmol) dropwise. The reaction was stirred at room temperature overnight. The reaction was deemed incomplete and 1 mL (cyclopropyl)magnesium bromide was added dropwise and continued to stir at room temperature for 5.5 hours. The reaction was poured into a seperatory funnel containing iced NH$_4$Cl and extracted with EtOAc. The combined organic extracts were washed with brine, dried over MgSO4, filtered, and concentrated. The residue was purified by flash chromatography using EtOAc and heptanes to yield 4-[4-cyclopropyl-5-[(4-methoxyphenyl)methoxy]quinazolin-7-yl]morpholine (176 mg, 84.8% yield). $^1$H-NMR (300 MHz, CDCl$_3$) δ 8.79 (s, 1H), 7.48-7.35 (m, 2H), 7.00-6.88 (m, 2H), 6.83 (d, J=2.3 Hz, 1H), 6.65 (d, J=2.3 Hz, 1H), 5.15 (s, 2H), 3.93-3.85 (m, 4H), 3.84 (s, 3H), 3.48-3.28 (m, 5H), 1.35-1.22 (m, 2H), 0.99-0.86 (m, 2H). ESI-MS m/z calc. 391.1896, found 392.25 (M+1)$^+$.

Preparation of Compound 57: 5-[(4-methoxyphenyl)methoxy]-N-methyl-7-morpholino-quinazolin-4-amine

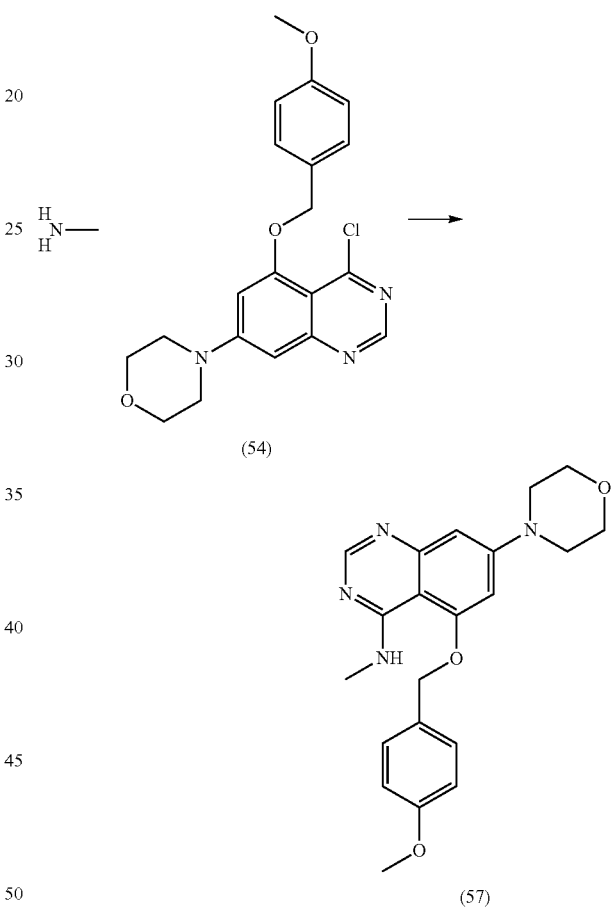

To a solution of 4-[4-chloro-5-[(4-methoxyphenyl)methoxy]quinazolin-7-yl]morpholine (500 mg, 1.296 mmol) in 1,4-dioxane (6.480 mL) was added methylamine (3.240 mL of 2 M, 6.480 mmol) in THF. The reaction was heated for 15 minutes at 60° C. The reaction was diluted with water and extracted with EtOAc (3×). The combined organics were washed with brine, concentrated to dryness, dissolved in minimal EtOAc, and dropped into cold heptanes while stirring vigorously. The resulting light orange ppt was filtered and dried overnight under vacuum at 50° C. to obtain 5-[(4-methoxyphenyl)methoxy]-N-methyl-7-morpholino-quinazolin-4-amine (378 mg, 0.9638 mmol, 74.36%). 1H NMR (300 MHz, DMSO) δ 8.22 (s, 1H), 7.88 (t, J=4.6 Hz, 1H), 7.48 (dd, J=9.1, 2.4 Hz, 2H), 7.02-6.93 (m, 2H), 6.74 (d, J=2.2 Hz, 1H), 6.51 (d, J=2.1 Hz, 1H), 5.33 (s, 2H), 3.77-3.71 (m, 7H), 3.28-3.18 (m, 4H), 2.92 (d, J=4.7 Hz, 3H). ESI-MS m/z calc. 380.18484, found 381.0 (M+1)+; Retention time: 0.73 minutes.

Preparation of Compound 58: 5-[(4-methoxyphenyl)methoxy]-N,N-dimethyl-7-morpholino-quinazolin-4-amine

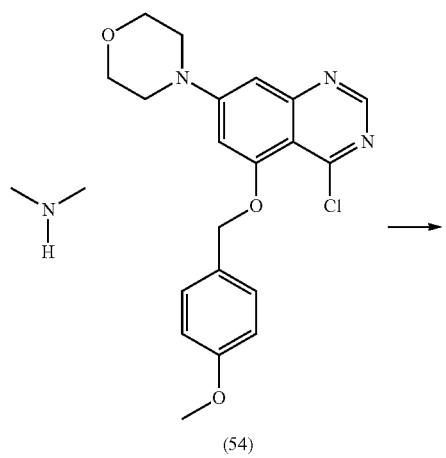

(54)

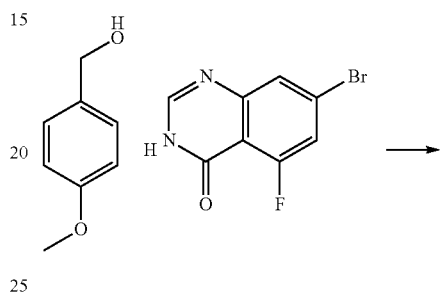

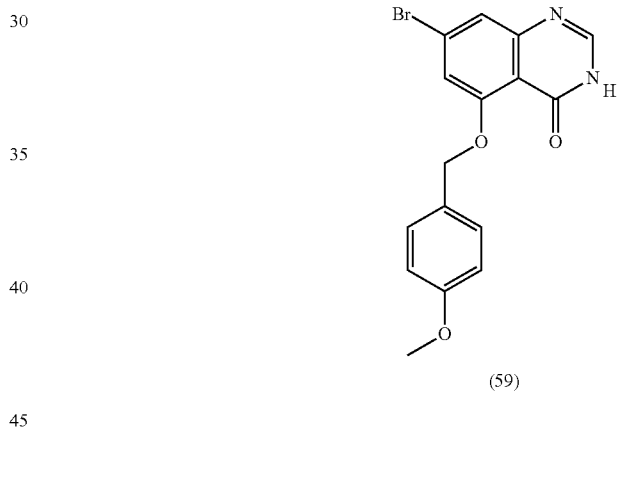

(58)

4-[4-chloro-5-[(4-methoxyphenyl)methoxy]quinazolin-7-yl]morpholine (500 mg, 1.296 mmol), dimethylamine (Hydrochloric Acid (1)) (528.4 mg, 563.3 µL, 6.480 mmol) and triethylamine (1.311 g, 1.806 mL, 12.96 mmol) in 1,4-dioxane (6.480 mL) were stirred at 60° C. for 2 h. The reaction mixture was diluted with water and extracted 3×EtOAc. The combined organics were concentrated to dryness, dissolved in minimal EtOAc, and dropped into cold heptane while stirring vigorously. The resulting tan ppt was filtered and dried overnight under vacuum at 50 deg C. to give 384 mg (71.4%) of 5-[(4-methoxyphenyl)methoxy]-N,N-dimethyl-7-morpholino-quinazolin-4-amine which was carried on as is to the next reaction. 5-[(4-methoxyphenyl)methoxy]-N,N-dimethyl-7-morpholino-quinazolin-4-amine (384 mg, 0.9248 mmol, 71.36%) 1H NMR (300 MHz, DMSO) δ 8.21 (s, 1H), 7.42 (t, J=5.7 Hz, 2H), 7.05-6.94 (m, 2H), 6.79 (d, J=2.2 Hz, 1H), 6.57 (d, J=2.1 Hz, 1H), 5.14 (s, 2H), 3.79-3.73 (m, 7H), 3.35-3.31 (m, 4H), 2.91 (s, 6H). ESI-MS m/z calc. 394.2005, found 395.0 (M+1)+; Retention time: 0.74 minutes.

Preparation of 7-bromo-5-[(4-methoxyphenyl)methoxy]-3H-quinazolin-4-one: Compound 59

(59)

To a solution of (4-methoxyphenyl)methanol (31.1 g, 225.1 mmol) in DMF (279.9 mL) was added NaH (9.31 g, 232.8 mmol). The resultant mixture was stirred at room temperature for 1 h. 7-bromo-5-fluoro-3H-quinazolin-4-one (27.33 g, 112.5 mmol) was added, and stirring was continued for an additional 2 h. Quenched by adding water (600 mL), then added AcOH to effect precipitation of a solid. The solid was collected by vacuum filtration, washing with water then Et2O. The solid was dried on high vacuum overnight to 7-bromo-5-[(4-methoxyphenyl)methoxy]-3H-quinazolin-4-one (34.32 g, 80.2%). 1H NMR (300 MHz, DMSO-d6) δ 12.07 (s, 1H), 8.02 (s, 1H), 7.55-7.42 (m, 2H), 7.37 (d, J=1.8 Hz, 1H), 7.28 (d, J=1.9 Hz, 1H), 7.03-6.90 (m, 2H), 5.20 (s, 2H), 3.76 (s, 3H)

Example 2: Biological Assay of Compounds of the Invention

A. DNA-PK Inhibition Assay

Compounds were screened for their ability to inhibit DNA-PK kinase using a standard radiometric assay. Briefly, in this kinase assay the transfer of the terminal $^{33}$P-phosphate in $^{33}$P-ATP to a peptide substrate is interrogated. The assay was carried out in 384-well plates to a final volume of 50 μL per well containing approximately 6 nM DNA-PK, 50 mM HEPES (pH 7.5), 10 mM $MgCl_2$, 25 mM NaCl, 0.01% BSA, 1 mM DTT, 10 μg/mL sheared double-stranded DNA (obtained from Sigma), 0.8 mg/mL DNA-PK peptide (Glu-Pro-Pro-Leu-Ser-Gln-Glu-Ala-Phe-Ala-Asp-Leu-Trp-Lys-Lys-Lys, obtained from American Peptide), and 100 μM ATP. Accordingly, compounds of the invention were dissolved in DMSO to make 10 mM initial stock solutions. Serial dilutions in DMSO were then made to obtain the final solutions for the assay. A 0.75 μL aliquot of DMSO or inhibitor in DMSO was added to each well, followed by the addition of ATP substrate solution containing $^{33}$P-ATP (obtained from Perkin Elmer). The reaction was started by the addition of DNA-PK, peptide and ds-DNA. After 45 min, the reaction was quenched with 25 μL of 5% phosphoric acid. The reaction mixture was transferred to MultiScreen HTS 384-well PH plates (obtained from Millipore), allowed to bind for one hour, and washed three times with 1% phosphoric acid. Following the addition of 50 μL of Ultima Gold™ high efficiency scintillant (obtained from Perkin Elmer), the samples were counted in a Packard TopCount NXT Microplate Scintillation and Luminescence Counter (Packard BioScience). The $K_i$ values were calculated using Microsoft Excel Solver macros to fit the data to the kinetic model for competitive tight-binding inhibition. In Tables 1 and 2 below, $K_i$ of less than 0.001 micromolar for the inhibition of DNA-PK is indicated as "A"; $K_i$ of equal to or greater than 0.001 micromolar and less than 0.01 micromolar for the inhibition of DNA-PK as "B"; $K_i$ of equal to or greater than 0.01 micromolar and less than 0.1 micromolar for the inhibition of DNA-PK as "C"; $K_i$ of equal to or greater than 0.1 micromolar and less than 1 micromolar for the inhibition of DNA-PK for "D"; and $K_i$ of equal to or greater than 1 micromolar as "E."

B. DNA-PK Cellular Assay

DNA-PK is recruited to and activated by double-strand breaks (DSB) in DNA and plays a critical role in the non-homologous end-joining (NHEJ) repair mechanism. Upon activation, DNA-PK undergoes rapid autophosphorylation at Ser2056. The measure of pDNA-PK (Ser2056) in response to DNA DSBs provides a cellular signaling assay to evaluate potential DNA-PK kinase inhibitors.

Neocarzinostatin (NCS) was used as a radiomimetic to induce DNA DSBs. The sandwich ELISA used the Meso Scale Discovery electrochemiluminescence technology platform which typically provides greater sensitivity than traditional ELISA formats. Internal validation has demonstrated that this assay enables highly specific and quantitative measurement of pDNA-PK (Ser2056).

A549 (human NSCLC) cells are plated at 25,000 cells/well in 100 uL of DMEM (Invitrogen cat #11995-040) supplemented with 1% Pen/Strep (Invitrogen cat #15070-063) and 10% FBS (Hyclone cat #SH30071.03HI) on black clear bottom 96 well plates (Costar #3904) and allowed to adhere overnight at 37° C. in 5% $CO_2$. The following day, the compounds and NCS solutions are prepared by adding 100 ul of DMEM growth media per well in a Corning polypropylene V-bottom deep well plate (cat #3357). The HP Compound Dilution D300 instrument was used to add compounds to the appropriate wells using the setting logarithmic and 16-point titration singlet.

The DMEM NCS solution was prepared by adding NCS to DMEM media at 200 ng/ml (final assay concentration, 50 ng/ml). 100 ul of the DMEM/NCS solution is added to the wells with the compounds. 100 ul of this solution is then immediately added to the A549 cells. The cells are then incubated for 15 minutes at 37° C.

The complete lysis buffer is prepared by adding 1% Phosphatase inhibitor (Sigma cat #P2850) and 1% Protease Inhibitor (Sigma cat #P8340) to the Lanthascreen cellular assay lysis buffer (Invitrogen cat #PV5598). The media from the plate was removed by flicking and patting dry. 60 uL/well of the complete lysis buffer is added to each well. These plates are then incubated for at least 5 minutes in the lysis buffer at room temperature to ensure complete lysis. At this point the lysates can be transferred to prepared ELISA plates.

The prepared ELISA plates were prepared blocking the Mesoscale Goat-Anti-Mouse (GAM) plates with 150 uL/well of 3% Blocker A (Mesoscale cat #R93-BA) for one hour at room temperature with shaking. The capture antibody is prepared by diluting the mouse monoclonal anti-total DNA-PK (AbCAM cat #ab1832) to 3 ug/mL in 1% Blocker A. The blocked plates rinsed once with 200 uL D-PBS. The capture antibody (25 ul/well) was added to each well and allowed to incubate for an hour at room temperature while shaking. This was rinsed once with 200 ul D-PBS before adding 25 uL of the prepared cell lysate from the cell plates to the Mesoscale GAM ELISA plate. The lysate is then incubated on the plates for one hour at room temperature with shaking. The detection antibody (Epitomics rabbit anti-pS2056-DNA-PK) is prepared at a 1/1000 dilution (to a final concentration of 450 ng/mL) in 1% Blocker A. The GAM plates are washed once with 200 uL of D-PBS and then 25 uL/well of the detection antibody is added to the plate. This incubates for one hour at room temperature with shaking. The Sulfotag is prepared by adding Sulfo-Tag Goat-Anti-Rabbit antibody (Mesoscale cat #R32AB-1) at a 1/500 dilution (1 ug/mL) to 1% Blocker A. The GAM plates are washed with 200 uL of D-PBS and then 25 uL of the Sulfotag preparation is added to each well. Once the plates have been incubated with the final solution, the Sulfotag, for 1 hour, they are washed once with 200 uL of D-PBS. The 1× Read Buffer (Mesoscale cat #R32-TC) is made by diluting the 4× buffer in ddH20. 150 uL of 1× buffer is added to each well of the GAM plate and then the plate is read on the Sector Imager 2400. The readout (electrochemiluminescence) was plotted against the concentration of each compound and the IC50s were generated using Prism software (GraphPad Prism version 6.0e for Macintosh).

In Tables 1 and 2 below, $IC_{50}$ of less than 0.10 micromolar for the inhibition of DNA-PK is indicated as "A"; $IC_{50}$ equal to or greater than 0.10 micromolar and less than 1.0 micromolar for the inhibition of DNA-PK as "B"; and $IC_{50}$ equal to or greater than 1.0 micromolar for the inhibition of DNA-PK as "C".

TABLE 1

Characterization Data and Ki and IC$_{50}$ Values for Certain Compounds of the Invention

| Comp. Nos. | Molecule | M + 1 | LCMS Retention Time (Method) | NMR | Ki (μM) DNA-PK | IC$_{50}$ (μM) |
|---|---|---|---|---|---|---|
| 1 | | 463.26 | 0.5 (A) | 1H NMR (400 MHz, CDCl3) δ 9.43 (s, 1H), 9.09 (s, 1H), 6.78 (s, 1H), 6.58 (d, J = 1.5 Hz, 1H), 4.75 (s, 1H), 4.59 (t, J = 9.0 Hz, 2H), 4.52 (d, J = 8.1 Hz, 1H), 4.24-4.11 (m, 1H), 3.94-3.83 (m, 4H), 3.42-3.31 (m, 4H), 3.19 (t, J = 9.0 Hz, 2H), 2.48 (s, 3H), 2.21 (d, J = 13.1 Hz, 2H), 1.99 (dd, J = 12.6, 3.6 Hz, 2H), 1.90-1.72 (m, 4H). | A | A |
| 2 | | 488.34 | 0.63 (A) | 1H NMR (300 MHz, CDCl3) δ 9.08 (s, 1H), 6.83 (d, J = 2.1 Hz, 1H), 6.67 (d, J = 2.0 Hz, 1H), 4.84 (s, 1H), 4.64 (dd, J = 8.6, 4.2 Hz, 1H), 4.62-4.52 (m, 2H), 4.27-4.17 (m, 1H), 3.94-3.85 (m, 4H), 3.51-3.40 (m, 4H), 3.18 (t, J = 9.1 Hz, 2H), 2.49 (s, 3H), 2.33-2.22 (m, 2H), 2.07-1.86 (m, 6H). | A | A |
| 3 | | 421.42 | 0.55 (A) | 1H NMR (300 MHz, Chloroform-d) δ 9.45 (s, 1H), 9.12 (s, 1H), 8.12 (d, J = 5.9 Hz, 1H), 6.86-6.77 (m, 1H), 6.60 (d, J = 2.2 Hz, 1H), 6.18 (d, J = 5.9 Hz, 1H), 4.87 (s, 1H), 4.79 (d, J = 3.5 Hz, 1H), 4.02-3.80 (m, 5H), 3.48-3.30 (m, 4H), 2.52 (s, 3H), 2.32-2.20 (m, 2H), 2.07-1.95 (m, 2H), 1.94-1.76 (m, 4H). | A | A |
| 4 | | 446.35 | 0.61 (A) | 1H NMR (300 MHz, Chloroform-d) δ 9.08 (s, 1H), 8.06 (d, J = 5.9 Hz, 1H), 6.83 (d, J = 2.3 Hz, 1H), 6.71-6.63 (m, 1H), 6.14 (d, J = 60 Hz, 1H), 4.93 (s, 1H), 4.85 (s, 1H), 4.06-3.79 (m, 5H), 3.49 (s, 3H), 3.48-3.40 (m, 4H), 2.49 (s, 3H), 2.34-2.21 (m, 2H), 2.13-1.85 (m, 6H). | A | A |

TABLE 1-continued

Characterization Data and Ki and IC$_{50}$ Values for Certain Compounds of the Invention

| Comp. Nos. | Molecule | M + 1 | LCMS Retention Time (Method) | NMR | Ki (μM) DNA-PK | IC$_{50}$ (μM) |
|---|---|---|---|---|---|---|
| 5 | | 493.34 | 0.58 (A) | 1H NMR (300 MHz, Chloroform-d) δ 8.58 (s, 1H), 6.80 (d, J = 2.4 Hz, 1H), 6.56 (d, J = 2.4 Hz, 1H), 4.68 (s, 1H), 4.58 (t, J = 9.1 Hz, 2H), 4.46 (d, J = 8.3 Hz, 1H), 4.13 (s, 3H), 3.93-3.82 (m, 4H), 3.38-3.27 (m, 4H), 3.19 (t, J = 9.1 Hz, 2H), 2.49 (s, 3H), 2.25-2.13 (m, 2H), 1.99-1.74 (m, 6H). | A | A |
| 6 | | 451.35 | 0.57 (A) | 1H NMR (300 MHz, Chloroform-d) δ 8.58 (s, 1H), 8.12 (d, J = 5.9 Hz, 1H), 6.81 (d, J = 2.4 Hz, 1H), 6.55 (d, J = 2.1 Hz, 1H), 6.17 (d, J = 5.9 Hz, 1H), 4.86 (s, 1H), 4.69 (s, 1H), 4.12 (s, 3H), 3.94-3.84 (m, 4H), 3.70 (d, J = 12.4 Hz, 1H), 3.41-3.25 (m, 4H), 2.49 (s, 3H), 2.21 (d, J = 11.0 Hz, 2H), 1.98-1.73 (m, 6H). | A | A |
| 7 | | 459.31 | 0.66 (A) | 1H NMR (300 MHz, Chloroform-d) δ 9.80 (d, J = 0.6 Hz, 1H), 9.15 (s, 1H), 7.89-7.78 (m, 2H), 7.78-7.65 (m, 2H), 6.80 (dd, J = 2.3, 0.6 Hz, 1H), 6.61 (d, J = 2.0 Hz, 1H), 4.86 (s, 1H), 4.30 (tt, J = 12.5, 4.1 Hz, 1H), 3.96-3.82 (m, 4H), 3.47-3.30 (m, 4H), 2.83 (qd, J = 12.8, 3.4 Hz, 2H), 2.35 (d, J = 15.0 Hz, 2H), 1.84-1.62 (m, 4H). | B | B |
| 8 | | 464.35 | 0.58 (A) | 1H NMR (300 MHz, Chloroform-d) δ 9.45 (s, 1H), 9.10 (s, 1H), 8.49 (d, J = 4.8 Hz, 1H), 7.76 (d, J = 4.5 Hz, 1H), 7.32 (d, J = 4.9 Hz, 1H), 6.79 (d, J = 2.2 Hz, 1H), 6.59 (d, J = 2.2 Hz, 1H), 5.18 (d, J = 7.6 Hz, 1H), 4.86-4.70 (m, 1H), 4.15-3.96 (m, 1H), 3.96-3.78 (m, 4H), 3.49-3.33 (m, 4H), 3.00 (d, J = 5.2 Hz, 3H), 2.32-2.14 (m, 2H), 2.10-1.96 (m, 2H), 1.96-1.74 (m, 4H). 1H NMR (300 MHz, Chloroform-d) δ 9.45 (s, 1H), 9.10 (s, 1H), 8.50 (d, J = 4.9 Hz, 1H), 7.77 (s, 1H), 7.33 (d, J = 4.9 Hz, 1H), 6.86-6.74 (m, 1H), 6.59 (d, J = 2.0 Hz, 1H), 5.16 (d, J = 7.6 Hz, 1H), 4.77 (s, 1H), 4.03 (d, J = 7.9 Hz, 1H), | A | A |

TABLE 1-continued

Characterization Data and Ki and IC$_{50}$ Values for Certain Compounds of the Invention

| Comp. Nos. | Molecule | M + 1 | LCMS Retention Time (Method) | NMR | Ki (μM) DNA-PK | IC$_{50}$ (μM) |
|---|---|---|---|---|---|---|
|  |  |  |  | 3.95-3.82 (m, 4H), 3.39 (dd, J = 5.7, 4.1 Hz, 4H), 3.01 (d, J = 5.1 Hz, 3H), 2.24 (d, J = 10.1 Hz, 2H), 2.08-1.96 (m, 2H), 1.96-1.68 (m, 4H). |  |  |
| 9 |  | 494.33 | 0.6 (A) | 1H NMR (300 MHz, Chloroform-d) δ 8.60 (s, 1H), 8.49 (d, J = 4.9 Hz, 1H), 7.73 (s, 1H), 7.38-7.30 (m, 1H), 6.91 (d, J = 3.6 Hz, 1H), 6.55 (d, J = 2.5 Hz, 1H), 5.09 (s, 1H), 4.71 (s, 1H), 4.18 (d, J = 2.0 Hz, 3H), 4.04-3.83 (m, 5H), 3.42-3.32 (m, 4H), 3.01 (d, J = 5.2 Hz, 3H), 2.22 (d, J = 9.3 Hz, 2H), 2.06-1.93 (m, 2H), 1.83 (t, J = 9.4 Hz, 4H). | A | A |
| 10 |  | 443.2 | 0.6 (C) | 1H NMR (400 MHz, Chloroform-d) δ 9.32 (s, 1H), 6.80 (s, 1H), 6.50 (d, J = 2.0 Hz, 1H), 4.71 (s, 1H), 4.56 (s, 1H), 3.89 (t, J = 4.9 Hz, 4H), 3.63 (s, 1H), 3.42 (t, J = 4.9 Hz, 4H), 2.84 (s, 3H), 2.17 (d, J = 13.4 Hz, 2H), 1.97-1.60 (m, 6H), 1.47 (s, 9H). | B | C |
| 11 |  | 480.33 | 0.57 (A) | 1H NMR (300 MHz, Chloroform-d) δ 8.46 (d, J = 4.9 Hz, 1H), 8.02 (s, 1H), 7.87 (dd, J = 5.4, 4.5 Hz, 1H), 7.29 (d, J = 4.8 Hz, 1H), 6.70 (d, J = 2.4 Hz, 1H), 6.48 (d, J = 2.5 Hz, 1H), 5.76-5.31 (m, 1H), 4.72 (s, 1H), 3.99 (dt, J = 8.1, 4.0 Hz, 1H), 3.92-3.74 (m, 4H), 3.42-3.22 (m, 4H), 2.98 (d, J = 5.1 Hz, 3H), 2.32-2.12 (m, 2H), 2.12-1.84 (m, 4H), 1.77 (td, J = 13.2, 11.9, 3.2 Hz, 2H). | A | C |
| 12 |  | 435.2 | 0.49 (A) | 1H NMR (300 MHz, Chloroform-d) δ 9.38 (s, 1H), 8.10 (d, J = 6.0 Hz, 1H), 6.80-6.69 (m, 1H), 6.54 (d, J = 1.9 Hz, 1H), 6.21 (d, J = 6.0 Hz, 1H), 5.09 (s, 1H), 4.76 (s, 1H), 4.01-3.82 (m, 4H), 3.38 (dd, J = 6.0, 3.9 Hz, 4H), 2.81 (s, 3H), 2.54 (s, 3H), 2.25 (d, J = 11.5 Hz, 2H), 2.12-1.68 (m, 6H)., 1H NMR (400 MHz, CDCl3) δ 9.27 (d, J = 1.7 Hz, 1H), 8.01 (d, J = 5.8 Hz, 1H), 6.65 (d, J = 2.0 Hz, 1H), 6.44 (d, J = 2.1 Hz, 1H), 6.19-6.05 (m, 1H), 4.87 (s, 1H), 4.66 (s, 1H), 3.80 (t, J = 4.9 Hz, 5H), 3.29 (dd, J = 6.8, 3.1 Hz, 4H), 2.71 (d, J = 1.9 Hz, 3H), 2.43 (d, J = 1.8 Hz, 4H), 2.14 (d, J = 13.8 Hz, 2H), 2.01-1.68 (m, 6H). | B | B |

TABLE 1-continued

Characterization Data and Ki and IC$_{50}$ Values for Certain Compounds of the Invention

| Comp. Nos. | Molecule | M + 1 | LCMS Retention Time (Method) | NMR | Ki (μM) DNA-PK | IC$_{50}$ (μM) |
|---|---|---|---|---|---|---|
| 13 | | 478.44 | 0.59 (A) | 1H NMR (300 MHz, Chloroform-d) δ 8.87 (s, 1H), 8.49 (d, J = 4.8 Hz, 1H), 7.75 (d, J = 4.9 Hz, 1H), 7.34 (d, J = 4.8 Hz, 1H), 6.82 (d, J = 2.4 Hz, 1H), 6.56 (d, J = 2.4 Hz, 1H), 5.18 (d, J = 7.4 Hz, 1H), 4.79-4.69 (m, 1H), 4.03 (ddt, J = 13.1, 7.8, 4.4 Hz, 1H), 3.89 (dd, J = 5.7, 4.1 Hz, 4H), 3.42-3.27 (m, 4H), 3.05 (s, 3H), 3.01 (d, J = 5.1 Hz, 3H), 2.31-2.16 (m, 2H), 2.13-2.00 (m, 2H), 2.00-1.75 (m, 4H). | A | A |
| 14 | | 505.44 | 0.53 (A) | 1H NMR (300 MHz, Chloroform-d) δ 9.42 (s, 1H), 9.08 (s, 1H), 8.18 (d, J = 0.8 Hz, 1H), 6.77 (d, J = 2.0 Hz, 1H), 6.56 (d, J = 2.2 Hz, 1H), 5.44 (d, J = 1.0 Hz, 1H), 4.85-4.62 (m, 2H), 3.97-3.74 (m, 5H), 3.60-3.55 (m, 4H), 3.45-3.27 (m, 4H), 2.52-2.46 (m, 4H), 2.33 (d, J = 2.5 Hz, 3H), 2.26-2.15 (m, 2H), 2.05-1.91 (m, 2H), 1.91-1.64 (m, 4H). | A | A |
| 15 | | 435.35 | 2.48 (A) | 1H NMR (300 MHz, Chloroform-d) δ 9.47 (s, 1H), 9.26 (d, J = 1.4 Hz, 1H), 9.10 (s, 1H), 8.97 (d, J = 5.0 Hz, 1H), 8.12 (dd, J = 5.1, 1.5 Hz, 1H), 8.02 (d, J = 8.2 Hz, 1H), 6.82-6.75 (m, 1H), 6.58 (d, J = 2.2 Hz, 1H), 4.83-4.73 (m, 1H), 4.20-4.07 (m, 1H), 3.95-3.82 (m, 4H), 3.43-3.31 (m, 4H), 2.33-2.17 (m, 2H), 2.06-1.82 (m, 6H). | A | A |
| 16 | | 397.44 | 0.58 (A) | 1H NMR (300 MHz, Chloroform-d) δ 9.43 (s, 1H), 9.09 (s, 1H), 6.78 (d, J = 2.3 Hz, 1H), 6.56 (d, J = 2.2 Hz, 1H), 5.73-5.54 (m, 1H), 4.74 (t, J = 3.9 Hz, 1H), 3.97 (ddd, J = 14.9, 6.4, 4.1, Hz, 1H), 3.92-3.81 (m, 4H), 3.45-3.30 (m, 4H), 2.19 (dd, J = 12.1, 2.7 Hz, 2H), 1.95-1.59 (m, 6H), 1.34 (tt, J = 7.7, 4.6 Hz, 1H), 1.03-0.91 (m, 2H), 0.79-0.68 (m, 2H).; 1H NMR (400 MHz, Chloroform-d) δ 9.44 (s, 1H), 9.09 (d, J = 1.4 Hz, 1H), 6.78 (d, J = 1.6 Hz, 1H), 6.60-6.52 (m, 1H), 5.73-5.52 (m, 1H), 4.73 (d, J = 3.5 Hz, 1H), 3.97 (ddt, J = 10.2, 7.3, 3.8 Hz, 1H), 3.89 (td, | A | A |

TABLE 1-continued

Characterization Data and Ki and IC₅₀ Values for Certain Compounds of the Invention

| Comp. Nos. | Molecule | M + 1 | LCMS Retention Time (Method) | NMR | Ki (μM) DNA-PK | IC₅₀ (μM) |
|---|---|---|---|---|---|---|
| | | | | J = 4.9, 1.3 Hz, 4H), 3.38 (td, J = 4.9, 1.3 Hz, 4H), 2.28-2.09 (m, 2H), 1.89 (dt, J = 13.0, 4.2 Hz, 2H), 1.85-1.60 (m, 4H), 1.39-1.28 (m, 1H), 1.03-0.90 (m, 2H), 0.80-0.69 (m, 2H). | | |
| 17 | | 447.12 | 0.55 (A) | 1H NMR (300 MHz, Chloroform-d) δ 9.49 (s, 1H), 9.12 (s, 1H), 8.51 (s, 1H), 7.76 (d, J = 2.2 Hz, 1H), 6.87 (d, J = 2.2 Hz, 1H), 6.82 (dd, J = 2.2, 0.5 Hz, 1H), 6.62 (d, J = 2.3 Hz, 1H), 5.17 (d, J = 7.9 Hz, 1H), 4.83 (d, J = 2.9 Hz, 1H), 4.45-4.29 (m, 1H), 3.94-3.90 (m, 4H), 3.45-3.39 (m, 4H), 2.30 (d, J = 9.4 Hz, 2H), 2.15-2.06 (m, 2H), 1.99-1.86 (m, 4H). | A | A |
| 18 | | 505.49 | 0.53 (A) | 1H NMR (300 MHz, Chloroform-d) δ 9.43 (s, 1H), 9.09 (s, 1H), 7.89 (d, J = 5.8 Hz, 1H), 6.85-6.72 (m, 1H), 6.57 (d, J = 2.2 Hz, 1H), 5.68 (d, J = 5.9 Hz, 1H), 4.74 (s, 1H), 4.60 (d, J = 7.9 Hz, 1H), 3.95-3.70 (m, 9H), 3.44-3.32 (m, 4H), 2.49-2.39 (m, 4H), 2.32 (s, 3H), 2.27-2.14 (m, 2H), 2.05-1.92 (m, 2H), 1.92-1.76 (m, 4H). | A | A |
| 19 | | 478.2 | 0.53 (C) | 1H NMR (400 MHz, CDCl3) δ 9.17 (s, 1H), 8.28 (d, J = 4.9 Hz, 1H), 7.56 (s, 1H), 7.12 (dd, J = 4.8, 0.7 Hz, 1H), 6.52 (d, J = 2.0 Hz, 1H), 6.32 (d, J = 2.0 Hz, 1H), 4.94 (d, J = 8.0 Hz, 1H), 4.54 (d, J = 4.3 Hz, 1H), 3.82 (dp, J = 13.9, 4.2 Hz, 1H), 3.67 (dd, J = 5.9, 3.8 Hz, 4H), 3.21-3.12 (m, 4H), 2.80 (d, J = 5.0 Hz, 3H), 2.59 (s, 3H), 2.12-1.95 (m, 2H), 1.88-1.75 (m, 2H), 1.73-1.51 (m, 4H). [1] | B | A |
| 20 | | 401.32 | 0.56 (C) | 1H NMR (400 MHz, CDCl3) δ 9.45 (s, 1H), 9.09 (s, 1H), 6.79 (d, J = 2.0 Hz, 1H), 6.57 (d, J = 2.1 Hz, 1H), 6.52 (d, J = 8.4 Hz, 1H), 4.75 (p, J = 3.2 Hz, 1H), 4.06-3.93 (m, 1H), 3.94-3.84 (m, 6H), 3.45 (s, 3H), 3.42-3.33 (m, 4H), 2.26-2.14 (m, 2H), 1.93-1.61 (m, 6H). | B | C |

TABLE 1-continued

Characterization Data and Ki and IC$_{50}$ Values for Certain Compounds of the Invention

| Comp. Nos. | Molecule | M + 1 | LCMS Retention Time (Method) | NMR | Ki (μM) DNA-PK | IC$_{50}$ (μM) |
|---|---|---|---|---|---|---|
| 21 | | 451.33 | 0.51 (A) | 1H NMR (300 MHz, CDCl3) δ 8.08 (d, J = 5.9 Hz, 1H), 7.93 (s, 1H), 6.65 (d, J = 2.3 Hz, 1H), 6.48 (d, J = 2.2 Hz, 1H), 6.18 (d, J = 6.1 Hz, 1H), 5.22 (s, 1H), 4.72 (s, 1H), 3.97-3.81 (m, 4H), 3.53 (d, J = 10.6 Hz, 3H), 3.40-3.25 (m, 4H), 2.52 (s, 3H), 2.23 (d, J = 12.9 Hz, 2H), 2.05-1.70 (m, 7H). | | B |
| 22 | | 401.32 | 0.63 (C) | 1H NMR (400 MHz, CDCl3) δ 9.41 (s, 1H), 9.09 (s, 1H), 6.85-6.72 (m, 1H), 6.56 (d, J = 2.0 Hz, 1H), 4.78-4.56 (m, 2H), 4.12 (q, J = 7.1 Hz, 2H), 3.96-3.82 (m, 4H), 3.66 (d, J = 9.7 Hz, 1H), 3.46-3.31 (m, 4H), 2.25-2.08 (m, 2H), 1.90 (dt, J = 12.5, 4.1 Hz, 2H), 1.84-1.61 (m, 4H), 1.25 (t, J = 7.1 Hz, 3H). | A | A |
| 23 | | 411.31 | 0.62 (C) | 1H NMR (400 MHz, CDCl3) δ 9.46 (s, 1H), 9.09 (s, 1H), 6.85-6.74 (m, 1H), 6.56 (d, J = 2.1 Hz, 1H), 5.67 (d, J = 8.1 Hz, 1H), 4.74 (t, J = 3.2 Hz, 1H), 4.04-3.80 (m, 5H), 3.47-3.32 (m, 4H), 2.28-2.14 (m, 2H), 1.96-1.83 (m, 2H), 1.83-1.51 (m, 4H), 1.35 (s, 3H), 1.19 (q, J = 3.8 Hz, 2H), 0.65-0.53 (m, 2H). | A | A |
| 24 | | 409.33 | 0.51 (C) | 1H NMR (400 MHz, CDCl3) δ 9.43 (d, J = 1.5 Hz, 1H), 9.09 (d, J = 1.6 Hz, 1H), 7.10 (d, J = 2.2 Hz, 1H), 6.78 (d, J = 2.1 Hz, 1H), 6.57 (d, J = 1.9 Hz, 1H), 5.53 (t, J = 2.0 Hz, 1H), 4.76-4.66 (m, 1H), 3.88 (dt, J = 5.0, 3.0 Hz, 4H), 3.72 (d, J = 1.5 Hz, 3H), 3.49-3.33 (m, 5H), 2.18 (dd, J = 13.8, 4.1 Hz, 3H), 1.99 (dt, J = 11.7, 3.7 Hz, 2H), 1.89-1.63 (m, 4H). | A | A |

TABLE 1-continued

Characterization Data and Ki and IC$_{50}$ Values for Certain Compounds of the Invention

| Comp. Nos. | Molecule | M + 1 | LCMS Retention Time (Method) | NMR | Ki (μM) DNA-PK | IC$_{50}$ (μM) |
|---|---|---|---|---|---|---|
| 25 | | 494.37 | 0.6 (C) | 1H NMR (400 MHz, CDCl3) δ 8.47 (d, J = 4.8 Hz, 1H), 7.91 (s, 1H), 7.76 (s, 1H), 7.28 (d, J = 4.9 Hz, 1H), 6.63 (d, J = 2.4 Hz, 1H), 6.47 (d, J = 2.4 Hz, 1H), 5.32 (s, 1H), 4.67 (s, 1H), 3.99 (d, J = 9.4 Hz, 1H), 3.92-3.80 (m, 4H), 3.50 (s, 3H), 3.37-3.23 (m, 4H), 3.01 (d, J = 5.1 Hz, 3H), 2.27-2.15 (m, 2H), 2.07-1.95 (m, 2H), 1.90 (dd, J = 13.0, 4.2 Hz, 2H), 1.79 (t, J = 12.8 Hz, 2H). | B | |
| 26 | | 433.05 | 0.25 (C) | 1H NMR (400 MHz, CDCl3) δ 9.44 (s, 1H), 9.10 (s, 1H), 7.51 (d, J = 1.3 Hz, 1H), 7.40-7.34 (m, 1H), 7.09 (d, J = 8.4 Hz, 1H), 6.78 (d, J = 1.9 Hz, 1H), 6.57 (d, J = 2.0 Hz, 1H), 4.74 (d, J = 3.9 Hz, 1H), 4.11 (tq, J = 9.9, 6.2, 5.3 Hz, 1H), 3.89 (dd, J = 5.9, 3.9 Hz, 4H), 3.73 (s, 3H), 3.43-3.33 (m, 4H), 2.29-2.17 (m, 2H), 2.04-1.73 (m, 6H). | B | |
| 27 | | 408.35 | 0.63 (C) | 1H NMR (300 MHz, Chloroform-d) δ 9.45 (s, 1H), 9.10 (s, 1H), 8.53 (d, J = 4.8 Hz, 2H), 6.93 (t, J = 4.8 Hz, 1H), 6.85-6.72 (m, 1H), 6.60 (d, J = 2.1 Hz, 1H), 5.20 (dq, J = 7.6, 3.7 Hz, 1H), 4.67 (dt, J = 6.3, 3.1 Hz, 1H), 3.99-3.79 (m, 4H), 3.51-3.15 (m, 4H), 2.38-2.06 (m, 4H), 2.11-1.78 (m, 4H). | A | |
| 28 | | 408.39 | 0.62 (C) | 1H NMR (300 MHz, Chloroform-d) δ 9.43 (s, 1H), 9.10 (s, 1H), 8.54 (d, J = 4.8 Hz, 2H), 6.95 (t, J = 4.8 Hz, 1H), 6.80 (dd, J = 2.1, 0.8 Hz, 1H), 6.62 (d, J = 2.0 Hz, 1H), 5.29-5.24 (m, 1H), 4.80-4.59 (m, 1H), 4.11-3.77 (m, 4H), 3.58-3.30 (m, 4H), 2.33-2.20 (m, 4H), 2.04-1.70 (m, 4H). | A | |

TABLE 1-continued

Characterization Data and Ki and IC$_{50}$ Values for Certain Compounds of the Invention

| Comp. Nos. | Molecule | M + 1 | LCMS Retention Time (Method) | NMR | Ki (µM) DNA-PK | IC$_{50}$ (µM) |
|---|---|---|---|---|---|---|
| 29 | | 397.26 | 0.53 (A) | 1H NMR (300 MHz, CDCl3) δ 9.47 (s, 1H), 9.09 (s, 1H), 7.74 (d, J = 3.3 Hz, 1H), 7.27 (d, J = 3.3 Hz, 1H), 6.84 (d, J = 1.6 Hz, 1H), 6.61 (d, J = 1.9 Hz, 1H), 4.87 (s, 1H), 3.96-3.84 (m, 4H), 3.51-3.38 (m, 4H), 3.31-3.16 (m, 1H), 2.42-2.27 (m, 2H), 2.22-2.05 (m, 4H), 1.96-1.82 (m, 2H). | | |
| 30 | | 406.36 | 0.51 (A) | 1H NMR (300 MHz, CDCl3) δ 9.51 (s, 1H), 9.10 (s, 1H), 8.59 (d, J = 5.2 Hz, 1H), 7.06 (d, J = 5.2 Hz, 1H), 6.84 (d, J = 1.7 Hz, 1H), 6.61 (d, J = 1.9 Hz, 1H), 4.96-4.82 (m, 1H), 4.03-3.82 (m, 4H), 3.51-3.30 (m, 4H), 2.90-2.77 (m, 1H), 2.75 (s, 3H), 2.44-2.28 (m, 2H), 2.19-1.75 (m, 6H). | | |
| 31 | | 386.28 | 0.58 (A) | 1H NMR (300 MHz, CDCl3) δ 9.46 (s, 1H), 9.10 (s, 1H), 6.81 (d, J = 1.7 Hz, 1H), 6.57 (d, J = 1.9 Hz, 1H), 4.83-4.66 (m, 1H), 4.19 (q, J = 7.1 Hz, 2H), 4.01-3.83 (m, 4H), 3.51-3.29 (m, 4H), 2.48 (tt, J = 10.3, 3.9 Hz, 1H), 2.30-2.12 (m, 2H), 2.12-1.65 (m, 6H), 1.30 (t, J = 7.1 Hz, 3H). | | |
| 32 | | 397.31 | 0.53 (A) | 1H NMR (300 MHz, CDCl3) δ 9.47 (s, 1H), 9.11 (s, 1H), 6.81 (d, J = 1.7 Hz, 1H), 6.56 (d, J = 1.8 Hz, 1H), 5.65 (s, 1H), 4.87-4.72 (m, 1H), 4.02-3.83 (m, 4H), 3.48-3.35 (m, 4H), 2.82-2.68 (m, 1H), 2.37-2.17 (m, 3H), 2.02-1.68 (m, 8H), 0.90-0.75 (m, 2H), 0.59-0.41 (m, 2H). | | |

TABLE 1-continued

Characterization Data and Ki and IC$_{50}$ Values for Certain Compounds of the Invention

| Comp. Nos. | Molecule | M + 1 | LCMS Retention Time (Method) | NMR | Ki (μM) DNA-PK | IC$_{50}$ (μM) |
|---|---|---|---|---|---|---|
| 33 | | 425.33 | 0.57 (A) | 1H NMR (300 MHz, CDCl3) δ 9.45 (s, 1H), 9.09 (s, 1H), 6.78 (d, J = 1.9 Hz, 1H), 6.57 (d, J = 2.0 Hz, 1H), 5.57 (d, J = 8.2 Hz, 1H), 4.74 (q, J = 3.2 Hz, 1H), 4.05-3.84 (m, 5H), 3.46-3.31 (m, 4H), 2.19 (dq, J = 9.9, 3.3 Hz, 2H), 1.97-1.55 (m, 6H), 1.26 (dd, J = 8.0, 5.3 Hz, 1H), 1.17 (s, 3H), 1.15 (s, 3H), 1.09 (t, J = 4.8 Hz, 1H), 0.73 (dd, J = 8.0, 4.3 Hz, 1H). | | |
| 34 | | 413.46 | 0.55 (A) | 1H NMR (300 MHz, CDCl3) δ 9.42 (s, 1H), 9.08 (d, J = 2.2 Hz, 1H), 6.79 (d, J = 1.9 Hz, 1H), 6.57 (d, J = 2.1 Hz, 1H), 5.51 (d, J = 8.1 Hz, 1H), 4.95-4.72 (m, 5H), 4.10-3.84 (m, 5H), 3.70 (tt, J = 8.3, 6.7 Hz, 1H), 3.39 (dd, J = 5.8, 4.0 Hz, 5H), 2.30-2.15 (m, 3H), 1.98-1.58 (m, 4H). | | |
| 35 | | 397.32 | 0.57 (A) | 1H NMR (300 MHz, CDCl3) δ 9.42 (s, 1H), 9.09 (s, 1H), 7.74 (d, J = 3.3 Hz, 1H), 7.26 (d, J = 3.3 Hz, 1H), 6.83 (d, J = 1.8 Hz, 1H), 6.63 (d, J = 2.0 Hz, 1H), 4.63-4.42 (m, 1H), 4.01-3.84 (m, 4H), 3.49-3.31 (m, 4H), 3.30-3.10 (m, 1H), 2.39 (d, J = 9.6 Hz, 4H), 2.04-1.58 (m, 4H). | | |
| 36 | | 449.32 | 0.5 (D) | 1H NMR (300 MHz, CDCl3) δ 8.13 (d, J = 6.0 Hz, 1H), 6.76 (d, J = 2.2 Hz, 1H), 6.50 (d, J = 2.1 Hz, 1H), 6.18 (d, J = 6.0 Hz, 1H), 4.93 (d, J = 7.9 Hz, 1H), 4.73 (d, J = 4.2 Hz, 1H), 3.96-3.85 (m, 4H), 3.42-3.28 (m, 4H), 3.01 (s, 3H), 2.73 (s, 3H), 2.51 (s, 3H), 2.32-2.19 (m, 2H), 2.08-1.73 (m, 9H). | | |

TABLE 1-continued

Characterization Data and Ki and IC$_{50}$ Values for Certain Compounds of the Invention

| Comp. Nos. | Molecule | M + 1 | LCMS Retention Time (Method) | NMR | Ki (μM) DNA-PK | IC$_{50}$ (μM) |
|---|---|---|---|---|---|---|
| 37 | | 434.33 | 0.48 (A) | 1H NMR (300 MHz, CDCl3) δ 9.49 (s, 1H), 9.11 (s, 1H), 8.28 (d, J = 7.7 Hz, 2H), 8.16 (s, 1H), 7.84-7.68 (m, 1H), 7.15-7.02 (m, 1H), 6.83 (d, J = 1.7 Hz, 1H), 6.59 (d, J = 1.9 Hz, 1H), 4.88-4.76 (m, 1H), 4.05-3.81 (m, 4H), 3.40 (dd, J = 14.8, 10.0 Hz, 4H), 2.59-2.42 (m, 1H), 2.42-2.25 (m, 2H), 2.25-2.04 (m, 2H), 2.04-1.71 (m, 4H). | | |
| 38 | | 406.29 | 0.5 (A) | 1H NMR (300 MHz, CDCl3) δ 9.41 (s, 1H), 9.08 (s, 1H), 8.57 (d, J = 5.2 Hz, 1H), 7.02 (d, J = 5.1 Hz, 1H), 6.83 (d, J = 1.7 Hz, 1H), 6.64 (d, J = 2.0 Hz, 1H), 4.63-4.41 (m, 1H), 4.05-3.83 (m, 4H), 3.53-3.29 (m, 4H), 2.86-2.76 (m, 1H), 2.75 (s, 3H), 2.51-2.33 (m, 2H), 2.25-2.10 (m, 2H), 1.96-1.62 (m, 6H). | | |
| 39 | | 414.17 | 0.55 (A) | 1H NMR (300 MHz, CDCl3) δ 9.72 (s, 1H), 9.33 (s, 1H), 8.12 (d, J = 6.1 Hz, 1H), 7.81 (d, J = 0.7 Hz, 1H), 7.08 (d, J = 1.3 Hz, 1H), 6.22 (d, J = 6.0 Hz, 1H), 5.04 (s, 1H), 4.90-4.75 (m, 1H), 3.90 (s, 1H), 2.54 (s, 3H), 2.36-2.18 (m, 2H), 2.14-1.59 (m, 6H). | | |
| 40 | | 371.38 | 0.53 (A) | 1H NMR (300 MHz, CDCl3) δ 9.47 (s, 1H), 9.09 (s, 1H), 6.83 (d, J = 1.7 Hz, 1H), 6.57 (d, J = 1.9 Hz, 1H), 5.67-5.49 (m, 1H), 4.83-4.75 (m, 1H), 3.95-3.85 (m, 4H), 3.48-3.36 (m, 4H), 2.87 (d, J = 4.8 Hz, 3H), 2.38-2.24 (m, 3H), 2.11-1.84 (m, 4H), 1.83-1.67 (m, 2H). | | |

TABLE 1-continued

Characterization Data and Ki and IC$_{50}$ Values for Certain Compounds of the Invention

| Comp. Nos. | Molecule | M + 1 | LCMS Retention Time (Method) | NMR | Ki (μM) DNA-PK | IC$_{50}$ (μM) |
|---|---|---|---|---|---|---|
| 41 | | 429.29 | 0.52 (A) | 1H NMR (300 MHz, CDCl3) δ 9.47 (s, 1H), 9.10 (s, 1H), 6.81 (d, J = 1.7 Hz, 1H), 6.57 (d, J = 1.9 Hz, 1H), 6.38-6.21 (m, 1H), 4.83-4.72 (m, 1H), 3.98-3.84 (m, 4H), 3.53 (t, J = 5.6 Hz, 2H), 3.49-3.29 (m, 9H), 2.40-2.19 (m, 3H), 2.12-1.63 (m, 8H). | | |
| 42 | | 492.3 | 0.54 (A) | 1H NMR (300 MHz, CDCl3) δ 8.52 (d, J = 4.9 Hz, 1H), 7.78 (s, 1H), 7.36 (d, J = 4.9 Hz, 1H), 6.78 (d, J = 2.2 Hz, 1H), 6.55-6.47 (m, 1H), 5.19 (s, 1H), 4.75 (s, 1H), 4.15-4.00 (m, 0H), 3.90 (dd, J = 6.0, 3.8 Hz, 4H), 3.43-3.32 (m, 4H), 3.11-2.98 (m, 6H), 2.80 (s, 0H), 2.33-2.18 (m, 2H), 2.13-1.77 (m, 6H). | | |
| 43 | | 431.25 | 2.19 (A) | 1H NMR (300 MHz, DMSO-d6) δ 8.48 (s, 1H), 7.54 (d, J = 7.5 Hz, 1H), 6.78 (d, J = 2.2 Hz, 1H), 6.68 (d, J = 2.1 Hz, 1H), 4.84 (m, 1H), 4.04 (s, 3H), 3.79 (s, 2H), 3.75 (m, 5H), 3.35 (m, 4H), 3.30 (s, 3H), 2.01 (m, 2H), 1.84-1.53 (m, 6H). | | |
| 44 | | 507 | 0.64 (C) | 1H NMR (300 MHz, CDCl3) δ 8.49 (d, J = 4.9 Hz, 1H), 8.42 (s, 1H), 7.76 (d, J = 4.8 Hz, 1H), 7.34 (d, J = 4.9 Hz, 1H), 6.78 (d, J = 2.3 Hz, 1H), 6.54 (d, J = 2.3 Hz, 1H), 5.13 (s, 1H), 4.55 (s, 1H), 4.06-3.78 (m, 5H), 3.31 (dd, J = 14.5, 9.7 Hz, 4H), 3.15 (s, 6H), 3.02 (d, J = 5.1 Hz, 3H), 2.12-2.00 (m, 2H), 1.81 (dd, J = 30.2, 11.2 Hz, 6H). | | |

TABLE 2

Characterization Data and Ki and IC₅₀ Values for Certain Compounds of the Invention

| Comp. Nos. | Molecule | M + 1 | LCMS Retention Time | NMR | Ki(μM) DNA-PK | IC₅₀ (μM) |
|---|---|---|---|---|---|---|
| 51 | | 368.14 | 0.63 (A) | 1H NMR (400 MHz, DMSO-d6) δ 11.47 (s, 1H), 7.83 (s, 1H), 7.51 (d, J = 8.6 Hz, 2H), 6.95 (d, J = 8.7 Hz, 2H), 6.65 (d, J = 2.0 Hz, 1H), 6.55 (d, J = 2.0 Hz, 1H), 5.13 (s, 2H), 3.88-3.59 (m, 7H), 3.33-3.27 (m, 4H). | D | C |
| 52 | | 352.16 | 0.58 (A) | 1H NMR (400 MHz, CDCl3) δ 9.42 (s, 1H), 9.09 (s, 1H), 7.41 (d, J = 8.5 Hz, 2H), 7.01-6.92 (m, 2H), 6.79 (d, J = 1.8 Hz, 1H), 6.64 (d, J = 2.0 Hz, 1H), 5.16 (s, 2H), 3.95-3.86 (m, 4H), 3.84 (s, 3H), 3.44-3.31 (m, 4H). | B | C |
| 53 | | 382.14 | 0.62 (A) | 1H NMR (400 MHz, CDCl3) δ 8.59 (s, 1H), 7.47 (d, J = 8.8 Hz, 2H), 6.99-6.92 (m, 2H), 6.82 (d, J = 2.3 Hz, 1H), 6.59 (d, J = 2.3 Hz, 1H), 5.13 (s, 2H), 4.11 (s, 3H), 3.90-3.85 (m, 4H), 3.84 (s, 3H), 3.37-3.31 (m, 4H). 1H NMR (300 MHz, Chloroform-d) δ 8.61 (s, 1H), 7.55-7.43 (m, 2H), 7.04-6.93 (m, 2H), 6.84 (d, J = 2.4 Hz, 1H), 6.61 (d, J = 2.4 Hz, 1H), 5.16 (s, 2H), 4.13 (s, 3H), 3.95-3.86 (s, 3H), 3.42-3.30 (m, 4H). | C | C |
| 54 | | 386.1 | 0.74 (A) | 1H NMR (400 MHz, CDCl3) δ 8.71 (s, 1H), 7.45 (d, J = 8.6 Hz, 2H), 6.98-6.91 (m, 2H), 6.84 (d, J = 2.3 Hz, 1H), 6.66 (d, J = 2.3 Hz, 1H), 5.16 (s, 2H), 3.97-3.85 (m, 4H), 3.84 (s, 3H), 3.48-3.29 (m, 4H). | | C |

TABLE 2-continued

Characterization Data and Ki and IC$_{50}$ Values for Certain Compounds of the Invention

| Comp. Nos. | Molecule | LCMS M + 1 | Retention Time | NMR | Ki(μM) DNA-PK | IC$_{50}$ (μM) |
|---|---|---|---|---|---|---|
| 55 | | 377.14 | 0.77 (A) | 1H NMR (400 MHz, CDCl3) δ 9.07 (s, 1H), 7.48 (d, J = 8.4 Hz, 2H), 6.94 (d, J = 8.6 Hz, 2H), 6.80 (s, 1H), 6.69 (s, 1H), 5.29 (s, 2H), 3.94-3.84 (m, 4H), 3.82 (s, 3H), 3.48-3.35 (m, 4H). 1H NMR (300 MHz, Chloroform-d) δ 9.09 (s, 1H), 7.58-7.44 (m, 2H), 7.03-6.90 (m, 2H), 6.82 (d, J = 2.3 Hz, 1H), 6.71 (d, J = 2.3 Hz, 1H), 5.31 (s, 2H), 3.98-3.86 (m, 4H), 3.84 (s, 3H), 3.51-3.38 (m, 4H). | B | C |
| 56 | | 392.25 | 0.63 (A) | 1H NMR (300 MHz, CDCl3) δ 8.79 (s, 1H), 7.48-7.35 (m, 2H), 7.00-6.88 (m, 2H), 6.83 (d, J = 2.3 Hz, 1H), 6.65 (d, J = 2.3 Hz, 1H), 5.15 (s, 2H), 3.93-3.85 (m, 4H), 3.84 (s, 3H), 3.48-3.28 (m, 5H), 1.35-1.22 (m, 2H), 0.99-0.86 (m, 2H). | | B |
| 57 | | 381 | 0.73 (C) | 1H NMR (300 MHz, DMSO) δ 8.22 (s, 1H), 7.88 (t, J = 4.6 Hz, 1H), 7.48 (dd, J = 9.1, 2.4 Hz, 2H), 7.02-6.93 (m, 2H), 6.74 (d, J = 2.2 Hz, 1H), 6.51 (d, J = 2.1 Hz, 1H), 5.33 (s, 2H), 3.77-3.71 (m, 7H), 3.28-3.18 (m, 4H), 2.92 (d, J = 4.7 Hz, 3H). | | |

TABLE 2-continued

Characterization Data and Ki and IC$_{50}$ Values for Certain Compounds of the Invention

| Comp. Nos. | Molecule | LCMS M + 1 | Retention Time | NMR | Ki(µM) DNA-PK | IC$_{50}$ (µM) |
|---|---|---|---|---|---|---|
| 58 | 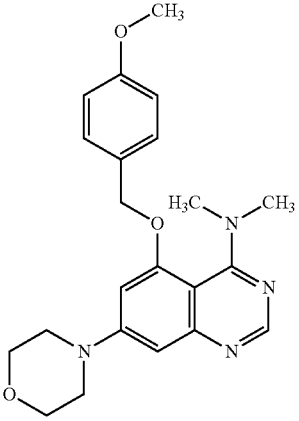 [SMILES: COc1ccc(COc2cc(N3CCOCC3)cc3ncnc(N(C)C)c23)cc1] | 395 | 0.74 (C) | 1H NMR (300 MHz, DMSO) δ 8.21 (s, 1H), 7.42 (t, J = 5.7 Hz, 2H), 7.05-6.94 (m, 2H), 6.79 (d, J = 2.2 Hz, 1H), 6.57 (d, J = 2.1 Hz, 1H), 5.14 (s, 2H), 3.79-3.73 (m, 7H), 3.35-3.31 (m, 4H), 2.91 (s, 6H). | | |
| 59 | 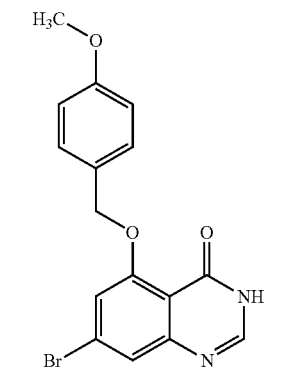 [SMILES: COc1ccc(COc2cc(Br)cc3nc[nH]c(=O)c23)cc1] | | | 1H NMR (300 MHz, DMSO-d6) δ 12.07 (s, 1H), 8.02 (s, 1H), 7.55-7.42 (m, 2H), 7.37 (d, J = 1.8 Hz, 1H), 7.28 (d, J = 1.9 Hz, 1H), 7.03-6.90 (m, 2H), 5.20 (s, 2H), 3.76 (s, 3H). | | |

Gene Editing Examples

The following examples, including the experiments conducted and results achieved are provided for illustrative purposes only and are not to be construed as limiting upon the present disclosure.

Example 3: Materials and Methods

Traffic light reporter (TLR) assay: The HEK293-EGIP (Enhanced Green Fluorescent inhibited Protein) stable cell line was purchased from System Biosciences (SBI). The HEK293-EGIP cell line harbors a disrupted GFP coding sequence with a stop codon and a 53-bp genomic fragment from the AAVS1 locus. Cells were maintained in DMEM (Life Technologies, cat. no. 10313-039) with high glucose (Life Technologies, cat. no. 10313-039) supplemented with 10% heat-inactivated FBS (Fetal Bovine Serum, Expression Systems Inc.), Glutamax and Penicillin+ Streptomycin and cultured at 37° C. and 5% CO2.

Cell transfection and NHEJ inhibitor treatment: The HEK293-EGIP stable cells will be transfected with the two-in-one gRNA/CRISPR-Cas9 dual plasmid vector, plasmid repair donor (both plasmids from System Biosciences). Transfection will be carried out using the Amaxa nucleofector system (Lonza) following manufacturer's protocol. After 16 hours, cells will be treated with Compounds represented by Formula (I) at various concentrations, including 1 µM, 2.5 µM, 5 µM and 10 µM of compound. The structure of Scr7 is shown as follows:

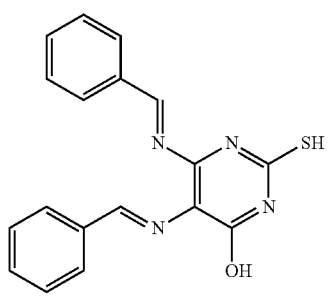 [SMILES: Oc1nc(S)nc(/N=C/c2ccccc2)c1/N=C/c1ccccc1]

and may be used as a control. The media will be changed following an additional 24 hour incubation. FACS analysis will be performed 5 days post transfection; cells will then be collected for genomic DNA isolation and PCR genotyping.

Cell Sorting and Flow Cytometry: For flow cytometry analysis, HEK293 cells will be trypsinized and resuspended in PBS/1% BSA FACS buffer and analyzed with a Fortessa flow cytometer (Becton Dickinson). A portion of cells will be centrifuged and used for the isolation of genomic DNA.

Cell viability assay upon compound treatment: To assess potential toxicity of the NHEJ inhibitor treatment, cell viability will be assessed after exposure to different concentrations of compounds. Cell viability of HEK293-EGIP will be determined by CellTiter Glo (Promega) kit. The cells transfected with the plasmid donor will be grown in the presence of compound (1 uM, 2.5 uM, 5 uM and 10 uM) for 24, 48 or 72 h, and subjected to the CellTiter Glo assay. Each experiment will be repeated three independent times in triplicates. To maintain healthy cells capable of entering S/G2, which is necessary for HDR, cells will be treated with compound at a concentration of 2.5 µM.

Genomic DNA isolation, PCR Genotyping, and Gel Quantification:

Specially designed PCR primer pairs will provide another means to assess HDR-mediated genome editing to obtain functional eGFP positive cells. The genotyping PCR primer pair is shown below, corresponding to SEQ ID NOs: 6 and 7. A 219 bp PCR product corresponds to unmodified cells and a 163 bp nucleotide corresponds to modification through HDR. Intensity of these bands on a >2.5% gel allows for estimation of HDR by densitometry using a Bio-Imager. The technique allows for the relative ranking of improvement of HDR by inhibitors. Intensities measured for each lane will be normalized by calculating the ratios of PCR bands corresponding to 'insertions' divided by 'total' (inserted and unmodified). The fold-change will be calculated by comparing the ratio of insertions with compound over that without compound.

Example 4: Assay for Monitoring HDR Efficiency

Assays will be performed to ascertain HDR efficiency in HEK293-EGIP cells. To this end, a bicistronic construct will be used that targets the human AAVS1 locus (FIG. 1A). The bicistronic vector system co-expresses human codon optimized Cas9 driven by the EF1 promoter as well as custom guide RNA (gRNA) consisting of a chimeric crRNA-tracrRNA transcript driven by the H1 promoter. The hsp-Cas9 contains two nuclear localization signals (NLS) at the N-terminus and C-terminus to ensure efficient import of the hspCas9 protein into the nucleus. The hspCas9 open reading frame (ORF) is followed by a regulatory element called WPRE (Woodchuck virus post-transcriptional regulatory element) to boost gene expression and stabilize the mRNA transcript.

The engineered human cell line, EGIP HEK293 will be used to monitor HDR efficiency using the bicistronic construct described above and in FIG. 1A. The EGIP HEK293 reporter cell line was purchased from SBI. The HEK293-EGIP cell line harbors a disrupted GFP coding sequence with a stop codon and a 53-bp genomic fragment from the AAVS1 locus. The stable line was generated by lentiviral infection of 293T cells with an EF1alpha promoter to drive the expression of eGFP followed by puromycin selection. The eGFP sequence was modified to insert a 56 nucleotide insert (uppercase) from the human AAVS1 safe harbor site. This sequence contains a stop codon (TAA in red) after amino acid T109 in the eGFP translated sequence. The guide sequences targeted are in bold letters. Upon transfection with the guide and donor, the AAVS1 site within the broken eGFP was cut and the donor construct provided a homologous sequence to repair the eGFP, by removing the stop codon and the AAVS1 insert. Using this system, edited cells which undergo HDR donor repair will generate GFP positive cells. Accordingly, co-transfecting Cas9, gRNA targeting AAVS1 and a AAVS1/EGFP rescue donor restored sequence by HDR to give GFP+ cells.

The population of GFP positive cells will be directly proportional with the efficiency of the homology directed repair.

For these assays, two-in-one Cas9-sgRNAs and eGFP donor template vectors will be introduced into the HEK293 EGIP cells by electroporation using the Amaxa nucleofector (Lonza) to drive the synthesis of Cas9-sgRNAs and the eGFP donor template. Compounds will be added 16 h post transfection followed by media change 48 hours later. Cells will then be allowed to propagate for an additional 72 hours before FACS analysis.

The HDR donor template sequence contained a 266 nucleotide 5' homology arm (in bold, black and underlined) and a 378 nucleotide 3' homology arm (in italics and underlined) (see SEQ ID NO: 1 below). Upon transfection with the guide RNA and donor template, the AAVS1 site within the broken eGFP will be cut and the donor construct will provide a homologous sequence to repair the eGFP, removing the stop codon and the AAVS1 insert.

The HDR template sequence to be used in the traffic light reporter assay is shown below (SEQ ID NO: 1):

(SEQ ID NO: 1)
TCGCGCGTTTCGGTGATGACGGTGAAAACCTCTGACACATGCAGCTCCCG

GAGACGGTCACAGCTTGTCTGTAAGCGGATGCCGGGAGCAGACAAGCCCG

TCAGGGCGCGTCAGCGGGTGTTGGCGGGTGTCGGGGCTGGCTTAACTATG

CGGCATCAGAGCAGATTGTACTGAGAGTGCACCATATGCGGTGTGAAATA

CCGCACAGATGCGTAAGGAGAAAATACCGCATCAGGCGCCATTCGCCATT

CAGGCTGCGCAACTGTTGGGAAGGGCGATCGGTGCGGGCCTCTTCGCTAT

TACGCCAGCTGGCGAAAGGGGATGTGCTGCAAGGCGATTAAGTTGGGTA

ACGCCAGGGTTTTCCCAGTCACGACGTTGTAAAACGACGGCCAGTGAAAC

TAGTGCGACGTAAACGGCCACAAGTTCAGCGTGTCCGGCGAGGGCGAGGG

CGATGCCACCTACGGCAAGCTGACCCTGAAGTTCATCTGCACCACCGGCA

AGCTGCCCGTGCCCTGGCCCACCCTCGTGACCACCCTGACCTACGGCGTG

CAGTGCTTCAGCCGCTACCCCGACCACATGAAGCAGCACGACTTCTTCAA

GTCCGCCATGCCCGAAGGCTACGTCCAGGAGCGCACCATCTTCTTCAAGG

ACGACGGCAACTACAAGACCCGCGCCGAGGTGAAGTTCGAGGGCGACACC

*CTGGTGAACCGCATCGAGCTGAAGGGCATCGACTTCAAGGAGGACGGCAA*

*CATCCTGGGGCACAAGCTGGAGTACAACTACAACAGCCACAACGTCTATA*

*TCATGGCCGACAAGCAGAAGAACGGCATCAAGGTGAACTTCAAGATCCGC*

*CACAACATCGAGGACGGCAGCGTGCAGCTCGCCGACCACTACCAGCAGAA*

*CACCCCCATCGGCGACGGCCCCGTGCTGCTGCCCGACAACCACTACCTGA*

*GCACCCAGTCCGCCCTGAGCAAAGACCCCAACGAGAAGCGCGATCACATG*

*GTCCTGCTGGAGTTCGTGACCGCCGCCGGGATCACTCTCGGCATGGAC*GT

CGACACCGGTGATATCAAGCTTGGCGTAATCATGGTCATAGCTGTTTCCT

GTGTGAAATTGTTATCCGCTCACAATTCCACACAACATACGAGCCGGAAG

CATAAAGTGTAAAGCCTGGGGTGCCTAATGAGTGAGCTAACTCACATTAA

TTGCGTTGCGCTCACTGCCCGCTTTCCAGTCGGGAAACCTGTCGTGCCAG

-continued

CTGCATTAATGAATCGGCCAACGCGCGGGGAGAGGCGGTTTGCGTATTGG

GCGCTCTTCCGCTTCCTCGCTCACTGACTCGCTGCGCTCGGTCGTTCGGC

TGCGGCGAGCGGTATCAGCTCACTCAAAGGCGGTAATACGGTTATCCACA

GAATCAGGGGATAACGCAGGAAAGAACATGTGAGCAAAAGGCCAGCAAAA

GGCCAGGAACCGTAAAAAGGCCGCGTTGCTGGCGTTTTTCCATAGGCTCC

GCCCCCCTGACGAGCATCACAAAAATCGACGCTCAAGTCAGAGGTGGCGA

AACCCGACAGGACTATAAAGATACCAGGCGTTTCCCCCTGGAAGCTCCCT

CGTGCGCTCTCCTGTTCCGACCCTGCCGCTTACCGGATACCTGTCCGCCT

TTCTCCCTTCGGGAAGCGTGGCGCTTTCTCATAGCTCACGCTGTAGGTAT

CTCAGTTCGGTGTAGGTCGTTCGCTCCAAGCTGGGCTGTGTGCACGAACC

CCCCGTTCAGCCCGACCGCTGCGCCTTATCCGGTAACTATCGTCTTGAGT

CCAACCCGGTAAGACACGACTTATCGCCACTGGCAGCAGCCACTGGTAAC

AGGATTAGCAGAGCGAGGTATGTAGGCGGTGCTACAGAGTTCTTGAAGTG

GTGGCCTAACTACGGCTACACTAGAAGAACAGTATTTGGTATCTGCGCTC

TGCTGAAGCCAGTTACCTTCGGAAAAAGAGTTGGTAGCTCTTGATCCGGC

AAACAAACCACCGCTGGTAGCGGTGGTTTTTTTGTTTGCAAGCAGCAGAT

TACGCGCAGAAAAAAGGATCTCAAGAAGATCCTTTGATCTTTTCTACGG

GGTCTGACGCTCAGTGGAACGAAAACTCACGTTAAGGGATTTTGGTCATG

AGATTATCAAAAGGATCTTCACCTAGATCCTTTTGATCCCCGCCACGGT

TGATGAGAGCTTTGTTGTAGGTGGACCAGTTGGTGATTTTGAACTTTTGC

TTTGCCACGGAACGGTCTGCGTTGTCGGGAAGATGCGTGATCTGATCCTT

CAACTCAGCAAAAGTTCGATTTATTCAACAAAGCCGCCGTCCCGTCAAGT

CAGCGTAATGCTCTGCCAGTGTTACAACCAATTAACCAATTCTGATTAGA

AAAACTCATCGAGCATCAAATGAAACTGCAATTTATTCATATCAGGATTA

TCAATACCATATTTTTGAAAAAGCCGTTTCTGTAATGAAGGAGAAAACTC

ACCGAGGCAGTTCCATAGGATGGCAAGATCCTGGTATCGGTCTGCGATTC

CGACTCGTCCAACATCAATACAACCTATTAATTTCCCCTCGTCAAAAATA

AGGTTATCAAGTGAGAAATCACCATGAGTGACGACTGAATCCGGTGAGAA

TGGCAAAAGTTTATGCATTTCTTTCCAGACTTGTTCAACAGGCCAGCCAT

TACGCTCGTCATCAAAATCACTCGCATCAACCAAACCGTTATTCATTCGT

GATTGCGCCTGAGCGAGACGAAATACGCGATCGCTGTTAAAAGGACAATT

ACAAACAGGAATCGAATGCAACCGGCGCAGGAACACTGCCAGCGCATCAA

CAATATTTTCACCTGAATCAGGATATTCTTCTAATACCTGGAATGCTGTT

TTTCCGGGGATCGCAGTGGTGAGTAACCATGCATCATCAGGAGTACGGAT

AAAATGCTTGATGGTCGGAAGAGGCATAAATTCCGTCAGCCAGTTTAGTC

TGACCATCTCATCTGTAACATCATTGGCAACGCTACCTTTGCCATGTTTC

AGAAACAACTCTGGCGCATCGGGCTTCCCATACAATCGATAGATTGTCGC

ACCTGATTGCCCGACATTATCGCGAGCCCATTTATACCCATATAAATCAG

CATCCATGTTGGAATTTAATCGCGGCCTCGAGCAAGACGTTTCCCGTTGA

ATATGGCTCATAACACCCCTTGTATTACTGTTTATGTAAGCAGACAGTTT

-continued

TATTGTTCATGATGATATATTTTTATCTTGTGCAATGTAACATCAGAGAT

TTTGAGACACAATTCATCGATGATGGTTGAGATGTGTATAAGAGACAGAT

TATTGAAGCATTTATCAGGGTTATTGTCTCATGAGCGGATACATATTTGA

ATGTATTTAGAAAAATAAACAAATAGGGGTTCCGCGCACATTTCCCCGAA

AAGTGCCACCTGACGTCTAAGAAACCATTATTATCATGACATTAACCTAT

AAAAATAGGCGTATCACGAGGCCCTTTCGTC

The primer sites used for the assay described herein are shown below. These primer sites are located within the donor sequence. The PCR reaction on the genomic template will generate a 700 nucleotide product with NHEJ expected to produce fragments around 300 nucleotides and 400 nucleotides in length. Following HDR evened the expected PCR product using the supplied donor template is 644 nucleotides. The primer sites used for the assay include the following sequences.

Guide RNA_1:
(SEQ ID NO: 2)
GTCCCCTCCACCCCACAGTG

Guide RNA_2:
(SEQ ID NO: 3)
GGGGCCACTAGGGACAGGAT

Forward Surveyor primer:
(SEQ ID NO: 4)
GCGACGTAAACGGCCACAAG

Reverse Surveyor primer:
(SEQ ID NO: 5)
GTCCATGCCGAGAGTGATCC

HDR primer_1 :
(SEQ ID NO: 6)
ACTTCTTCAAGTCCGCCATGCCC

HDR primer_2 :
(SEQ ID NO: 7)
ATGTTGCCGTCCTCCTTGAAGTCG

Example 3: Evaluation of DNA-PK Inhibitors for Increasing CRISPR-Genome Editing HDR Efficacy HEK293-EGIP cells will be nucleofected with the following constructs and cultured as described: dual expression gRNA-Cas9 only, dual expression gRNA-Cas9 with donor repair template, dual expression gRNA-Cas9 with donor template and culture of the cells with 2.5 µM Compound 1, and dual expression gRNA-Cas9 with donor repair template and culture of the cells with 2.5 µM of the putative ligase IV inhibitor Scr7. The cells will contacted with compounds of Formula (I) or with Scr7 for 24 hours.

The amount of CRISPR-genome edited HEK-EGIP cells in comparison to the gRNA-Cas9 and donor template condition only increase will be evaluated. Addition of the compounds of Formula (I) to the culture medium of HEK293-EGIP cells nucleofected with gRNA-Cas9 and donor template will be evaluated for increase in the amount of CRISPR-genome edited HEK-EGIP cells in comparison to the gRNA-Cas9 and donor template condition only.

In some embodiments, the fold-increase in enhancement of the DNA repair process using the CRISPR-Cas9 system in the presence of a donor repair template will be quantitated by Fluorescence Activated Cell Sorter (FACS). Flow cytometry analysis 10 days post transfection will be conducted. Flow cytometry experiments will be carried out in triplicate.

Figure 1B:
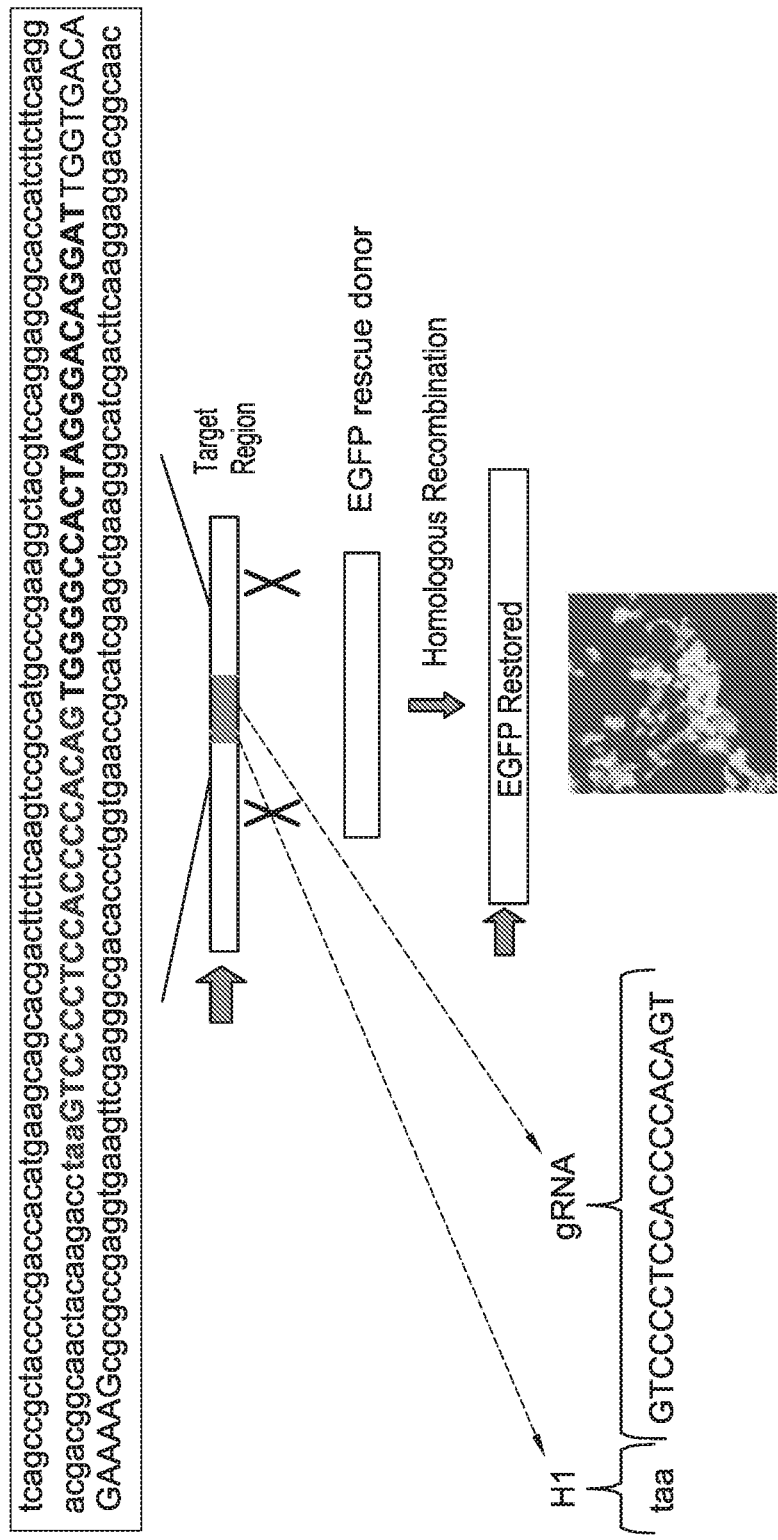
Figure 1C:
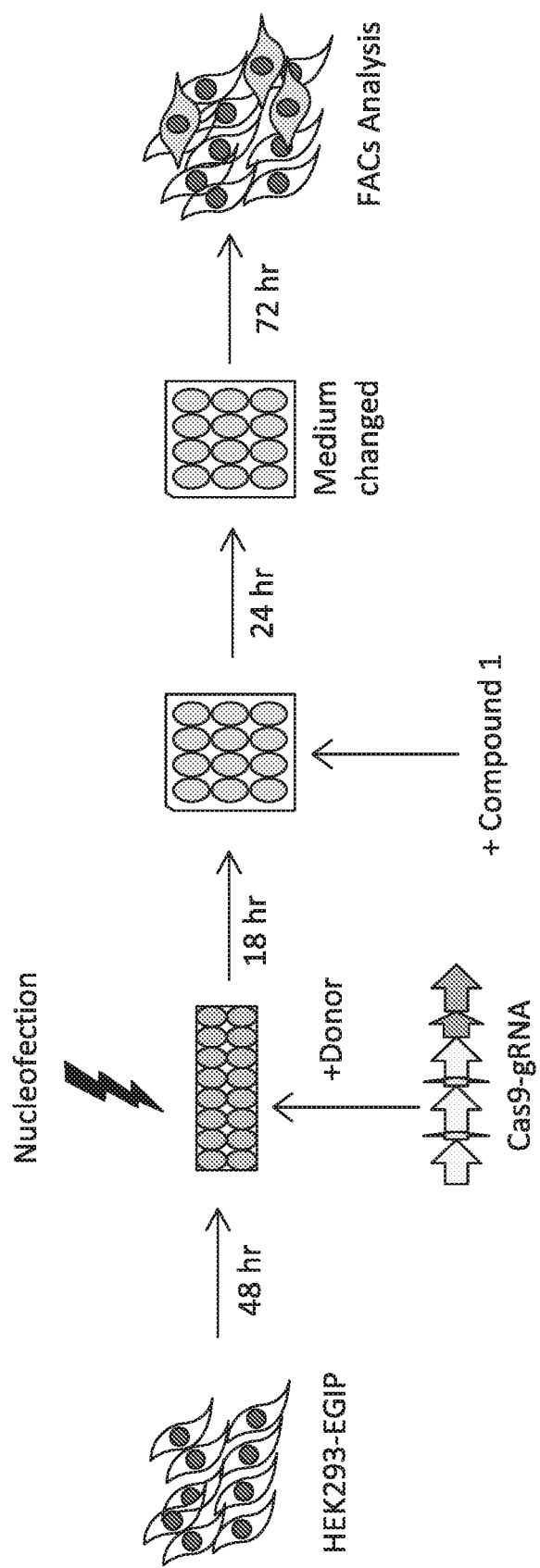

In some embodiments, the robust "Traffic Light Reporter" (TLR) assay will be used (FIG. 1B) to quantitate the fold-increase in enhancement of HDR-mediated DNA repair process in the CRISPR-Cas9 system. In the TLR system, the HEK293-EGIP stable cell line expressing the "broken" green fluorescent protein eGFP, relies on HDR-mediated repair to generate functional eGFP in the presence of DNA donor template (see FIGS. 1B and 1C). As shown in the experimental workflow in FIG. 1C, functional GFP positive cells appear through HDR pathway where the 56 nt insertion is replaced with the correct DNA sequence. Forty-eight hours post transfection through electroporation, GFP positive cells will usually emerge. Flow cytometry analysis will be conducted in triplicate.

Example 5: Comparison of Small Molecule NHEJ Inhibitors for Increasing HDR Genome Editing Further experiments will be conducted utilizing the HEK293-EGIP cell line to ascertain HDR efficiency following contact with a DNA-PK inhibitor for any of the compounds described herein.

For these experiments, HEK293-EGIP cells will be nucleofected with donor template only or donor template and Cas9-sgRNA. To test the ability the compounds described herein to enhance HDR editing, cells that will be nucleofected with either donor template alone, or donor template and Cas9-sgRNA will be administered either Scr7 or a DNA-PK inhibitor describe herein.

HDR recombination status will be ascertained by traditional "end-point" PCR primer genotyping and quantitation based on agarose band intensities. The primers produced distinct amplicons: a 219 bp nucleotide band corresponded to unmodified cells and a 163 bp nucleotide product for HDR event. Intensity of these bands on a >2.5% gel allows for estimation of HDR by densitometry using a Bio-Imager. The technique allows for the relative ranking of conditions for improvement of HDR by inhibitors of NHEJ. The genotyping PCR primer pairs for these assays is shown below.

```
HDR primer_1
                                    (SEQ ID NO: 6)
ACTTCTTCAAGTCCGCCATGCCC HDR primer_2
                                    (SEQ ID NO: 7)
ATGTTGCCGTCCTCCTTGAAGTCG
```

The Cas9 protein and sgRNAs can be delivered in the form of synthetic RNAs instead of the vector systems purchased from SBI. In addition to boosting HDR efficiency, our internal genome editing experiments indicated higher cell viability following ribonucleoprotein protein (RNP) transfection compared with DNA transfection. Furthermore cell synchronization of the S/G2 phase can also stimulate HDR (Lin S et al. Elife. 2014 Dec. 15; 3, 2014). These new strategies and robust detection of genome editing such as digital droplet PCR and next-generation sequencing will be used to streamline genome editing for both therapeutic and research purposes.

Example 6: Evaluation of Administration of DNA-PK Inhibitor Compounds for Increased Gene Editing Assays will be performed to ascertain the ability of a DNA-PK inhibitor to allow for the editing of a target gene. For these assays, the editing of the Serpin A1 gene from M to Z form will be assessed. To this end, Huh7 hepato cellular carcinoma cells will be nucleofected with gRNA and Cas9 protein, with or without a donor repair template in which a KpnI site was introduced. The nucleofected cells will then be cultured in the presence of DMSO or 2.5 µM DNA-PK inhibitor compounds described herein for three days, following which, the genomic DNA will be amplified and assessed for the introduction of the Kpn site.

The assay works as follows: when the SerpinA1 gene is edited, Kpn endonuclease is able to digest the gene fragment, resulting in the appearance of a digested band on a gel only when the SerpinA1 gene is edited. Conversely, when the SerpinA1 is not edited, the Kpn endonuclease is not able cut the gene fragment, and thus there will not be an appearance of a new, digested band on a gel.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

All references provided herein are incorporated herein in its entirety by reference. As used herein, all abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997.

---

What is claimed is:

1. A compound represented by the following formula:

(I)

or a pharmaceutically acceptable salt thereof, wherein

Ring A is an aromatic ring system selected from

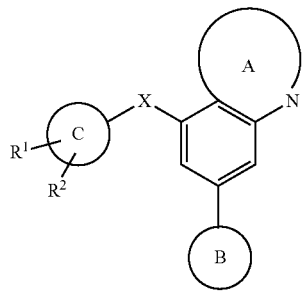

Ring B is a ring system selected from

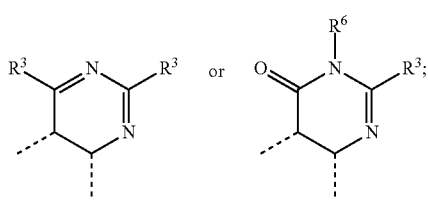

wherein Ring B is optionally substituted with one or more substituents selected from the group consisting of —F, —OH, and $C_{1-4}$alkyl optionally substituted with one or more substituents selected from the group consisting of —F, —Cl, —OH, and —$OC_{1-2}$alkyl;

Ring C is a $C_{4-6}$ cycloalkyl, 5-6-membered heteroaryl, or phenyl group, wherein Ring C is optionally further substituted with one or more substituents selected from the group consisting of halogen, $C_{1-2}$ alkyl, —OH, and —$OC_{1-2}$alkyl;

X is —NH—, —O—, —$OC_{1-4}$ alkyl-, —S—, or —$CH_2$—;

each of $R^1$ and $R^2$ is, independently, hydrogen, —C(O)$NHR^4$, —C(O)$OR^4$, —NHC(O)$R^4$, —NHC(O)$OR^4$, —NHC(O)$NHR^4$, —NHS(O)$_2R^4$, —$NHR^4$, —$C_{1-4}$ alkyl-$NHR^4$, —$OR^4$, or $R^7$ wherein $R^1$ and $R^2$ cannot simultaneously be hydrogen;

each $R^3$ independently is hydrogen, —$C_{1-4}$alkyl, halogen, —$OC_{1-2}$alkyl, —C(O)OH, —C(O)$OC_{1-2}$alkyl, —CN, —C(O)$NHC_{1-2}$alkyl, —C(O)$NH_2$, $C_{3-4}$ cycloalkyl, or —NRR', wherein each of said $R^3$ alkyl and cycloalkyl independently is optionally substituted with one or more substituents selected from the group consisting of —F, —Cl, —OH and —OC$_{1-2}$alkyl;

each R$^4$ independently is hydrogen, C$_{1-4}$alkyl, C$_{2-4}$alkenyl, C$_{2-4}$alkynyl, C$_{3-10}$ cycloalkyl, 6-10 membered aryl, 5-10-membered heteroaryl, or 4-10-membered heterocyclyl, wherein each of said R$^4$ groups is optionally and independently substituted with one or more substituents selected from the group consisting of —Br, —Cl, —F, C$_{1-4}$alkyl, CN, NO$_2$, C$_{2-4}$alkenyl, C$_{2-4}$alkynyl, C$_{3-6}$cycloalkyl, C$_{0-4}$ alkyl-C$_{3-5}$ cycloalkyl, C$_{0-4}$ alkyl-O—C$_{1-4}$ alkyl, C$_{0-4}$ alkyl-O—C$_{0-4}$ alkyl-C$_{3-5}$ cycloalkyl, C(O)OC$_{1-4}$ alkyl, C(O)OC$_{0-4}$ alkyl-C$_{3-5}$ cycloalkyl, C$_{0-4}$ alkyl-C(O)NH$_2$, C(O)NHC$_{1-4}$ alkyl, C(O)N(C$_{1-4}$ alkyl)$_2$, C(O)NH(Co$_{1-4}$ alkyl-C$_{3-5}$ cycloalkyl), CH$_2$OR$^5$, C$_{0-4}$ alkyl-C(O)R$^5$, C$_{0-4}$ alkyl-C(O)N(R$^5$)$_2$, C$_{0-4}$ alkyl-C(O)OR$^5$, C$_{0-4}$ alkyl-NHC(O)R$^5$, C$_{0-4}$ alkyl-N(R$^5$)$_2$, 5-6 membered heterocyclyl, —O(C$_{1-4}$ alkyl)OR$^5$, —OR$^5$, and oxo, and wherein each of said optional R$^4$ substituents is optionally and independently substituted with one or more substituents selected from the group consisting of —F, —Cl, C$_{1-4}$alkyl, —OH, —OC$_{1-4}$alkyl, —SC$_{1-4}$alkyl, —C(O)C$_{1-4}$ alkyl, —C(O)OC$_{1-4}$ alkyl, and —C(O)OC$_{0-4}$ alkyl-C$_{3-5}$ cycloalkyl; and each R$^5$ independently is hydrogen, C$_{1-4}$alkyl, phenyl, 5-6-membered heteroaryl, or 4-7-membered heterocyclyl, wherein each R$^5$ is optionally and independently substituted with one or more substituents selected from the group consisting of —F, —Cl, C$_{1-2}$alkyl, —CH$_2$OH, —CN, —OH, —OC$_{1-2}$alkyl, 5-6-membered heteroaryl, and 4-7 membered heterocyclyl, or two R$^5$ groups together with the intervening nitrogen atom optionally form a morpholine ring, azetidine ring, pyrrolidine ring, piperidine ring, or piperazine ring; and R$^6$ is hydrogen or C$_{1-4}$alkyl optionally substituted with one or more substituents selected from the group consisting of —F, —Cl, —CH$_2$OH, —CN, —OH, and —OC$_{1-2}$alkyl;

R$^7$ is 6-10-membered aryl, 5-10-membered heteroaryl, or 4-7-membered heterocyclyl, each of which is optionally and independently substituted with one or more substituents selected from the group consisting of —F, —Cl, C$_{1-2}$alkyl, —CH$_2$OH, —CN, and —OR; and each of R and R' independently is hydrogen or C$_{1-4}$alkyl, or R and R' together with the nitrogen atom to which they are attached optionally form a morpholine ring, azetidine ring, pyrrolidine ring, piperidine ring, or piperazine ring.

2. The compound of claim 1, wherein said aryl group for R$^4$ is optionally substituted and selected from phenyl or naphthalene; the heteroaryl group for R$^4$ is optionally substituted and selected from a pyrrole, imidazole, pyrazole, triazole, thiazole, isothiazole, oxazole, pyridine, furopyridine, pyrimidine, pyrimidinone, pyrazine, pyridazine, quinolone, furopyrimidine, pyrrolopyrimidine, benzimidazole, benzothiazole, or benzoxazole; and said heterocyclyl group for R$^4$ is optionally substituted and selected from a tetrahydrofuran, oxetane, tetrahydropyran, dihydroisoxazole, pyrimidine-2,4(1H,3H)-dione, dihydrofuropyrimidine, dihydropyranopyrimidine, dihydropyrrolopyrimidine, tetrahydropyridopyrimidine, dihydropyridopyrimidine, dihydrofuropyridine, dihydropyridopyridine, tetrahydropteridine, or isoindoline-1,3-dione.

3. The compound of claim 1, wherein said heterocyclic group for the R$^4$ substituents is optionally substituted and selected from oxetane, azetidine, tetrahydrofuran, dihydropyran, tetrahydropyran, morpholine, piperidine, pyrrolidine, piperazine, furan, oxazole, oxadiazole, pyrrole, pyrazole, triazole, oxadiazole or tetrazole.

4. The compound of claim 1, wherein said heteroaryl group for R$^5$ is optionally substituted and selected from imidazole, triazole, thiazole, pyridine, or pyrimidine, and wherein said heterocyclyl group for R$^5$ is optionally substituted and selected from oxetane, tetrahydrofuran, or tetrahydropyran.

5. The compound of claim 1, wherein Ring C is optionally substituted C$_{4-6}$ cycloalkyl or optionally substituted 5-6 membered heteroaryl.

6. The compound of claim 1, wherein X is —O— or —NH—.

7. The compound of claim 1, wherein

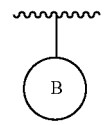

B is optionally substituted and selected from

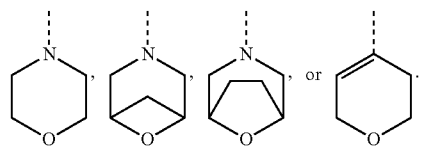

8. The compound of claim 1, wherein each R$^3$ independently is hydrogen, —C$_{1-4}$alkyl, halogen, —OC$_{1-2}$alkyl, —CN, —C$_{3-4}$ cycloalkyl, or —NRR', wherein each of said R$^3$ alkyl and cycloalkyl independently is optionally substituted.

9. The compound of claim 1, wherein
each R$^4$ independently is hydrogen or an optionally substituted group selected from C$_{1-4}$alkyl, C$_{2-4}$alkenyl, C$_{2-4}$alkynyl, C$_{3-5}$cycloalkyl, or phenyl.

10. The compound of claim 1, wherein each R$^4$ independently is an optionally substituted group selected from a pyrrole, imidazole, pyrazole, triazole, thiazole, isothiazole, oxazole, pyridine, furopyridine, pyrimidine, pyrimidinone, pyrazine, pyridazine, quinolone, furopyrimidine, pyrrolopyrimidine, benzimidazole, benzothiazole, benzoxazole, tetrahydrofuran, oxetane, tetrahydropyran, dihydroisoxazole, pyrimidine-2,4(1H,3H)-dione, dihydrofuropyrimidine, dihydropyranopyrimidine, dihydropyrrolopyrimidine, tetrahydropyridopyrimidine, dihydropyridopyrimidine, dihydrofuropyridine, dihydropyridopyridine, tetrahydropteridine, or isoindoline-1,3-dione.

11. The compound of claim 1, wherein each R$^4$ independently is an optionally substituted group selected from imidazole, pyrazole, pyrimidine, furopyrimidine, oxetane or dihydrofuropyrimidine.

12. The compound of claim 1, wherein each $R^4$ independently is hydrogen or an optionally substituted group selected from $C_{1-4}$ alkyl,

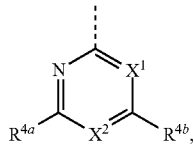

or a ring group selected from $C_{3-5}$ cycloalkyl, pyrrole, imidazole, pyrazole, triazole, thiazole, isothiazole, oxazole, tetrahydrofuran, oxetane, tetrahydropyran, dihydroisoxazole, or phenyl, wherein $X^1$ is N or $CR^{4d}$;

$X^2$ is N or $CR^{4c}$, wherein $X^1$ and $X^2$ cannot simultaneously be N;

each of $R^{4a}$, $R^{4b}$, and $R^{4c}$ independently is hydrogen, F, Cl, Br, CN, $NO_2$, $C_{1-4}$ alkyl, $C_{0-4}$ alkyl-$C_{3-5}$ cycloalkyl, $C_{0-4}$ alkyl-O—$C_{1-4}$ alkyl, $C_{0-4}$ alkyl-O—$C_{0-4}$ alkyl-$C_{3-5}$ cycloalkyl, $C_{2-4}$ alkenyl, $C_{2-4}$ alkynyl, C(O)O$C_{1-4}$ alkyl, C(O)O$C_{0-4}$ alkyl-$C_{3-5}$ cycloalkyl, C(O)$NH_2$, C(O)NH$C_{1-4}$ alkyl, C(O)N($C_{1-4}$ alkyl)$_2$, C(O)NH ($C_{0-4}$ alkyl-$C_{3-5}$ cycloalkyl), a heterocyclic group selected from oxetane, azetidine, tetrahydrofuran, dihydropyran, tetrahydropyran, morpholine, piperidine, or piperazine, or a heteroaryl group selected from furan, oxazole, oxadiazole, pyrrole, pyrazole, triazole, or tetrazole; or $R^{4c}$ and $R^{4a}$, or $R^{4c}$ and $R^{4b}$, together with the intervening atoms, optionally form a dihydrofuran, dihydropyran, or tetrahydropiperidine heterocyclic ring group;

$R^{4d}$ independently is hydrogen, F, Cl, Br, CN, $NO_2$, $C_{1-4}$ alkyl, $C_{0-4}$ alkyl-O—$C_{1-4}$ alkyl, $C_{2-4}$ alkenyl, $C_{2-4}$ alkynyl, C(O)O$C_{1-4}$ alkyl, C(O)$NH_2$, C(O)NH$C_{1-4}$ alkyl, or C(O)N($C_{1-4}$ alkyl)$_2$;

wherein each of the $R^4$ ring groups is optionally and independently substituted with one or more substituents selected from the group consisting of F, Cl, Br, CN, $NO_2$, $C_{1-4}$ alkyl, $C_{0-4}$ alkyl-$C_{3-5}$ cycloalkyl, $C_{0-4}$ alkyl-O—$C_{1-4}$ alkyl, $C_{0-4}$ alkyl-O—$C_{0-4}$ alkyl-$C_{3-5}$ cycloalkyl, $C_{2-4}$ alkenyl, $C_{2-4}$ alkynyl, C(O)O$C_{1-4}$ alkyl, C(O)O$C_{0-4}$ alkyl-$C_{3-5}$ cycloalkyl, C(O)$NH_2$, C(O)NH$C_{1-4}$ alkyl, C(O)N ($C_{1-4}$ alkyl)$_2$, C(O)NH($C_{0-4}$ alkyl-$C_{3-5}$ cycloalkyl), a heterocyclic group selected from oxetane, azetidine, tetrahydrofuran, dihydropyran, tetrahydropyran, morpholine, piperidine, or piperazine, and a heteroaryl group selected from furan, oxazole, oxadiazole, pyrrole, pyrazole, triazole, or tetrazole;

each of said heterocyclic and heteroaryl groups for $R^{4a}$, $R^{4b}$ and $R^{4c}$, and for the substituents of $R^4$ is optionally and independently substituted with one or more substituents selected from the group consisting of —F, $C_{1-4}$ alkyl, —OH, —C(O)$C_{1-4}$ alkyl, —C(O)O$C_{1-4}$ alkyl, or —C(O)O$C_{0-4}$ alkyl-$C_{3-5}$ cycloalkyl; and wherein each of said alkyl and cycloalkyl groups for $R^{4a}$, $R^{4b}$ and $R^{4c}$, and for the substituents of $R^4$ is optionally and independently substituted with one or more substituents selected from the group consisting of —F and —OH.

13. The compound of claim 1, wherein each $R^4$ independently is $C_{1-4}$ alkyl or a ring group selected from $C_{3-5}$ cycloalkyl, pyrazole, imidazole, oxetane,

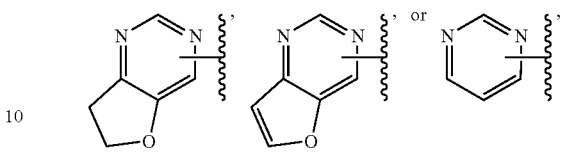

wherein said $R^4$ $C_{1-4}$ alkyl is optionally substituted with one or more substituents selected from the group consisting of —Br, —Cl, —F, and —O($C_{1-4}$ alkyl), and wherein each of said $R^4$ ring groups is optionally and independently substituted with one or more substituents selected from the group consisting of —Br, —Cl, —F, $C_{1-4}$alkyl, —CN, —O($C_{1-4}$ alkyl), $C_{3-6}$cycloalkyl, $C_{0-4}$ alkyl-O—$C_{1-4}$ alkyl, C(O) NH$C_{1-4}$ alkyl, C(O)N($C_{1-4}$ alkyl)$_2$, and a piperazine, wherein each of said optional $R^4$ substituents is optionally and independently substituted with one or more substitutents selected from the group consisting of —F, $C_{1-4}$alkyl, —OH, and —O$C_{1-4}$alkyl.

14. The compound of claim 13, wherein said $R^4$ $C_{1-4}$ alkyl is optionally substituted with one or more substituents selected from the group consisting of —F and —O($C_{1-4}$ alkyl), and wherein each of said $R^4$ ring groups is optionally and independently substituted with one or more substituents selected from the group consisting of $C_{1-4}$alkyl, —O($C_{1-4}$ alkyl), $C_{0-4}$ alkyl-O—$C_{1-4}$ alkyl, C(O)NH$C_{1-4}$ alkyl, C(O)N ($C_{1-4}$ alkyl)$_2$, and a piperazine, wherein each of said optional $R^4$ substituents is optionally substituted with one or more $C_{1-4}$alkyl.

15. The compound of claim 1, wherein each of $R^1$ and $R^2$ independently is hydrogen, —C(O)NH$R_4$, —C(O)O$R^4$, —NHC(O)$R^4$, —NHC(O)O$R_4$, —$C_{0-4}$ alkyl-NH$R^4$, —O$R^4$, or $R^7$.

16. The compound of claim 1, wherein $R^7$ is optionally substituted and selected from a pyrrole, imidazole, pyrazole, triazole, thiazole, isothiazole, oxazole, pyridine, furopyridine, pyrimidine, pyrimidinone, pyrazine, pyridazine, quinolone, furopyrimidine, pyrrolopyrimidine, benzimidazole, benzothiazole, benzoxazole, tetrahydrofuran, oxetane, tetrahydropyran, dihydroisoxazole, pyrimidine-2,4(1H,3H)-dione, dihydrofuropyrimidine, dihydropyranopyrimidine, dihydropyrrolopyrimidine, tetrahydropyridopyrimidine, dihydropyridopyrimidine, dihydrofuropyridine, dihydropyridopyridine, tetrahydropteridine, or isoindoline-1,3-dione.

17. The compound of claim 16, wherein $R^7$ is optionally substituted and selected from a pyrimidine, imidazole, pyrazole, thiazole, furopyrimidine, pyrrolopyrimidine, benzimidazole, benzothiazole, benzoxazole, oxetane, dihydrofuropyrimidine, or isoindoline-1,3-dione.

18. The compound of claim 17, wherein $R^7$ is optionally substituted and selected from a pyrimidine, pyrazole, furopyrimidine, thiazole, or isoindoline-1,3-dione.

19. The compound of claim 1, wherein X is —O—.

20. The compound of claim 1, wherein Ring C is optionally substituted $C_{4-6}$ cycloalkyl.

21. The compound of claim 20, wherein Ring C is optionally substituted cyclohexane.

22. The compound of claim 1, represented by the following formula:

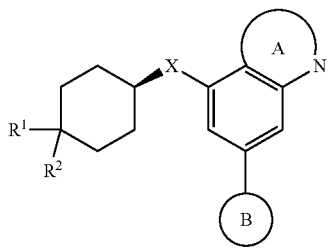

(II)

or a pharmaceutically acceptable salt thereof, wherein $R^1$ is —C(O)NHR$^4$, —C(O)OR$^4$, —NHC(O)R$^4$, —NHC(O)OR$^4$, —NHC(O)NHR$^4$, —NHS(O)$_2$R$^4$, —C$_{0-4}$ alkyl-NHR$^4$, —OR$^4$, or R$^7$; and $R^2$ is hydrogen.

23. The compound of claim 1, represented by the following formula:

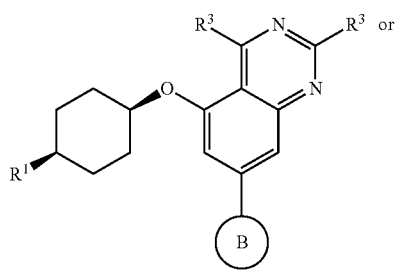

(III-A-1)

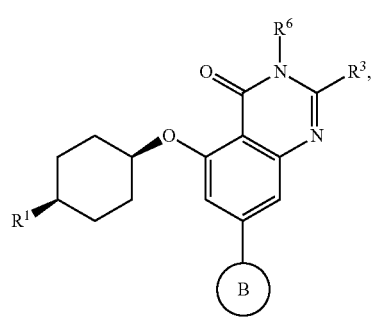

(III-B-1)

(III-B-1), or a pharmaceutically acceptable salt thereof.

24. The compound of claim 23, wherein each $R^1$ independently is

—C(O)NHR$^4$, —C(O)OR$^4$, —NHC(O)R$^4$, —NHC(O)OR$^4$, —C$_{1-4}$ alkyl-NHR$^4$, —NHR$^4$, —OR$^4$, or R$^7$.

25. The compound of claim 24, wherein $R^1$ is —C$_{1-4}$ alkyl-NHR$^4$, —NHR$^4$, or —OR$^4$.

26. The compound of claim 1, represented by following formula:

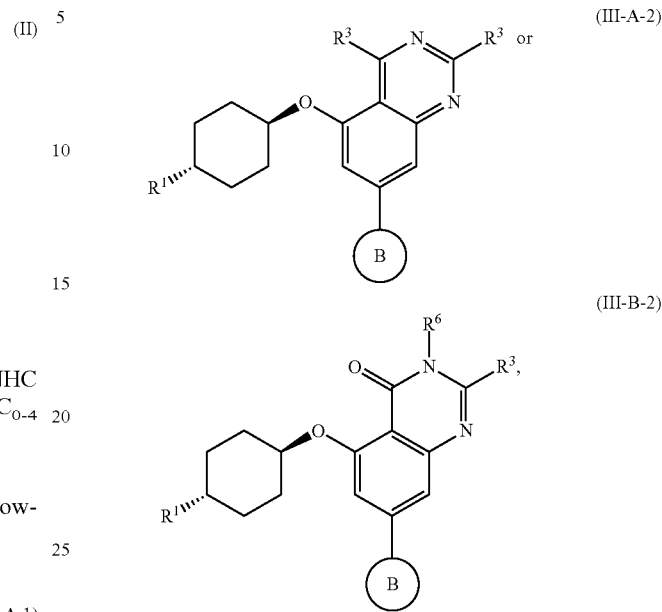

(III-A-2)

(III-B-2)

or a pharmaceutically acceptable salt thereof.

27. The compound of claim 26, wherein each $R^1$ independently is

—C(O)NHR$^4$, —C(O)OR$^4$, —NHC(O)R$^4$, —NHC(O)OR$^4$, —C$_{0-4}$ alkyl-NHR$^4$, —OR$^4$, or R$^7$.

28. The compound of claim 1, wherein each $R^3$ independently is hydrogen, methyl, —Cl, —OCH$_3$, —CN, cyclopropyl, —NHCH$_3$, or —N(CH$_3$)$_2$; and $R^6$ is hydrogen or methyl.

29. The compound of claim 1, wherein Ring C is optionally substituted 5-6 membered heteroaryl.

30. The compound of claim 1, wherein

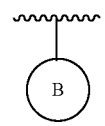

is optionally substituted

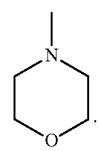

.

31. The compound of claim 1, wherein Ring C is optionally substituted phenyl.

32. The compound of claim 1, wherein X is —OC$_{1-4}$ alkyl-.

33. The compound of claim 32, represented by the following formula:

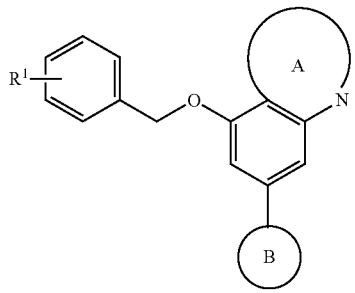

(IV)

or a pharmaceutically acceptable salt thereof, wherein:
R$^1$ is hydrogen, —C(O)NHR$^4$, —C(O)OR$^4$, —NHC(O)R$^4$, —NHC(O)OR$^4$, —NHC(O)NHR$^4$, —NHS(O)$_2$R$^4$, —C$_{0-4}$ alkyl-NHR$^4$, —OR$^4$, or R$^7$.

34. The compound of claim 31, wherein

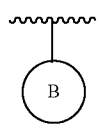

is optionally substituted

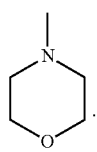

35. The compound of claim 31, represented by the following formula:

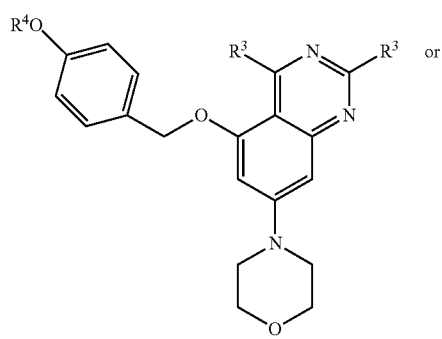

(V-A)

-continued

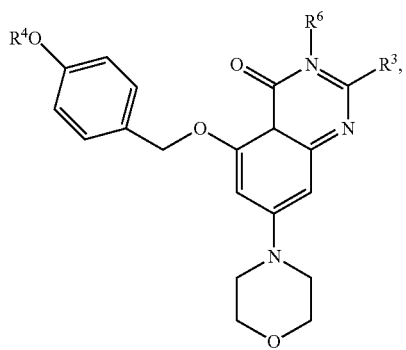

(V-B)

or a pharmaceutically acceptable salt thereof.

36. The compound of claim 35, wherein
R$^3$ is hydrogen, methyl, cyclopropyl, —F, —Cl, —OC$_{1-2}$alkyl, —NRR', or —CN, wherein each of said R$^3$ alkyl is optionally substituted with one or more substituents selected from the group consisting of —F, —OH, and —O(C$_{1-2}$ alkyl);
each R$^4$ independently is optionally substituted C$_{1-4}$ alkyl optionally substituted with one or more substituents selected from the group consisting of —F, —OH, and —O(C$_{1-2}$ alkyl);
R and R' are each and independently hydrogen or C$_{1-2}$ alkyl.

37. The compound of claim 36, wherein
each R$^3$ independently is hydrogen, methyl, —Cl, —OCH$_3$, —CN, cyclopropyl, —NHCH$_3$, or —N(CH$_3$)$_2$; and
R$^6$ is hydrogen or methyl.

38. A compound selected from the list of compounds in Tables 1 and 2, or a pharmaceutically acceptable salt thereof.

39. A pharmaceutical composition comprising a compound of claim 1 and a pharmaceutically acceptable excipient.

40. A method of sensitizing a cell to a therapeutic agent or a disease state that induces a DNA lesion comprising the step of contacting the cell with the compound of claim 1, or a pharmaceutical composition comprising said compound.

41. A method of potentiating a therapeutic regimen for the treatment of cancer in a patient comprising the step of administering to said patient an effective amount of the compound of claim 1, or a pharmaceutical composition comprising said compound.

42. A method of treating cancer or inhibiting cancer cell growth in a patient comprising administering to said patient an effective amount of the compound of claim 1, or a pharmaceutical composition comprising said compound, either alone or in combination with one or more additional therapeutic agent.

43. A method of preparing a compound of claim 1, or a pharmaceutically acceptable salt thereof, wherein the method comprises:
reacting Compound (X-1) with Compound (Y-1) to form a compound represented by Formula (I) or a pharmaceutically acceptable salt thereof:

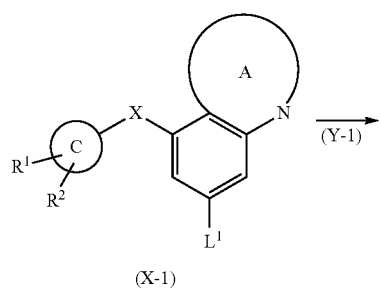

(X-1)

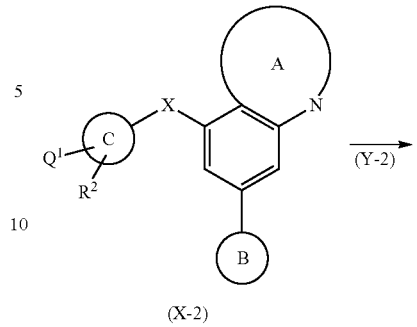

(X-2)

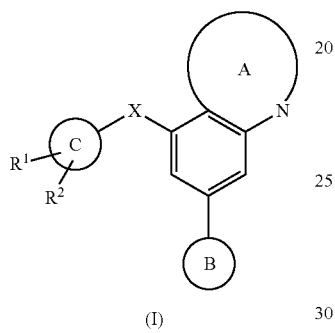

(I)

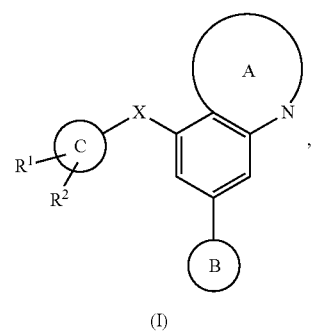

(I)

wherein:

L¹ of Compound (X-1) is a halogen, toluenesulfonate, methanesulfonate or trifluoromethanesulfonate, and the other variables of Compound (X-1) are each and independently as described in claim 1; and Compound (Y-1) is

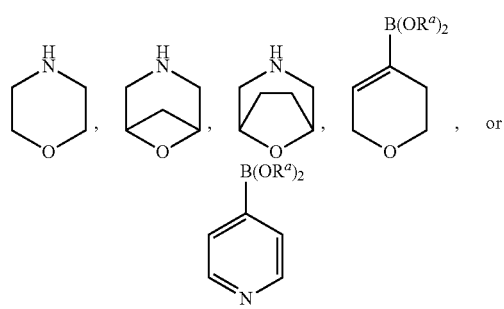

wherein $R^a$ is —H or two $R^a$, together with the oxygen atom to which they are attached, form a dioxane ring optionally substituted with one or more $C_{1-2}$ alkyl.

44. A method of preparing a compound of claim 1, or a pharmaceutically acceptable salt thereof, wherein $R^1$ is —NHC(O)R⁴, —NHC(O)OR⁴, —NHC(O)NHR⁴, —NHS(O)₂R⁴, —NHR⁴, or —OR⁴; and the other variables of Formula (I) are each and independently as described in claim 1; and wherein the method comprises:

reacting Compound (X-2) with Compound (Y-2) to form a compound represented by Formula (I) or a pharmaceutically acceptable salt thereof:

$Q^1$ of Compound (X-2) is —NH₂ or —OH, and the other variables of Compound (X-2) are each and independently as described in claim 1; and Compound (Y-2) is R⁴—C(O)-L², R⁴—O—C(O)-L², NHR⁴—C(O)-L², R⁴S(O)₂-L², R⁴-L², R⁴C(O)OR^b, or R⁴—N═C═O, wherein each R⁴ is as described in claim 1, L² is a halogen, toluenesulfonate, methanesulfonate or trifluoromethanesulfonate, and R^b is $C_{1-4}$ alkyl.

45. A method of preparing a compound of claim 1, or a pharmaceutically acceptable salt thereof, wherein X is —NH— or —O—, and the other variables of Formula (I) are each and independently as described in claim 1, and wherein the method comprises:

(i) reacting Compound (X-3) with Compound (Y-3) to form a compound represented by Formula (I) or a pharmaceutically acceptable salt thereof:

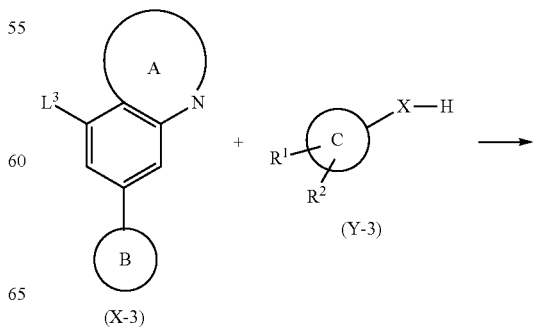

-continued

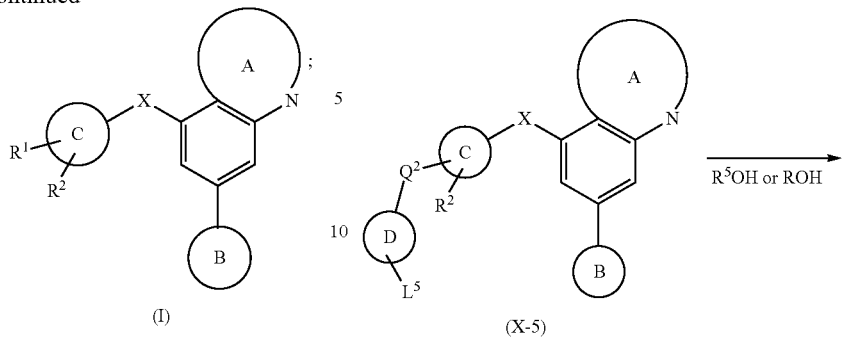

(I)

or (ii) reacting Compound X-4 with Compound Y-4 to form a compound represented by formula (I) or a pharmaceutically acceptable salt thereof:

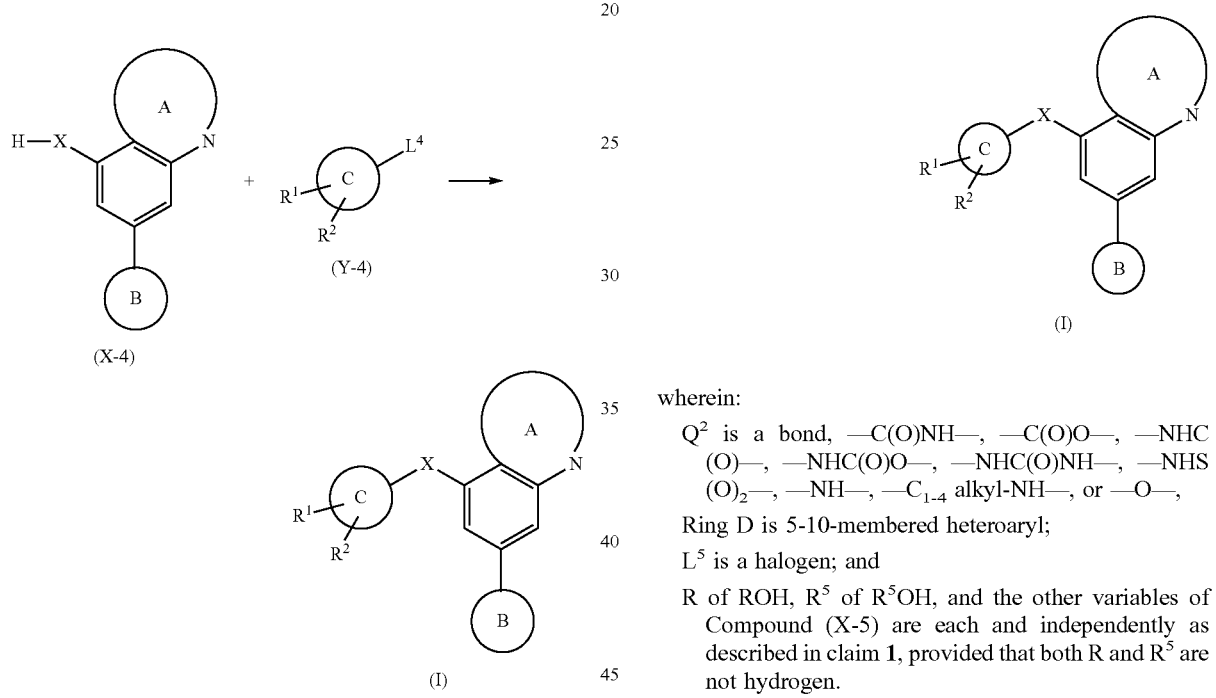

wherein $L^3$ is a halogen; $L^4$ is a halogen, toluenesulfonate, methanesulfonate, or trifluoromethanesulfonate, and wherein the variables of each of Compounds (X-3), (X-4), (Y-3), and (Y-4) are each and independently as described in claim 1.

46. A method of preparing a compound of claim 1 or a pharmaceutically acceptable salt thereof, wherein
$R^1$ is —C(O)NHR$^4$, —C(O)OR$^4$, —NHC(O)R$^4$, —NHC(O)OR$^4$, —NHC(O)NHR$^4$, —NHS(O)$_2$R$^4$, —NHR$^4$, —C$_{1-4}$ alkyl-NHR$^4$, —OR$^4$, or R$^7$; $R^2$ is hydrogen; each of R$^4$ independently is 5-10 membered heteroaryl substituted with —OR$^5$; R$^7$ independently is 5-10 membered heteroaryl substituted with —OR; R, R$^5$, and the other variables of formula (I) are each and independently as described in claim 1, provided that both R and R$^5$ are not hydrogen, and wherein the method comprises:

reacting Compound (X-5) with R$^5$OH or ROH to form a compound represented by formula (I) or a pharmaceutically acceptable salt thereof:

wherein:

$Q^2$ is a bond, —C(O)NH—, —C(O)O—, —NHC(O)—, —NHC(O)O—, —NHC(O)NH—, —NHS(O)$_2$—, —NH—, —C$_{1-4}$ alkyl-NH—, or —O—, Ring D is 5-10-membered heteroaryl;

$L^5$ is a halogen; and

R of ROH, R$^5$ of R$^5$OH, and the other variables of Compound (X-5) are each and independently as described in claim 1, provided that both R and R$^5$ are not hydrogen.

47. A method of preparing a compound of claim 1, or a pharmaceutically acceptable salt thereof, wherein X is —O—, and the other variables of Formula (I) are each and independently as described in claim 1, and wherein the method comprises:

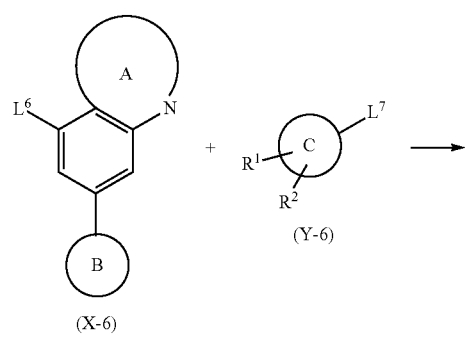

-continued
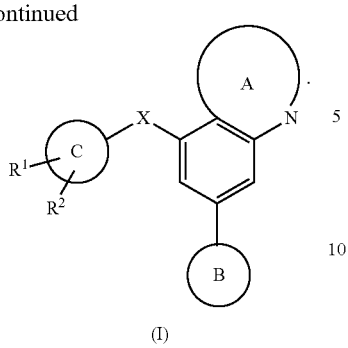
(I)
wherein $L^6$ is —OH; $L^7$ is —OH; and the remaining variables of each of Compounds (X-6), and (Y-6) are each and independently as described in claim 1.
48. A kit or composition for editing one or more target genomic regions, comprising:
 a genome editing system; and
 a compound of claim 1 or a pharmaceutically acceptable salt thereof.
* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: AAVS1 target site

<400> SEQUENCE: 1
accccacagt ggggccacta                    20

```
<210> SEQ ID NO 2
<211> LENGTH: 20
<212> TYPE: DNA
<213> ORGANISM: Artificial Sequence
<220> FEATURE:
<223> OTHER INFORMATION: NAV1.7 target

<400> SEQUENCE: 2
ggctgagcgt ccatcaacca                                                 20

<210> SEQ ID NO 3
<211> LENGTH: 100
<212> TYPE: RNA
<213> ORGANISM: Artificial Sequence
<220> FEATURE:
<223> OTHER INFORMATION: AAVS1 sgRNA
<220> FEATURE:
<221> NAME/KEY: misc_feature
<222> LOCATION: (1)..(3)
<223> OTHER INFORMATION: 2'-O-methyl 3'-phosphorothioate
<220> FEATURE:
<221> NAME/KEY: misc_feature
<222> LOCATION: (97)..(99)
<223> OTHER INFORMATION: 2'-O-methyl 3'-phosphorothioate

<400> SEQUENCE: 3
accccacagu ggggccacua guuuuagagc uagaaauagc aaguuaaaau aaggcuaguc      60
cguuaucaac uugaaaaagu ggcaccgagu cggugcuuuu                          100

<210> SEQ ID NO 4
<211> LENGTH: 100
<212> TYPE: RNA
<213> ORGANISM: Artificial Sequence
<220> FEATURE:
<223> OTHER INFORMATION: NAV1.7 sgRNA
<220> FEATURE:
<221> NAME/KEY: misc_feature
<222> LOCATION: (1)..(3)
<223> OTHER INFORMATION: 2'-O-methyl 3'-phosphorothioate
<220> FEATURE:
<221> NAME/KEY: misc_feature
<222> LOCATION: (97)..(99)
<223> OTHER INFORMATION: 2'-O-methyl 3'-phosphorothioate

<400> SEQUENCE: 4
ggcugagcgu ccaucaacca guuuuagagc uagaaauagc aaguuaaaau aaggcuaguc      60
cguuaucaac uugaaaaagu ggcaccgagu cggugcuuuu                          100

<210> SEQ ID NO 5
<211> LENGTH: 90
<212> TYPE: DNA
<213> ORGANISM: Artificial Sequence
<220> FEATURE:
<223> OTHER INFORMATION: AAVS1 PAM
<220> FEATURE:
<221> NAME/KEY: misc_feature
<222> LOCATION: (1)..(3)
<223> OTHER INFORMATION: 2'-O-methyl 3'-phosphorothioate
<220> FEATURE:
<221> NAME/KEY: misc_feature
<222> LOCATION: (87)..(89)
<223> OTHER INFORMATION: 2'-O-methyl 3'-phosphorothioate

<400> SEQUENCE: 5
gggtactttt atctgtcccc tccacccac agtggggcca gaattctcag ctagggacag       60
gattggtgac agaaaagccc catccttagg                                      90
```

```
<210> SEQ ID NO 6
<211> LENGTH: 90
<212> TYPE: DNA
<213> ORGANISM: Artificial Sequence
<220> FEATURE:
<223> OTHER INFORMATION: AAVS1 Non-PAM
<220> FEATURE:
<221> NAME/KEY: misc_feature
<222> LOCATION: (1)..(3)
<223> OTHER INFORMATION: 2'-O-methyl 3'-phosphorothioate
<220> FEATURE:
<221> NAME/KEY: misc_feature
<222> LOCATION: (87)..(89)
<223> OTHER INFORMATION: 2'-O-methyl 3'-phosphorothioate

<400> SEQUENCE: 6
cctaaggatg gggctttct gtcaccaatc ctgtccctag ctgagaattc tggccccact      60
gtggggtgga ggggacagat aaaagtaccc                                     90

<210> SEQ ID NO 7
<211> LENGTH: 90
<212> TYPE: DNA
<213> ORGANISM: Artificial Sequence
<220> FEATURE:
<223> OTHER INFORMATION: NAV1.7 PAM
<220> FEATURE:
<221> NAME/KEY: misc_feature
<222> LOCATION: (1)..(3)
<223> OTHER INFORMATION: 2'-O-methyl 3'-phosphorothioate
<220> FEATURE:
<221> NAME/KEY: misc_feature
<222> LOCATION: (87)..(89)
<223> OTHER INFORMATION: 2'-O-methyl 3'-phosphorothioate

<400> SEQUENCE: 7
agctgtccat tggggagcat gagggctgag cgtccatcaa ctgagaattc ccagggagac      60
cacaccgttg cagtccacag cactgtgcat                                      90

<210> SEQ ID NO 8
<211> LENGTH: 90
<212> TYPE: DNA
<213> ORGANISM: Artificial Sequence
<220> FEATURE:
<223> OTHER INFORMATION: NAV1.7 Non-PAM
<220> FEATURE:
<221> NAME/KEY: misc_feature
<222> LOCATION: (1)..(3)
<223> OTHER INFORMATION: 2'-O-methyl 3'-phosphorothioate
<220> FEATURE:
<221> NAME/KEY: misc_feature
<222> LOCATION: (87)..(89)
<223> OTHER INFORMATION: 2'-O-methyl 3'-phosphorothioate

<400> SEQUENCE: 8
atgcacagtg ctgtggactg caacggtgtg gtctccctgg gaattctcag ttgatggacg      60
ctcagccctc atgctcccca atggacagct                                      90

<210> SEQ ID NO 9
<211> LENGTH: 20
<212> TYPE: DNA
<213> ORGANISM: Artificial Sequence
<220> FEATURE:
<223> OTHER INFORMATION: AAVS1 FW

<400> SEQUENCE: 9 ggacaaccc aaagtacccc                                                  20

<210> SEQ ID NO 10
```

```
<211> LENGTH: 20
<212> TYPE: DNA
<213> ORGANISM: Artificial Sequence
<220> FEATURE:
<223> OTHER INFORMATION: AAVS1 RV

<400> SEQUENCE: 10
aggatcagtg aaacgcacca                                              20

<210> SEQ ID NO 11
<211> LENGTH: 20
<212> TYPE: DNA
<213> ORGANISM: Artificial Sequence
<220> FEATURE:
<223> OTHER INFORMATION: NAV1.7 FW

<400> SEQUENCE: 11
gccagtgggt tcagtggtat                                              20

<210> SEQ ID NO 12
<211> LENGTH: 25
<212> TYPE: DNA
<213> ORGANISM: Artificial Sequence
<220> FEATURE:
<223> OTHER INFORMATION: NAV1.7 RV

<400> SEQUENCE: 12
tcagcattat ccttgcattt tctgt                                        25
```